(12) United States Patent
McClure et al.

(10) Patent No.: US 6,696,464 B2
(45) Date of Patent: Feb. 24, 2004

(54) TRIAZOLO-PYRIDINES ANTI-INFLAMMATORY COMPOUNDS

(75) Inventors: Kim F. McClure, Mystic, CT (US); Michael A. Letavic, Mystic, CT (US); Mark A. Dombroski, Waterford, CT (US); Allen J. Duplantier, Ledyard, CT (US); Ellen R. Laird, Longmont, CO (US)

(73) Assignee: Pfizer Inc, New York, NY (US)

( * ) Notice: Subject to any disclaimer, the term of this patent is extended or adjusted under 35 U.S.C. 154(b) by 0 days.

(21) Appl. No.: 10/094,760

(22) Filed: Mar. 11, 2002

(65) Prior Publication Data
US 2003/0096838 A1 May 22, 2003

Related U.S. Application Data
(60) Provisional application No. 60/274,840, filed on Mar. 9, 2001.

(51) Int. Cl.[7] .............. A61K 31/44; C07D 471/02
(52) U.S. Cl. ........................... 514/303; 546/119
(58) Field of Search .................. 546/119; 514/303

(56) References Cited

U.S. PATENT DOCUMENTS

| | | | |
|---|---|---|---|
| 5,716,955 A | 2/1998 | Adams et al. | 514/235.8 |
| 5,716,972 A | 2/1998 | Adams et al. | 514/341 |
| 5,717,100 A | 2/1998 | Selnick et al. | 546/194 |
| 5,756,499 A | 5/1998 | Adams et al. | 514/235.8 |
| 5,777,097 A | 7/1998 | Lee et al. | 536/24.31 |

FOREIGN PATENT DOCUMENTS

| | | | |
|---|---|---|---|
| EP | 0 662 477 | * 7/1995 | |
| WO | 9901449 | 1/1999 | C07D/401/04 |
| WO | 9961440 | 12/1999 | C07D/403/14 |
| WO | 0006563 | 2/2000 | C07D/401/04 |
| WO | 0031065 | 6/2000 | C07D/401/04 |
| WO | 0035911 | 6/2000 | C07D/405/14 |
| WO | 0040243 | 7/2000 | A61K/31/444 |
| WO | 0041698 | 7/2000 | A61K/31/535 |
| WO | 0063204 | 10/2000 | C07D/413/00 |

OTHER PUBLICATIONS

The Journal of Biological Chemistry, vol. 271, No. 40, pp. 24313–24316 (1996).
Bioorganic & Medicinal Chemistry Letters, 10, pp. 2047–2050 (2000).
Bioorganic & Medicinal Chemistry Letters, 11, pp. 9–12 (2001).

* cited by examiner

Primary Examiner—D. Margaret Seaman
(74) Attorney, Agent, or Firm—Peter C. Richardson; Garth Butterfield

(57) ABSTRACT

The present invention relates to novel triazolo-pyridines of the formula I

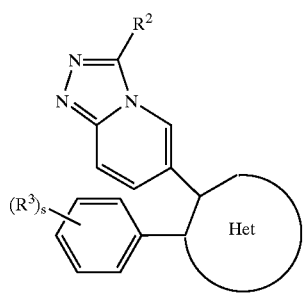

wherein Het is an optionally substituted 5-membered heterocycle containing one to two heteroatoms selected from nitrogen, sulfur and oxygen wherein at least one of said heteroatoms atoms must be nitrogen;

$R^2$ is selected from the group consisting of hydrogen, $(C_1-C_6)$alkyl or other suitable substituents;

$R^3$ is selected from the group consisting of hydrogen, $(C_1-C_6)$alkyl or other suitable substituents;

s is an integer from 0–5;

to intermediates for their preparation, to pharmaceutical compositions containing them and to their medicinal use. The compounds of the present invention are potent inhibitors of MAP kinases, preferably p38 kinase. They are useful in the treatment of inflammation, osteoarthritis, rheumatoid arthritis, cancer, repurfusion or ischemia in stroke or heart attack, autoimmune diseases and other disorders.

53 Claims, 1 Drawing Sheet

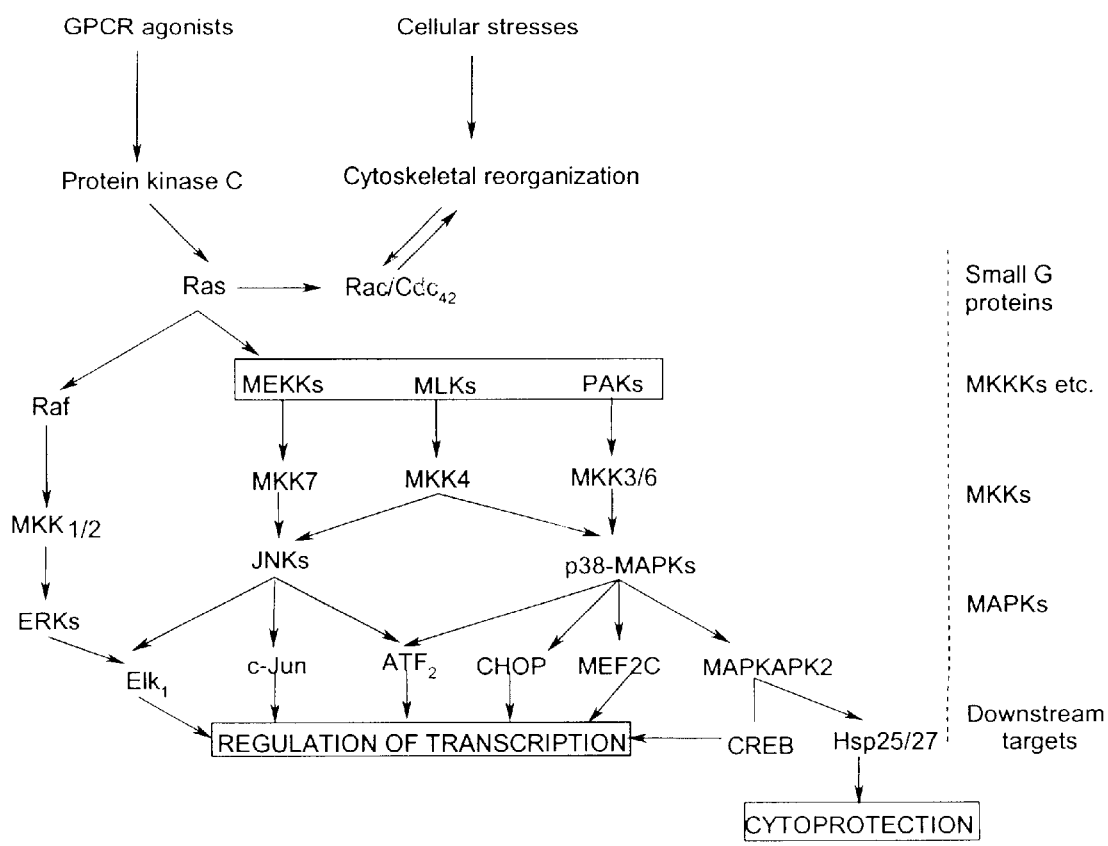
-- FIGURE 1
MAP Kinase Family: General Feature

TRIAZOLO-PYRIDINES ANTI-INFLAMMATORY COMPOUNDS

This application claims the benefit of U.S. Provisional Application No. 60/274,840, filed Mar. 9, 2001.

The present invention relates to novel triazolo-pyridines, to intermediates for their preparation, to pharmaceutical compositions containing them and to their medicinal use. The compounds of the present invention are potent inhibitors of MAP kinases, preferably p38 kinase. They are useful in the treatment of inflammation, osteoarthritis, rheumatoid arthritis, cancer, reperfusion or ischemia in stroke or heart attack, autoimmune diseases and other disorders.

Intracellular signal transduction is the means by which cells respond to extracellular stimuli. Regardless of the nature of the cell surface receptor (e. g. protein tyrosine kinase or seven-transmembrane G-protein coupled), protein kinases and phosphatases along with phopholipases are the essential machinery by which the signal is further transmitted within the cell [Marshall, J. C. Cell, 80, 179–278 (1995)]. Protein kinases can be categorized into five classes with the two major classes being, tyrosine kinases and serine/threonine kinases depending upon whether the enzyme phosphorylates its substrate(s) on specific tyrosine(s) or serine/threonine(s) residues [Hunter, T. Methods in Enzymology (Protein Kinase Classification) p. 3, Hunter, T.; Sefton, B. M.; eds. vol. 200, Academic Press; San Diego, 1991].

For most biological responses, multiple intracellular kinases are involved and an individual kinase can be involved in more than one signaling pathway. These kinases are often cytosolic and can translocate to the nucleus or the ribosomes where they can affect transcriptional and translational events, respectively. The involvement of kinases in transcriptional control is presently much better understood than their effect on translation as illustrated by the studies on growth factor induced signal transduction involving MAP/ERK kinase [Marshall, C. J. Cell, 80, 179 (1995); Herskowitz, I. Cell, 80, 187 (1995); Hunter, T. Cell, 80, 225 (1995); Seger, R., and Krebs, E. G. FASEB J., 726–735 (1995)].

While many signaling pathways are part of normal cell homeostasis, numerous cytokines (e.g., IL-1 and TNF) and certain other mediators of inflammation (e.g., COX-2, and iNOS) are produced only as a response to stress signals such as bacterial lipopolysaccharide (LPS). Early evidence suggesting that the signal transduction pathway leading to LPS-induced cytokine biosynthesis involved protein kinases came from studies of Weinstein [Weinstein, et al., J. Immunol, 151, 3829(1993)] but the specific protein kinases involved were not identified. Working from a similar perspective, Han [Han, et al., Science 265, 808(1994)] identified murine p38 as a kinase which is tyrosine phosphorylated in response to LPS. Additional evidence of the involvement of the p38 kinase in LPS-stimulated signal transduction pathway leading to the initiation of proinflammatory cytokine biosynthesis was provided by the discovery of p38 kinase (CSBP 1 and 2) by Lee [Lee; et al,. Nature, 372, 739(1994)] as the molecular target for a novel class of anti-inflammatory agents. Thus, compounds which inhibit p38 will inhibit IL-1 and TNF synthesis in human monocytes. Such results have been reported by [Lee, et al., Int. J. Immunopharmac., 10(7), 835(1988)] and [Lee; et al.,Annals N.Y. Acad. Sci., 696, 149(1993)].

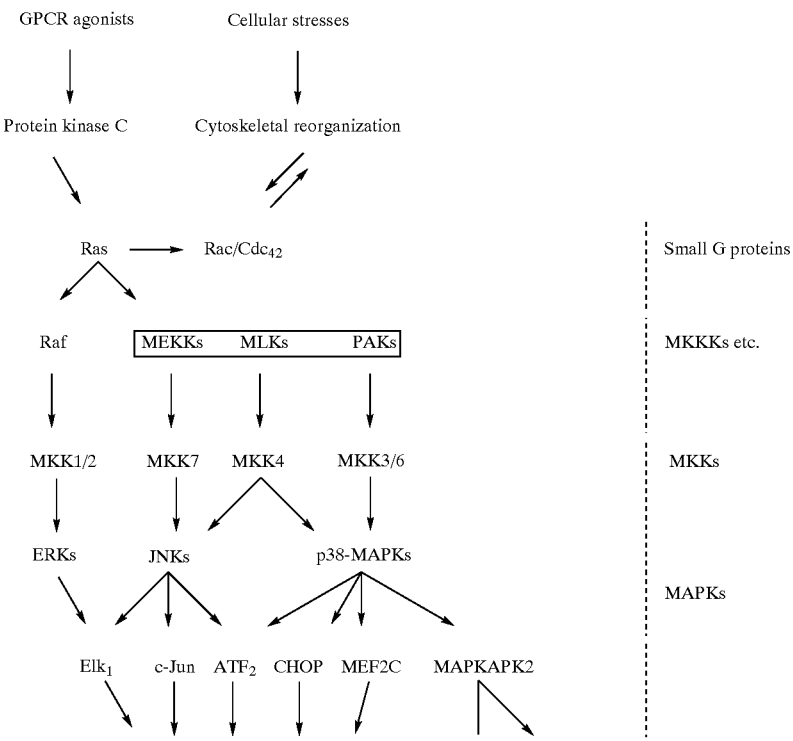

FIG. 1
MAP Kinase Family: General Feature

-continued

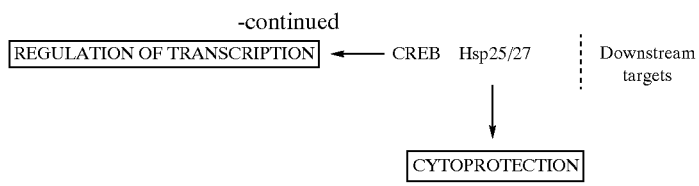

It is now accepted that CSBP/p38 is a one of several kinases involved in a stress-response signal transduction pathway which is parallel to and largely independent of the analogous mitogen-activated protein kinase (MAP) kinase cascade (FIG. 1). Stress signals, including LPS, pro-inflammatory cytokines, oxidants, UV light and osmotic stress, activate kinases upstream from CSBP/p38 which in turn phosphorylate CSBP/p38 at threonine 180 and tyrosine 182 resulting in CSBP/p38 activation. MAPKAP kinase-2 and MAPKAP kinase-3 have been identified as downstream substrates of CSBP/p38 which in turn phosphorylate heat shock protein Hsp 27. It is now known that MAPKAP-2 is essential for LPS induced TNFα biosynthesis [Kotlyarov et al. *Nature Cell Biol.*, 1, 94 (1999), see also Cohen, P. *Trends Cell Biol.*, 353–361(1997)].

In addition to inhibiting IL-1 and TNF, CSBP/p38 kinase inhibitors also decrease the synthesis of a wide variety of pro-inflammatory proteins including, IL-6, IL-8, GM-CSF and COX-2. Inhibitors of CSBP/p38 kinase have also been shown to suppress the TNF-induced expression of VCAM-1 on endothelial cells, the TNF-induced phosphorylation and activation of cytosolic PLA2 and the IL-1 stimulated synthesis of collagenase and stromelysin. These and additional data demonstrate that CSBP/p38 is involved not only cytokine synthesis, but also in cytokine signaling [CSBP/p38 kinase reviewed in Cohen, P. *Trends Cell Biol.*, 353–361 (1997)].

Interleukin-1 (IL-1) and Tumor Necrosis Factor (TNF) are biological substances produced by a variety of cells, such as monocytes or macrophages. IL-1 has been demonstrated to mediate a variety of biological activities thought to be important in immunoregulation and other physiological conditions such as inflammation [See, e.g., Dinarello et al., Rev. Infect. Disease, 6, 51 (1984)]. The myriad of known biological activities of IL-1 include the activation of T helper cells, induction of fever, stimulation of prostaglandin or collagenase production, neutrophil chemotaxis, induction of acute phase proteins and the suppression of plasma iron levels.

There are many disease states in which excessive or unregulated IL-1 production is implicated in exacerbating and/or causing the disease. These include rheumatoid arthritis, osteoarthritis, endotoxemia and/or toxic shock syndrome, other acute or chronic inflammatory disease states such as the inflammatory reaction induced by endotoxin or inflammatory bowel disease, tuberculosis, atherosclerosis, muscle degeneration, cachexia, psoriatic arthritis, Reiter's syndrome, rheumatoid arthritis, gout, traumatic arthritis, rubella arthritis, and acute synovitis. Recent evidence also links IL-1 activity to diabetes and pancreatic β cells, Dinarello, *J. Clinical Immunology*, 5 (5), 287–297 (1985).

Excessive or unregulated TNF production has been implicated in mediating or exacerbating a number of diseases including rheumatoid arthritis, rheumatoid spondylitis, osteoarthritis, gouty arthritis and other arthritic conditions; sepsis, septic shock, endotoxic shock, gram negative sepsis, toxic shock syndrome, adult respiratory distress syndrome, cerebral malaria, chronic pulmonary inflammatory disease, silicosis, pulmonary sarcoidosis, bone resorption diseases, reperfusion injury, graft vs. host reaction, allograft rejections, fever and myalgias due to infection, such as influenza, cachexia secondary to infection or malignancy, cachexia secondary to acquired immune deficiency syndrome (AIDS), AIDS, ARC (AIDS related complex), keloid information, scar tissue formation, Crohn's disease, ulcerative colitis, or pyrosis.

Interleukin-8 (IL-8) is a chemotactic factor produced by several cell types including mononuclear cells, fibroblasts, endothelial cells, and keratinocytes. Its production from endothelial cells is induced by IL-1, TNF, or lipopolysaccharide (LPS). IL-8 stimulates a number of functions in vitro. It has been shown to have chemoattractant properties for neutrophils, T-lymphocytes, and basophils. In addition it induces histamine release from basophils from both normal and atopic individuals as well lysosomal enzyme release and respiratory burst from neutrophils. IL-8 has also been shown to increase the surface expression of Mac-1 (CD11b/CD18) on neutrophils without de novo protein synthesis, this may contribute to increased adhesion of the neutrophils to vascular endothelial cells. Many diseases are characterized by massive neutrophil infiltration. Conditions associated with an increase in IL-8 production (which is responsible for chemotaxis of neutrophils into the inflammatory site) would benefit by compounds which are suppressive of IL-8 production.

IL-1 and TNF affect a wide variety of cells and tissues and these cytokines as well as other leukocyte derived cytokines are important and critical inflammatory mediators of a wide variety of disease states and conditions. The inhibition of these cytokines is of benefit in controlling, reducing and alleviating many of these disease states.

Inhibition of signal transduction via CSBP/p38, which in addition to IL-1, TNF and IL-8 described above is also required for the synthesis and/or action of several additional pro-inflammatory proteins (i.e., IL-6, GM-CSF, COX-2, collagenase and stromelysin), is expected to be a highly effective mechanism for regulating the excessive and destructive activation of the immune system. This expectation is supported by the potent and diverse anti-inflammatory activities described for CSBP/p38 kinase inhibitors [Badger, et al., *J. Pharm. Exp. Thera.*, 279 (3); 1453–1461. (1996); Griswold et al., *Pharmacol. Comm.*, 7, 323–229 (1996)].

There remains a need for treatment, in this field, for compounds which are cytokine suppressive anti-inflammatory drugs, i.e., compounds which are capable of inhibiting the CSBP/p38/RK kinase.

CSBP/p38/RK kinase inhibitors are well known to those skilled in the art. International Patent Publication WO 00/40243, published Jul. 13, 2000, refers to pyridine substituted pyridine compounds and states that these compounds are p38 inhibitors. International Patent Publication WO 00/63204, published Oct. 26, 2000, refers to substituted azole compounds and states that these compounds are p38 inhibitors. International Patent Publication WO 00/31065, published Jun. 2, 2000, refers to certain heterocyclic compounds and states that these compounds are p38 inhibitors. International Patent Publication WO 00/06563, published Feb. 10, 2000, refers to substituted imidazole compounds and states that these compounds are p38 inhibitors. International Patent Publication WO 00/41698, published Jul. 20, 2000, refers to certain ω-carboxy aryl substituted diphenyl urea compounds and states that these compounds are p38 inhibitors. U.S. Pat. No. 5,716,955 refers to certain substituted imidazole compounds and states that these compounds are p38 inhibitors. U.S. Pat. No. 5,716,972 refers to certain pyridinyl substituted imidazole compounds and states that these compounds are p38 inhibitors. U.S. Pat. No. 5,756,499 refers to certain substituted imidazole compounds and states that these compounds are p38 inhibitors.

SUMMARY OF THE INVENTION

The present invention relates to a compound of the formula I

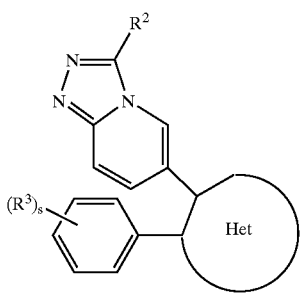

wherein Het is an optionally substituted 5-membered heteroaryl containing one to two heteroatoms selected from nitrogen, sulfur and oxygen wherein at least one of said heteroatoms atoms must be nitrogen;

$R^2$ is selected from the group consisting of hydrogen, $(C_1-C_6)$alkyl or other suitable substituents;

$R^3$ is selected from the group consisting of hydrogen, $(C_1-C_6)$alkyl or other suitable substituents;

s is an integer from zero to five;

and pharmaceutically acceptable salts and prodrugs thereof.

The present invention also relates to the pharmaceutically acceptable acid addition salts of compounds of the formula I. The acids which are used to prepare the pharmaceutically acceptable acid addition salts of the aforementioned base compounds of this invention are those which form non-toxic acid addition salts, i.e., salts containing pharmacologically acceptable anions, such as the chloride, bromide, iodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate [i.e., 1,1'-methylene-bis-(2-hydroxy-3-naphthoate)]salts.

The invention also relates to base addition salts of formula I. The chemical bases that may be used as reagents to prepare pharmaceutically acceptable base salts of those compounds of formula I that are acidic in nature are those that form non-toxic base salts with such compounds. Such non-toxic base salts include, but are not limited to those derived from such pharmacologically acceptable cations such as alkali metal cations (e.g., potassium and sodium) and alkaline earth metal cations (e.g., calcium and magnesium), ammonium or water-soluble amine addition salts such as N-methylglucamine-(meglumine), and the lower alkanolammonium and other base salts of pharmaceutically acceptable organic amines.

The compounds of this invention include all stereoisomers (e.g., cis and trans isomers) and all optical isomers of compounds of the formula I (e.g., R and S enantiomers), as well as racemic, diastereomeric and other mixtures of such isomers.

The compounds and prodrugs of the present invention can exist in several tautomeric forms, including the enol and imine form, the keto and enamine form and geometric isomers and mixtures thereof. All such tautomeric forms are included within the scope of the present invention. Tautomers exist as mixtures of tautomers in solution. In solid form, usually one tautomer predominates. Even though one tautomer may be described, the present invention includes all tautomers of the present compounds.

The present invention also includes atropisomers of the present invention. Atropisomers refer to compounds of formula I that can be separated into rotationally restricted isomers.

The compounds of this invention may contain olefin-like double bonds. When such bonds are present, the compounds of the invention exist as cis and trans configurations and as mixtures thereof.

A "suitable substituent" is intended to mean a chemically and pharmaceutically acceptable functional group i.e., a moiety that does not negate the inhibitory activity of the inventive compounds. Such suitable substituents may be routinely selected by those skilled in the art. Illustrative examples of suitable substituents include, but are not limited to halo groups, perfluoroalkyl groups, perfluoroalkoxy groups, alkyl groups, alkenyl groups, alkynyl groups, hydroxy groups, oxo groups, mercapto groups, alkylthio groups, alkoxy groups, aryl or heteroaryl groups, aryloxy or heteroaryloxy groups, aralkyl or heteroaralkyl groups, aralkoxy or heteroaralkoxy groups, HO—(C=O)— groups, amino groups, alkyl- and dialkylamino groups, carbamoyl groups, alkylcarbonyl groups, alkoxycarbonyl groups, alkylaminocarbonyl groups dialkylamino carbonyl groups, arylcarbonyl groups, aryloxycarbonyl groups, alkylsulfonyl groups, arylsulfonyl groups and the like.

More specifically, the present invention also relates to a compound of the formula

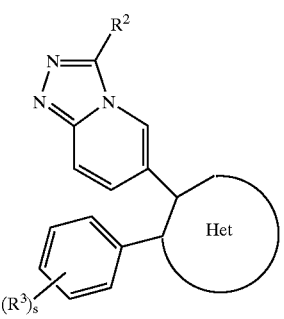

wherein Het is an optionally substituted 5-membered heteroaryl which taken together with $(R^3)_s$-phenyl is selected from the group consisting of:

(a)
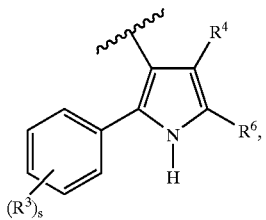

(b)
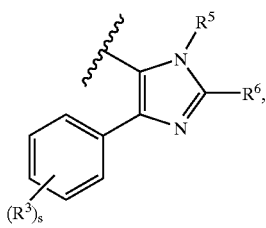

(c)
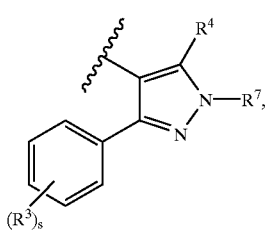

(d)
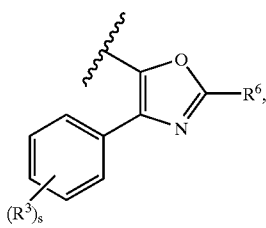

(e)
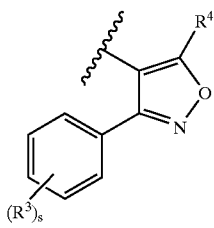

(f)
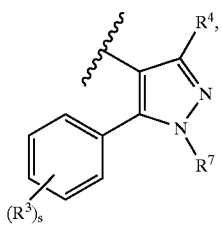

(g)
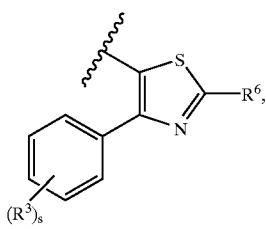

-continued (h)
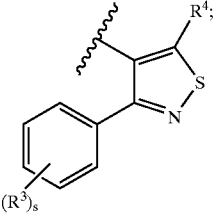

each $R^1$ is independently selected from hydrogen, $(C_1-C_6)$ alkyl, phenyl, $(C_1-C_{10})$heteroaryl, $(C_1-C_{10})$heterocyclic and $(C_3-C_{10})$cycloalkyl; wherein each of the aforesaid $R^1$ $(C_1-C_6)$alkyl, phenyl, $(C_1-C_{10})$heteroaryl, $(C_1-C_{10})$ heterocyclic and $(C_3-C_{10})$cycloalkyl substituents may optionally be substituted by one to four moieties independently selected from the group consisting of halo, $(C_1-C_6)$ alkyl, $(C_2-C_6)$alkenyl, $(C_2-C_6)$alkynyl, perhalo$(C_1-C_6)$ alkyl, phenyl, $(C_1-C_{10})$heteroaryl, $(C_1-C_{10})$heterocyclic, $(C_3-C_{10})$cycloalkyl, hydroxy, $(C_1-C_6)$alkoxy, perhalo $(C_1-C_6)$alkoxy, phenoxy, $(C_1-C_{10})$heteroaryl-O—, $(C_1-C_{10})$heterocyclic-O—, $(C_3-C_{10})$cycloalkyl-O—, $(C_1-C_6)$alkyl-S—, $(C_1-C_6)$alkyl-SO$_2$—, $(C_1-C_6)$alkyl-NH—SO$_2$—, —NO$_2$, amino, $(C_1-C_6)$alkylamino, $[(C_1-C_6)$ alkyl]$_2$-amino, $(C_1-C_6)$alkyl-SO$_2$—NH—, $(C_1-C_6)$alkyl-(C=O)—NH—, $(C_1-C_6)$alkyl-(C=O)—[((C_1-C_6)alkyl)-N]—, phenyl-(C=O)—NH—, phenyl-(C=O)—[((C_1-C_6)alkyl)-N]—, —CN, $(C_1-C_6)$alkyl-(C=O)—, phenyl-(C=O)—, $(C_1-C_{10})$heteroaryl-(C=O)—, $(C_1-C_{10})$ heterocyclic-(C=O)—, $(C_3-C_{10})$cycloalkyl-(C=O)—, HO—(C=O)—, $(C_1-C_6)$alkyl-O—(C=O)—, H$_2$N (C=O)— $(C_1-C_6)$alkyl-NH—(C=O)—, $[(C_1-C_6)$alkyl]$_2$—N—(C=O)—, phenyl-NH—(C=O)—, phenyl-[((C_1-C_6)alkyl)-N]—(C=O)—, $(C_1-C_{10})$heteroaryl-NH—(C=O)—, $(C_1-C_{10})$heterocyclic-NH—(C=O)—, $(C_3-C_{10})$cycloalkyl-NH—(C=O)—, $(C_1-C_6)$alkyl-(C=O)—O— and phenyl-(C=O)—O—; wherein two $R^1$ $(C_1-C_6)$alkyl groups may be taken together with the nitrogen atom to which they are attached to form a five to six membered heterocyclic or heteroaryl ring;

$R^2$ is selected from the group consisting of hydrogen, —C≡N, $(C_1-C_6)$alkyl, $(C_2-C_6)$alkenyl, $(C_2-C_6)$alkynyl, $(C_3-C_{10})$cycloalkyl, phenyl, $(C_1-C_{10})$heteroaryl, $(C_1-C_{10})$ heterocyclic and $(R^1)_2$—N—; wherein each of the aforesaid $(C_1-C_6)$alkyl, $(C_3-C_{10})$cycloalkyl, phenyl, $(C_1-C_{10})$ heteroaryl and $(C_1-C_{10})$heterocyclic substituents may optionally be independently substituted by one to four moieties independently selected from the group consisting of halo, $(C_1-C_6)$alkyl, $(C_2-C_6)$alkenyl, $(C_2-C_6)$alkynyl, perhalo$(C_1-C_6)$alkyl, phenyl, $(C_3-C_{10})$cycloalkyl, $(C_1-C_{10})$ heteroaryl, $(C_1-C_{10})$heterocyclic, formyl, —CN, $(C_1-C_6)$ alkyl-(C=O)—, phenyl-(C=O)—, HO-(C=O)—, $(C_1-C_6)$ alkyl-O—(C=O)—, $(C_1-C_6)$alkyl-NH—(C=O)—, $[(C_1-C_6)$alkyl]$_2$—N—(C=O)—, phenyl-NH—(C=O)—, phenyl-[((C_1-C_6)alkyl)-N]—(C=O)—, —NO$_2$, amino, $(C_1-C_6)$alkylamino, $[(C_1-C_6)$alkyl]$_2$-amino, $(C_1-C_6)$alkyl-(C=O)—NH—, $(C_1-C_6)$alkyl-(C=O)—[((C_1-C_6)alkyl)-N]—, phenyl-(C=O)—NH—, phenyl-(C=O)—[((C_1-C_6) alkyl)-N]—, H$_2$N—(C=O)—NH—, $(C_1-C_6)$alkyl-HN—(C=O)—NH—, $[(C_1-C_6)$alkyl-]$_2$N—(C=O)—NH—, $(C_1-C_6)$alkyl-HN—(C=O)—[((C_1-C_6)alkyl)-N]—, $[(C_1-C_6)$alkyl-]$_2$N—(C=O)—[((C_1-C_6)alkyl)-N]—, phenyl-HN—(C=O)—NH—, (phenyl-)$_2$N—(C=O)—NH—, phenyl-HN—(C=O)—[((C_1-C_6)alkyl)-N]—, (phenyl-)$_2$N—(C=O)—[((C_1-C_6)alkyl)-N]—, $(C_1-C_6)$ alkyl-O—(C=O)—NH—, $(C_1-C_6)$alkyl-O—(C=O)—

[((C$_1$–C$_6$)alkyl)-N]—, phenyl-O—(C=O)—NH—, phenyl-O—(C=O)—[((C$_1$–C$_6$)alkyl)-N]—, (C$_1$–C$_6$)alkyl-SO$_2$NH—, phenyl-SO$_2$NH—, (C$_1$–C$_6$)alkyl-SO$_2$—, phenyl-SO$_2$—, hydroxy, (C$_1$–C$_6$)alkoxy, perhalo(C$_1$–C$_6$)alkoxy, phenoxy, (C$_1$–C$_6$)alkyl-(C=O)—O—, phenyl-(C=O)—O—, H$_2$N—(C=O)—O—, (C$_1$–C$_6$)alkyl-HN—(C=O)—O—, [(C$_1$–C$_6$)alkyl-]$_2$N—(C=O)—O—, phenyl-HN—(C=O)—O—, (phenyl-)$_2$N—(C=O)—O—; wherein when said R$^2$ phenyl contains two adjacent substituents, such substituents may optionally be taken together with the carbon atoms to which they are attached to form a five to six membered carbocyclic or heterocyclic ring; wherein each of said moieties containing a phenyl alternative may optionally be substituted by one or two radicals independently selected from the group consisting of (C$_1$–C$_6$)alkyl, halo, (C$_1$–C$_6$)alkoxy, perhalo(C$_1$–C$_6$)alkyl and perhalo(C$_1$–C$_6$)alkoxy;

each R$^3$ is independently selected from the group consisting of halo, (C$_1$–C$_6$)alkyl, (C$_2$–C$_6$)alkenyl, (C$_2$–C$_6$)alkynyl, perhalo(C$_1$–C$_6$)alkyl, phenyl, (C$_1$–C$_{10}$)heteroaryl, (C$_1$–C$_{10}$)heterocyclic, (C$_3$–C$_{10}$)cycloalkyl, hydroxy, (C$_1$–C$_6$)alkoxy, perhalo(C$_1$–C$_6$)alkoxy, phenoxy, (C$_1$–C$_{10}$)heteroaryl-O—, (C$_1$–C$_{10}$)heterocyclic-O—, (C$_3$–C$_{10}$)cycloalkyl-O—, (C$_1$–C$_6$)alkyl-S—, (C$_1$–C$_6$)alkyl-SO$_2$—, (C$_1$–C$_6$)alkyl-NH—SO$_2$—, —NO$_2$, amino, (C$_1$–C$_6$)alkylamino, [(C$_1$–C$_6$)alkyl]$_2$-amino, (C$_1$–C$_6$)alkyl-SO$_2$—NH—, (C$_1$–C$_6$)alkyl-(C=O)—NH—, (C$_1$–C$_6$)alkyl-(C=O)—[((C$_1$–C$_6$)alkyl)-N]—, phenyl-(C=O)—NH—, phenyl-(C=O)—[((C$_1$–C$_6$)alkyl)-N]—, —CN, (C$_1$–C$_6$)alkyl-(C=O)—, phenyl-(C=O)—, (C$_1$–C$_{10}$)heteroaryl-(C=O)—, (C$_1$–C$_{10}$)heterocyclic-(C=O)—, (C$_3$–C$_{10}$)cycloalkyl-(C=O)—, HO—(C=O)—, (C$_1$–C$_6$)alkyl-O—(C=O)—, H$_2$N(C=O)—, (C$_1$–C$_6$)alkyl-NH—(C=O)—, [(C$_1$–C$_6$)alkyl]$_2$—N—(C=O)—, phenyl-NH—(C=O)—, phenyl-[((C$_1$–C$_6$)alkyl)-N]—(C=O)—, (C$_1$–C$_{10}$)heteroaryl-NH—(C=O)—, (C$_1$–C$_{10}$)heterocyclic-NH—(C=O)—, (C$_3$–C$_{10}$)cycloalkyl-NH—(C=O)— and (C$_1$–C$_6$)alkyl-(C=O)—O—; wherein two adjacent R$^3$ substituents may be optionally taken together with the carbon atoms to which they are attached to form a five to six membered carbocyclic or heterocyclic ring;

s is an integer from zero to five;

R$^4$ and R$^6$ are each independently selected from the group consisting of hydrogen, halo or R$^9$—B—(CH$_2$)$_n$—;

n is an integer from zero to six;

each B is independently a bond, —(CHR$^{10}$)—, —O—, —S—, —(SO$_2$)—, —(C=O)—, —O—(C=O)—, —(C=O)—O—, —(C=O)—NR$^{10}$—, —(R$^{10}$—N)—, —(R$^{10}$—N)—SO$_2$—, —(R$^{10}$—N)—(C=O)—, —SO$_2$—(NR$^{10}$)—, —(R$^{10}$—N)—(C=O)—(NR$^{11}$)—, —(O)—(C=O)—(NR$^{10}$)— or —(R$^{10}$—N)—(C=O)—O—;

R$^5$ and R$^7$ are each independently selected from the group consisting of hydrogen, R$^{14}$—(CR$^{15}$H)$_p$—, phenyl, (C$_1$–C$_{10}$)heteroaryl, (C$_1$–C$_{10}$)heterocyclic, (C$_3$–C$_{10}$)cycloalkyl, (C$_1$–C$_6$)alkyl-(SO$_2$)—, phenyl-(SO$_2$)—, H$_2$N—(SO$_2$)—, (C$_1$–C$_6$)alkyl-NH—(SO$_2$)—, [(C$_1$–C$_6$)alkyl-]$_2$N—(SO$_2$)—, phenyl-NH—(SO$_2$)—, (phenyl-)$_2$N—(SO$_2$)—, R$^{16}$—(C$_1$–C$_6$)alkyl-(C=O)—, phenyl-(C=O)—, (C$_1$–C$_{10}$)heteroaryl-(C=O)—, (C$_1$–C$_{10}$)heterocyclic-(C=O)—, (C$_3$–C$_{10}$)cycloalkyl-(C=O)—, (C$_1$–C$_6$)alkyl-O—(C=O)—, (C$_1$–C$_{10}$)heterocyclic-O—(C=O)—, (C$_3$–C$_{10}$)cycloalkyl-O—(C=O)—, H$_2$N—(C=O)—, (C$_1$–C$_6$)alkyl-NH—(C=O)—, phenyl-NH—(C=O)—, (C$_1$–C$_{10}$)heteroaryl-NH—(C=O)—, (C$_1$–C$_{10}$)heterocyclic-NH—(C=O)—, (C$_3$–C$_{10}$)cycloalkyl-NH—(C=O)—, [(C$_1$–C$_6$)alkyl-]$_2$N—(C=O)—, (phenyl-)$_2$N—(C=O)—, phenyl-[((C$_1$–C$_6$)alkyl)-N]—(C=O)—, (C$_1$–C$_{10}$)heteroaryl-[((C$_1$–C$_6$)alkyl)-N]—(C=O)—, (C$_1$–C$_{10}$)heterocyclic-[((C$_1$–C$_6$)alkyl)-N]—(C=O)—, and (C$_3$–C$_{10}$)cycloalkyl-[((C$_1$–C$_6$)alkyl)-N]—(C=O)—; wherein each of the aforesaid phenyl, heterocyclic, heteroaryl or cycloalkyl R$^5$ and R$^7$ substituents may optionally be independently substituted by one to four moieties independently selected from the group consisting of halo, R$^{16}$—(C$_1$–C$_6$)alkyl, (C$_2$–C$_6$)alkenyl, (C$_2$–C$_6$)alkynyl, perhalo(C$_1$–C$_6$)alkyl, (C$_3$–C$_{10}$)cycloalkyl, phenyl, benzyl, (C$_1$–C$_{10}$)heterocyclic, (C$_1$–C$_{10}$)heteroaryl, (C$_1$–C$_6$)alkyl-SO$_2$—, formyl, —CN, (C$_1$–C$_6$)alkyl-(C=O)—, (C$_3$–C$_{10}$)cycloalkyl-(C=O)—, phenyl-(C=O)—, (C$_1$–C$_{10}$)heterocyclic-(C=O)—, (C$_1$–C$_{10}$)heteroaryl-(C=O)—, HO—(C=O)—, (C$_1$–C$_6$)alkyl-O—(C=O)—, (C$_3$–C$_{10}$)cycloalkyl-O—(C=O)—, (C$_1$–C$_{10}$)heterocyclic-O—(C=O)—, (C$_1$–C$_6$)alkyl-NH—(C=O)—, (C$_3$–C$_{10}$)cycloalkyl-NH—(C=O)—, phenyl-NH—(C=O)—, (C$_1$–C$_{10}$)heterocyclic-NH—(C=O)—, (C$_1$–C$_{10}$)heteroaryl-NH—(C=O)—, [(C$_1$–C$_6$)alkyl]$_2$—N—(C=O)—, phenyl-[((C$_1$–C$_6$)alkyl)-N]—(C=O)—, hydroxy, (C$_1$–C$_6$)alkoxy, perhalo(C$_1$–C$_6$)alkoxy, (C$_3$–C$_{10}$)cycloalkyl-O—, phenoxy, (C$_1$–C$_{10}$)heterocyclic-O—, (C$_1$–C$_{10}$)heteroaryl-O—, (C$_1$–C$_6$)alkyl-(C=O)—O—, (C$_3$–C$_{10}$)cycloalkyl-(C=O)—O—, phenyl-(C=O)—O—, (C$_1$–C$_{10}$)heterocyclic-(C=O)—O—, (C$_1$–C$_{10}$)heteroaryl-(C=O)—O—, —NO$_2$, amino, (C$_1$–C$_6$)alkylamino, [(C$_1$–C$_6$)alkyl]$_2$-amino, formamidyl, (C$_1$–C$_6$)alkyl-(C=O)—NH—, (C$_3$–C$_{10}$)cycloalkyl-(C=O)—NH—, phenyl-(C=O)—NH—, (C$_1$–C$_{10}$)heterocyclic-(C=O)—NH—, (C$_1$–C$_{10}$)heteroaryl-(C=O)—NH—, (C$_1$–C$_6$)alkyl-(C=O)—[((C$_1$–C$_6$)alkyl)-N]—, phenyl-(C=O)—[((C$_1$–C$_6$)alkyl-N]—, (C$_1$–C$_6$)alkyl-SO$_2$NH—, (C$_3$–C$_{10}$)cycloalkyl-SO$_2$NH—, phenyl-SO$_2$NH—, (C$_1$–C$_{10}$)heterocyclic-SO$_2$NH— and (C$_1$–C$_{10}$)heteroaryl-SO$_2$NH—; wherein each of said phenyl and heteroaryl moieties may optionally be substituted by one or two radicals independently selected from halo, (C$_1$–C$_6$)alkyl, (C$_1$–C$_6$)alkoxy, perfluoro(C$_1$–C$_6$)alkyl and perfluoro(C$_1$–C$_6$)alkoxy;

p is an integer from one to six;

R$^9$ is selected from the group consisting of hydrogen, —CF$_3$, —C≡N, R$^{13}$—(R$^{12}$CH)$_m$—, phenyl, (C$_1$–C$_{10}$)heterocyclic, (C$_1$–C$_{10}$)heteroaryl and (C$_3$–C$_{10}$)cycloalkyl; wherein each of the aforesaid R$^9$ phenyl, (C$_1$–C$_{10}$)heteroaryl, (C$_1$–C$_{10}$)heterocyclic and (C$_3$–C$_{10}$)cycloalkyl substituents may optionally be substituted by one to four moieties independently selected from the group consisting of halo, (C$_1$–C$_6$)alkyl, (C$_2$–C$_6$)alkenyl, (C$_2$–C$_6$)alkynyl, perhalo(C$_1$–C$_6$)alkyl, phenyl, (C$_1$–C$_{10}$)heteroaryl, (C$_1$–C$_{10}$)heterocyclic, (C$_3$–C$_{10}$)cycloalkyl, hydroxy, (C$_1$–C$_6$)alkoxy, perhalo(C$_1$–C$_6$)alkoxy, phenoxy, (C$_1$–C$_{10}$)heteroaryl-O—, (C$_1$–C$_{10}$)heterocyclic-O—, (C$_3$–C$_{10}$)cycloalkyl-O—, (C$_1$–C$_6$)alkyl-S—, (C$_1$–C$_6$)alkyl-SO$_2$—, (C$_1$–C$_6$)alkyl-NH—SO$_2$—, —NO$_2$, amino, (C$_1$–C$_6$)alkylamino, [(C$_1$–C$_6$)alkyl]$_2$-amino, (C$_1$–C$_6$)alkyl-SO$_2$—NH—, (C$_1$–C$_6$)alkyl-(C=O)—NH—, (C$_1$–C$_6$)alkyl-(C=O)—[((C$_1$–C$_6$)alkyl)-N]—, phenyl-(C=O)—NH—, phenyl-(C=O)—[((C$_1$–C$_6$)alkyl)-N]—, —CN, (C$_1$–C$_6$)alkyl-(C=O)—, phenyl-(C=O)—, (C$_1$–C$_{10}$)heteroaryl-(C=O)—, (C$_1$–C$_{10}$)heterocyclic-(C=O)—, (C$_3$–C$_{10}$)cycloalkyl-(C=O)—, HO—(C=O)—, (C$_1$–C$_6$)alkyl-O—(C=O)—, H$_2$N(C=O)— (C$_1$–C$_6$)alkyl-NH—(C=O)—, [(C$_1$–C$_6$)alkyl]$_2$—N—(C=O)—, phenyl-NH—(C=O)—, phenyl-[((C$_1$–C$_6$)alkyl)-N]—(C=O)—, (C$_1$–C$_{10}$)heteroaryl-NH—(C=O)—, (C$_1$–C$_{10}$)heterocyclic-NH—(C=O)—, (C$_3$–C$_{10}$)cycloalkyl-NH—(C=O)—, (C$_1$–C$_6$)alkyl-(C=O)—O— and phenyl-(C=O)—O—; wherein two adjacent substituents of said phenyl, (C$_1$–C$_{10}$)heteroaryl, (C$_1$–C$_{10}$)heterocyclic and (C$_3$–C$_{10}$)cycloalkyl R$^9$ substituents may optionally be taken together with the carbon or heteroatom to which they are attached to form a five or six membered carbocyclic or heterocyclic ring;

m is an integer from one to six;

$R^{10}$ is hydrogen, $(C_1-C_6)$alkyl-$SO_2$— or $(C_1-C_6)$alkyl;

$R^{11}$ is hydrogen or $(C_1-C_6)$alkyl;

each $R^{12}$ is independently selected from the group consisting of hydrogen, amino, $(C_1-C_6)$alkoxy and $(C_1-C_6)$alkyl;

$R^{13}$ is selected from the group consisting of hydrogen, $(C_1-C_6)$alkyl, $(C_2-C_6)$alkenyl, $(C_2-C_6)$alkynyl, phenyl, $(C_1-C_{10})$heteroaryl, $(C_1-C_{10})$heterocyclic, $(C_3-C_{10})$cycloalkyl, hydroxy, $(C_1-C_6)$alkoxy, perhalo$(C_1-C_6)$alkoxy, phenoxy, $(C_1-C_{10})$heteroaryl-O—, $(C_1-C_{10})$heterocyclic-O—, $(C_3-C_{10})$cycloalkyl-O—, $(C_1-C_6)$alkyl-S—, $(C_1-C_6)$alkyl-$SO_2$—, $(C_1-C_6)$alkyl-NH—$SO_2$—, —$NO_2$, amino, $(C_1-C_6)$alkylamino, [$(C_1-C_6)$alkyl]$_2$-amino, $(C_1-C_6)$alkyl-$SO_2$—NH—, phenyl-$SO_2$—NH—, $(C_1-C_6)$alkyl-$SO_2$—[(($C_1-C_6$)alkyl)-N]—, phenyl-$SO_2$—[(($C_1-C_6$)alkyl)-N]—, $(C_1-C_6)$alkyl-(C=O)—NH—, $(C_1-C_6)$alkyl-(C=O)—[(($C_1-C_6$)alkyl)-N]—, phenyl-(C=O)—NH—, phenyl-(C=O)—[(($C_1-C_6$)alkyl)-N]—, —CN, $(C_1-C_6)$alkyl-(C=O)—, phenyl-(C=O)—, $(C_1-C_{10})$heteroaryl-(C=O)—, $(C_1-C_{10})$heterocyclic-(C=O)—, $(C_3-C_{10})$cycloalkyl-(C=O)—, HO—(C=O)—, $(C_1-C_6)$alkyl-O—(C=O)—, $H_2N$(C=O)—, $(C_1-C_6)$alkyl-NH—(C=O)—, [$(C_1-C_6)$alkyl]$_2$—N—(C=O)—, phenyl-NH—(C=O)—, phenyl-[(($C_1-C_6$)alkyl)-N]—(C=O)—, $(C_1-C_{10})$heteroaryl-NH—(C=O)—, $(C_1-C_{10})$heterocyclic-NH—(C=O)—, $(C_3-C_{10})$cycloalkyl-NH—(C=O)—, $(C_1-C_6)$alkyl-(C=O)—O— and phenyl-(C=O)—O—;

$R^{14}$ is selected from the group consisting of hydrogen, halo, $(C_1-C_6)$alkyl, $(C_2-C_6)$alkenyl, $(C_2-C_6)$alkynyl, perhalo$(C_1-C_6)$alkyl, $(C_3-C_{10})$cycloalkyl, phenyl, $(C_1-C_{10})$heterocyclic, $(C_1-C_{10})$heteroaryl, phenyl-(S=O)—, $(C_1-C_6)$alkyl-$SO_2$—, phenyl-$SO_2$—, $H_2N$—$SO_2$—, $(C_1-C_6)$alkyl-NH—$SO_2$—, phenyl-NH—$SO_2$—, [$(C_1-C_6)$alkyl-]$_2$N—$SO_2$—, (phenyl-)$_2$N—$SO_2$—, formyl, —CN, $(C_1-C_6)$alkyl-(C=O)—, phenyl-(C=O)—, $(C_1-C_{10})$heteroaryl-(C=O)—, $(C_1-C_{10})$heterocyclic-(C=O)—, $(C_3-C_{10})$cycloalkyl-(C=O)—, HO—(C=O)—, $R^{16}$—$(C_1-C_6)$alkyl-O—(C=O)—, $(C_3-C_{10})$cycloalkyl-O—(C=O)—, $(C_1-C_{10})$heterocyclic-O—(C=O)—, $H_2N$—(C=O)—, $R^{16}$—$(C_1-C_6)$alkyl-NH—(C=O)—, $(C_3-C_{10})$cycloalkyl-NH—(C=O)—, phenyl-NH—(C=O)—, $(C_1-C_{10})$heterocyclic-NH—(C=O)—, $(C_1-C_{10})$heteroaryl-NH—(C=O)—, [$(C_1-C_6)$alkyl]$_2$—N—(C=O)—, phenyl-[(($C_1-C_6$)alkyl)-N]—(C=O)—, $(C_1-C_{10})$heteroaryl-[(($C_1-C_6$)alkyl)-N]—(C=O)—, $(C_1-C_{10})$heterocyclic-[(($C_1-C_6$)alkyl)-N]—(C=O)—, $(C_3-C_{10})$cycloalkyl[(($C_1-C_6$)alkyl)-N]—(C=O)—, hydroxy, $R^{16}$—$(C_1-C_6)$alkoxy, perhalo$(C_1-C_6)$alkoxy, $(C_3-C_{10})$cycloalkyl-O—, phenoxy, $(C_1-C_{10})$heterocyclic-O—, $(C_1-C_{10})$heteroaryl-O—, $R^{16}$—$(C_1-C_6)$alkyl-(C=O)—O—, $(C_3-C_{10})$cycloalkyl-(C=O)—O—, phenyl-(C=O)—O—, $(C_1-C_{10})$heterocyclic-(C=O)—O—, $(C_1-C_{10})$heteroaryl-(C=O)—O—, —$NO_2$, amino, $R^{16}$—$(C_1-C_6)$alkylamino, [$(C_1-C_6)$alkyl]$_2$-amino, formamidyl, $R^{16}$—$(C_1-C_6)$alkyl-(C=O)—NH—, $(C_3-C_{10})$cycloalkyl-(C=O)—NH—, phenyl-(C=O)—NH—, $(C_1-C_{10})$heterocyclic-(C=O)—NH—, $(C_1-C_{10})$heteroaryl-(C=O)—NH—, $R^{16}$—$(C_1-C_6)$alkyl-(C=O)—[(($C_1-C_6$)alkyl)-N]—, phenyl-(C=O)—[(($C_1-C_6$)alkyl)-N]—, $R^{16}$—$(C_1-C_6)$alkyl-$SO_2NH$—, $(C_3-C_{10})$cycloalkyl-$SO_2NH$—, phenyl-$SO_2NH$—, $(C_1-C_{10})$heterocyclic-$SO_2NH$— and $(C_1-C_{10})$heteroaryl-$SO_2NH$—; wherein each of the aforesaid phenyl, heterocyclic, heteroaryl or cycloalkyl $R^{14}$ substituents may optionally be independently substituted by one to four moieties independently selected from the group consisting of halo, $R^{16}$—$(C_1-C_6)$alkyl, $(C_2-C_6)$alkenyl, $(C_2-C_6)$alkynyl, perhalo$(C_1-C_6)$alkyl, $(C_3-C_{10})$cycloalkyl, phenyl, benzyl, $(C_1-C_{10})$heterocyclic, $(C_1-C_{10})$heteroaryl, $(C_1-C_6)$alkyl-$SO_2$—, formyl, —CN, $R^{16}$—$(C_1-C_6)$alkyl-(C=O)—, $(C_3-C_{10})$cycloalkyl-(C=O)—, phenyl-(C=O)—, $(C_1-C_{10})$heterocyclic-(C=O)—, $(C_1-C_{10})$heteroaryl-(C=O)—, HO—(C=O)—, $(C_1-C_6)$alkyl-O—(C=O)—, $(C_3-C_{10})$cycloalkyl-O—(C=O)—, $(C_1-C_{10})$heterocyclic-O—(C=O)—, $(C_1-C_{10})$heteroaryl-O—(C=O)—, $H_2N$—(C=O)—, $R^{16}$—$(C_1-C_6)$alkyl-NH—(C=O)—, $(C_3-C_{10})$cycloalkyl-NH—(C=O)—, phenyl-NH—(C=O)—, $(C_1-C_{10})$heterocyclic-NH—(C=O)—, $(C_1-C_{10})$heteroaryl-NH—(C=O)—, [$(C_1-C_6)$alkyl]$_2$—N—(C=O)—, phenyl-[(($C_1-C_6$)alkyl)-N]—(C=O)—, hydroxy, $R^{16}$—$(C_1-C_6)$alkoxy, perhalo$(C_1-C_6)$alkoxy, $(C_3-C_{10})$cycloalkyl-O—, phenoxy, $(C_1-C_{10})$heterocyclic-O—, $(C_1-C_{10})$heteroaryl-O—, $R^{16}$—$(C_1-C_6)$alkyl-(C=O)—O—, $(C_3-C_{10})$cycloalkyl-(C=O)—O—, phenyl-(C=O)—O—, $(C_1-C_{10})$heterocyclic-(C=O)—O—, $(C_1-C_{10})$heteroaryl-(C=O)—O—, —$NO_2$, amino, $R^{16}$—$(C_1-C_6)$alkylamino, [$(C_1-C_6)$alkyl]$_2$-amino, formamidyl, $R^{16}$—$(C_1-C_6)$alkyl-(C=O)—NH—, $(C_3-C_{10})$cycloalkyl-(C=O)—NH—, phenyl-(C=O)—NH—, $(C_1-C_{10})$heterocyclic-(C=O)—NH—, $(C_1-C_{10})$heteroaryl-(C=O)—NH—, $R^{16}$—$(C_1-C_6)$alkyl-(C=O)—[(($C_1-C_6$)alkyl)-N]—, phenyl-(C=O)—[(($C_1-C_6$)alkyl)-N]—, $R^{16}$—$(C_1-C_6)$alkyl-$SO_2NH$—, $(C_3-C_{10})$cycloalkyl-$SO_2NH$—, phenyl-$SO_2NH$—, $(C_1-C_{10})$heterocyclic-$SO_2NH$— and $(C_1-C_{10})$heteroaryl-$SO_2NH$—; wherein each of said phenyl and heteroaryl moieties may optionally be substituted by one or two radicals independently selected from the group consisting of halo, $(C_1-C_6)$alkyl, $(C_1-C_6)$alkoxy, perfluoro$(C_1-C_6)$alkyl and perfluoro$(C_1-C_6)$alkoxy;

each $R^{15}$ is independently selected from the group consisting of hydrogen, halo, $(C_1-C_6)$alkyl, $(C_2-C_6)$alkenyl, perhalo$(C_1-C_6)$alkyl, HO—(C=O)—, $(C_1-C_6)$alkyl-O—(C=O)—, $H_2N$—(C=O)—, $(C_1-C_6)$alkyl-NH—(C=O)—, [$(C_1-C_6)$alkyl]$_2$—N—(C=O)—, hydroxy, $(C_1-C_6)$alkoxy, $(C_1-C_6)$alkyl-(C=O)—O—, amino, $(C_1-C_6)$alkylamino, [$(C_1-C_6)$alkyl]$_2$-amino, formamidyl and $(C_1-C_6)$alkyl-(C=O)—NH—;

each $R^{16}$ is independently selected from the group consisting of hydrogen, halo, $(C_1-C_6)$alkyl, $(C_2-C_6)$alkenyl, $(C_2-C_6)$alkynyl, perhalo$(C_1-C_6)$alkyl, $(C_1-C_{10})$heterocyclic, HO—(C=O)—, $(C_1-C_6)$alkyl-O—(C=O)—, $H_2N$—(C=O)—, $(C_1-C_6)$alkyl-NH—(C=O)—, [$(C_1-C_6)$alkyl]$_2$—N—(C=O)—, hydroxy, $(C_1-C_6)$alkoxy, perhalo$(C_1-C_6)$alkoxy, $(C_1-C_6)$alkyl-(C=O)—O—, —$NO_2$, amino, $(C_1-C_6)$alkylamino, [$(C_1-C_6)$alkyl]$_2$-amino, formamidyl and $(C_1-C_6)$alkyl-(C=O)—NH—; wherein said $(C_1-C_{10})$heterocyclic may optionally be substituted by one to three substituents independently selected from the group consisting of halo, $(C_1-C_6)$alkyl, $(C_1-C_6)$alkoxy, benzyl, amino, $(C_1-C_6)$alkylamino and [$(C_1-C_6)$alkyl]$_2$-amino;

or $R^4$ and $R^6$ or $R^4$ and $R^7$ or $R^5$ and $R^6$ may be taken together with the atoms to which they are attached to form an optionally substituted five to ten membered saturated, unsaturated or aromatic ring optionally containing two to three heteroatoms independently selected from NH, N, O, S, SO or $SO_2$; wherein said ring may be optionally substituted by one to three substituents independently selected from the group consisting of oxo, halo, $(C_1-C_6)$alkyl, phenyl, $(C_1-C_{10})$ heteroaryl, $(C_1-C_{10})$heterocyclic, $(C_3-C_{10})$cycloalkyl, hydroxy, $(C_1-C_6)$alkoxy, phenoxy, $(C_1-C_{10})$heteroaryl-O—, $(C_1-C_{10})$heterocyclic-O—, $(C_3-C_{10})$cycloalkyl-O—, $(C_1-C_6)$alkyl-S—, $(C_1-C_6)$alkyl-SO$_2$—, phenyl-S—, phenyl-(S=O)—, phenyl-SO$_2$—, $(C_1-C_6)$alkyl-NH—SO$_2$—, $[(C_1-C_6)$alkyl$]_2$—N—SO$_2$—, phenyl-NH—SO$_2$—, (phenyl)$_2$—N—SO$_2$—, phenyl-[N $(C_1-C_6)$alkyl]-SO$_2$—, formyl, $(C_1-C_6)$alkyl-(C=O)—, phenyl-(C=O)—, $(C_1-C_{10})$heteroaryl-(C=O)—, $(C_1-C_{10})$heterocyclic-(C=O)—, $(C_3-C_{10})$ cycloalkyl-(C=O)—, HO—(C=O)—, $(C_1-C_6)$alkyl-O—(C=O)—, $(C_1-C_{10})$heterocyclic-O—(C=O)—, $(C_3-C_{10})$cycloalkyl-O—(C=O)—, H$_2$N—(C=O)—, $(C_1-C_6)$alkyl-NH—(C=O)—, $[(C_1-C_6)$alkyl$]_2$—N—(C=O)—, phenyl-NH—(C=O)—, phenyl-$[(C_1-C_6)$ alkyl)-N]—(C=O)—, $(C_1-C_{10})$heteroaryl-NH—(C=O)—, $(C_1-C_{10})$heteroaryl-$[(C_1-C_6)$alkyl)-N]—(C=O)—, $(C_1-C_{10})$heterocyclic-NH—(C=O)—, $(C_1-C_{10})$heterocyclic-$[((C_1-C_6)$alkyl)-N]—(C=O)—, $(C_3-C_{10})$cycloalkyl-NH—(C=O)—, $(C_3-C_{10})$ cycloalkyl-$[((C_1-C_6)$alkyl)-N]—(C=O)—, amino, $(C_1-C_6)$alkylamino, $[(C_1-C_6)$alkyl$]_2$amino, $(C_1-C_6)$ alkyl-SO$_2$—NH—, phenyl-SO$_2$—NH—, $(C_1-C_6)$ alkyl-SO$_2$—$[((C_1-C_6)$alkyl)-N]—, phenyl-SO$_2$—$[((C_1-C_6)$alkyl)-N]—, formamidyl, $(C_1-C_6)$alkyl-(C=O)—NH—, $(C_1-C_6)$alkyl-(C=O)—$[((C_1-C_6)$ alkyl)-N]—, phenyl-(C=O)—NH—, phenyl-(C=O)—$[((C_1-C_6)$alkyl)-N]-, $(C_1-C_{10})$heteroaryl-(C=O)—NH—, $(C_1-C_{10})$heteroaryl-(C=O)—$[((C_1-C_6)$alkyl)-N]—, $(C_1-C_{10})$heterocyclic-(C=O)—NH—, $(C_1-C_{10})$heterocyclic-(C=O)—$[((C_1-C_6)$alkyl)-N]—, $(C_3-C_{10})$cycloalkyl-(C=O)—NH—, $(C_3-C_{10})$cycloalkyl-(C=O)—$[((C_1-C_6)$alkyl)-N]—, H$_2$N(C=O)—NH—, $(C_1-C_6)$alkyl-HN—(C=O)—NH—, $(C_1-C_6)$alkyl-HN—(C=O)—$[((C_1-C_6)$alkyl)-N]—, $[(C_1-C_6)$alkyl$]_2$—N—(C=O)—NH—, $[(C_1-C_6)$alkyl$]_2$—N—(C=O)—$[((C_1-C_6)$alkyl)-N]—, phenyl-HN—(C=O)—NH—, phenyl-HN—(C=O)—$[((C_1-C_6)$alkyl)-N]—, (phenyl)$_2$—N—(C=O)—NH—, (phenyl)$_2$—N—(C=O)—$[((C_1-C_6)$alkyl)-N]—, $(C_1-C_{10})$heteroaryl-HN—(C=O)—NH—, $(C_1-C_{10})$heteroaryl-HN—(C=O)—$[((C_1-C_6)$alkyl)-N]—, $[(C_1-C_{10})$heteroaryl]$_2$—N—(C=O)—$[((C_1-C_6)$alkyl)-N]—, $[(C_1-C_{10})$ heteroaryl]$_2$—N—(C=O)—NH—, $(C_1-C_{10})$ heterocyclic-HN—(C=O)—NH—, $(C_1-C_{10})$ heterocyclic-HN—(C=O)—$[((C_1-C_6)$alkyl)-N]—, $[(C_1-C_{10})$heterocyclic]$_2$—N—(C=O)—$[((C_1-C_6)$ alkyl)-N]—, $[(C_1-C_{10})$heterocyclic]$_2$—N—(C=O)—NH—, $(C_3-C_{10})$cycloalkyl-HN—(C=O)—NH—, $(C_3-C_{10})$cycloalkyl-HN—(C=O)—$[((C_1-C_6)$alkyl)-N]—, $[(C_3-C_{10})$cycloalkyl]$_2$—N—(C=O)—$[((C_1-C_6)$alkyl)-N]—, $[(C_3-C_{10})$cycloalkyl]$_2$—N—(C=O)—NH—, $(C_1-C_6)$alkyl-(C=O)—O—, phenyl-(C=O)—O—, $(C_1-C_{10})$heteroaryl-(C=O)—O—, $(C_1-C_{10})$heterocyclic-(C=O)—O—, $(C_3-C_{10})$ cycloalkyl-(C=O)—O—, $(C_1-C_6)$alkyl-NH—(C=O)—O—, $[(C_1-C_6)$alkyl$]_2$—N—(C=O)—O—, phenyl-NH—(C=O)—O—, $(C_1-C_{10})$heteroaryl-NH—(C=O)—O—, $(C_1-C_{10})$heterocyclic-NH—(C=O)—O— and $(C_3-C_{10})$cycloalkyl-NH—(C=O)—O—;

or the pharmaceutically acceptable salts thereof.

As used herein, the term "alkyl," as well as the alkyl moieties of other groups referred to herein (e.g., alkoxy), may be linear or branched (such as methyl, ethyl, n-propyl, isopropyl, n-butyl, iso-butyl, secondary-butyl, tertiary-butyl), and they may also be cyclic (e.g., cyclopropyl or cyclobutyl); optionally substituted by 1 to 3 suitable substituents as defined above such as fluoro, chloro, trifluoromethyl, $(C_1-C_6)$alkoxy, $(C_6-C_{10})$aryloxy, trifluoromethoxy, difluoromethoxy or $(C_1-C_6)$alkyl. The phrase "each of said alkyl" as used herein refers to any of the preceding alkyl moieties within a group such alkoxy, alkenyl or alkylamino. Preferred alkyls include $(C_1-C_4)$alkyl, most preferably methyl.

As used herein, the term "cycloalkyl" refers to a mono or bicyclic carbocyclic ring (e.g., cyclopropyl, cyclobutyl, cyclopentyl, cyclohexyl, cycloheptyl, cyclooctyl, cyclononyl, cyclopentenyl, cyclohexenyl, bicyclo[2.2.1] heptanyl, bicyclo[3.2.1]octanyl and bicyclo[5.2.0]nonanyl, etc.); optionally containing 1–2 double bonds and optionally substituted by 1 to 3 suitable substituents as defined above such as fluoro, chloro, trifluoromethyl, $(C_1-C_6)$alkoxy, $(C_6-C_{10})$aryloxy, trifluoromethoxy, difluoromethoxy or $(C_1-C_6)$alkyl. The phrase "each of said alkyl" as used herein refers to any of the preceding alkyl moieties within a group such alkoxy, alkenyl or alkylamino. Preferred cycloalkyls include cyclobutyl, cyclopentyl and cyclohexyl.

As used herein, the term "halogen" includes fluoro, chloro, bromo or iodo or fluoride, chloride, bromide or iodide.

As used herein, the term "halo-substituted alkyl" refers to an alkyl radical as described above substituted with one or more halogens included, but not limited to, chloromethyl, dichloromethyl, fluoromethyl, difluoromethyl, trifluoromethyl, 2,2,2-trichloroethyl, and the like; optionally substituted by 1 to 3 suitable substituents as defined above such as fluoro, chloro, trifluoromethyl, $(C_1-C_6)$alkoxy, $(C_6-C_{10})$aryloxy, trifluoromethoxy, difluoromethoxy or $(C_1-C_6)$alkyl.

As used herein, the term "alkenyl" means straight or branched chain unsaturated radicals of 2 to 6 carbon atoms, including, but not limited to ethenyl, 1-propenyl, 2-propenyl (allyl), iso-propenyl, 2-methyl-1-propenyl, 1-butenyl, 2-butenyl, and the like; optionally substituted by 1 to 3 suitable substituents as defined above such as fluoro, chloro, trifluoromethyl, $(C_1-C_6)$alkoxy, $(C_6-C_{10})$aryloxy, trifluoromethoxy, difluoromethoxy or $(C_1-C_6)$alkyl.

As used herein, the term "$(C_2-C_6)$alkynyl" is used herein to mean straight or branched hydrocarbon chain radicals having one triple bond including, but not limited to, ethynyl, propynyl, butynyl, and the like; optionally substituted by 1 to 3 suitable substituents as defined above such as fluoro, chloro, trifluoromethyl, $(C_1-C_6)$alkoxy, $(C_6-C_{10})$aryloxy, trifluoromethoxy, difluoromethoxy or $(C_1-C_6)$alkyl.

As used herein, the term "carbonyl" or "(C=O)" (as used in phrases such as alkylcarbonyl, alkyl-(C=O)— or alkoxycarbonyl) refers to the joinder of the >C=O moiety to a second moiety such as an alkyl or amino group (i.e. an amido group). Alkoxycarbonylamino (i.e. alkoxy(C=O)—NH—) refers to an alkyl carbamate group. The carbonyl group is also equivalently defined herein as (C=O). Alkylcarbonylamino refers to groups such as acetamide.

As used herein, the term "phenyl-$[(C_1-C_6)$alkyl)-N]—(C=O)—," as used herein, refers to a disubstituted amide group of the formula

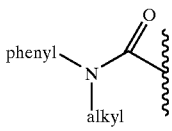

As used herein, the term "aryl" means aromatic radicals such as phenyl, naphthyl, tetrahydronaphthyl, indanyl and the like; optionally substituted by 1 to 3 suitable substituents as defined above such as fluoro, chloro, trifluoromethyl, $(C_1-C_6)$alkoxy, $(C_6-C_{10})$aryloxy, trifluoromethoxy, difluoromethoxy or $(C_1-C_6)$alkyl.

As used herein, the term "heteroaryl" refers to an aromatic heterocyclic group usually with one heteroatom selected from O, S and N in the ring. In addition to said heteroatom, the aromatic group may optionally have up to four N atoms in the ring. For example, heteroaryl group includes pyridyl, pyrazinyl, pyrimidinyl, pyridazinyl, thienyl, furyl, imidazolyl, pyrrolyl, oxazolyl (e.g., 1,3-oxazolyl, 1,2-oxazolyl), thiazolyl (e.g., 1,2-thiazolyl, 1,3-thiazolyl), pyrazolyl, tetrazolyl, triazolyl (e.g., 1,2,3-triazolyl, 1,2,4-triazolyl), oxadiazolyl (e.g., 1,2,3-oxadiazolyl), thiadiazolyl (e.g., 1,3,4-thiadiazolyl), quinolyl, isoquinolyl, benzothienyl, benzofuryl, indolyl, and the like; optionally substituted by 1 to 3 suitable substituents as defined above such as fluoro, chloro, trifluoromethyl, $(C_1-C_6)$alkoxy, $(C_6-C_{10})$aryloxy, trifluoromethoxy, difluoromethoxy or $(C_1-C_6)$alkyl. Particularly preferred heteroaryl groups include oxazolyl, imidazolyl, pyridyl, thienyl, furyl, thiazolyl and pyrazolyl (these heteroaryls are most preferred of the $R^4$, $R^5$, $R^6$ and $R^7$ heteroaryls).

The term "heterocyclic" as used herein refers to a cyclic group containing 1–9 carbon atoms and 1–4 hetero atoms selected from N, O, S or NR'. Examples of such rings include azetidinyl, tetrahydrofuranyl, imidazolidinyl, pyrrolidinyl, piperidinyl, piperazinyl, oxazolidinyl, thiazolidinyl, pyrazolidinyl, thiomorpholinyl, tetrahydrothiazinyl, tetrahydrothiadiazinyl, morpholinyl, oxetanyl, tetrahydrodiazinyl, oxazinyl, oxathiazinyl, indolinyl, isoindolinyl, quinuclidinyl, chromanyl, isochromanyl, benzoxazinyl and the like. Examples of such monocyclic saturated or partially saturated ring systems are tetrahydrofuran-2-yl, tetrahydrofuran-3-yl, imidazolidin-1-yl, imidazolidin-2-yl, imidazolidin-4-yl, pyrrolidin-1-yl, pyrrolidin-2-yl, pyrrolidin-3-yl, piperidin-1-yl, piperidin-2-yl, piperidin-3-yl, piperazin-1-yl, piperazin-2-yl, piperazin-3-yl, 1,3-oxazolidin-3-yl, isothiazolidine, 1,3-thiazolidin-3-yl, 1,2-pyrazolidin-2-yl, 1,3-pyrazolidin-1-yl, thiomorpholinyl, 1,2-tetrahydrothiazin-2-yl, 1,3-tetrahydrothiazin-3-yl, tetrahydrothiadiazinyl, morpholinyl, 1,2-tetrahydrodiazin-2-yl, 1,3-tetrahydrodiazin-1-yl, 1,4-oxazin-2-yl, 1,2,5-oxathiazin-4-yl and the like; optionally substituted by 1 to 3 suitable substituents as defined above such as fluoro, chloro, trifluoromethyl, $(C_1-C_6)$alkoxy, $(C_6-C_{10})$aryloxy, trifluoromethoxy, difluoromethoxy or $(C_1-C_6)$alkyl. Preferred heterocyclics include tetrahydrofuranyl, pyrrolidinyl, piperidinyl, piperazinyl and morpholinyl.

An embodiment of the present invention are those compounds of formula I wherein $R^2$ is $(C_1-C_6)$alkyl, phenyl, $(C_3-C_{10})$cycloalkyl, $(C_1-C_{10})$heteroaryl or $(C_1-C_{10})$heterocyclic.

Another embodiment of the present invention are those compounds of formula I wherein $R^2$ is $(C_1-C_6)$alkyl, optionally substituted with one to four groups independently selected from halo, hydroxy, $(C_1-C_6)$alkyl, $(C_2-C_6)$alkenyl, $(C_2-C_6)$alkynyl, $(C_1-C_6)$alkoxy, perhalo$(C_1-C_6)$alkyl, perhalo$(C_1-C_6)$alkoxy, —CN, —NO$_2$, amino, $(C_1-C_6)$alkylamino, $[(C_1-C_6)$alkyl$]_2$-amino, HO—(C=O)—, $(C_1-C_6)$alkyl-(C=O)—, $(C_1-C_6)$alkyl-O—(C=O)—, $(C_1-C_6)$alkyl-CO$_2$—, $(C_1-C_6)$alkyl-(C=O)—NH—, $(C_1-C_6)$alkyl-NH—(C=O)—, $(C_1-C_6)$alkyl-(C=O)—[$((C_1-C_6)$alkyl)-N]—, $(C_1-C_6)$alkyl-[$((C_1-C_6)$alkyl)-N]—(C=O)—, $(C_1-C_6)$alkyl-SO$_2$NH—, $(C_1-C_6)$alkyl-SO$_2$—, optionally substituted phenyl-(C=O)—, optionally substituted phenyl-(C=O)—O—, optionally substituted phenoxy, optionally substituted phenyl-NH—(C=O)—, optionally substituted phenyl-[$((C_1-C_6)$alkyl)-N]—(C=O)—, optionally substituted phenyl-(C=O)—NH— optionally substituted phenyl-(C=O)—[$((C_1-C_6)$alkyl)-N]—.

A preferred embodiment of the present invention are those compounds of formula I wherein $R^2$ is $(C_1-C_4)$alkyl.

Another embodiment of the present invention are those compounds of formula I wherein $R^2$ is optionally substituted $(C_3-C_6)$cycloalkyl; wherein said substituents are independently selected from the group consisting of halo, $(C_1-C_6)$alkyl, $(C_2-C_6)$alkenyl, $(C_2-C_6)$alkynyl, perhalo$(C_1-C_6)$alkyl, phenyl, $(C_3-C_{10})$cycloalkyl, $(C_1-C_{10})$heteroaryl, $(C_1-C_{10})$heterocyclic, formyl, —CN, $(C_1-C_6)$alkyl-(C=O)—, phenyl-(C=O)—, HO—(C=O)—, $(C_1-C_6)$alkyl-O—(C=O)—, $(C_1-C_6)$alkyl-NH—(C=O)—, $[(C_1-C_6)$alkyl$]_2$—N—(C=O)—, phenyl-NH—(C=O)—, phenyl-[$((C_1-C_6)$alkyl)-N]—(C=O)—, —NO$_2$, amino, $(C_1-C_6)$alkylamino, $[(C_1-C_6)$alkyl$]_2$-amino, $(C_1-C_6)$alkyl-(C=O)—NH—, $(C_1-C_6)$alkyl-(C=O)—[$((C_1-C_6)$alkyl)-N]—, phenyl-(C=O)—NH—, phenyl-(C=O)—[$((C_1-C_6)$alkyl)-N]—, H$_2$N—(C=O)—NH—, $(C_1-C_6)$alkyl-HN—(C=O)—NH—, $[(C_1-C_6)$alkyl-$]_2$N—(C=O)—NH—, $(C_1-C_6)$alkyl-HN—(C=O)—[$((C_1-C_6)$alkyl)-N]—, $[(C_1-C_6)$alkyl-$]_2$N—(C=O)—[$((C_1-C_6)$alkyl)-N]—, phenyl-HN—(C=O)—NH—, (phenyl-)$_2$N—(C=O)—NH—, phenyl-HN—(C=O)—[$((C_1-C_6)$alkyl)-N]—, (phenyl-)$_2$N—(C=O)—[$((C_1-C_6)$alkyl)-N]—, $(C_1-C_6)$alkyl-O—(C=O)—NH—, $(C_1-C_6)$alkyl-O—(C=O)—[$((C_1-C_6)$alkyl)-N]—, phenyl-O—(C=O)—NH—, phenyl-O—(C=O)—[$((C_1-C_6)$alkyl)-N]—, $(C_1-C_6)$alkyl-SO$_2$NH—, phenyl-SO$_2$NH—, $(C_1-C_6)$alkyl-SO$_2$—, phenyl-SO$_2$—, hydroxy, $(C_1-C_6)$alkoxy, perhalo$(C_1-C_6)$alkoxy, phenoxy, $(C_1-C_6)$alkyl-(C=O)—O—, phenyl-(C=O)—O—, H$_2$N—(C=O)—O—, $(C_1-C_6)$alkyl-HN—(C=O)—O—, $[(C_1-C_6)$alkyl-$]_2$N—(C=O)—O—, phenyl-HN—(C=O)—O—, (phenyl-)$_2$N—(C=O)—O—; wherein each of said moieties containing a phenyl alternative may optionally be substituted by one or two radicals independently selected from the group consisting of $(C_1-C_6)$alkyl, halo, $(C_1-C_6)$alkoxy, perhalo$(C_1-C_6)$alkyl and perhalo$(C_1-C_6)$alkoxy; more preferably said substituents are independently selected from the group consisting of halo, $(C_1-C_6)$alkyl, $(C_2-C_6)$alkenyl, perhalo$(C_1-C_6)$alkyl, —CN, $(C_1-C_6)$alkyl-(C=O)—, HO—(C=O)—, $(C_1-C_6)$alkyl-O—(C=O)—, $(C_1-C_6)$alkyl-NH—(C=O)—, $[(C_1-C_6)$alkyl$]_2$—N—(C=O)—, amino, $(C_1-C_6)$alkylamino, $[(C_1-C_6)$alkyl$]_2$-amino, $(C_1-C_6)$alkyl-(C=O)—NH—, $(C_1-C_6)$alkyl-(C=O)—[$((C_1-C_6)$alkyl)-N]—, H$_2$N—(C=O)—NH—, $(C_1-C_6)$alkyl-HN—(C=O)—NH—, $[(C_1-C_6)$alkyl-$]_2$N—(C=O)—NH—, $(C_1-C_6)$alkyl-HN—(C=O)—[$((C_1-C_6)$alkyl)-N]—, $[(C_1-C_6)$alkyl-$]_2$N—(C=O)—[$((C_1-C_6)$alkyl)-N]—, hydroxy, $(C_1-C_6)$alkoxy, perhalo$(C_1-C_6)$alkoxy, $(C_1-C_6)$alkyl-(C=O)—O—, H$_2$N—(C=O)—O—, $(C_1-C_6)$alkyl-HN—(C=O)—O— and $[(C_1-C_6)$alkyl-$]_2$N—(C=O)—O—.

Another embodiment of the present invention are those compounds of formula I wherein $R^2$ is optionally substituted ($C_1$-$C_{10}$)heterocyclic; wherein said substituents are independently selected from the group consisting of halo, ($C_1$-$C_6$)alkyl, ($C_2$-$C_6$)alkenyl, ($C_2$-$C_6$)alkynyl, perhalo($C_1$-$C_6$)alkyl, phenyl, ($C_3$-$C_{10}$)cycloalkyl, ($C_1$-$C_{10}$)heteroaryl, ($C_1$-$C_{10}$)heterocyclic, formyl, —CN, ($C_1$-$C_6$)alkyl-(C=O)—, phenyl-(C=O)—, HO—(C=O)—, ($C_1$-$C_6$)alkyl-O—(C=O)—, ($C_1$-$C_6$)alkyl-NH—(C=O)—, [($C_1$-$C_6$)alkyl]$_2$—N—(C=O)—, phenyl-NH—(C=O)—, phenyl-[(($C_1$-$C_6$)alkyl)-N]—(C=O)—, —NO$_2$, amino, ($C_1$-$C_6$)alkylamino, [($C_1$-$C_6$)alkyl]$_2$-amino, ($C_1$-$C_6$)alkyl-(C=O)—NH—, ($C_1$-$C_6$)alkyl-(C=O)—[(($C_1$-$C_6$)alkyl)-N]—, phenyl-(C=O)—NH—, phenyl-(C=O)—[(($C_1$-$C_6$)alkyl)-N]—, H$_2$N—(C=O)—NH—, ($C_1$-$C_6$)alkyl-HN—(C=O)—NH—, [($C_1$-$C_6$)alkyl-]$_2$N—(C=O)—NH—, ($C_1$-$C_6$)alkyl-HN—(C=O)—[(($C_1$-$C_6$)alkyl)-N]—, [($C_1$-$C_6$)alkyl-]$_2$N—(C=O)—[(($C_1$-$C_6$)alkyl)-N]—, phenyl-HN—(C=O)—NH—, (phenyl-)$_2$N—(C=O)—NH—, phenyl-HN—(C=O)—[(($C_1$-$C_6$)alkyl)-N]—, (phenyl-)$_2$N—(C=O)—[(($C_1$-$C_6$)alkyl)-N]—, ($C_1$-$C_6$)alkyl-O—(C=O)—NH—, ($C_1$-$C_6$)alkyl-O—(C=O)—[(($C_1$-$C_6$)alkyl)-N]—, phenyl-O—(C=O)—NH—, phenyl-O—(C=O)—[(($C_1$-$C_6$)alkyl)-N]—, ($C_1$-$C_6$)alkyl-SO$_2$NH—, phenyl-SO$_2$NH—, ($C_1$-$C_6$)alkyl-SO$_2$—, phenyl-SO$_2$—, hydroxy, ($C_1$-$C_6$)alkoxy, perhalo($C_1$-$C_6$)alkoxy, phenoxy, ($C_1$-$C_6$)alkyl-(C=O)—O—, phenyl-(C=O)—O—, H$_2$N—(C=O)—O—, ($C_1$-$C_6$)alkyl-HN—(C=O)—O—, [($C_1$-$C_6$)alkyl-]$_2$N—(C=O)—O—, phenyl-HN—(C=O)—O—, (phenyl-)$_2$N—(C=O)—O—; wherein each of said moieties containing a phenyl alternative may optionally be substituted by one or two radicals independently selected from the group consisting of ($C_1$-$C_6$) alkyl, halo, ($C_1$-$C_6$)alkoxy, perhalo($C_1$-$C_6$)alkyl and perhalo($C_1$-$C_6$)alkoxy; more preferably said substituents are independently selected from the group consisting of halo, ($C_1$-$C_6$)alkyl, ($C_2$-$C_6$)alkenyl, perhalo($C_1$-$C_6$)alkyl, —CN, ($C_1$-$C_6$)alkyl-(C=O)—, HO—(C=O)—, ($C_1$-$C_6$)alkyl-O—(C=O)—, ($C_1$-$C_6$)alkyl-NH—(C=O)—, [($C_1$-$C_6$)alkyl]$_2$—N—(C=O)—, amino, ($C_1$-$C_6$)alkylamino, [($C_1$-$C_6$)alkyl]$_2$-amino, ($C_1$-$C_6$)alkyl-(C=O)—NH—, ($C_1$-$C_6$)alkyl-(C=O)—[(($C_1$-$C_6$)alkyl)-N]—, H$_2$N—(C=O)—NH—, ($C_1$-$C_6$)alkyl-HN—(C=O)—NH—, [($C_1$-$C_6$)alkyl-]$_2$N—(C=O)—NH—, ($C_1$-$C_6$)alkyl-HN—(C=O)—[(($C_1$-$C_6$)alkyl)-N]—, [($C_1$-$C_6$)alkyl-]$_2$N—(C=O)—[(($C_1$-$C_6$)alkyl)-N]—, hydroxy, ($C_1$-$C_6$)alkoxy, perhalo($C_1$-$C_6$)alkoxy, ($C_1$-$C_6$)alkyl-(C=O)—O—, H$_2$N—(C=O)—O—, ($C_1$-$C_6$)alkyl-HN—(C=O)—O— and [($C_1$-$C_6$)alkyl-]$_2$N—(C=O)—O—.

Another embodiment of the present invention are those compounds of formula I wherein $R^2$ is optionally substituted ($C_1$-$C_{10}$)heteroaryl; wherein said substituents are independently selected from the group consisting of halo, ($C_1$-$C_6$) alkyl, ($C_2$-$C_6$)alkenyl, ($C_2$-$C_6$)alkynyl, perhalo($C_1$-$C_6$) alkyl, phenyl, ($C_3$-$C_{10}$)cycloalkyl, ($C_1$-$C_{10}$)heteroaryl, ($C_1$-$C_{10}$)heterocyclic, formyl, —CN, ($C_1$-$C_6$)alkyl-(C=O)—, phenyl-(C=O)—, HO—(C=O)—, ($C_1$-$C_6$)alkyl-O—(C=O)—, ($C_1$-$C_6$)alkyl-NH—(C=O)—, [($C_1$-$C_6$)alkyl]$_2$—N—(C=O)—, phenyl-NH—(C=O)—, phenyl-[(($C_1$-$C_6$)alkyl)-N]—(C=O)—, —NO$_2$, amino, ($C_1$-$C_6$)alkylamino, [($C_1$-$C_6$)alkyl]$_2$-amino, ($C_1$-$C_6$)alkyl-(C=O)—NH—, ($C_1$-$C_6$)alkyl-(C=O)—[(($C_1$-$C_6$)alkyl)-N]—, phenyl-(C=O)—NH—, phenyl-(C=O)—[(($C_1$-$C_6$)alkyl)-N]—, H$_2$N—(C=O)—NH—, ($C_1$-$C_6$)alkyl-HN—(C=O)—NH—, [($C_1$-$C_6$)alkyl-]$_2$N—(C=O)—NH—, ($C_1$-$C_6$)alkyl-HN—(C=O)—[(($C_1$-$C_6$)alkyl)-N]—, [($C_1$-$C_6$)alkyl-]$_2$N—(C=O)—[(($C_1$-$C_6$)alkyl)-N]—, phenyl-HN—(C=O)—NH—, (phenyl-)$_2$N—(C=O)—NH—, phenyl-HN—(C=O)—[(($C_1$-$C_6$)alkyl)-N]—, (phenyl-)$_2$N—(C=O)—[(($C_1$-$C_6$)alkyl)-N]—, ($C_1$-$C_6$)alkyl-O—(C=O)—NH—, ($C_1$-$C_6$)alkyl-O—(C=O)—[(($C_1$-$C_6$)alkyl)-N]—, phenyl-O—(C=O)—NH—, phenyl-O—(C=O)—[(($C_1$-$C_6$)alkyl)-N]—, ($C_1$-$C_6$)alkyl-SO$_2$NH—, phenyl-SO$_2$NH—, ($C_1$-$C_6$)alkyl-SO$_2$—, phenyl-SO$_2$—, hydroxy, ($C_1$-$C_6$)alkoxy, perhalo($C_1$-$C_6$)alkoxy, phenoxy, ($C_1$-$C_6$)alkyl-(C=O)—O—, phenyl-(C=O)—O—, H$_2$N—(C=O)—O—, ($C_1$-$C_6$)alkyl-HN—(C=O)—O—, [($C_1$-$C_6$)alkyl-]$_2$N—(C=O)—O—, phenyl-HN—(C=O)—O—, (phenyl-)$_2$N—(C=O)—O—; wherein each of said moieties containing a phenyl alternative may optionally be substituted by one or two radicals independently selected from the group consisting of ($C_1$-$C_6$)alkyl, halo, ($C_1$-$C_6$)alkoxy, perhalo($C_1$-$C_6$)alkyl and perhalo($C_1$-$C_6$)alkoxy; more preferably said substituents are independently selected from the group consisting of halo, ($C_1$-$C_6$)alkyl, ($C_2$-$C_6$)alkenyl, perhalo($C_1$-$C_6$)alkyl, —CN, ($C_1$-$C_6$)alkyl-(C=O)—, HO—(C=O)—, ($C_1$-$C_6$)alkyl-($C_1$-$C_6$)alkyl-O—(C=O)—, ($C_1$-$C_6$)alkyl-NH—(C=O)—, [($C_1$-$C_6$)alkyl]$_2$—N—(C=O)—, amino, ($C_1$-$C_6$)alkylamino, [($C_1$-$C_6$)alkyl]$_2$-amino, ($C_1$-$C_6$)alkyl-(C=O)—NH—, ($C_1$-$C_6$)alkyl-(C=O)—[(($C_1$-$C_6$)alkyl)-N]—, H$_2$N—(C=O)—NH—, ($C_1$-$C_6$)alkyl-HN—(C=O)—NH—, [($C_1$-$C_6$)alkyl-]$_2$N—(C=O)—NH—, ($C_1$-$C_6$)alkyl-HN—(C=O)—[(($C_1$-$C_6$) alkyl)-N]—, [($C_1$-$C_6$)alkyl-]$_2$N—(C=O)—[(($C_1$-$C_6$) alkyl)-N]—, hydroxy, ($C_1$-$C_6$)alkoxy, perhalo($C_1$-$C_6$) alkoxy, ($C_1$-$C_6$)alkyl-(C=O)—O—, H$_2$N—(C=O)—O—, ($C_1$-$C_6$)alkyl-HN—(C=O)—O— and [($C_1$-$C_6$)alkyl-]$_2$N—(C=O)—O—.

Another preferred embodiment of the present invention are those groups of compounds of formula I wherein $R^2$ is optionally substituted phenyl; wherein said substituents are independently selected from the group consisting of halo, ($C_1$-$C_6$)alkyl, ($C_2$-$C_6$)alkenyl, ($C_2$-$C_6$)alkynyl, perhalo ($C_1$-$C_6$)alkyl, phenyl, ($C_3$-$C_{10}$)cycloalkyl, ($C_1$-$C_{10}$)heteroaryl, ($C_1$-$C_{10}$)heterocyclic, formyl, —CN, ($C_1$-$C_6$)alkyl-(C=O)—, phenyl-(C=O)—, HO—(C=O)—, ($C_1$-$C_6$)alkyl-O—(C=O)—, ($C_1$-$C_6$)alkyl-NH—(C=O)—, [($C_1$-$C_6$)alkyl]$_2$—N—(C=O)—, phenyl-NH—(C=O)—, phenyl-[(($C_1$-$C_6$)alkyl)-N]—(C=O)—, —NO$_2$, amino, ($C_1$-$C_6$)alkylamino, [($C_1$-$C_6$)alkyl]$_2$-amino, ($C_1$-$C_6$)alkyl-(C=O)—NH—, ($C_1$-$C_6$)alkyl-(C=O)—[(($C_1$-$C_6$)alkyl)-N]—, phenyl-(C=O)—NH—, phenyl-(C=O)—[(($C_1$-$C_6$)alkyl)-N]—, H$_2$N—(C=O)—NH—, ($C_1$-$C_6$)alkyl-HN—(C=O)—NH—, [($C_1$-$C_6$)alkyl-]$_2$N—(C=O)—NH—, ($C_1$-$C_6$)alkyl-HN—(C=O)—[(($C_1$-$C_6$) alkyl)-N]—, [($C_1$-$C_6$)alkyl-]$_2$N—(C=O)—[(($C_1$-$C_6$) alkyl)-N]—, phenyl-HN—(C=O)—NH—, (phenyl-)$_2$N—(C=O)—NH—, phenyl-HN—(C=O)—[(($C_1$-$C_6$)alkyl)-N]—, (phenyl-)$_2$N—(C=O)—[(($C_1$-$C_6$)alkyl)-N]—, ($C_1$-$C_6$)alkyl-O—(C=O)—NH—, ($C_1$-$C_6$)alkyl-O—(C=O)—[(($C_1$-$C_6$)alkyl)-N]—, phenyl-O—(C=O)—NH—, phenyl-O—(C=O)—[(($C_1$-$C_6$)alkyl)-N]—, ($C_1$-$C_6$)alkyl-SO$_2$NH—, phenyl-SO$_2$NH—, ($C_1$-$C_6$)alkyl-SO$_2$—, phenyl-SO$_2$—, hydroxy, ($C_1$-$C_6$)alkoxy, perhalo ($C_1$-$C_6$)alkoxy, phenoxy, ($C_1$-$C_6$)alkyl-(C=O)—O—, phenyl-(C=O)—O—, H$_2$N—(C=O)—O—, ($C_1$-$C_6$)alkyl-HN—(C=O)—O—, [($C_1$-$C_6$)alkyl-]$_2$N—(C=O)—O—, phenyl-HN—(C=O)—O—, (phenyl-)$_2$N—(C=O)—O—; wherein each of said moieties containing a phenyl alternative may optionally be substituted by one or two radicals independently selected from the group consisting of ($C_1$-$C_6$) alkyl, halo, ($C_1$-$C_6$)alkoxy, perhalo($C_1$-$C_6$)alkyl and perhalo($C_1$-$C_6$)alkoxy; more preferably said substituents are independently selected from the group consisting of halo, ($C_1$-$C_6$)alkyl, ($C_2$-$C_6$)alkenyl, perhalo($C_1$-$C_6$)alkyl, —CN, ($C_1$-$C_6$)alkyl-(C=O)—, HO—(C=O)—, ($C_1$-$C_6$)alkyl- O—(C=O)—, $(C_1-C_6)$alkyl-NH—(C=O)—, $[(C_1-C_6)$alkyl$]_2$—N—(C=O)—, amino, $(C_1-C_6)$alkylamino, $[(C_1-C_6)$alkyl$]_2$-amino, $(C_1-C_6)$alkyl-(C=O)—NH—, $(C_1-C_6)$alkyl-(C=O)—$[((C_1-C_6)$alkyl)-N]—, $H_2N$—(C=O)—NH—, $(C_1-C_6)$alkyl-HN—(C=O)—NH—, $[(C_1-C_6)$alkyl-$]_2N$—(C=O)—NH—, $(C_1-C_6)$alkyl-HN—(C=O)—$[((C_1-C_6)$alkyl)-N]—, $[(C_1-C_6)$alkyl-$]_2N$—(C=O)—$[((C_1-C_6)$alkyl)-N]—, hydroxy, $(C_1-C_6)$alkoxy, perhalo$(C_1-C_6)$alkoxy, $(C_1-C_6)$alkyl-(C=O)—O—, $H_2N$—(C=O)—O—, $(C_1-C_6)$alkyl-HN—(C=O)—O— and $[(C_1-C_6)$alkyl-$]_2N$—(C=O)—O—.

Another embodiment of the present invention are those groups of compounds of formula I wherein $R^2$ is $(R^1)_2$—N—0 wherein each $R^1$ is independently selected from hydrogen, $(C_1-C_6)$alkyl, phenyl, $(C_1-C_{10})$heterocyclic and $(C_3-C_{10})$cycloalkyl; wherein each of the aforesaid $R^1$ $(C_1-C_6)$alkyl, phenyl, $(C_1-C_{10})$heteroaryl, $(C_1-C_{10})$heterocyclic and $(C_3-C_{10})$cycloalkyl substituents may optionally be substituted by one to four moieties independently selected from the group consisting of halo, $(C_1-C_6)$alkyl, $(C_2-C_6)$alkenyl, $(C_2-C_6)$alkynyl, perhalo$(C_1-C_6)$alkyl, phenyl, $(C_1-C_{10})$heteroaryl, $(C_1-C_{10})$heterocyclic, $(C_3-C_{10})$cycloalkyl, hydroxy, $(C_1-C_6)$alkoxy, perhalo $(C_1-C_6)$alkoxy, phenoxy, $(C_1-C_{10})$heteroaryl-O—, $(C_1-C_{10})$heterocyclic-O—, $(C_3-C_{10})$cycloalkyl-O—, $(C_1-C_6)$alkyl-S—, $(C_1-C_6)$alkyl-$SO_2$—, $(C_1-C_6)$alkyl-NH—$SO_2$—, —$NO_2$, amino, $(C_1-C_6)$alkylamino, $[(C_1-C_6)$alkyl$]_2$-amino, $(C_1-C_6)$alkyl-$SO_2$—NH—, $(C_1-C_6)$alkyl-(C=O)—NH—, $(C_1-C_6)$alkyl-(C=O)—$[((C_1-C_6)$alkyl)-N]—, phenyl-(C=O)—NH—, phenyl-(C=O)—$[((C_1-C_6)$alkyl)-N]—, —CN, $(C_1-C_6)$alkyl-(C=O)—, phenyl-(C=O)—, $(C_1-C_{10})$heteroaryl-(C=O)—, $(C_1-C_{10})$heterocyclic-(C=O)—, $(C_3-C_{10})$cycloalkyl-(C=O)—, HO—(C=O)—, $(C_1-C_6)$alkyl-O—(C=O)—, $H_2N$(C=O)— $(C_1-C_6)$alkyl-NH—(C=O)—, $[(C_1-C_6)$alkyl$]_2$—N—(C=O)—, phenyl-NH—(C=O)—, phenyl-$[((C_1-C_6)$alkyl)-N]—(C=O)—, $(C_1-C_{10})$heteroaryl-NH—(C=O)—, $(C_1-C_{10})$heterocyclic-NH—(C=O)—, $(C_3-C_{10})$cycloalkyl-NH—(C=O)—, $(C_1-C_6)$alkyl-(C=O)—O— and phenyl-(C=O)—O—; wherein two $R^1$ $(C_1-C_6)$alkyl groups may be taken together with the nitrogen atom to form a five to six membered heterocyclic or heteroaryl ring.

A more preferred embodiment of the present invention are those groups of compounds of formula I wherein $R^2$ is $(R^1)_2$—N— wherein each $R^1$ is independently selected from hydrogen, $(C_1-C_4)$alkyl, phenyl and $(C_1-C_{10})$heterocyclic; wherein said $(C_1-C_4)$alkyl, phenyl and $(C_1-C_{10})$heterocyclic may optionally be substituted by one to four moieties independently selected from the group consisting of halo, $(C_1-C_6)$alkyl, $(C_2-C_6)$alkenyl, $(C_2-C_6)$alkynyl, perhalo$(C_1-C_6)$alkyl, hydroxy, $(C_1-C_6)$alkoxy, perhalo $(C_1-C_6)$alkoxy, amino, $(C_1-C_6)$alkylamino, $[(C_1-C_6)$alkyl$]_2$-amino, $(C_1-C_6)$alkyl-$SO_2$—NH—, $(C_1-C_6)$alkyl-(C=O)—NH—, —CN, $(C_1-C_6)$alkyl-(C=O)—, HO—(C=O)—, $(C_1-C_6)$alkyl-O—(C=O)—, $H_2N$(C=O)— $(C_1-C_6)$alkyl-NH—(C=O)—, $[(C_1-C_6)$alkyl$]_2$—N—(C=O)— and $(C_1-C_6)$alkyl-(C=O)—O—; more preferably optionally substituted with 1–3 substituents independently selected from halo, methyl, hydroxy and amino.

Another embodiment of the present invention, referred to as the phenyl-pyrolyl-triazolopyridines, are those group of compounds of formula I wherein the compound has the formula

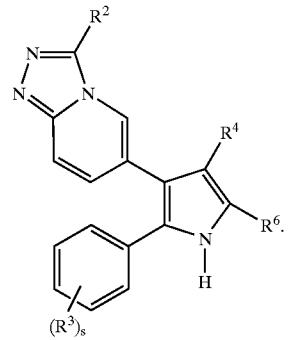

I(a)

Other embodiments of the present invention include those compounds of formula I(a) in combination with each of the aforementioned embodiments of $R^2$.

Preferred embodiments of the present invention, referred to as the phenyl-imdazolyl-triazolopyridines, are those group of compounds of formula I wherein the compound has the formula

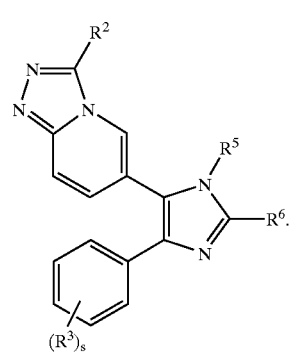

I(b)

Other embodiments of the present invention include those compounds of formula I(b) in combination with each of the aforementioned embodiments of $R^2$.

Another preferred embodiment of the present invention, referred to as the phenyl-pyrazolyl-triazolopyridines, are those group of compounds of formula I wherein the compound has the formula

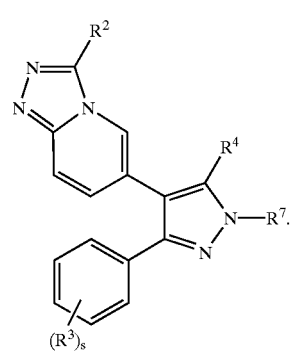

I(c)

Other embodiments of the present invention include those compounds of formula I(c) in combination with each of the aforementioned embodiments of $R^2$.

Another preferred embodiment of the present invention, referred to as the phenyl-oxazolyl-triazolopyridines, are those group of compounds of formula I wherein the compound has the formula I(d)

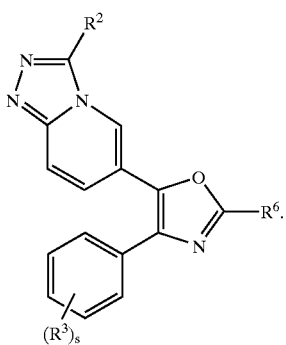

Other embodiments of the present invention include those compounds of formula I(d) in combination with each of the aforementioned embodiments of $R^2$.

Another preferred embodiment of the present invention, referred to as the phenyl-isoxazolyl-triazolopyridines, are those group of compounds of formula I wherein the compound has the formula I(e)

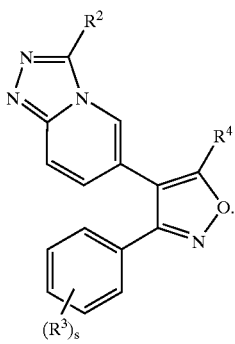

Other embodiments of the present invention include those compounds of formula I(e) in combination with each of the aforementioned embodiments of $R^2$.

Another embodiment of the present invention, referred to as the phenyl-pyrazolyl-triazolopyridines, are those group of compounds of formula I wherein the compound has the formula I(f)

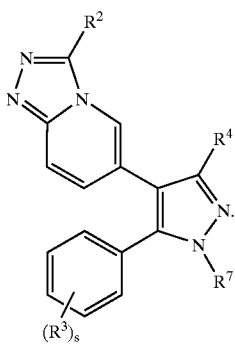

Other embodiments of the present invention include those compounds of formula I(f) in combination with each of the aforementioned embodiments of $R^2$.

Another embodiment of the present invention, referred to as the phenyl-thiazolyl-triazolopyridines, are those group of compounds of formula I wherein the compound has the formula I(g)

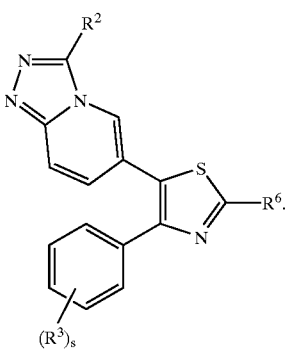

Other embodiments of the present invention include those compounds of formula I(g) in combination with each of the aforementioned embodiments of $R^2$.

Another embodiment of the present invention, referred to as the phenyl-isothiazolyl-triazolopyridines, are those group of compounds of formula I wherein the compound has the formula I(h)

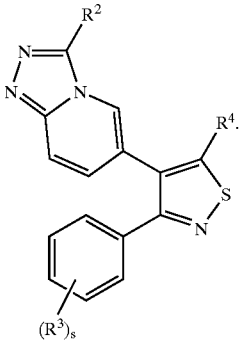

Other embodiments of the present invention include those compounds of formula I(h) in combination with each of the aforementioned embodiments of $R^2$.

Another embodiment of the present invention are those group of compounds of formula I (and I(a), I(c), I(e), I(f), and I(h)) wherein $R^4$ is hydrogen. Other embodiments of the present invention include those compounds of formula I (and I(a), I(c), I(e), I(f), and I(h)) wherein $R^4$ is hydrogen in combination with the aforementioned embodiments of $R^2$.

Another embodiment of the present invention are those group of compounds of formula I (and I(a), I(c), I(e), I(f), and I(h)) wherein $R^4$ is $R^9$—B—$(CH_2)_n$— and n is zero. Other embodiments of the present invention include those compounds of formula I (and I(a), I(c), I(e), I(f), and I(h)) wherein $R^4$ is $R^9$—B—$(CH_2)_n$— and n is zero in combination with the aforementioned embodiments of $R^2$.

Another embodiment of the present invention are those group of compounds of formula I (and I(a), I(c), I(e), I(f), and I(h)) wherein $R^4$ is $R^9$—B—$(CH_2)_n$— and n is an integer from one to six, more preferably one to five, more preferably one to three. Other embodiments of the present invention include those compounds of formula I (and I(a), I(c), I(e), I(f), and I(h)) wherein $R^4$ is $R^9$—B—$(CH_2)_n$— and n is an integer from one to six, more preferably one to five, more preferably one to three, in combination with the aforementioned embodiments of $R^2$.

Another preferred embodiment of the present invention are those group of compounds of formula I (and I(a), I(c), I(e), I(f), and I(h)) wherein $R^4$ is $R^9$—B—$(CH_2)_n$—; n is zero; B is a bond and $R^9$ is $R^{13}$—$(R^{12}CH)_m$—. Other embodiments of the present invention include those compounds of formula I (and I(a), I(c), I(e), I(f), and I(h)) wherein $R^4$ is $R^9$—B—$(CH_2)_n$—, n is zero and $R^9$ is $R^{13}$—$(R^{12}CH)$ in combination with the aforementioned embodiments of $R^2$. More preferred embodiments of the invention are those compounds of formula I (and I(c), (e) and (f)) wherein $R^4$ is $R^9$—B—$(CH_2)_n$—, n is zero, $R^9$ is $R^{13}$—$(R^{12}CH)_m$—, m is one to six, and $R^{12}$ and $R^{13}$ are each hydrogen.

Another embodiment of the present invention are those group of compounds of formula I (and I(a), I(c), I(e), I(f), and I(h)) wherein $R^4$ is $R^9$—B—$(CH_2)_n$—; n is zero; B is —(C=O)—$(R^{10}$—N)—, —$(R^{10}$—N)—, —$SO_2$—$(R^{10}$—N)—, —$(R^{10}$—N)—(C=O)—$(NR^{11})$— or —$(R^{10}$—N)—(C=O)—O—; and $R^9$ is selected from the group consisting of hydrogen and $R^{13}$—$(R^{12}CH)_m$—; more preferably wherein $R^9$ is $R^{13}$—$(R^{12}CH)_m$—; m is 1–6; $R^{10}$ is hydrogen or methyl; each $R^{12}$ is independently selected from the groups consisting of hydrogen or methyl; and $R^{13}$ is selected from the group consisting of hydrogen, $(C_1$–$C_6)$alkyl, $(C_2$–$C_6)$alkenyl, phenyl, $(C_1$–$C_{10})$heteroaryl, $(C_1$–$C_{10})$heterocyclic, $(C_3$–$C_{10})$cycloalkyl, hydroxy, $(C_1$–$C_6)$alkoxy, perhalo$(C_1$–$C_6)$alkoxy, phenoxy, $(C_1$–$C_{10})$heteroaryl-O—, $(C_1$–$C_{10})$heterocyclic-O—, $(C_3$–$C_{10})$cycloalkyl-O—, $(C_1$–$C_6)$alkyl-S—, $(C_1$–$C_6)$alkyl-$SO_2$—, $(C_1$–$C_6)$alkyl-NH—$SO_2$—, —$NO_2$, amino, $(C_1$–$C_6)$alkylamino, [$(C_1$–$C_6)$alkyl]$_2$-amino, $(C_1$–$C_6)$alkyl-$SO_2$—NH—, $(C_1$–$C_6)$alkyl-(C=O)—NH—, $(C_1$–$C_6)$alkyl-(C=O)—[(($C_1$–$C_6)$alkyl)-N]—, phenyl-(C=O)—NH—, phenyl-(C=O)—[(($C_1$–$C_6)$alkyl)-N]—, $(C_1$–$C_6)$alkyl-$SO_2$—NH—, phenyl-$SO_2$—NH—, $(C_1$–$C_6)$alkyl-$SO_2$—[(($C_1$–$C_6)$alkyl)-N]—, phenyl-$SO_2$—[(($C_1$–$C_6)$alkyl)-N]—, —CN, $(C_1$–$C_6)$alkyl-(C=O)—, phenyl-(C=O)—, $(C_1$–$C_{10})$heteroaryl-(C=O)—, $(C_1$–$C_{10})$heterocyclic-(C=O)—, $(C_3$–$C_{10})$cycloalkyl-(C=O)—, $(C_1$–$C_{10})$heteroaryl-NH—(C=O)—, $(C_1$–$C_{10})$heterocyclic-NH—(C=O)—, $(C_3$–$C_{10})$cycloalkyl-NH—(C=O)—, HO—(C=O)—, $(C_1$–$C_6)$alkyl-O—(C=O)—, $H_2N$(C=O)—, $(C_1$–$C_6)$alkyl-NH—(C=O)—, [$(C_1$–$C_6)$alkyl]$_2$—N—(C=O)—, phenyl-NH—(C=O)—, phenyl-[(($C_1$–$C_6)$alkyl)-N]-(C=O)—, $(C_1$–$C_6)$alkyl-(C=O)—O— and phenyl-(C=O)—O—. Other embodiments of the present invention include those compounds of formula I (and I(a), I(c), I(e), I(f), and I(h)) wherein $R^4$ is $R^9$—B—$(CH_2)_n$—; n is zero; B is —(C=O)—$(R^{10}$—N)—, —$(R^{10}$—N)—, —$SO_2$—$(R^{10}$—N)—, —$(R^{10}$—N)—(C=O)—$(NR^{11})$— or —$(R^{10}$—N)—(C=O)—O—; $R^9$ is hydrogen or $R^{13}$—$(R^{12}CH)_m$—(more preferably wherein $R^9$ is $R^{13}$—$(R^{12}CH)_m$—); m is 1–6; $R^{10}$ is hydrogen or methyl; each $R^{12}$ is independently selected from the groups consisting of hydrogen or methyl; and $R^{13}$ is as described above, in combination with the aforementioned embodiments of $R^2$.

Another preferred embodiment of the present invention are those group of compounds of formula I (and I(a), I(c), I(e), I(f), and I(h)) wherein $R^4$ is $R^9$—B—$(CH_2)_n$—; n is zero; B is —$(R^{10}$—N)—; $R^9$ is hydrogen or $R^{13}$—$(R^{12}CH)_m$—; m is 1–6; $R^{10}$ is hydrogen or methyl; $R^{12}$ is hydrogen or methyl; and $R^{13}$ is selected from the group consisting of hydrogen, $(C_1$–$C_6)$alkyl, hydroxy, $(C_1$–$C_6)$alkoxy, amino, $(C_1$–$C_6)$alkylamino, [$(C_1$–$C_6)$alkyl]$_2$amino, $(C_2$–$C_6)$alkenyl, $(C_2$–$C_6)$alkynyl, phenyl, $(C_1$–$C_{10})$heteroaryl, $(C_1$–$C_{10})$heterocyclic and $(C_3$–$C_{10})$cycloalkyl. Other embodiments of the present invention include those compounds of formula I (and I(a), I(c), I(e), I(f), and I(h)) wherein $R^4$ is $R^9$—B—$(CH_2)_n$—; n is zero; B is —$(R^{10}$—N)—; $R^9$ is hydrogen or $R^{13}$—$(R^{12}CH)_m$—; m is 1–6; $R^{10}$ is hydrogen or methyl; $R^{12}$ is hydrogen or methyl; and $R^{13}$ is selected from the group consisting of hydrogen, $(C_1$–$C_6)$alkyl, hydroxy, $(C_1$–$C_6)$alkoxy, amino, $(C_1$–$C_6)$alkylamino, [$(C_1$–$C_6)$alkyl]$_2$amino, $(C_2$–$C_6)$alkenyl, $(C_2$–$C_6)$alkynyl, phenyl, $(C_1$–$C_{10})$heteroaryl, $(C_1$–$C_{10})$heterocyclic and $(C_3$–$C_{10})$cycloalkyl, in combination with the aforementioned embodiments of $R^2$. More preferred embodiments of the invention are those compounds of formula I (and I(c), I(e) and I(f)) wherein $R^4$ is $R^9$—B—$(CH_2)_n$—; n is zero; B is —$(R^{10}$—N)—; $R^9$ is $R^{13}$—$(R^{12}CH)_n$—; m is 1–6; and $R^{10}$, $R^{12}$ and $R^{13}$ are each hydrogen.

Another embodiment of the present invention are those group of compounds of formula I (and I(a), I(c), I(e), I(f), and I(h)) wherein $R^4$ is $R^9$—B—$(CH_2)_n$—; n is zero; B is a bond, and $R^9$ is selected from the group consisting of optionally substituted phenyl, $(C_1$–$C_{10})$heterocyclic, $(C_1$–$C_{10})$heteroaryl and $(C_3$–$C_{10})$cycloalkyl; wherein each of the aforesaid $R^9$ phenyl, $(C_1$–$C_{10})$heteroaryl, $(C_1$–$C_{10})$heterocyclic and $(C_3$–$C_{10})$cycloalkyl substituents may optionally be substituted by one to four moieties independently selected from the group consisting of halo, $(C_1$–$C_6)$alkyl, $(C_2$–$C_6)$alkenyl, $(C_2$–$C_6)$alkynyl, perhalo$(C_1$–$C_6)$alkyl, phenyl, $(C_1$–$C_{10})$heteroaryl, $(C_1$–$C_{10})$heterocyclic, $(C_3$–$C_{10})$cycloalkyl, hydroxy, $(C_1$–$C_6)$alkoxy, perhalo $(C_1$–$C_6)$alkoxy, phenoxy, $(C_1$–$C_{10})$heteroaryl-O—, $(C_1$–$C_{10})$heterocyclic-O—, $(C_3$–$C_{10})$cycloalkyl-O—, $(C_1$–$C_6)$alkyl-S—, $(C_1$–$C_6)$alkyl-$SO_2$—, $(C_1$–$C_6)$alkyl-NH—$SO_2$—, —$NO_2$, amino, $(C_1$–$C_6)$alkylamino, [$(C_1$–$C_6)$alkyl]$_2$-amino, $(C_1$–$C_6)$alkyl-$SO_2$—NH—, $(C_1$–$C_6)$alkyl-(C=O)—NH—, $(C_1$–$C_6)$alkyl-(C=O)—[(($C_1$–$C_6)$alkyl)-N]—, phenyl-(C=O)—NH—, phenyl-(C=O)—[(($C_1$–$C_6)$alkyl)-N]—, —CN, $(C_1$–$C_6)$alkyl-(C=O)—, phenyl-(C=O)—, $(C_1$–$C_{10})$heteroaryl-(C=O)—, $(C_1$–$C_{10})$heterocyclic-(C=O)—, $(C_3$–$C_{10})$cycloalkyl-(C=O)—, HO—(C=O)—, $(C_1$–$C_6)$alkyl-O—(C=O)—, $H_2N$(C=O)— $(C_1$–$C_6)$alkyl-NH—(C=O)—, [$(C_1$–$C_6)$alkyl]$_2$—N—(C=O)—, phenyl-NH—(C=O)—, phenyl-[(($C_1$–$C_6)$alkyl)-N]—(C=O)—, $(C_1$–$C_{10})$heteroaryl-NH—(C=O)—, $(C_1$–$C_{10})$heterocyclic-NH—(C=O)—, $(C_3$–$C_{10})$cycloalkyl-NH—(C=O)—, $(C_1$–$C_6)$alkyl-(C=O)—O— and phenyl-(C=O)—O—. Other embodiments of the present invention include those compounds of formula I (and I(a), I(c), I(e), I(f), and I(h)) wherein $R^4$ is $R^9$—B—$(CH_2)_n$—; n is zero; B is a bond, and $R^9$ is as described above, in combination with the aforementioned embodiments of $R^2$.

Another embodiment of the present invention are those group of compounds of formula I (and I(a), I(c), I(e), I(f), and I(h)) wherein $R^4$ is $R^9$—B—$(CH_2)_n$—; n is zero; B is —(C=O)—$(R^{10}$—N)—, —$(R^{10}$—N)—, —$SO_2$—$(R^{10}$—N)—, —$(R^{10}$—N)—(C=O)—$(NR^{11})$— or —$(R^{10}$—N)—(C=O)—O—; and $R^9$ is selected from the group consisting of optionally substituted phenyl, $(C_1$–$C_{10})$heterocyclic, $(C_1$–$C_{10})$heteroaryl and $(C_3$–$C_{10})$cycloalkyl; wherein each of the aforesaid $R^9$ phenyl, $(C_1$–$C_{10})$heteroaryl, $(C_1$–$C_{10})$heterocyclic and $(C_3$–$C_{10})$cycloalkyl substituents may optionally be substituted by one to four moieties independently selected from the group consisting of halo, $(C_1$–$C_6)$alkyl, $(C_2$–$C_6)$alkenyl, $(C_2$–$C_6)$alkynyl, perhalo$(C_1$–$C_6)$alkyl, phenyl, $(C_1$–$C_{10})$heteroaryl, $(C_1$–$C_{10})$heterocyclic, $(C_3$–$C_{10})$cycloalkyl, hydroxy, $(C_1$–$C_6)$alkoxy, perhalo $(C_1$–$C_6)$alkoxy, phenoxy, $(C_1$–$C_{10})$heteroaryl-O—, $(C_1$–$C_{10})$heterocyclic-O—, $(C_3$–$C_{10})$cycloalkyl-O—, $(C_1$–$C_6)$alkyl-S—, $(C_1$–$C_6)$alkyl-$SO_2$—, $(C_1$–$C_6)$alkyl-NH—$SO_2$—, —$NO_2$, amino, $(C_1$–$C_6)$alkylamino, [$(C_1$–$C_6)$ alkyl]$_2$-amino, (C$_1$–C$_6$)alkyl-SO$_2$—NH—, (C$_1$–C$_6$)alkyl-(C=O)—NH—, (C$_1$–C$_6$)alkyl-(C=O)—[((C$_1$–C$_6$)alkyl)-N]—, phenyl-(C=O)—NH—, phenyl-(C=O)—[((C$_1$–C$_6$) alkyl)-N]—, —CN, (C$_1$–C$_6$)alkyl-(C=O)—, phenyl-(C=O)—, (C$_1$–C$_{10}$)heteroaryl-(C=O)—, (C$_1$–C$_{10}$) heterocyclic-(C=O)—, (C$_3$–C$_{10}$)cycloalkyl-(C=O)—, HO—(C=O)—, (C$_1$–C$_6$)alkyl-O—(C=O)—, H$_2$N (C=O)— (C$_1$–C$_6$)alkyl-NH—(C=O)—, [(C$_1$–C$_6$)alkyl]$_2$—N—(C=O)—, phenyl-NH—(C=O)—, phenyl-[((C$_1$–C$_6$)alkyl)-N]—(C=O)—, (C$_1$–C$_{10}$)heteroaryl-NH—(C=O)—, (C$_1$–C$_{10}$)heterocyclic-NH—(C=O)—, (C$_3$–C$_{10}$)cycloalkyl-NH—(C=O)—, (C$_1$–C$_6$)alkyl-(C=O)—O— and phenyl-(C=O)—O—. Other embodiments of the present invention include those compounds of formula I (and I(a), I(c), I(e), I(f), and I(h)) wherein R$^4$ is R$^9$—B—(CH$_2$)$_n$—; n is zero; B is —(C=O)—(R$^{10}$—N)—, —(R$^{10}$—N)—, —SO$_2$—(R$^{10}$—N)—, —(R$^{10}$—N)—(C=O)—(NR$^{11}$)— or —(R$^{10}$—N)—(C=O)—O—; and R$^9$ is as described above, in combination with the aforementioned embodiments of R$^2$.

Another embodiment of the present invention are those group of compounds of formula I (and I(a), I(c), I(e), I(f), and I(h)) wherein R$^4$ is R$^9$—B—(CH$_2$)$_n$—; n is an integer from one to six, more preferably one to five, more preferably one to three; B is a bond, and R$^9$ is selected from the group consisting of optionally substituted phenyl, (C$_1$–C$_{10}$) heterocyclic, (C$_1$–C$_{10}$)heteroaryl and (C$_3$–C$_{10}$)cycloalkyl; wherein each of the aforesaid R$^9$ phenyl, (C$_1$–C$_{10}$) heteroaryl, (C$_1$–C$_{10}$)heterocyclic and (C$_3$–C$_{10}$)cycloalkyl substituents may optionally be substituted by one to four moieties independently selected from the group consisting of halo, (C$_1$–C$_6$)alkyl, (C$_2$–C$_6$)alkenyl, (C$_2$–C$_6$)alkynyl, perhalo(C$_1$–C$_6$)alkyl, phenyl, (C$_1$–C$_{10}$)heteroaryl, (C$_1$–C$_{10}$) heterocyclic, (C$_3$–C$_{10}$)cycloalkyl, hydroxy, (C$_1$–C$_6$)alkoxy, perhalo(C$_1$–C$_6$)alkoxy, phenoxy, (C$_1$–C$_{10}$)heteroaryl-O—, (C$_1$–C$_{10}$)heterocyclic-O—, (C$_3$–C$_{10}$)cycloalkyl-O—, (C$_1$–C$_6$)alkyl-S—, (C$_1$–C$_6$)alkyl-SO$_2$—, (C$_1$–C$_6$)alkyl-NH—SO$_2$—, —NO$_2$, amino, (C$_1$–C$_6$)alkylamino, [(C$_1$–C$_6$) alkyl]$_2$-amino, (C$_1$–C$_6$)alkyl-SO$_2$—NH—, (C$_1$–C$_6$)alkyl-(C=O)—NH—, (C$_1$–C$_6$)alkyl-(C=O)—[((C$_1$–C$_6$)alkyl)-N]—, phenyl-(C=O)—NH—, phenyl-(C=O)—[((C$_1$–C$_6$) alkyl)-N]—, —CN, (C$_1$–C$_6$)alkyl-(C=O)—, phenyl-(C=O)—, (C$_1$–C$_{10}$)heteroaryl-(C=O)—, (C$_1$–C$_{10}$) heterocyclic-(C=O)—, (C$_3$–C$_{10}$)cycloalkyl-(C=O)—, HO—(C=O)—, (C$_1$–C$_6$)alkyl-O—(C=O)—, H$_2$N (C=O)— (C$_1$–C$_6$)alkyl-NH—(C=O)—, [(C$_1$–C$_6$)alkyl]$_2$—N—(C=O)—, phenyl-NH—(C=O)—, phenyl-[((C$_1$–C$_6$)alkyl)-N]—(C=O)—, (C$_1$–C$_{10}$)heteroaryl-NH—(C=O)—, (C$_1$–C$_{10}$)heterocyclic-NH—(C=O)—, (C$_3$–C$_{10}$)cycloalkyl-NH—(C=O)—, (C$_1$–C$_6$)alkyl-(C=O)—O— and phenyl-(C=O)—O—. Other embodiments of the present invention include those compounds of formula I (and I(a), I(c), I(e), I(f), and I(h)) wherein R$^4$ is R$^9$—B—(CH$_2$)$_n$—; n is an integer from one to six, more preferably one to five, more preferably one to three; B is a bond, and R$^9$ is as described above, in combination with the aforementioned embodiments of R$^2$.

Another embodiment of the present invention are those group of compounds of formula I (and I(a), I(c), I(e), I(f), and I(h)) wherein R$^4$ is R$^9$—B—(CH$_2$)$_n$—; n is an integer from one to six, more preferably one to five, more preferably one to three; B is —(C=O)—(R$^{10}$—N)—, —(R$^{10}$—N)—, —SO$_2$—(R$^{10}$—N)—, —(R$^{10}$—N)—(C=O)—(NR$^{11}$)— or —(R$^{10}$—N)—(C=O)—O—; and R$^9$ is selected from the group consisting of optionally substituted phenyl, (C$_1$–C$_{10}$) heterocyclic, (C$_1$–C$_{10}$)heteroaryl and (C$_3$–C$_{10}$)cycloalkyl; wherein each of the aforesaid R$^9$ phenyl, (C$_1$–C$_{10}$) heteroaryl, (C$_1$–C$_{10}$)heterocyclic and (C$_3$–C$_{10}$)cycloalkyl substituents may optionally be substituted by one to four moieties independently selected from the group consisting of halo, (C$_1$–C$_6$)alkyl, (C$_2$–C$_6$)alkenyl, (C$_2$–C$_6$)alkynyl, perhalo(C$_1$–C$_6$)alkyl, phenyl, (C$_1$–C$_{10}$)heteroaryl, (C$_1$–C$_{10}$) heterocyclic, (C$_3$–C$_{10}$)cycloalkyl, hydroxy, (C$_1$–C$_6$)alkoxy, perhalo(C$_1$–C$_6$)alkoxy, phenoxy, (C$_1$–C$_{10}$)heteroaryl-O—, (C$_1$–C$_{10}$)heterocyclic-O—, (C$_3$–C$_{10}$)cycloalkyl-O—, (C$_1$–C$_6$)alkyl-S—, (C$_1$–C$_6$)alkyl-SO$_2$—, (C$_1$–C$_6$)alkyl-NH—SO$_2$—, —NO$_2$, amino, (C$_1$–C$_6$)alkylamino, [(C$_1$–C$_6$) alkyl]$_2$-amino, (C$_1$–C$_6$)alkyl-SO$_2$—NH—, (C$_1$–C$_6$)alkyl-(C=O)—NH—, (C$_1$–C$_6$)alkyl-(C=O)—[((C$_1$–C$_6$)alkyl)-N]—, phenyl-(C=O)—NH—, phenyl-(C=O)—[((C$_1$–C$_6$) alkyl)-N]—, —CN, (C$_1$–C$_6$)alkyl-(C=O)—, phenyl-(C=O)—, (C$_1$–C$_{10}$)heteroaryl-(C=O)—, (C$_1$–C$_{10}$) heterocyclic-(C=O)—, (C$_3$–C$_{10}$)cycloalkyl-(C=O)—, HO—(C=O)—, (C$_1$–C$_6$)alkyl-O—(C=O)—, H$_2$N (C=O)— (C$_1$–C$_6$)alkyl-NH—(C=O)—, [(C$_1$–C$_6$)alkyl]$_2$—N—(C=O)—, phenyl-NH—(C=O)—, phenyl-[((C$_1$–C$_6$)alkyl)-N]—(C=O)—, (C$_1$–C$_{10}$)heteroaryl-NH—(C=O)—, (C$_1$–C$_{10}$)heterocyclic-NH—(C=O)—, (C$_3$–C$_{10}$)cycloalkyl-NH—(C=O)—, (C$_1$–C$_6$)alkyl-(C=O)—O— and phenyl-(C=O)—O—. Other embodiments of the present invention include those compounds of formula I (and I(a), I(c), I(e), I(f), and I(h)) wherein R$^4$ is R$^9$—B—(CH$_2$)$_n$—; n is an integer from one to six, more preferably one to five, more preferably one to three; B is —(C=O)—(R$^{10}$—N)—, —(R$^{10}$—N)—, —SO$_2$—(R$^{10}$—N)—, —(R$^{10}$—N)—(C=O)—(NR$^{11}$)— or —(R$^{10}$—N)—(C=O)—O—; and R$^9$ is as described above, in combination with the aforementioned embodiments of R$^2$.

Another embodiment of the present invention are those group of compounds of formula I (and I(a), I(c), I(e), I(f), and I(h)) wherein R$^4$ is R$^9$—B—(CH$_2$)$_n$—; n is an integer from one to six, more preferably one to five, more preferably one to three; B is a bond, and R$^9$ is R$^{13}$—(R$^{12}$CH)$_m$—; m is 1–6; R$^{10}$ is hydrogen or methyl; each R$^{12}$ is independently selected from the groups consisting of hydrogen or methyl; and R$^{13}$ is selected from the group consisting of hydrogen, (C$_1$–C$_6$)alkyl, (C$_1$–C$_6$)alkoxy, phenyl, (C$_1$–C$_{10}$)heteroaryl, (C$_1$–C$_{10}$)heterocyclic, (C$_3$–C$_{10}$)cycloalkyl, hydroxy, (C$_1$–C$_6$)alkoxy, perhalo(C$_1$–C$_6$)alkoxy, phenoxy, (C$_1$–C$_{10}$) heteroaryl-O—, (C$_1$–C$_{10}$)heterocyclic-O—, (C$_3$–C$_{10}$) cycloalkyl-O—, (C$_1$–C$_6$)alkyl-S—, (C$_1$–C$_6$)alkyl-SO$_2$—, (C$_1$–C$_6$)alkyl-NH—SO$_2$—, —NO$_2$, amino, (C$_1$–C$_6$) alkylamino, [(C$_1$–C$_6$)alkyl]$_2$-amino, (C$_1$–C$_6$)alkyl-SO$_2$—NH—, (C$_1$–C$_6$)alkyl-(C=O)—NH—, (C$_1$–C$_6$)alkyl-(C=O)—[((C$_1$–C$_6$)alkyl)-N]—, phenyl-(C=O)—NH—, phenyl-(C=O)—[((C$_1$–C$_6$)alkyl)-N]—, (C$_1$–C$_6$)alkyl-SO$_2$—NH—, phenyl-SO$_2$—NH—, (C$_1$–C$_6$)alkyl-SO$_2$—[((C$_1$–C$_6$)alkyl)-N]—, phenyl-SO$_2$—[((C$_1$–C$_6$)alkyl)-N]—, —CN, (C$_1$–C$_6$)alkyl-(C=O)—, phenyl-(C=O)—, (C$_1$–C$_{10}$)heteroaryl-(C=O)—, (C$_1$–C$_{10}$)heterocyclic-(C=O)—, (C$_3$–C$_{10}$)cycloalkyl-(C=O)—, (C$_1$–C$_{10}$) heteroaryl-NH—(C=O)—, (C$_1$–C$_{10}$)heterocyclic-NH—(C=O)—, (C$_3$–C$_{10}$)cycloalkyl-NH—(C=O)—, HO—(C=O)—, (C$_1$–C$_6$)alkyl-O—(C=O)—, H$_2$N(C=O)—, (C$_1$–C$_6$)alkyl-NH—(C=O)—, [(C$_1$–C$_6$)alkyl]$_2$—N—(C=O)—, phenyl-NH—(C=O)—, phenyl-[((C$_1$–C$_6$) alkyl)-N]—(C=O)—, (C$_1$–C$_6$)alkyl-(C=O)—O— and phenyl-(C=O)—O—. Other embodiments of the present invention include those compounds of formula I (and I(a), I(c), I(e), I(f), and I(h)) wherein R$^4$ is R$^9$—B—(CH$_2$)$_n$—; n is an integer from one to six, more preferably one to five, more preferably one to three; B is a bond, and R$^{13}$ is R$^9$—(R$^{12}$CH)$_m$—; m is 1–6; R$^{10}$ is hydrogen or methyl; each R$^{12}$ is independently selected from the groups consisting of hydrogen or methyl; and $R^{13}$ as described above, in combination with the aforementioned embodiments of $R^2$.

Another embodiment of the present invention are those group of compounds of formula I (and I(a), I(c), I(e), I(f), and I(h)) wherein $R^4$ is $R^9$—B—$(CH_2)_n$—; n is an integer from one to six, more preferably one to five, more preferably one to three; B is —(C=O)—($R^{10}$—N)—, —($R^{10}$—N)—, —$SO_2$—($R^{10}$—N)—, —($R^{10}$—N)—(C=O)—($NR^{11}$)— or —($R^{10}$—N)—(C=O)—O—; and $R^9$ is $R^{13}$—($R^{12}$CH)$_m$—; m is 1–6; $R^{10}$ is hydrogen or methyl; each $R^{12}$ is independently selected from the groups consisting of hydrogen or methyl; and $R^{13}$ is selected from the group consisting of hydrogen, $(C_1-C_6)$alkyl, $(C_1-C_6)$alkoxy, phenyl, $(C_1-C_{10})$heteroaryl, $(C_1-C_{10})$heterocyclic, $(C_3-C_{10})$cycloalkyl, hydroxy, $(C_1-C_6)$alkoxy, perhalo$(C_1-C_6)$alkoxy, phenoxy, $(C_1-C_{10})$heteroaryl-O—, $(C_1-C_{10})$heterocyclic-O—, $(C_3-C_{10})$cycloalkyl-O—, $(C_1-C_6)$alkyl-S—, $(C_1-C_6)$alkyl-$SO_2$—, $(C_1-C_6)$alkyl-NH-$SO_2$—, —$NO_2$, amino, $(C_1-C_6)$alkylamino, $[(C_1-C_6)$alkyl$]_2$-amino, $(C_1-C_6)$alkyl-$SO_2$—NH—, $(C_1-C_6)$alkyl-(C=O)—NH—, $(C_1-C_6)$alkyl-(C=O)—$[((C_1-C_6)$alkyl$)$-N]—, phenyl-(C=O)—NH—, phenyl-(C=O)—$[((C_1-C_6)$alkyl$)$-N]—, $(C_1-C_6)$alkyl-$SO_2$—NH—, phenyl-$SO_2$—NH—, $(C_1-C_6)$alkyl-$SO_2$—$[((C_1-C_6)$alkyl$)$-N]—, phenyl-$SO_2$—$[((C_1-C_6)$alkyl$)$-N]—, —CN, $(C_1-C_6)$alkyl-(C=O)—, phenyl-(C=O)—, $(C_1-C_{10})$heteroaryl-(C=O)—, $(C_1-C_{10})$heterocyclic-(C=O)—, $(C_3-C_{10})$cycloalkyl-(C=O)—, $(C_1-C_{10})$heteroaryl-NH—(C=O)—, $(C_1-C_{10})$heterocyclic-NH—(C=O)—, $(C_3-C_{10})$cycloalkyl-NH—(C=O)—, HO—(C=O)—, $(C_1-C_6)$alkyl-O—(C=O)—, $H_2N$(C=O)—, $(C_1-C_6)$alkyl-NH—(C=O)—, $[(C_1-C_6)$alkyl$]_2$—N—(C=O)—, phenyl-NH—(C=O)—, phenyl-$[((C_1-C_6)$alkyl$)$-N]—(C=O)—, $(C_1-C_6)$alkyl-(C=O)—O— and phenyl-(C=O)—O—. Other embodiments of the present invention include those compounds of formula I (and I(a), I(c), I(e), I(f), and I(h)) wherein $R^4$ is $R^9$—B—$(CH_2)_n$—; n is an integer from one to six, more preferably one to five, more preferably one to three; B is —(C=O)—($R^{10}$—N)—, —($R^{10}$—N)—, —$SO_2$—($R^{10}$—N)—, —($R^{10}$—N)—(C=O)—($NR^{11}$)— or —($R^{10}$—N)—(C=O)—O—; and $R^9$ is $R^{13}$—($R^{12}$CH)$_m$—; m is 1–6; $R^{10}$ is hydrogen or methyl; each $R^{12}$ is independently selected from the groups consisting of hydrogen or methyl; and $R^{13}$ is as described above, in combination with the aforementioned embodiments of $R^2$.

Another embodiment of the present invention are those group of compounds of formula I (and I(c) and I(f)) wherein $R^7$ is selected from the group consisting of $R^{16}$—$(C_1-C_6)$alkyl-(C=O)—, phenyl-(C=O)—, $(C_1-C_{10})$heteroaryl-(C=O)—, $(C_1-C_{10})$heterocyclic-(C=O)—, $(C_3-C_{10})$cycloalkyl-(C=O)—, $(C_1-C_6)$alkyl-O—(C=O)—, $H_2N$—(C=O)—, $(C_1-C_6)$alkyl-NH—(C=O)—, phenyl-NH—(C=O)—, $(C_1-C_{10})$heteroaryl-NH—(C=O)—, $(C_1-C_{10})$heterocyclic-NH—(C=O)— and $(C_3-C_{10})$cycloalkyl-NH—(C=O)—; wherein each of the aforesaid phenyl, heterocyclic, heteroaryl or cycloalkyl $R^7$ substituents may optionally be independently substituted by one to four moieties independently selected from the group consisting of halo, $R^{16}(C_1-C_6)$alkyl, $(C_2-C_6)$alkenyl, $(C_2-C_6)$alkynyl, perhalo$(C_1-C_6)$alkyl, $(C_3-C_{10})$cycloalkyl, phenyl, benzyl, $(C_1-C_{10})$heterocyclic, $(C_1-C_{10})$heteroaryl, $(C_1-C_6)$alkyl-$SO_2$—, formyl, —CN, $(C_1-C_6)$alkyl-(C=O)—, $(C_3-C_{10})$cycloalkyl-(C=O)—, phenyl-(C=O)—, $(C_1-C_{10})$heterocyclic-(C=O)—, $(C_1-C_{10})$heteroaryl-(C=O)—, HO—(C=O)—, $(C_1-C_6)$alkyl-O—(C=O)—, $(C_3-C_{10})$cycloalkyl-O—(C=O)—, $(C_1-C_{10})$heterocyclic-O—(C=O)—, $(C_1-C_{10})$heteroaryl-O—(C=O)—, $(C_1-C_6)$alkyl-NH—(C=O)—, $(C_3-C_{10})$cycloalkyl-NH—(C=O)—, phenyl-NH—(C=O)—, $(C_1-C_{10})$heterocyclic-NH—(C=O)—, $(C_1-C_{10})$heteroaryl-NH—(C=O)—, $[(C_1-C_6)$alkyl$]_2$—N—(C=O)—, phenyl-$[((C_1-C_6)$alkyl$)$-N]—(C=O)—, hydroxy, $(C_1-C_6)$alkoxy, perhalo$(C_1-C_6)$alkoxy, $(C_3-C_{10})$cycloalkyl-O—, phenoxy, $(C_1-C_{10})$heterocyclic-O—, $(C_1-C_{10})$heteroaryl-O—, $(C_1-C_6)$alkyl-(C=O)—O—, $(C_3-C_{10})$cycloalkyl-(C=O)—O—, phenyl-(C=O)—O—, $(C_1-C_{10})$heterocyclic-(C=O)—O—, $(C_1-C_{10})$heteroaryl-(C=O)—O—, —$NO_2$, amino, $(C_1-C_6)$alkylamino, $[(C_1-C_6)$alkyl$]_2$-amino, formamidyl, $(C_1-C_6)$alkyl-(C=O)—NH—, $(C_3-C_{10})$cycloalkyl-(C=O)—NH—, phenyl-(C=O)—NH—, $(C_1-C_{10})$heterocyclic-(C=O)—NH—, $(C_1-C_{10})$heteroaryl-(C=O)—NH—, $(C_1-C_6)$alkyl-(C=O)—$[((C_1-C_6)$alkyl$)$-N]—, phenyl-(C=O)—$[((C_1-C_6)$alkyl$)$-N]—, $(C_1-C_6)$alkyl-$SO_2$NH—, $(C_3-C_{10})$cycloalkyl-$SO_2$NH—, phenyl-$SO_2$NH—, $(C_1-C_{10})$heterocyclic-$SO_2$NH— and $(C_1-C_{10})$heteroaryl-$SO_2$NH—; wherein each of said phenyl and heteroaryl moieties may optionally be substituted by one or two radicals independently selected from the group consisting of halo, $(C_1-C_6)$alkyl, $(C_1-C_6)$alkoxy, amino, $(C_1-C_6)$alkylamino and $[(C_1-C_6)$alkyl$]_2$-amino. More preferred embodiments of the present invention are those group of compounds of formula I(c) wherein $R^7$ is hydrogen. Other embodiments of the present invention include those compounds of formula I (and I(c) and I(f)) wherein $R^7$ is as defined above, in combination with each of the aforementioned I(c) and I(f) $R^4$ embodiments and with each of the aforementioned $R^2$ embodiments.

Another embodiment of the present invention are those group of compounds of formula I (and I(c) and I(f)) wherein $R^7$ is selected from the group consisting of hydrogen and optionally substituted phenyl, $(C_1-C_{10})$heteroaryl, $(C_1-C_{10})$heterocyclic and $(C_3-C_{10})$cycloalkyl. Other embodiments of the present invention include those compounds of formula I (and I(c) and I(f)) wherein $R^7$ is as defined above, in combination with each of the aforementioned I(c) and I(f) $R^4$ embodiments and with each of the aforementioned $R^2$ embodiments.

Another preferred embodiment of the present invention are those group of compounds of formula I (and I(c) and I(f)) wherein $R^7$ is $R^{14}$—$(CR^{15}H)_p$—; p is one to six, preferably one to four; and $R^{14}$ is selected from the group consisting of hydrogen, halo, $(C_1-C_6)$alkyl, $(C_2-C_6)$alkenyl, $(C_2-C_6)$alkynyl, perhalo$(C_1-C_6)$alkyl, $(C_3-C_{10})$cycloalkyl, phenyl, $(C_1-C_{10})$heterocyclic, $(C_1-C_{10})$heteroaryl, formyl, —CN, $(C_1-C_6)$alkyl-(C=O)—, phenyl-(C=O)—, $(C_1-C_{10})$heteroaryl-(C=O)—, $(C_1-C_{10})$heterocyclic-(C=O)—, $(C_3-C_{10})$cycloalkyl-(C=O)—, HO—(C=O)—, $R^{16}$—$(C_1-C_6)$alkyl-O—(C=O)—, $(C_3-C_{10})$cycloalkyl-O—(C=O)—, $(C_1-C_{10})$heterocyclic-O—(C=O)—, $(C_1-C_{10})$heteroaryl-O—(C=O)—, $H_2N$—(C=O)—, $R^{16}$—$(C_1-C_6)$alkyl-NH—(C=O)—, $(C_3-C_{10})$cycloalkyl-NH—(C=O)—, phenyl-NH—(C=O)—, $(C_1-C_{10})$heterocyclic-NH—(C=O)—, $(C_1-C_{10})$heteroaryl-NH—(C=O)—, $[(C_1-C_6)$alkyl$]_2$—N—(C=O)—, phenyl-$[((C_1-C_6)$alkyl$)$-N]—(C=O)—, $(C_1-C_{10})$heteroaryl-$[((C_1-C_6)$alkyl$)$-N]—(C=O)—, $(C_1-C_{10})$heterocyclic-$[((C_1-C_6)$alkyl$)$-N]—(C=O)—, $(C_3-C_{10})$cycloalkyl-$[((C_1-C_6)$alkyl$)$-N]—(C=O)—, hydroxy, $R^{16}$—$(C_1-C_6)$alkoxy, perhalo$(C_1-C_6)$alkoxy, $(C_3-C_{10})$cycloalkyl-O—, phenoxy, $(C_1-C_{10})$heterocyclic-O—, $(C_1-C_{10})$heteroaryl-O—, $R^{16}$—$(C_1-C_6)$alkyl-(C=O)—O—, $(C_3-C_{10})$cycloalkyl-(C=O)—O—, phenyl-(C=O)—O—, $(C_1-C_{10})$heterocyclic-(C=O)—O—, $(C_1-C_{10})$heteroaryl-(C=O)—O—, amino, $R^{16}$—$(C_1-C_6)$alkylamino, $[(C_1-C_6)$alkyl$]_2$-amino, formamidyl, $R^{16}$—$(C_1-C_6)$alkyl-(C=O)—NH—, $(C_3-C_{10})$cycloalkyl- (C=O)—NH—, phenyl-(C=O)—NH—, $(C_1-C_{10})$ heterocyclic-(C=O)—NH—, $(C_1-C_{10})$heteroaryl-(C=O)—NH—, $R^{16}$—$(C_1-C_6)$alkyl-(C=O)—[(($C_1-C_6$)alkyl)-N]—, phenyl-(C=O)—[$(C_1-C_6)$alkyl-N]—, $R^{16}$—$(C_1-C_6)$alkyl-SO$_2$NH—, $(C_3-C_{10})$cycloalkyl-SO$_2$NH—, phenyl-SO$_2$NH—, $(C_1-C_{10})$heterocyclic-SO$_2$NH— and $(C_1-C_{10})$heteroaryl-SO$_2$NH—; wherein each of the aforesaid phenyl, heterocyclic, heteroaryl or cycloalkyl $R^{14}$ substituents may optionally be independently substituted by one to four moieties independently selected from the group consisting of halo, $R^{16}$—$(C_1-C_6)$alkyl, $(C_2-C_6)$alkenyl, $(C_2-C_6)$alkynyl, perhalo$(C_1-C_6)$alkyl, $(C_3-C_{10})$cycloalkyl, phenyl, benzyl, $(C_1-C_{10})$heterocyclic, $(C_1-C_{10})$heteroaryl, $(C_1-C_6)$alkyl-SO$_2$—, formyl, —CN, $R^{16}$—$(C_1-C_6)$alkyl-(C=O)—, $(C_3-C_{10})$cycloalkyl-(C=O)—, phenyl-(C=O)—, $(C_1-C_{10})$heterocyclic-(C=O)—, $(C_1-C_{10})$heteroaryl-(C=O)—, HO—(C=O)—, $(C_1-C_6)$alkyl-O—(C=O)—, $(C_3-C_{10})$cycloalkyl-O—(C=O)—, $(C_1-C_{10})$heterocyclic-O—(C=O)—, $(C_1-C_{10})$heteroaryl-O—(C=O)—, H$_2$N—(C=O)—, $R^{16}$—$(C_1-C_6)$alkyl-NH—(C=O)—, $(C_3-C_{10})$cycloalkyl-NH—(C=O)—, phenyl-NH—(C=O)—, $(C_1-C_{10})$heterocyclic-NH—(C=O)—, $(C_1-C_{10})$heteroaryl-NH—(C=O)—, $[(C_1-C_6)$alkyl]$_2$—N—(C=O)—, phenyl-[(($C_1-C_6$)alkyl)-N]—(C=O)—, hydroxy, $R^{16}$—$(C_1-C_6)$alkoxy, perhalo$(C_1-C_6)$alkoxy, $(C_3-C_{10})$cycloalkyl-O—, phenoxy, $(C_1-C_{10})$heterocyclic-O—, $(C_1-C_{10})$heteroaryl-O—, $R^{16}$—$(C_1-C_6)$alkyl-(C=O)—O—, $(C_3-C_{10})$cycloalkyl-(C=O)—O—, phenyl-(C=O)—O—, $(C_1-C_{10})$heterocyclic-(C=O)—O—, $(C_1-C_{10})$heteroaryl-(C=O)—O—, —NO$_2$, amino, $R^{16}$—$(C_1-C_6)$alkylamino, $[(C_1-C_6)$alkyl]$_2$-amino, formamidyl, $R^{16}$—$(C_1-C_6)$alkyl-(C=O)—NH—, $(C_3-C_{10})$cycloalkyl-(C=O)—NH—, phenyl-(C=O)—NH—, $(C_1-C_{10})$heterocyclic-(C=O)—NH—, $(C_1-C_{10})$heteroaryl-(C=O)—NH—, $R^{16}$—$(C_1-C_6)$alkyl-(C=O)—[(($C_1-C_6$)alkyl)-N]—, phenyl-(C=O)—[(($C_1-C_6$)alkyl)-N]—, $R^{16}$—$(C_1-C_6)$alkyl-SO$_2$NH—, $(C_3-C_{10})$cycloalkyl-SO$_2$NH—, phenyl-SO$_2$NH—, $(C_1-C_{10})$heterocyclic-SO$_2$NH— and $(C_1-C_{10})$heteroaryl-SO$_2$NH—; wherein each of said phenyl and heteroaryl moieties may optionally be substituted by one or two radicals independently selected from the group consisting of halo, $(C_1-C_6)$alkyl, $(C_1-C_6)$alkoxy, amino, $(C_1-C_6)$alkylamino or $[(C_1-C_6)$alkyl]$_2$-amino;

each $R^{15}$ is independently selected from the group consisting of hydrogen, halo, $(C_1-C_6)$alkyl, $(C_2-C_6)$alkenyl, perhalo$(C_1-C_6)$alkyl, HO—(C=O)—, $(C_1-C_6)$alkyl-O—(C=O)—, H$_2$N—(C=O)—, $(C_1-C_6)$alkyl-NH—(C=O)—, $[(C_1-C_6)$alkyl]$_2$—N—(C=O)—, hydroxy, $(C_1-C_6)$alkoxy, perhalo$(C_1-C_6)$alkoxy, amino, $(C_1-C_6)$alkylamino, $[(C_1-C_6)$alkyl]$_2$-amino, formamidyl and $(C_1-C_6)$alkyl-(C=O)—NH—; and each $R^{16}$ is independently selected from the group consisting of hydrogen, halo, $(C_1-C_6)$alkyl, $(C_2-C_6)$alkenyl, $(C_2-C_6)$alkynyl, perhalo$(C_1-C_6)$alkyl, HO—(C=O)—, $(C_1-C_6)$alkyl-O—(C=O)—, H$_2$N—(C=O)—, $(C_1-C_6)$alkyl-NH—(C=O)—, $[(C_1-C_6)$alkyl]$_2$—N—(C=O)—, hydroxy, $(C_1-C_6)$alkoxy, perhalo$(C_1-C_6)$alkoxy, $(C_1-C_6)$alkyl-(C=O)—O—, —NO$_2$, amino, $(C_1-C_6)$alkylamino, $[(C_1-C_6)$alkyl]$_2$-amino, formamidyl and $(C_1-C_6)$alkyl-(C=O)—NH—.

Other embodiments of the present invention include those compounds of formula I (and I(c) and I(f)) wherein $R^7$ is as defined above, in combination with each of the aforementioned I(c) and I(f) $R^4$ embodiments and with each of the aforementioned $R^2$ embodiments.

A more preferred embodiment of the present invention are those group of compounds of formula I (and I(c) and I(f)) wherein $R^7$ is $R^{14}$—(CR$^{15}$H)$_p$—; p is one to six, preferably one to four; $R^{14}$ is selected from the group consisting of hydrogen, halo, $(C_1-C_6)$alkyl, $(C_2-C_6)$alkenyl, $(C_3-C_{10})$cycloalkyl, phenyl, $(C_1-C_{10})$heterocyclic, $(C_1-C_{10})$heteroaryl, HO—(C=O)—, $R^{16}$—$(C_1-C_6)$alkyl-O—(C=O)—, H$_2$N—(C=O)—, $R^{16}$—$(C_1-C_6)$alkyl-NH—(C=O)—, phenyl-NH—(C=O)—, $(C_1-C_{10})$heterocyclic-NH—(C=O)—, $[(C_1-C_6)$alkyl]$_2$—N—(C=O)—, phenyl-[(($C_1-C_6$)alkyl)-N]—(C=O)—, hydroxy, $R^{16}$—$(C_1-C_6)$alkoxy, phenoxy, amino, $R^{16}$—$(C_1-C_6)$alkylamino, $[(C_1-C_6)$alkyl]$_2$-amino, $R^{16}$—$(C_1-C_6)$alkyl-(C=O)—NH—, wherein each of the aforesaid phenyl, heterocyclic, heteroaryl or cycloalkyl $R^{14}$ substituents may optionally be independently substituted by one to four moieties independently selected from the group consisting of halo, $R^{16}$—$(C_1-C_6)$alkyl, $(C_2-C_6)$alkenyl, $(C_2-C_6)$alkynyl, perhalo$(C_1-C_6)$alkyl, $(C_1-C_6)$alkyl-SO$_2$—, formyl, —CN, $R^{16}$—$(C_1-C_6)$alkyl-(C=O)—, HO—(C=O)—, $(C_1-C_6)$alkyl-O—(C=O)—, H$_2$N—(C=O)—, $R^{16}$—$(C_1-C_6)$alkyl-NH—(C=O)—, $[(C_1-C_6)$alkyl]$_2$—N—(C=O)—, hydroxy, $R^{16}$—$(C_1-C_6)$alkoxy, perhalo$(C_1-C_6)$alkoxy, $R^{16}$—$(C_1-C_6)$alkyl-(C=O)—O—, amino, $R^{16}$-$(C_1-C_6)$alkylamino, $[(C_1-C_6)$alkyl]$_2$-amino, formamidyl, $R^{16}$—$(C_1-C_6)$alkyl-(C=O)—NH—, $R^{16}$—$(C_1-C_6)$alkyl-(C=O)—[(($C_1-C_6$)alkyl)-N]— and $R^{16}$—$(C_1-C_6)$alkyl-SO$_2$NH—;

each $R^{15}$ is independently selected from the group consisting of hydrogen, halo, $(C_1-C_6)$alkyl, $(C_2-C_6)$alkenyl, perhalo$(C_1-C_6)$alkyl, HO—(C=O)—, $(C_1-C_6)$alkyl-O—(C=O)—, H$_2$N—(C=O)—, $(C_1-C_6)$alkyl-NH—(C=O)—, $[(C_1-C_6)$alkyl]$_2$—N—(C=O)—, hydroxy, $(C_1-C_6)$alkoxy, perhalo$(C_1-C_6)$alkoxy, amino, $(C_1-C_6)$alkylamino, $[(C_1-C_6)$alkyl]$_2$-amino, formamidyl and $(C_1-C_6)$alkyl-(C=O)—NH—; wherein no more than two of said $R^{15}$ groups may be other than hydrogen; and each $R^{16}$ is independently selected from the group consisting of hydrogen, halo, $(C_1-C_6)$alkyl, $(C_2-C_6)$alkenyl, $(C_2-C_6)$alkynyl, perhalo$(C_1-C_6)$alkyl, HO—(C=O)—, $(C_1-C_6)$alkyl-O—(C=O)—, H$_2$N—(C=O)—, $(C_1-C_6)$alkyl-NH—(C=O)—, $[(C_1-C_6)$alkyl]$_2$—N—(C=O)—, hydroxy, $(C_1-C_6)$alkoxy, perhalo$(C_1-C_6)$alkoxy, $(C_1-C_6)$alkyl-(C=O)—O—, —NO$_2$, amino, $(C_1-C_6)$alkylamino, $[(C_1-C_6)$alkyl]$_2$-amino, formamidyl and $(C_1-C_6)$alkyl-(C=O)—NH—.

Other embodiments of the present invention include those compounds of formula I (and I(c) and I(f)) wherein $R^7$ is as defined above, in combination with each of the aforementioned I(c) and I(f) $R^4$ embodiments and with each of the aforementioned $R^2$ embodiments.

A more preferred embodiment of the present invention are those group of compounds of formula I(c) wherein $R^7$ is $R^{14}$—(CR$^{15}$H)$_p$—; p is one to four; $R^{14}$ is selected from the group consisting of hydrogen, $(C_2-C_4)$alkenyl, HO—(C=O)—, $(C_1-C_3)$alkyl-O—(C=O)—, H$_2$N—(C=O)—, $(C_1-C_3)$alkyl-NH—(C=O)—, $[(C_1-C_2)$alkyl]$_2$—N—(C=O)—, hydroxy, $(C_1-C_3)$alkoxy, amino, $(C_1-C_4)$alkylamino, $[(C_1-C_4)$alkyl]$_2$-amino and $(C_1-C_3)$alkyl-(C=O)—NH—; and each $R^{15}$ is independently selected from the group consisting of hydrogen, $(C_1-C_2)$alkyl, hydroxy, and amino. More preferred compounds of formula I(c) are those compounds wherein the combined molecular weight of the $R^4$ and $R^7$ substituents is less than 200 AMU. More preferably, the combined molecular weight of the $R^4$ and $R^7$ substituents is less than 100 AMU.

Another embodiment of the present invention are those group of compounds of formula I (and I(b)) wherein $R^5$ is hydrogen. Other embodiments of the present invention include those compounds of formula I (and I(b)) wherein $R^5$ is hydrogen, in combination with each of the aforementioned $R^2$ embodiments.

Another preferred embodiment of the present invention are those group of compounds of formula I (and I(b)) wherein $R^5$ is $(C_1-C_{10})$heterocyclic or $(C_1-C_{10})$heteroaryl; wherein each of the aforesaid heterocyclic and heteroaryl substituents may optionally be independently substituted by one to four moieties independently selected from the group consisting of halo, $(C_1-C_6)$alkyl, $(C_1-C_6)$alkoxy, HO—(C=O)—, $(C_1-C_6)$alkyl-O—(C=O)—, $H_2N$—(C=O)—, $(C_1-C_6)$alkyl-NH—(C=O)— and $[(C_1-C_6)alkyl]_2$—N—(C=O)—. Other embodiments of the present invention include those compounds of formula I (and I(b)) wherein $R^5$ is said optionally substituted $(C_1-C_{10})$heterocyclic or $(C_1-C_{10})$heteroaryl, in combination with each of the aforementioned $R^2$ embodiments. More preferred heterocyclic compounds are pyrrolidinyl, piperidinyl, and azetidinyl.

Another preferred embodiment of the present invention are those group of compounds of formula I (and I(b)) wherein $R^5$ is $R^{14}$—$(CHR^{15})_p$—, p is 1–6; and $R^{14}$ is selected from the group consisting of hydrogen, $(C_1-C_6)$alkyl, $(C_2-C_6)$alkenyl, perhalo$(C_1-C_6)$alkyl, $(C_3-C_{10})$cycloalkyl, phenyl, $(C_1-C_{10})$heterocyclic, $(C_1-C_{10})$heteroaryl, phenyl-(S=O)—, $(C_1-C_6)$alkyl-$SO_2$—, phenyl-$SO_2$—, $H_2N$—$SO_2$—, $(C_1-C_6)$alkyl-NH—$SO_2$—, phenyl-NH—$SO_2$—, $[(C_1-C_6)alkyl-]_2N$—$SO_2$—, $(C_1-C_6)$alkyl-(C=O)—, phenyl-(C=O)—, $(C_1-C_{10})$heteroaryl-(C=O)—, $(C_1-C_{10})$heterocyclic-(C=O)—, $(C_3-C_{10})$cycloalkyl-(C=O)—, HO—(C=O)—, $R^{16}$—$(C_1-C_6)$alkyl-O—(C=O)—, $(C_3-C_{10})$cycloalkyl-O—(C=O)—, $(C_1-C_{10})$heterocyclic-O—(C=O)—, $(C_1-C_{10})$heteroaryl-O—(C=O)—, $H_2N$—(C=O)—, $(C_1-C_6)$alkyl-NH—(C=O)—, $(C_3-C_{10})$cycloalkyl-NH—(C=O)—, phenyl-NH—(C=O)—, $(C_1-C_{10})$heterocyclic-NH—(C=O)—, $(C_1-C_{10})$heteroaryl-NH—(C=O)—, $[(C_1-C_6)alkyl]_2$—N—(C=O)—, phenyl-$[((C_1-C_6)alkyl)-N]$—(C=O)—, $(C_1-C_{10})$heteroaryl-$[N-(C_1-C_6)alkyl]$-(C=O)—, $(C_1-C_{10})$heterocyclic-$[((C_1-C_6)alkyl)-N]$—(C=O)—, $(C_3-C_{10})$cycloalkyl$[((C_1-C_6)alkyl)-N]$—(C=O)—, hydroxy, $R^{16}$—$(C_1-C_6)$alkoxy, perhalo$(C_1-C_6)$alkoxy, $(C_3-C_{10})$cycloalkyl-O—, phenoxy, $(C_1-C_{10})$heterocyclic-O—, $(C_1-C_{10})$heteroaryl-O—, $R^{16}$—$(C_1-C_6)$alkyl-(C=O)—O—, $(C_3-C_{10})$cycloalkyl-(C=O)—O—, phenyl-(C=O)—O—, $(C_1-C_{10})$heterocyclic-(C=O)—O—, $(C_1-C_{10})$heteroaryl-(C=O)—O—, —$NO_2$, amino, $R^{16}$—$(C_1-C_6)$alkylamino, $[(C_1-C_6)alkyl]_2$-amino, formamidyl, $R^{16}$—$(C_1-C_6)$alkyl-(C=O)—NH—, $(C_3-C_{10})$cycloalkyl-(C=O)—NH—, phenyl-(C=O)—NH—, $R^{16}$—$(C_1-C_6)$alkyl-$SO_2NH$—, $(C_3-C_{10})$cycloalkyl-$SO_2NH$—, phenyl-$SO_2NH$—, $(C_1-C_{10})$heterocyclic-$SO_2NH$— and $(C_1-C_{10})$heteroaryl-$SO_2NH$—; wherein each of the aforesaid phenyl, heterocyclic, heteroaryl or cycloalkyl $R^{14}$ substituents may optionally be independently substituted by one to four moieties independently selected from the group consisting of halo, $R^{16}$—$(C_1-C_6)$alkyl, $(C_2-C_6)$alkenyl, $(C_2-C_6)$alkynyl, perhalo$(C_1-C_6)$alkyl, $(C_3-C_{10})$cycloalkyl, phenyl, benzyl $(C_1-C_{10})$heterocyclic, $(C_1-C_{10})$heteroaryl, $(C_1-C_6)$alkyl-$SO_2$—, formyl, —CN, $R^{16}$—$(C_1-C_6)$alkyl-(C=O)—, $(C_3-C_{10})$cycloalkyl-(C=O)—, phenyl-(C=O)—, $(C_1-C_{10})$heterocyclic-(C=O)—, $(C_1-C_{10})$heteroaryl-(C=O)—, HO—(C=O)—, $(C_1-C_6)$alkyl-O—(C=O)—, $(C_3-C_{10})$cycloalkyl-O—(C=O)—, $(C_1-C_{10})$heterocyclic-O—(C=O)—, $(C_1-C_{10})$heteroaryl-O—(C=O)—, $H_2N$—(C=O)—, $R^{16}$—$(C_1-C_6)$alkyl-NH—(C=O)—, $(C_3-C_{10})$cycloalkyl-NH—(C=O)—, phenyl-NH—(C=O)—, $(C_1-C_{10})$heterocyclic-NH—(C=O)—, $(C_1-C_{10})$heteroaryl-NH—(C=O)—, $[(C_1-C_6)alkyl]_2$—N—(C=O)—, phenyl-$[((C_1-C_6)alkyl)-N]$—(C=O)—, hydroxy, $R^{16}$—$(C_1-C_6)$alkoxy, perhalo$(C_1-C_6)$alkoxy, $(C_3-C_{10})$cycloalkyl-O—, phenoxy, $(C_1-C_{10})$heterocyclic-O—, $(C_1-C_{10})$heteroaryl-O—, $R^{16}$—$(C_1-C_6)$alkyl-(C=O)—O—, $(C_3-C_{10})$cycloalkyl-(C=O)—O—, phenyl-(C=O)—O—, $(C_1-C_{10})$heterocyclic-(C=O)—O—, $(C_1-C_{10})$heteroaryl-(C=O)—O—, —$NO_2$, amino, $R^{16}$—$(C_1-C_6)$alkylamino, $[(C_1-C_6)alkyl]_2$-amino, formamidyl, $R^{16}$—$(C_1-C_6)$alkyl-(C=O)—NH—, $(C_3-C_{10})$cycloalkyl-(C=O)—NH—, phenyl-(C=O)—NH—, $(C_1-C_{10})$heterocyclic-(C=O)—NH—, $(C_1-C_{10})$heteroaryl-(C=O)—NH—, $R^{16}$—$(C_1-C_6)$alkyl-(C=O)—$[((C_1-C_6)alkyl)-N]$—, phenyl-(C=O)—$[((C_1-C_6)alkyl-N]$—, $R^{16}$—$(C_1-C_6)$alkyl-$SO_2NH$—, $(C_3-C_{10})$cycloalkyl-$SO_2NH$—, phenyl-$SO_2NH$—, $(C_1-C_{10})$heterocyclic-$SO_2NH$— and $(C_1-C_{10})$heteroaryl-$SO_2NH$—; and wherein each of said phenyl and heteroaryl moieties may optionally be substituted by one or two radicals independently selected from halo, $(C_1-C_6)$alkyl, $(C_1-C_6)$alkoxy, amino, $(C_1-C_6)$alkylamino and $[(C_1-C_6)alkyl]_2$-amino. Other embodiments of the present invention include those compounds of formula I (and I(b)) wherein $R^5$ is said $R^{14}$—$(CHR^{15})_p$—, p is 1–6; and $R^{14}$ is as defined above, in combination with each of the aforementioned $R^2$ embodiments.

Another preferred embodiment of the present invention are those group of compounds of formula I (and I(b)) wherein $R^5$ is $R^{14}$—$(CHR^{15})_p$—, p is 1–6; and $R^{14}$ is selected from the group consisting of hydrogen, $(C_1-C_6)$alkyl, $(C_2-C_6)$alkenyl, $(C_3-C_{10})$cycloalkyl, phenyl, $(C_1-C_{10})$heterocyclic, $(C_1-C_{10})$heteroaryl, HO—(C=O)—, $R^{16}$—$(C_1-C_6)$alkyl-O—(C=O)—, $H_2N$—(C=O)—, $R^{16}$—$(C_1-C_6)$alkyl-NH—(C=O)—, phenyl-NH—(C=O)—, $(C_1-C_{10})$heterocyclic-NH—(C=O)—, $[(C_1-C_6)alkyl]_2$—N—(C=O)—, phenyl-$[((C_1-C_6)alkyl)-N]$—(C=O)—, hydroxy, $R^{16}$—$(C_1-C_6)$alkoxy, phenoxy, amino, $R^{16}$—$(C_1-C_6)$alkylamino, $[(C_1-C_6)alkyl]_2$-amino, $R^{16}$—$(C_1-C_6)$alkyl-(C=O)—NH—, wherein each of the aforesaid phenyl, heterocyclic, heteroaryl or cycloalkyl $R^{14}$ substituents may optionally be independently substituted by one to four moieties independently selected from the group consisting of halo, $R^{16}$—$(C_1-C_6)$alkyl, $(C_2-C_6)$alkenyl, $(C_2-C_6)$alkynyl, perhalo$(C_1-C_6)$alkyl, $(C_1-C_6)$alkyl-$SO_2$—, formyl, —CN, $R^{16}$—$(C_1-C_6)$alkyl-(C=O)—, HO—(C=O)—, $(C_1-C_6)$alkyl-O—(C=O)—, $H_2N$—(C=O)—, $R^{16}$—$(C_1-C_6)$alkyl-NH—(C=O)—, $[(C_1-C_6)alkyl]_2$—N—(C=O)—, hydroxy, $R^{16}$—$(C_1-C_6)$alkoxy, perhalo $(C_1-C_6)$alkoxy, $R^{16}$—$(C_1-C_6)$alkyl-(C=O)—O—, amino, $R^{16}$—$(C_1-C_6)$alkylamino, $[(C_1-C_6)alkyl]_2$-amino, formamidyl, $R^{16}$—$(C_1-C_6)$alkyl-(C=O)—NH—, $R^{16}$—$(C_1-C_6)$alkyl-(C=O)—$[((C_1-C_6)alkyl)-N]$— and $R^{16}$—$(C_1-C_6)$alkyl-$SO_2NH$—;

each $R^{15}$ is independently selected from the group consisting of hydrogen, halo, $(C_1-C_6)$alkyl, $(C_2-C_6)$alkenyl, perhalo$(C_1-C_6)$alkyl, HO—(C=O)—, $(C_1-C_6)$alkyl-O—(C=O)—, $H_2N$—(C=O)—, $(C_1-C_8)$alkyl-NH—(C=O)—, $[(C_1-C_6)alkyl]_2$—N—(C=O)—, hydroxy, $(C_1-C_6)$alkoxy, perhalo$(C_1-C_6)$alkoxy, amino, $(C_1-C_6)$alkylamino, $[(C_1-C_6)alkyl]_2$-amino, formamidyl and $(C_1-C_6)$alkyl-(C=O)—NH—; wherein no more than two of said $R^{15}$ groups may be other than hydrogen; and each $R^{16}$ is independently selected from the group consisting of hydrogen, halo, $(C_1-C_6)$alkyl, $(C_2-C_6)$ alkenyl, $(C_2-C_6)$alkynyl, perhalo$(C_1-C_6)$alkyl, HO—(C=O)—, $(C_1-C_6)$alkyl-O—(C=O)—, $H_2N$—(C=O)—, $(C_1-C_6)$alkyl-NH—(C=O)—, [$(C_1-C_6)$alkyl]$_2$—N—(C=O)—, hydroxy, $(C_1-C_6)$alkoxy, perhalo$(C_1-C_6)$alkoxy, $(C_1-C_6)$alkyl-(C=O)—O—, —NO$_2$, amino, $(C_1-C_6)$alkylamino, [$(C_1-C_6)$alkyl]$_2$-amino, formamidyl and $(C_1-C_6)$alkyl-(C=O)—NH—.

Other embodiments of the present invention include those group of compounds of formula I (and I(b)) wherein $R^5$ is said $R^{14}$—(CHR$^{15}$)$_p$—, p is 1–6; and $R^{14}$, $R^{15}$ and $R^{16}$ are as defined above, in combination with each of the aforementioned $R^2$ embodiments.

A more preferred embodiment of the present invention are those group of compounds of formula I (and I(b)) wherein $R^5$ is $R^{14}$—(CHR$^{15}$)$_p$—, p is 1–6; and $R^{14}$ is selected from the group consisting of hydrogen, $(C_2-C_4)$alkenyl, $(C_1-C_{10})$heterocyclic, HO—(C=O)—, $(C_1-C_3)$alkyl-O—(C=O)—, $H_2N$—(C=O)—, $(C_1-C_3)$alkyl-NH—(C=O)—, hydroxy, $(C_1-C_3)$alkoxy, amino, $(C_1-C_3)$alkylamino, and [$(C_1-C_2)$alkyl]$_2$-amino; and each $R^{15}$ is independently selected from the group consisting of hydrogen, $(C_1-C_6)$alkyl, hydroxy, $(C_1-C_3)$alkoxy, perhalo$(C_1)$alkoxy, amino, $(C_1-C_2)$alkylamino, [$(C_1-C_2)$alkyl]$_2$-amino, formamidyl and $(C_1-C_6)$alkyl-(C=O)—NH—; wherein no more than two of said $R^{15}$ groups may be other than hydrogen.

Another embodiment of the present invention are those compounds of formula I (and I(a), I(b), I(d), I(g)) wherein $R^6$ is hydrogen. Other embodiments of the present invention include those compounds of formula I (and I(a), I(b), I(d), I(g)) wherein $R^6$ is hydrogen, in combination with each of the aforementioned I(a) $R^4$ embodiments, I(b) $R^5$ embodiments or with each of the aforementioned $R^2$ embodiments.

Another embodiment of the present invention are those group of compounds of formula I (and I(a), I(b), I(d), I(g)) wherein $R^6$ is $R^9$—B—(CH$_2$)$_n$— and n is zero. Other embodiments of the present invention include those compounds of formula I (and I(a), I(b), I(d), I(g)) wherein $R^6$ is $R^9$—B—(CH$_2$)$_n$— and n is zero, in combination with each of the aforementioned I(a) $R^4$ embodiments, I(b) $R^5$ embodiments or with each of the aforementioned $R^2$ embodiments.

Another embodiment of the present invention are those group of compounds of formula I (and I(a), I(b), I(d), I(g)) wherein $R^6$ is $R^9$—B—(CH$_2$)$_n$— and n is an integer from one to six, more preferably one to five, more preferably one to three. Other embodiments of the present invention include those compounds of formula I (and I(a), I(b), I(d), I(g)) wherein $R^6$ is $R^9$—B—(CH$_2$)$_n$— and n is an integer from one to five, in combination with each of the aforementioned I(a) $R^4$ embodiments, I(b) $R^5$ embodiments or with each of the aforementioned $R^2$ embodiments.

Another preferred embodiment of the present invention are those group of compounds of formula I (and I(a), I(b), I(d), I(g)) wherein $R^6$ is $R^9$—B—(CH$_2$)$_n$—; n is zero; B is a bond and $R^9$ is selected from the group consisting of hydrogen, —CF$_3$, —C≡N, $(C_1-C_{10})$heteroaryl, $(C_1-C_{10})$heterocyclic or $(C_3-C_{10})$cycloalkyl; wherein each of the aforesaid $(C_1-C_{10})$heteroaryl, $(C_1-C_{10})$heterocyclic and $(C_3-C_{10})$cycloalkyl may optionally be substituted by one to three moieties independently selected from the group consisting of halo, $(C_1-C_6)$alkyl, $(C_2-C_6)$alkenyl, $(C_1-C_6)$alkynyl, perhalo$(C_1-C_6)$alkyl, hydroxy, $(C_1-C_6)$alkoxy, perhalo$(C_1-C_6)$alkoxy, $(C_1-C_6)$alkyl-S—, $(C_1-C_6)$alkyl-SO$_2$—, $(C_1-C_6)$alkyl-NH—SO$_2$—, —NO$_2$, amino, $(C_1-C_6)$alkylamino, [$(C_1-C_6)$alkyl]$_2$-amino, $(C_1-C_6)$alkyl-SO$_2$—NH—, $(C_1-C_6)$alkyl-(C=O)—NH—, $(C_1-C_6)$alkyl-(C=O)—[(($C_1-C_6$)alkyl)-N]—, —CN, $(C_1-C_6)$alkyl-(C=O)—, HO—(C=O)—, $(C_1-C_6)$alkyl-O—(C=O)—, $H_2N$(C=O)—, $(C_1-C_6)$alkyl-NH—(C=O)—, [$(C_1-C_6)$alkyl]$_2$—N—(C=O)— and $(C_1-C_6)$alkyl-(C=O)—O—. Other embodiments of the present invention include those compounds of formula I (and I(a), I(b), I(d), I(g)) wherein $R^6$ is $R^9$—B—(CH$_2$)$_n$—0 and n is zero; B is a bond and $R^9$ is as defined above, in combination with each of the aforementioned I(a) $R^4$ embodiments, I(b) $R^5$ embodiments or with each of the aforementioned $R^2$ embodiments.

Another embodiment of the present invention are those compounds of formula I (and I(a), I(b), I(d), I(g)) wherein $R^6$ is $R^9$—B—(CH$_2$)$_n$—; n is zero; B is —(C=O)—NR$^{10}$—, —(R$^{10}$—N)—, —(R$^{10}$—N)—SO$_2$—, —(R$^{10}$—N)—(C=O)—, >C=O, —O—(C=O)—, SO$_2$(NR$^{10}$)—, —(R$^{10}$—N)—(C=O)—(NR$^{11}$)—; and $R^9$ is selected from the group consisting of hydrogen, $(C_3-C_{10})$cycloalkyl or phenyl; wherein the aforesaid phenyl and $(C_3-C_{10})$cycloalkyl may optionally be substituted by one to three moieties independently selected from the group consisting of halo, $(C_1-C_6)$alkyl, $(C_2-C_6)$alkenyl, $(C_2-C_6)$alkynyl, perhalo$(C_1-C_6)$alkyl, hydroxy, $(C_1-C_6)$alkoxy, perhalo$(C_1-C_6)$alkoxy, $(C_1-C_6)$alkyl-S—, $(C_1-C_6)$alkyl-SO$_2$—, $(C_1-C_6)$alkyl-NH—SO$_2$—, —NO$_2$, amino, $(C_1-C_6)$alkylamino, [$(C_1-C_6)$alkyl]$_2$-amino, $(C_1-C_6)$alkyl-SO$_2$—NH—, $(C_1-C_6)$alkyl-(C=O)—NH—, $(C_1-C_6)$alkyl-(C=O)—[N($(C_1-C_6)$alkyl]-, —CN, $(C_1-C_6)$alkyl-(C=O)—, HO—(C=O)—, $(C_1-C_6)$alkyl-O—(C=O)—, $H_2N$(C=O)— $(C_1-C_6)$alkyl-NH—(C=O)—, [$(C_1-C_6)$alkyl]$_2$—N—(C=O)— and $(C_1-C_6)$alkyl-(C=O)—O—. Other embodiments of the present invention include those compounds of formula I (and I(a), I(b), I(d), I(g)) wherein $R^6$ is $R^9$—B—(CH$_2$)$_n$— and n is zero; B is —(C=O)—NR$^{10}$—, —(R$^{10}$—N)—, —(R$^{10}$—N)—SO$_2$—, —(R$^{10}$—N)—(C=O)—, >C=O, —O—(C=O)—, —SO$_2$—(NR$^{10}$)—, —(R$^{10}$—N)—(C=O)—(NR$^{11}$)—; and $R^9$ is as defined above, in combination with each of the aforementioned I(a) $R^4$ embodiments, I(b) $R^5$ embodiments or with each of the aforementioned $R^2$ embodiments.

Another preferred embodiment of the present invention are those compounds of formula I (and I(a), I(b), I(d), I(g)) wherein $R^6$ is $R^9$—B—(CH$_2$)$_n$—; n is zero; B is —(C=O)—NR$^{10}$—, —(R$^{10}$—N)—, >C=O, —O—(C=O)—, —(R$^{10}$—N)—(C=O)— or —(R$^{10}$—N)—(C=O)—(NR$^{11}$)—; $R^9$ is $R^{13}$—(R$^{12}$CH)$_m$—; m is 1–6; $R^{10}$ is hydrogen or methyl; $R^{12}$ is hydrogen or methyl; and $R^{13}$ is selected from the group consisting of hydrogen, $(C_1-C_6)$alkyl, $(C_1-C_6)$alkoxy, phenyl, $(C_1-C_{10})$heteroaryl, $(C_1-C_{10})$heterocyclic, $(C_3-C_{10})$cycloalkyl, amino, $(C_1-C_6)$alkylamino, [$(C_1-C_6)$alkyl]$_2$amino, $(C_1-C_6)$alkyl-SO$_2$—NH—, phenyl-SO$_2$—NH—, $(C_1-C_6)$alkyl-SO$_2$—[N—$(C_1-C_6)$alkyl]-, phenyl-SO$_2$—[N—$(C_1-C_6)$alkyl]-, hydroxy, $(C_1-C_6)$alkoxy, perhalo$(C_1-C_6)$alkoxy, phenoxy, $(C_1-C_{10})$heteroaryl-O—, $(C_1-C_{10})$heterocyclic-O—, $(C_3-C_{10})$cycloalkyl-O—, $(C_1-C_6)$alkyl-S—, $(C_1-C_6)$alkyl-SO$_2$—, $(C_1-C_6)$alkyl-NH—SO$_2$—, —NO$_2$, amino, $(C_1-C_6)$alkylamino, [$(C_1-C_6)$alkyl]$_2$-amino, $(C_1-C_6)$alkyl-SO$_2$—NH—, $(C_1-C_6)$alkyl-(C=O)—NH—, $(C_1-C_6)$alkyl-(C=O)—[N($(C_1-C_6)$alkyl]-, phenyl-(C=O)—NH—, phenyl-(C=O)—[N—$(C_1-C_6)$alkyl]-, —CN, $(C_1-C_6)$alkyl-(C=O)—, phenyl-(C=O)—, $(C_1-C_{10})$heteroaryl-(C=O)—, $(C_1-C_{19})$heterocyclic-(C=O)—, $(C_3-C_{10})$cycloalkyl-(C=O)—, $(C_1-C_{10})$heteroaryl-NH—(C=O)—, $(C_1-C_{10})$heterocyclic-NH—(C=O)—, $(C_3-C_{10})$cycloalkyl-NH—(C=O)—, HO—(C=O)—, $(C_1-C_6)$alkyl-O—(C=O)—, $H_2N$(C=O)—, $(C_1-C_6)$alkyl-NH—(C=O)—, [$(C_1-C_8)$alkyl]$_2$—N—(C=O)—, phenyl-NH—(C=O)—, phenyl-[N—($(C_1-C_6)$alkyl)](C=O)—, $(C_1-C_6)$alkyl-(C=O)—O— and phenyl-(C=O)—O—. Other embodiments of the present invention include those compounds of formula I (and I(a), I(b), I(d), I(g)) wherein $R^6$ is $R^9$—B—$(CH_2)_n$— and n is zero; B is —(C=O)—$NR^{10}$—, —($R^{10}$—N)—, —($R^{10}$—N)—$SO_2$—, —($R^{10}$—N)—(C=O)—, >C=O, —O—(C=O)—, —$SO_2$—($NR^{10}$)—, —($R^{10}$—N)—(C=O)—($NR^{11}$)—; and $R^9$ is $R^{13}$—($R^{12}CH)_m$—; m is 1–6; $R^{10}$ is hydrogen or methyl; $R^{12}$ is hydrogen or methyl; and $R^{13}$ is as defined above, in combination with each of the aforementioned I(a) $R^4$ embodiments, I(b) $R^5$ embodiments or with each of the aforementioned $R^2$ embodiments.

Another preferred embodiment of the present invention are those compounds of formula I (and I(a), I(b), I(d), I(g)) wherein $R^6$ is $R^9$—B—$(CH_2)_n$—; n is zero; B is —($R^{10}$—N)—; $R^9$ is hydrogen or $R^{13}$—($R^{12}CH)_m$—; m is 1–6; $R^{10}$ is hydrogen or methyl; $R^{12}$ is hydrogen or methyl; and $R^{13}$ is selected from the group consisting of hydrogen, $(C_1-C_6)$alkyl, hydroxy, $(C_1-C_6)$alkoxy, amino, $(C_1-C_6)$alkylamino, $[(C_1-C_6)$alkyl$]_2$amino, $(C_2-C_6)$alkenyl, $(C_2-C_6)$alkynyl, phenyl, $(C_1-C_{10})$heteroaryl, $(C_1-C_{10})$heterocyclic and $(C_3-C_{10})$cycloalkyl. Other embodiments of the present invention include those compounds of formula I (and I(a), I(b), I(d), I(g)) wherein $R^6$ is $R^9$—B—$(CH_2)_n$— and n is zero; B is —($R^{10}$—N)—; $R^9$ is hydrogen or $R^{13}$—($R^{12}CH)_m$—; m is 1–6; $R^{10}$ is hydrogen or methyl; $R^{12}$ is hydrogen or methyl; and $R^{13}$ is as defined above, in combination with each of the aforementioned I(a) $R^4$ embodiments, I(b) $R^5$ embodiments or with each of the aforementioned $R^2$ embodiments.

Another embodiment of the present invention are those compounds of formula I (and I(a), I(b), I(d), I(g)) wherein $R^6$ is $R^9$—B—$(CH_2)_n$—; n is one to six, preferably one to four; B is —(C=O)—$NR^{10}$—, —($R^{10}$—N)—, —($R^{10}$—N)—(C=O)— or —($R^{10}$—N)—(C=O)—($NR^{11}$)—; $R^9$ is $R^{13}$—($R^{12}CH)_m$—; m is 1–6; $R^{10}$ is hydrogen or methyl; $R^{12}$ is hydrogen or methyl; and $R^{13}$ is selected from the group consisting of hydrogen, $(C_1-C_6)$alkyl, $(C_1-C_6)$alkoxy, phenyl, $(C_1-C_{10})$heteroaryl, $(C_1-C_{10})$heterocyclic, $(C_3-C_1)$cycloalkyl, amino, $(C_1-C_6)$alkylamino, $[(C_1-C_6)$alkyl$]_2$amino, $(C_1-C_6)$alkyl-$SO_2$—NH—, phenyl-$SO_2$—NH—, $(C_1-C_6)$alkyl-$SO_2$—[N—$(C_1-C_6)$alkyl]-, phenyl-$SO_2$—[N—$(C_1-C_6)$alkyl]-, hydroxy, $(C_1-C_6)$alkoxy, perhalo $(C_1-C_6)$alkoxy, phenoxy, $(C_1-C_{10})$heteroaryl-O—, $(C_1-C_{10})$heterocyclic-O—, $(C_3-C_{10})$cycloalkyl-O—, $(C_1-C_6)$alkyl-S—, $(C_1-C_6)$alkyl-$SO_2$—, $(C_1-C_6)$alkyl-NH—$SO_2$—, —$NO_2$, amino, $(C_1-C_6)$alkylamino, $[(C_1-C_6)$alkyl$]_2$-amino, $(C_1-C_6)$alkyl-$SO_2$—NH—, $(C_1-C_6)$alkyl-(C=O)—NH—, $(C_1-C_6)$alkyl-(C=O)—[(($C_1-C_6)$alkyl)-N]—, phenyl-(C=O)—NH—, phenyl-(C=O)—[(($C_1-C_6)$alkyl)-N]—, —CN, $(C_1-C_6)$alkyl-(C=O)—, phenyl-(C=O)—, $(C_1-C_{10})$heteroaryl-(C=O)—, $(C_1-C_{10})$heterocyclic-(C=O)—, $(C_3-C_{10})$cycloalkyl-(C=O)—, $(C_1-C_{10})$heteroaryl-NH—(C=O)—, $(C_1-C_{10})$heterocyclic-NH—(C=O)—, $(C_3-C_{10})$cycloalkyl-NH—(C=O)—, HO—(C=O)—, $(C_1-C_6)$alkyl-O—(C=O)—, $H_2N$(C=O)— $(C_1-C_6)$alkyl-NH—(C=O)—, $[(C_1-C_6)$alkyl$]_2$—N—(C=O)—, phenyl-NH—(C=O)—, phenyl-[(($C_1-C_6)$alkyl)-N]—(C=O)—, $(C_1-C_6)$alkyl-(C=O)—O— and phenyl-(C=O)—O—. Other embodiments of the present invention include those compounds of formula I (and I(a), I(b), I(d), I(g)) wherein $R^6$ is $R^9$—B—$(CH_2)_n$—; n is one to four; B is —(C=O)—$NR^{10}$—, —($R^{10}$—N)—, —($R^{10}$—N)—(C=O)— or —($R^{10}$—N)—(C=O)—($NR^{11}$)—; $R^9$ is $R^{13}$—($R^{12}CH)_m$—; m is 1–6; $R^{10}$ is hydrogen or methyl; $R^{12}$ is hydrogen or methyl; and $R^{13}$ is as defined above, in combination with each of the aforementioned I(a) $R^4$ embodiments, I(b) $R^5$ embodiments or with each of the aforementioned $(R^3)_s$ embodiments.

Another embodiment of the present invention are those group of compounds of formula I (and I(a), I(b), I(d), I(g)) wherein $R^6$ is $R^9$—B—$(CH_2)_n$—; n is an integer from one to six, more preferably one to five, more preferably one to three; B is a bond, and $R^9$ is selected from the group consisting of optionally substituted phenyl, $(C_1-C_{10})$heterocyclic, $(C_1-C_{10})$heteroaryl and $(C_3-C_{10})$cycloalkyl; wherein each of the aforesaid $R^9$ phenyl, $(C_1-C_{10})$heteroaryl, $(C_1-C_{10})$heterocyclic and $(C_3-C_{10})$cycloalkyl substituents may optionally be substituted by one to four moieties independently selected from the group consisting of halo, $(C_1-C_6)$alkyl, $(C_2-C_6)$alkenyl, $(C_2-C_6)$alkynyl, perhalo$(C_1-C_6)$alkyl, phenyl, $(C_1-C_{10})$heteroaryl, $(C_1-C_{10})$heterocyclic, $(C_3-C_{10})$cycloalkyl, hydroxy, $(C_1-C_6)$alkoxy, perhalo$(C_1-C_6)$alkoxy, phenoxy, $(C_1-C_{10})$heteroaryl-O—, $(C_1-C_{10})$heterocyclic-O—, $(C_3-C_{10})$cycloalkyl-O—, $(C_1-C_6)$alkyl-S—, $(C_1-C_6)$alkyl-$SO_2$—, $(C_1-C_6)$alkyl-NH—$SO_2$—, —$NO_2$, amino, $(C_1-C_6)$alkylamino $[(C_1-C_6)$alkyl$]_2$-amino, $(C_1-C_6)$alkyl-$SO_2$—NH—, $(C_1-C_6)$alkyl-(C=O)—NH—, $(C_1-C_6)$alkyl-(C=O)—[(($C_1-C_6)$alkyl)-N]—, phenyl-(C=O)—NH—, phenyl-(C=O)—[(($C_1-C_6)$alkyl)-N]—, —CN, $(C_1-C_6)$alkyl-(C=O)—, phenyl-(C=O)—, $(C_1-C_{10})$heteroaryl-(C=O)—, $(C_1-C_{10})$heterocyclic-(C=O)—, $(C_3-C_{10})$cycloalkyl-(C=O)—, HO—(C=O)—, $(C_1-C_6)$alkyl-O—(C=O)—, $H_2N$(C=O)— $(C_1-C_6)$alkyl-NH—(C=O)—, $[(C_1-C_6)$alkyl$]_2$—N—(C=O)—, phenyl-NH—(C=O)—, phenyl-[(($C_1-C_6)$alkyl)-N]—(C=O)—, $(C_1-C_{10})$heteroaryl-NH—(C=O)—, $(C_1-C_{10})$heterocyclic-NH—(C=O)—, $(C_3-C_{10})$cycloalkyl-NH—(C=O)—, $(C_1-C_6)$alkyl-(C=O)—O— and phenyl-(C=O)—O—. Other embodiments of the present invention include those compounds of formula I (and I(a), I(b), I(d), I(g)) wherein $R^6$ is $R^9$—B—$(CH_2)_n$—; n is an integer from one to six, more preferably one to five, more preferably one to three; B is a bond, and $R^9$ is as described above, in combination with each of the aforementioned I(a) $R^4$ embodiments, I(b) $R^5$ embodiments or with each of the aforementioned $R^2$ embodiments.

Another embodiment of the present invention are those group of compounds of formula I (and I(a), I(b), I(d), I(g)) wherein $R^6$ is $R^9$—B—$(CH_2)_n$—; n is an integer from one to six, more preferably one to five, more preferably one to three; B is —(C=O)—($R^{10}$—N)—, —($R^{10}$—N)—, —$SO_2$—($R^{10}$—N)—, —($R^{10}$—N)—(C=O)—($NR^{11}$)— or —($R^{10}$—N)—(C=O)—O—; and $R^9$ is selected from the group consisting of optionally substituted phenyl, $(C_1-C_{10})$heterocyclic, $(C_1-C_{10})$heteroaryl and $(C_3C_{10})$cycloalkyl; wherein each of the aforesaid $R^9$ phenyl, $(C_1C_{10})$heteroaryl, $(C_1-C_{10})$heterocyclic and $(C_3C_{10})$cycloalkyl substituents may optionally be substituted by one to four moieties independently selected from the group consisting of halo, $(C_1-C_6)$alkyl, $(C_2-C_6)$alkenyl, $(C_2-C_6)$alkynyl, perhalo $(C_1-C_6)$alkyl, phenyl, $(C_1-C_{10})$heteroaryl, $(C_1-C_{10})$heterocyclic, $(C_3-C_{10})$cycloalkyl, hydroxy, $(C_1-C_6)$alkoxy, perhalo$(C_1-C_6)$alkoxy, phenoxy, $(C_1-C_{10})$heteroaryl-O—, $(C_1-C_{10})$heterocyclic-O—, $(C_3-C_{10})$cycloalkyl-O—, $(C_1-C_6)$alkyl-S—, $(C_1-C_6)$alkyl-$SO_2$—, $(C_1-C_6)$alkyl-NH—$SO_2$—, —$NO_2$, amino, $(C_1-C_6)$alkylamino, $[(C_1-C_6)$alkyl$]_2$-amino, $(C_1-C_6)$alkyl-$SO_2$—NH—, $(C_1-C_6)$alkyl-(C=O)—NH—, $(C_1-C_6)$alkyl-(C=O)—[(($C_1-C_6)$alkyl)-N]—, phenyl-(C=O)—NH—, phenyl-(C=O)—[(($C_1-C_6)$alkyl)-N]—, —CN, $(C_1-C_6)$alkyl-(C=O)—, phenyl-(C=O)—, $(C_1C_{10})$heteroaryl-(C=O)—, $(C_1C_{10})$heterocyclic-(C=O)—, $(C_3-C_{10})$cycloalkyl-(C=O)—, HO—(C=O)—, $(C_1-C_6)$alkyl-O—(C=O)—, $H_2N$(C=O)— $(C_1-C_6)$alkyl-NH—(C=O)—, $[(C_1-C_6)$alkyl$]_2$—N—(C=O)—, phenyl-NH—(C=O)—, phenyl-

[((C$_1$-C$_6$)alkyl)-N]—(C=O)—, (C$_1$-C$_{10}$)heteroaryl-NH—(C=O)—, (C$_1$-C$_{10}$)heterocyclic-NH—(C=O)—, (C$_3$-C$_{10}$)cycloalkyl-NH—(C=O)—, (C$_1$-C$_6$)alkyl-(C=O)—O— and phenyl-(C=O)—O—. Other embodiments of the present invention include those compounds of formula I (and I(a), I(b), I(d), I(g)) wherein R$^6$ is R$^9$—B—(CH$_2$)$_n$—; n is an integer from one to six, more preferably one to five, more preferably one to three; B is —(C=O)—(R$^{10}$—N)—, —(R$^{10}$—N)—, —SO$_2$—(R$^{10}$—N)—, —(R$^{10}$—N)—(C=O)—(NR$^{11}$)— or —(R$^{10}$—N)—(C=O)—O—; and R$^9$ is as described above, in combination with each of the aforementioned I(a) R$^4$ embodiments, I(b) R$^5$ embodiments or with each of the aforementioned R$^2$ embodiments.

Another embodiment of the present invention are those group of compounds of formula I (and I(a), I(b), I(d), I(g)) wherein R$^6$ is R$^9$—B—(CH$_2$)$_n$—; n is an integer from one to six, more preferably one to five, more preferably one to three; B is a bond, and R$^9$ is R$^{13}$—(R$^{12}$CH)$_m$—; m is 1–6; R$^{10}$ is hydrogen or methyl; each R$^{12}$ is independently selected from the groups consisting of hydrogen or methyl; and R$^{13}$ is selected from the group consisting of hydrogen, (C$_1$-C$_6$)alkyl, (C$_1$-C$_6$)alkoxy, phenyl, (C$_1$C$_{10}$)heteroaryl, (C$_1$-C$_{10}$)heterocyclic, (C$_3$C$_{10}$)cycloalkyl, hydroxy, (C$_1$-C$_6$)alkoxy, perhalo(C$_1$-C$_6$)alkoxy, phenoxy, (C$_1$-C$_{10}$)heteroaryl-O—, (C$_1$-C$_{10}$)heterocyclic-O—, (C$_3$C$_{10}$)cycloalkyl-O—, (C$_1$-C$_6$)alkyl-S—, (C$_1$-C$_6$)alkyl-SO$_2$—, (C$_1$-C$_6$)alkyl-NH—SO$_2$—, —NO$_2$, amino, (C$_1$-C$_6$)alkylamino, [(C$_1$-C$_6$)alkyl]$_2$-amino, (C$_1$-C$_6$)alkyl-SO$_2$—NH—, (C$_1$-C$_6$)alkyl-(C=O)—NH—, (C$_1$-C$_6$)alkyl-(C=O)—[((C$_1$-C$_6$)alkyl)-N]—, phenyl-(C=O)—NH—, phenyl-(C=O)—[((C$_1$-C$_6$)alkyl)-N]—, (C$_1$-C$_6$)alkyl-SO$_2$—NH—, phenyl-SO$_2$—NH—, (C$_1$-C$_6$)alkyl-SO$_2$—[((C$_1$-C$_6$)alkyl)-N]—, phenyl-SO$_2$—[((C$_1$-C$_6$)alkyl)-N]—, —CN, (C$_1$-C$_6$)alkyl-(C=O)—, phenyl-(C=O)—, (C$_1$-C$_{10}$)heteroaryl-(C=O)—, (C$_1$-C$_{10}$)heterocyclic-(C=O)—, (C$_3$-C$_{10}$)cycloalkyl-(C=O)—, (C$_1$-C$_{10}$)heteroaryl-NH—(C=O)—, (C$_1$-C$_{10}$)heterocyclic-NH—(C=O)—, (C$_3$-C$_{10}$)cycloalkyl-NH—(C=O)—, HO—(C=O)—, (C$_1$-C$_6$)alkyl-O—(C=O)—, H$_2$N(C=O)—, (C$_1$-C$_6$)alkyl-NH—(C=O)—, [(C$_1$-C$_6$)alkyl]$_2$—N—(C=O)—, phenyl-NH—(C=O)—, phenyl-[((C$_1$-C$_6$)alkyl)-N]—(C=O)—, (C$_1$-C$_6$)alkyl-(C=O)—O— and phenyl-(C=O)—O—. Other embodiments of the present invention include those compounds of formula I (and I(a), I(c), I(e), I(f), and I(h)) wherein R$^6$ is R$^9$—B—(CH$_2$)$_n$—; n is an integer from one to six, more preferably one to five, more preferably one to three; B is —(C=O)—(R$^{10}$—N)—, —(R$^{10}$—N)—, —SO$_2$—(R$^{10}$—N)—, —(R$^{10}$—N)—(C=O)—(NR$^{11}$)— or —(R$^{10}$—N)—(C=O)—O—; R$^9$ is R$^{13}$—(R$^{12}$CH)$_m$—; m is 1–6; R$^{10}$ is hydrogen or methyl; each R$^{12}$ is independently selected from the groups consisting of hydrogen or methyl; and R$^{13}$ is as described above, in combination with each of the aforementioned I(a) R$^4$ embodiments, I(b) R$^5$ embodiments or with each of the aforementioned R$^2$ embodiments.

Another embodiment of the present invention are those compounds of formula I wherein s is an integer from zero to four and each R$^3$ is independently selected from the group consisting of halo, (C$_1$-C$_6$)alkyl, (C$_2$-C$_6$)alkenyl, (C$_2$-C$_6$)alkynyl, perhalo(C$_1$-C$_6$)alkyl, phenyl, (C$_1$-C$_{10}$)heteroaryl, (C$_1$-C$_{10}$)heterocyclic, (C$_3$-C$_{10}$)cycloalkyl, hydroxy, (C$_1$-C$_6$)alkoxy, perhalo(C$_1$-C$_6$)alkoxy, phenoxy, (C$_1$-C$_{10}$)heteroaryl-O—, (C$_1$-C$_{10}$)heterocyclic-O—, (C$_3$-C$_{10}$)cycloalkyl-O—, (C$_1$-C$_6$)alkyl-S—, (C$_1$-C$_6$)alkyl-SO$_2$—, (C$_1$-C$_6$)alkyl-NH—SO$_2$—, —NO$_2$, amino, (C$_1$-C$_6$)alkylamino, [(C$_1$-C$_6$)alkyl]$_2$-amino, (C$_1$-C$_6$)alkyl-SO$_2$—NH—, (C$_1$-C$_6$)alkyl-(C=O)—NH—, (C$_1$-C$_6$)alkyl-(C=O)—[((C$_1$-C$_6$)alkyl)-N]—, phenyl-(C=O)—NH—, phenyl-(C=O)—[((C$_1$-C$_6$)alkyl)-N]—, —CN, (C$_1$-C$_6$)alkyl-(C=O)—, phenyl-(C=O)—, (C$_1$-C$_{10}$)heteroaryl-(C=O)—, (C$_1$-C$_{10}$)heterocyclic-(C=O)—, (C$_3$-C$_{10}$)cycloalkyl-(C=O)—, HO—(C=O)—, (C$_1$-C$_6$)alkyl-O—(C=O)—, H$_2$N(C=O)—, (C$_1$-C$_6$)alkyl-NH—(C=O)—, [(C$_1$-C$_6$)alkyl]$_2$-N—(C=O)—, phenyl-NH—(C=O)—, phenyl-[((C$_1$-C$_6$)alkyl)-N]—(C=O)—, (C$_1$-C$_{10}$)heteroaryl-NH—(C=O)—, (C$_1$-C$_{10}$)heterocyclic-NH—(C=O)—, (C$_3$-C$_{10}$)cycloalkyl-NH—(C=O)— and (C$_1$-C$_6$)alkyl-(C=O)—O—. Other embodiments of the present invention include those compounds of formula I (and I(a), I(b), I(c), I(d), I(e), I(f) and I(g)) wherein R$^3$ is as defined above in combination with each of the aforementioned R$^6$ embodiments, R$^7$ embodiments, R$^4$ embodiments, R$^5$ embodiments or with each of the aforementioned R$^2$ embodiments.

Another embodiment of the present invention are those compounds of formula I wherein s is an integer from zero to four and each R$^3$ is independently selected from the group consisting of halo, —CN, (C$_1$-C$_6$)alkyl, (C$_2$-C$_6$)alkenyl, (C$_2$-C$_6$)alkynyl and perhalo(C$_1$-C$_6$)alkyl. Other embodiments of the present invention include those compounds of formula I (and I(a), I(b), I(c), I(d), I(e), I(f) and I(g)) wherein R$^3$ is as defined above in combination with each of the aforementioned R$^6$ embodiments, R$^7$ embodiments, R$^4$ embodiments, R$^5$ embodiments or with each of the aforementioned R$^2$ embodiments.

Another embodiment of the present invention are those compounds of formula I wherein s is an integer from zero to four and zero, one or two of R$^3$ are independently selected from the group consisting of halo, (C$_1$-C$_6$)alkyl, perhalo (C$_1$-C$_6$)alkyl, hydroxy, (C$_1$-C$_6$)alkoxy, perhalo(C$_1$-C$_6$)alkoxy, amino, (C$_1$-C$_6$)alkylamino, [(C$_1$-C$_6$)alkyl]$_2$-amino, —CN, and H$_2$N(C=O)—. Other embodiments of the present invention include those compounds of formula I (and I(a), I(b), I(c), I(d), I(e), I(f) and I(g)) wherein R$^3$ is as defined above in combination with each of the aforementioned R$^6$ embodiments, R$^7$ embodiments, R$^4$ embodiments, R$^5$ embodiments or with each of the aforementioned R$^2$ embodiments.

Another embodiment of the present invention are those compounds of formula I wherein s is an integer from zero to four and one of R$^3$ is selected from the group consisting of phenyl, (C$_1$-C$_{10}$)heteroaryl, (C$_1$-C$_{10}$)heterocyclic and (C$_3$-C$_{10}$)cycloalkyl. Other embodiments of the present invention include those compounds of formula I (and I(a), I(b), I(c), I(d), I(e), I(f) and I(g)) wherein R$^3$ is as defined above with each of the aforementioned R$^6$ embodiments, R$^7$ embodiments, R$^4$ embodiments, R$^5$ embodiments or with each of the aforementioned R$^2$ embodiments.

Another embodiment of the present invention are those compounds of formula I wherein s is an integer from zero to four and one of R$^3$ is selected from the group consisting of hydroxy, (C$_1$-C$_6$)alkoxy, perhalo(C$_1$-C$_6$)alkoxy, phenoxy, (C$_1$-C$_{10}$)heteroaryl-O—, (C$_1$-C$_{10}$)heterocyclic-O—, (C$_3$-C$_{10}$)cycloalkyl-O—, (C$_1$-C$_6$)alkyl-S—, (C$_1$-C$_6$)alkyl-SO$_2$— and (C$_1$-C$_6$)alkyl-NH—SO$_2$—. Other embodiments of the present invention include those compounds of formula I (and I(a), I(b), I(c), I(d), I(e), I(f) and I(g)) wherein R$^3$ is as defined above in combination with each of the aforementioned R$^6$ embodiments, R$^7$ embodiments, R$^4$ embodiments, R$^5$ embodiments or with each of the aforementioned R$^2$ embodiments.

Another embodiment of the present invention are those compounds of formula I wherein s is an integer from zero to four and one of R$^3$ is selected from the group consisting of amino, $(C_1-C_6)$alkylamino, $[(C_1-C_6)$alkyl$]_2$-amino, $(C_1-C_6)$alkyl-SO$_2$—NH—, $(C_1-C_6)$alkyl-(C=O)—NH—, $(C_1-C_6)$alkyl-(C=O)—$[((C_1-C_6)$alkyl)-N]$—, phenyl-(C=O)—NH— and phenyl-(C=O)—[N—$(C_1-C_6)$alkyl]-. Other embodiments of the present invention include those compounds of formula I (and I(a), I(b), I(c), I(d), I(e), I(f) and I(g)) wherein $R^3$ is as defined above in combination with each of the aforementioned $R^6$ embodiments, $R^7$ embodiments, $R^4$ embodiments, $R^5$ embodiments or with each of the aforementioned $R^2$ embodiments.

Another embodiment of the present invention are those compounds of formula I wherein s is an integer from zero to four and one of $R^3$ is selected from the group consisting of $(C_1-C_6)$alkyl-(C=O)—, phenyl-(C=O)—, $(C_1-C_{10})$heteroaryl-(C=O)—, $(C_1-C_{10})$heterocyclic-(C=O)—, $(C_3-C_{10})$cycloalkyl-(C=O)—, $(C_1-C_{10})$heteroaryl-NH—(C=O)—, $(C_1-C_{10})$heterocyclic-NH—(C=O)—, $(C_3-C_{10})$cycloalkyl-NH—(C=O)—, HO—(C=O)—, $(C_1-C_6)$alkyl-O—(C=O)—, H$_2$N(C=O)— $(C_1-C_6)$alkyl-NH—(C=O)—, $[(C_1-C_6)$alkyl$]_2$N—(C=O)—, phenyl-NH—(C=O)—, phenyl-$[((C_1-C_6)$alkyl)-N]$—(C=O)— and $(C_1-C_6)$alkyl-(C=O)—O—. Other embodiments of the present invention include those compounds of formula I (and I(a), I(b), I(c), I(d), I(e), I(f) and I(g)) wherein $R^3$ is as defined above in combination with each of the aforementioned $R^6$ embodiments, $R^7$ embodiments, $R^4$ embodiments, $R^5$ embodiments or with each of the aforementioned $R^2$ embodiments.

Another embodiment of the present invention are those compounds of formula I wherein s is an integer from zero to three and each $R^3$ is independently selected from the group consisting of halo, $(C_1-C_6)$alkyl, perhalo$(C_1-C_6)$alkyl, hydroxy, $(C_1-C_6)$alkoxy, perhalo$(C_1-C_6)$alkoxy, —NO$_2$, amino, $(C_1-C_6)$alkylamino, $[(C_1-C_6)$alkyl$]_2$-amino, —CN, and H$_2$N(C=O)—. Other embodiments of the present invention include those compounds of formula I (and I(a), I(b), I(c), I(d), I(e), I(f) and I(g)) wherein $R^3$ is as defined above in combination with each of the aforementioned $R^6$ embodiments, $R^7$ embodiments, $R^4$ embodiments, $R^5$ embodiments or with each of the aforementioned $R^2$ embodiments.

Another embodiment of the present invention are those compounds of formula I wherein s is an integer from zero to two and each $R^3$ is independently selected from the group consisting of halo, $(C_1-C_6)$alkyl, perhalo$(C_1-C_6)$alkyl, $(C_1-C_6)$alkoxy, perhalo$(C_1-C_6)$alkoxy and —ON. Other embodiments of the present invention include those compounds of formula I (and I(a), I(b), I(c), I(d), I(e), I(f) and I(g)) wherein $R^3$ is as defined above in combination with each of the aforementioned $R^6$ embodiments, $R^7$ embodiments, $R^4$ embodiments, $R^5$ embodiments or with each of the aforementioned $R^2$ embodiments.

Another embodiment of the present invention are those compounds of formula I wherein s is an integer from zero to three and each $R^3$ is independently selected from the group consisting of fluoro, chloro and methyl. Other embodiments of the present invention include those compounds of formula I (and I(a), I(b), I(c), I(d), I(e), I(f) and I(g)) wherein $R^3$ is as defined above in combination with each of the aforementioned $R^6$ embodiments, $R^7$ embodiments, $R^4$ embodiments, $R^5$ embodiments or with each of the aforementioned $R^2$ embodiments.

Examples of specific preferred compounds of the formula I are the following:

3-Isopropyl-6-(4-phenyl-oxazol-5-yl)-[1,2,4]triazolo[4,3-a]pyridine;

3-Ethyl-6-(4-m-tolyl-oxazol-5-yl)-[1,2,4]triazolo[4,3-a]pyridine;

3-Cyclopropyl-6-[4-(4-fluoro-phenyl)-oxazol-5-yl]-[1,2,4]triazolo[4,3-a]pyridine;

3-Cyclobutyl-6-[4-(4-fluoro-phenyl)-oxazol-5-yl]-[1,2,4]triazolo[4,3-a]pyridine;

3-Cyclobutyl-6-(4-phenyl-oxazol-5-yl)-[1,2,4]triazolo[4,3-a]pyridine;

3-Cyclopropyl-6-(4-phenyl-oxazol-5-yl)-[1,2,4]triazolo[4,3-a]pyridine;

3-Ethyl-6-(4-phenyl-oxazol-5-yl)-[1,2,4]triazolo[4,3-a]pyridine;

3-Ethyl-6-[4-(4-fluoro-phenyl)-oxazol-5-yl]-[1,2,4]triazolo[4, 3-a]pyridine;

6-[4-(4-Fluoro-phenyl)-oxazol-5-yl]-3-isopropyl-[1,2,4]triazolo[4,3-a]pyridine;

3-Cyclobutyl-6-(4-m-tolyl-oxazol-5-yl)-[1,2,4]triazolo[4,3-a]pyridine;

3-Isopropyl-6-(4-m-tolyl-oxazol-5-yl)-[1,2,4]triazolo[4,3-a]pyridine;

6-[4-(4-Fluoro-3-methyl-phenyl)-oxazol-5-yl]-3-isopropyl-[1,2,4]triazolo[4,3-a]pyridine;

3-Cyclopropyl-6-[4-(4-fluoro-3-methyl-phenyl)-oxazol-5-yl]-[1,2,4]triazolo[4,3-a]pyridine;

6-[4-(4-Fluoro-phenyl)-oxazol-5-yl]-3-phenyl-[1,2,4]triazolo[4,3-a]pyridine;

3-Isopropyl-6-(2-methyl-4-phenyl-oxazol-5-yl)-[1,2,4]triazolo[4,3-a]pyridine; and 6-[4-(4-Fluoro-phenyl)-2-methyl-oxazol-5-yl]-3-isopropyl-[1,2,4]triazolo[4,3-a]pyridine;

Other specific triazolopyridine compounds of formula I include the following:

6-[3-(4-Fluoro-phenyl)-5-methyl-isoxazol-4-yl]-3-isopropyl-[1,2,4]triazolo[4,3-a]pyridine;

3-Difluoromethyl-6-(4-phenyl-oxazol-5-yl)-[1,2,4]triazolo[4,3-a]pyridine;

3-Isoxazol-5-yl-6-(4-phenyl-oxazol-5-yl)-[1,2,4]triazolo[4, 3-a]pyridine;

6-(4-Phenyl-oxazol-5-yl)-3-(2,2,2-trifluoro-ethyl)-[1,2,4]triazolo[4,3-a]pyridine;

6-[3-(4-Fluoro-phenyl)-5-methyl-isoxazol-4-yl]-3-phenyl-[1,2,4]triazolo[4,3-a]pyridine;

6-[4-(2,4-Difluoro-phenyl)-oxazol-5-yl]-3-isopropyl-[1,2,4]triazolo[4,3-a]pyridine;

6-[4-(4-Fluoro-phenyl)-thiazol-5-yl]-3-isopropyl-[1,2,4]triazolo[4,3-a]pyridine;

6-[4-(2,4-Difluoro-phenyl)-thiazol-5-yl]-3-isopropyl-[1,2, 4]triazolo[4,3-a]pyridine;

6-[3-(2,4-Difluoro-phenyl)-5-methyl-isoxazol-4-yl]-3-isopropyl-[1,2,4]triazolo[4,3-a]pyridine;

6-[3-(2,4-Difluoro-phenyl)-5-methyl-isoxazol-4-yl]-3-phenyl-[1,2,4]triazolo[4,3-a]pyridine;

[3-(4-Fluoro-phenyl)-4-(3-isopropyl-1,2,4]triazolo[4,3-a]pyridin-6-yl)-isoxazol-methanol;

[3-(4-Fluoro-phenyl)-5-(3-isopropyl-[1,2,4]triazolo[4,3-a]pyridin-6-yl)-oxazol-2-yl]-methanol;

[4-(2,4-Difluoro-phenyl)-5-(3-isopropyl-[1,2,4]triazolo[4,3-a]pyridin-6-yl)-oxazol-2-yl]-methanol;

[4-(2,4Difluoro-phenyl)-5-(3-isopropyl-[1,2,4]triazolo[4,3-a]pyridin-6-yl)-oxazol-2-yl]-methanol;

6-[4-(3-Chloro-4-fluoro-phenyl)-oxazol-5-yl]-3-isopropyl-[1,2,4]triazolo[4,3-a]pyridine;

6-[5-(2,4-Difluoro-phenyl)-3H-imidazol-4-yl]-3-isopropyl-[1,2,4]triazolo[4,3-a]pyridine;

6-[5-(4-Fluoro-phenyl)-3H-imidazol-4-yl]-3-isopropyl-[1,2, 4]triazolo[4,3-a]pyridine;

6-[5-(4-Fluoro-phenyl)-3-methyl-3H-imidazol-4-yl]-3-isopropyl-[1,2,4]triazolo[4,3-a]pyridine;

6-[5-(4-Fluoro-phenyl)-3-pyrrolidin-3-yl-3H-imidazol-4-yl]-3-isopropyl-[1,2,4]triazolo[4,3-a]pyridine;

6-[4-(4-Fluoro-phenyl)-2-methyl-oxazol-5-yl]-3-phenyl-[1,2,4]triazolo[4,3-a]pyridine;
6-[5-(4-Fluoro-3-methyl-phenyl)-3H-imidazol-4-yl]-3-phenyl-[1,2,4]triazolo[4,3-a]pyridine;
6-[4-(4-Fluoro-3-methyl-phenyl)-oxazol-5-yl]-3-phenyl-[1,2,4]triazolo[4,3-a]pyridine;
6-[3-(2,4-Difluoro-phenyl)-5-methyl-1H-pyrazol-4-yl]-3-isopropyl-[1,2,4]triazolo[4,3-a]pyridine;
6-[3-(4-Fluoro-phenyl)-5-methyl-1H-pyrazol-4-yl]-3-phenyl-[1,2,4]triazolo[4,3-a]pyridine;
6-[3-(4-Fluoro-phenyl)-5-methyl-1H-pyrazol-4-yl]-3-isopropyl-[1,2,4]triazolo[4,3-a]pyridine;
6-[4-(3,4-Difluoro-phenyl)-oxazol-5-yl]-3-isopropyl-[1,2,4]triazolo[4,3-a]pyridine;
6-[5-(3,4-Difluoro-phenyl)-3H-imidazol-4-yl]-3-isopropyl-[1,2,4]triazolo[4,3-a]pyridine;
6-[5-(3,4-Difluoro-phenyl)-3-methyl-3H-imidazol-4-yl]-3-isopropyl-[1,2,4]triazolo[4,3-a]pyridine;
6-[5-(2,4-Difluoro-phenyl)-2-methyl-3H-imidazol-4-yl]-3-isopropyl-[1,2,4]triazolo[4,3-a]pyridine;
6-[3-Azetidin-3-yl-5-(4-fluoro-phenyl)-3H-imidazol-4-yl]-3-isopropyl-[1,2,4]triazolo[4,3-a]pyridine;
6-[4-(2,4-Difluoro-phenyl)-2-methyl-thiazol-5-yl]-3-isopropyl-[1,2,4]triazolo[4,3-a]pyridine;
6-[4-(4-Chloro-phenyl)-oxazol-5-yl]-3-isopropyl-[1,2,4]triazolo[4,3-a]pyridine;
6-[4-(3-Chloro-phenyl)-oxazol-5-yl]-3-isopropyl-[1,2,4]triazolo[4,3-a]pyridine
6-[5-(4-Chloro-phenyl)-3H-imidazol-4-yl]-3-isopropyl-[1,2,4]triazolo[4,3-a]pyridine;
6-[4-(3-Fluoro-phenyl)-oxazol-5-yl]-3-isopropyl-[1,2,4]triazolo[4,3-a]pyridine;
6-[5-(4-Fluoro-phenyl)-2-piperidin-4-yl-3H-imidazol-4-yl]-3-phenyl-[1,2,4]triazolo[4,3-a]pyridine;
2-[4-(4-Fluoro-phenyl)-5-(3-phenyl-[1,2,4]triazolo[4,3-a]pyridin-6-yl)-1H-imidazol-2-yl]-ethanesulfonic acid amide;
4-(4-Fluoro-phenyl)-5-(3-isopropyl-[1,2,4]triazolo[4,3-a]pyridin-6-yl)-1H-imidazole-2-carboxylic acid amide;
4-(4-Fluoro-phenyl)-5-(3-phenyl-[1,2,4]triazolo[4,3-a]pyridin-6-yl)-1H-imidazole-2-carboxylic acid;
6-[5-(4-Fluoro-phenyl)-1H-imidazol-4-yl]-3-phenyl-[1,2,4]triazolo[4,3-a]pyridine;
3-Isopropyl-6-(5-m-tolyl-1H-imidazol-4-yl)-[1,2,4]triazolo[4,3-a]pyridine;
3-Phenyl-6-(5-m-tolyl-1H-imidazol-4-yl)-[1,2,4]triazolo[4,3-a]pyridine;
6-[5-(4-Fluoro-phenyl)-3-pyrrolidin-3-yl-3H-imidazol-4-yl]-3-phenyl-[1,2,4]triazolo[4,3-a]pyridine;
6-[5-(4-Fluoro-phenyl)-2-methyl-1H-imidazol-4-yl]-3-phenyl-[1,2,4]triazolo[4,3-a]pyridine;
3-Isopropyl-6-(3-pyrrolidin-3-yl-5-m-tolyl-3H-imidazol-4-yl)-[1,2,4]triazolo[4,3-a]pyridine;
3-Isopropyl-6-(2-methyl-5-m-tolyl-1H-imidazol-4-yl)-[1,2,4]triazolo[4,3-a]pyridine;
6-[5-(4-Fluoro-phenyl)-2-pyrazin-2-yl-1H-imidazol-4-yl]-3-isopropyl-[1,2,4]triazolo[4,3-a]pyridine;
N-[4-(4-Fluoro-phenyl)-5-(3-isopropyl-[1,2,4]triazolo[4,3-a]pyridin-6-yl)-1H-imidazol-2-yl]-acetamide;
N-[4-(4-Fluoro-phenyl)-5-(3-phenyl-[1,2,4]triazolo[4,3-a]pyridin-6-yl)-1H-imidazol-2-yl]-acetamide;
3-Isopropyl-6-(2-pyrazin-2-yl-5-m-tolyl-1H-imidazol-4-yl)-[1,2,4]triazolo[4,3-a]pyridine;
N-[5-(3-Isopropyl-[1,2,4]triazolo[4,3-a]pyridin-6-yl)-4-m-tolyl-1H-imidazol-2-yl]-acetamide;
N-[5-(3-Phenyl-[1,2,4]triazolo[4,3-a]pyridin-6-yl)-4-m-tolyl-1H-imidazol-2-yl]-acetamide;
6-[5-(4-Fluoro-phenyl)-2-piperidin-4-yl-1H-imidazol-4-yl]-3-isopropyl-[1,2,4]triazolo[4,3-a]pyridine;
3-Isopropyl-6-(2-piperidin-4-yl-5-m-tolyl-3H-imidazol-4-yl)-[1,2,4]triazolo[4,3-a]pyridine;
6-[3-(4-Fluoro-phenyl)-isothiazol-4-yl]-3-isopropyl-[1,2,4]triazolo[4,3-a]pyridine;
3-(4-Fluoro-phenyl)-4-(3-isopropyl-[1,2,4]triazolo[4,3-a]pyridin-6-yl)-isothiazole-5-carboxylic acid amide;
6-[3-(4-Fluoro-phenyl)-isothiazol-4-yl]-3-phenyl-[1,2,4]triazolo[4,3-a]pyridine;
6-[3-(4-Fluoro-phenyl)-5-methyl-isothiazol-4-yl]-3-isopropyl-[1,2,4]triazolo[4,3-a]pyridine;
3-(2-Chloro-phenyl)-6-[3-(4-fluoro-phenyl)-1H-pyrazol-4-yl]-[1,2,4]triazolo[4,3-a]pyridine;
4-[3-(2-Chloro-phenyl)-[1,2,4]triazolo[4,3-a]pyridin-6-yl]-5-(4-fluoro-phenyl)-2H-pyrazol-3-ylamine;
3-(2-Chloro-phenyl)-6-(3-m-tolyl-1H-pyrazol-4-yl)-[1,2,4]triazolo[4,3-a]pyridine;
4-[3-(2-Chloro-phenyl)-[1,2,4]triazolo[4,3-a]pyridin-6-yl]-5-m-tolyl-2H-pyrazol-3-ylamine;
{6-[3-(4-Fluoro-phenyl)-1H-pyrazol-4-yl]-[1,2,4]triazolo[4,3-a]pyridin-3-yl}-ethyl ester;
{6-[5-Amino-3-(4-fluoro-phenyl)-1H-pyrazol-4-yl]-[1,2,4]triazolo[4,3-a]pyridin-3-yl}-acetic acid ethyl ester;
N-Ethyl-2-{6-[3-(4-fluoro-phenyl)-1H-pyrazol-4-yl]-[1,2,4]triazolo[4,3-a]pyridin-3-yl}-acetamide;
2-{6-[5-Amino-3-(4-fluoro-phenyl)-1H-pyrazol-4-yl]-[1,2,4]triazolo[4,3-a]pyridine-3-yl}-N-ethyl-acetamide;
6-[3-(3-Chloro-phenyl)-1H-pyrazol-4-yl]-3-phenyl-[1,2,4]triazolo[4,3-a]pyridine;
5-(3-Chloro-phenyl)-4-(3-phenyl-[1,2,4]triazolo[4,3-a]pyridin-6-yl)-2H-pyrazol-3-ylamine;
6-[3-(3-Chloro-phenyl)-1H-pyrazol-4-yl]-3-isopropyl-[1,2,4]triazolo[4,3-a]pyridine;
5-(3-Chloro-phenyl)-4-(3-isopropyl-[1,2,4]triazolo[4,3-a]pyridin-6-yl)-2H-pyrazol-3-ylamine;
6-[3-(4-Fluoro-phenyl)-1H-pyrazol-4-yl]-3-isopropyl-[1,2,4]triazolo[4,3-a]pyridine;
5-(4-Fluoro-phenyl)-4-(3-isopropyl-[1,2,4]triazolo[4,3-a]pyridin-6-yl)-2H-pyrazol-3-ylamine;
N-[5-(4-Fluoro-phenyl)-4-(3-isopropyl-[1,2,4]triazolo[4,3-a]pyridin-6-yl)-2H-pyrazol-3-yl]-N',N'-dimethyl-ethane-1,2-diamine;
2-[3-(4-Fluoro-phenyl)-4-(3-isopropyl-[1,2,4]triazolo[4,3-a] pyridin-6-yl)-pyrazol-1-yl]-N,N-dimethyl-acetamide;
6-[3-(4-Chloro-phenyl)-1H-pyrazol-4-yl]-3-isopropyl-[1,2,4]triazolo[4,3-a]pyridine;
6-[3-(4-Fluoro-phenyl)-i H-pyrazol-4-yl]-3-phenyl-[1,2,4]triazolo[4,3-a]pyridine;
5-(4-Fluoro-phenyl)-4-(3-phenyl-[1,2,4]triazolo[4,3-a]pyridin-6-yl)-2H-pyrazol-3-ylamine;
6-[3-(2,4-Difluoro-phenyl)-1H-pyrazol-4-yl]-3-phenyl-[1,2,4]triazolo[4,3-a]pyridine;
5-(2,4-Difluoro-phenyl)-4-(3-phenyl-[1,2,4]triazolo[4,3-a]pyridin-6-yl)-2H-pyrazol-3-ylamine;
2-[3-(4-Fluoro-phenyl)-4-(3-phenyl-[1,2,4]triazolo[4,3-a]pyridin-6-yl)-pyrazol-1-yl]-N,N-dimethyl-acetamide;
6-[3-(2,4-Difluoro-phenyl)-5-methyl-1H-pyrazol-4-yl]-3-phenyl-[1,2,4]triazolo[4,3-a]pyridine;
2-[3-(2,4-Difluoro-phenyl)-4-(3-phenyl-[1,2,4]triazolo[4,3-a]pyridin-6-yl)-pyrazol-1-yl]-N,N-dimethyl-acetamide;
6-[4-(3-Fluoro-phenyl)-oxazol-5-yl]-3-phenyl-[1,2,4]triazolo[4,3-a]pyridine;
[6-(4-m-Tolyl-oxazol-5-yl)-[1,2,4]triazolo[4,3-a]pyridin-3-yl]-acetic acid ethyl ester;
3-(2-Chloro-phenyl)-6-(4-m-tolyl-oxazol-5-yl)-[1,2,4]triazolo[4,3-a]pyridine; and
3-Phenyl-6-(4-m-tolyl-oxazol-5-yl)-[1,2,4]triazolo[4,3-a]pyridine.

The present invention also includes isotopically-labelled compounds, which are identical to those recited in Formula I, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Compounds of the present invention, prodrugs thereof, and pharmaceutically acceptable salts of said compounds or of said prodrugs which contain the aforementioned isotopes and/or other isotopes of other atoms are within the scope of this invention. Certain isotopically-labelled compounds of the present invention, for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labelled compounds of Formula I of this invention and prodrugs thereof can generally be prepared by carrying out the procedures disclosed in the Schemes and/or in the Examples and Preparations below, by substituting a readily available isotopically labelled reagent for a non-isotopically labelled reagent.

The compounds of Formula I or a pharmaceutically acceptable salt thereof can be used in the manufacture of a medicament for the prophylactic or therapeutic treatment of any disease state in a human, or other mammal, which is exacerbated or caused by excessive or unregulated cytokine production by such mammal's cells, such as but not limited to monocytes and/or macrophages.

Compounds of Formula (I) are capable of inhibiting proinflammatory cytokines, such as IL-1, IL-6, IL-8, and TNF and are therefore of use in therapy. IL-1, IL-6, IL-8 and TNF affect a wide variety of cells and tissues and these cytokines, as well as other leukocyte-derived cytokines, are important and critical inflammatory mediators of a wide variety of disease states and conditions. The inhibition of these pro-inflammatory cytokines is of benefit in controlling, reducing and alleviating many of these disease states.

Accordingly, the present invention provides a method of treating a cytokine mediated disease which comprises administering an effective cytokine-interfering amount of a compound of Formula (I) or a pharmaceutically acceptable salt thereof.

Certain compounds of Formula (I) are capable of inhibiting inducible pro-inflammatory proteins, such as COX-2, also referred to by many other names such as prostaglandin endoperoxide synthase-2 (PGHS-2) and are therefore of use in therapy. These proinflammatory lipid mediators of the cyclooxygenase (COX) pathway are produced by the inducible COX-2 enzyme. Regulation, therefore of COX-2 which is responsible for these products derived from arachidonic acid, such as prostaglandins, affect a wide variety of cells and tissues. Expression of COX-1 is not effected by compounds of Formula (I). This selective inhibition of COX-2 is accepted as alleviating or sparing ulcerogenic liability associated with inhibition of COX-1 thereby inhibiting prostoglandins essential for cytoprotective effects. Thus inhibition of these pro-inflammatory mediators is of benefit in controlling, reducing and alleviating many of these disease states. Most notably these inflammatory mediators, in particular prostaglandins, have been implicated in pain, such as in the sensitization of pain receptors, or edema. This aspect of pain management, therefore, includes treatment of neuromuscular pain, headache, cancer pain, and arthritis pain. Compounds of Formula (I), or a pharmaceutically acceptable salt thereof, are of use in therapy in a human, or other mammal, by inhibition of the synthesis of the COX-2 enzyme.

Accordingly, the present invention provides a method of inhibiting the synthesis of COX-2 which comprises administering an effective amount of a compound of Formula (I) or a pharmaceutically acceptable salt thereof. The present invention also provides for a method of treatment in a human, or other mammal, by inhibition of the synthesis of the COX-2 enzyme.

In particular, compounds of Formula (I) or a pharmaceutically acceptable salt thereof are of use in the therapy of any disease state in a human, or other mammal, which is exacerbated by or caused by excessive or unregulated IL-1, IL-8 or TNF production by such mammal's cells, such as, but not limited to, monocytes and/or macrophages.

Accordingly, in another aspect, this invention relates to a method of inhibiting the production of IL-1 in a mammal in need thereof which comprises administering to said mammal an effective amount of a compound of Formula (I) or a pharmaceutically acceptable salt thereof.

There are many disease states in which excessive or unregulated IL-1 production is implicated in exacerbating and/or causing the disease. These include rheumatoid arthritis, osteoarthritis, meningitis, ischemic and hemorrhagic stroke, neurotrauma/closed head injury, stroke, endotoxemia and/or toxic shock syndrome, other acute or chronic inflammatory disease states such as the inflammatory reaction induced by endotoxin or inflammatory bowel disease, tuberculosis, atherosclerosis, muscle degeneration, multiple sclerosis, cachexia, bone resorption, psoriatic arthritis, Reiter's syndrome, rheumatoid arthritis, gout, traumatic arthritis, rubella arthritis and acute synovitis. Recent evidence also links IL-1 activity to diabetes, pancreatic β cells disease, and Alzheimer's disease.

Use of a p38 inhibitor for the treatment of p38 mediated disease states, can include, but is not limited to neurodegenerative diseases, such as Alzheimer's disease, Parkinson's disease and multiple sclerosis, etc. In a further aspect, this invention relates to a method of inhibiting the production of TNF in a mammal in need thereof which comprises administering to said mammal an effective amount of a compound of Formula (I) or a pharmaceutically acceptable salt thereof.

Excessive or unregulated TNF production has been implicated in mediating or exacerbating a number of diseases including rheumatoid arthritis, rheumatoid spondylitis, osteoarthritis, gouty arthritis and other arthritic conditions, sepsis, septic shock, endotoxic shock, gram negative sepsis, toxic shock syndrome, adult respiratory distress syndrome, stroke, cerebral malaria, chronic obstructive pulmonary disease, chronic pulmonary inflammatory disease, silicosis, pulmonary sarcoidosis, bone resorption diseases, such as osteoporosis, cardiac, brain and renal reperfusion injury, graft vs. host reaction, allograft rejections, fever and myalgias due to infection, such as influenza, (including HIV-induced forms), cerebral malaria, meningitis, ischemic and hemorrhagic stroke, cachexia secondary to infection or malignancy, cachexia secondary to acquired immune deficiency syndrome (AIDS), AIDS, ARC (AIDS related complex), keloid formation, scar tissue formation, inflammatory bowel disease, Crohn's disease, ulcerative colitis and pyresis.

Compounds of Formula (I) are also useful in the treatment of viral infections, where such viruses are sensitive to upregulation by TNF or will elicit TNF production in vivo. The viruses contemplated for treatment herein are those that produce TNF as a result of infection, or those which are sensitive to inhibition, such as by decreased replication, directly or indirectly, by the TNF inhibiting-compounds of Formula (I). Such viruses include, but are not limited to HIV-1, HIV-2 and HIV-3, Cytomegalovirus (CMV), Influenza, adenovirus and the Herpes group of viruses, such as but not limited to, Herpes Zoster and Herpes Simplex. Accordingly, in a further aspect, this invention relates to a method of treating a mammal afflicted with a human immunodeficiency virus (HIV) which comprises administering to such mammal an effective TNF inhibiting amount of a compound of Formula (I) or a pharmaceutically acceptable salt thereof.

Compounds of Formula (I) may also be used in association with the veterinary treatment of mammals, other than in humans, in need of inhibition of TNF production. TNF mediated diseases for treatment, in animals include disease states such as those noted above, but in particular viral infections. Examples of such viruses include, but are not limited to, lentivirus infections such as, equine infectious anaemia virus, caprine arthritis virus, visna virus, or maedi virus or retrovirus infections, such as but not limited to feline immunodeficiency virus (FIV), bovine immunodeficiency virus, or canine immunodeficiency virus or other retroviral infections.

The compounds of Formula (I) may also be used topically in the treatment of topical disease states mediated by or exacerbated by excessive cytokine production, such as by IL-I or TNF respectively, such as inflamed joints, eczema, contact dermatitis psoriasis and other inflammatory skin conditions such as sunburn; inflammatory eye conditions including conjunctivitis; pyresis, pain and other conditions associated with inflammation. Periodontal disease has also been implemented in cytokine production, both topically and systemically. Hence, the use of compounds of Formula (I) to control the inflammation associated with cytokine production in such peroral diseases such as gingivitis and periodontitis is another aspect of the present invention.

Compounds of Formula (I) have also been shown to inhibit the production of IL-8 (Interleukin-8, NAP). Accordingly, in a further aspect, this invention relates to a method of inhibiting the production of IL-8 in a mammal in need thereof which comprises administering, to said mammal an effective amount of a compound of Formula (I) or a pharmaceutically acceptable salt thereof.

There are many disease states in which excessive or unregulated IL-8 production is implicated in exacerbating and/or causing the disease. These diseases are characterized by massive neutrophil infiltration such as, psoriasis, inflammatory bowel disease, asthma, cardiac and renal reperfusion injury, adult respiratory distress syndrome, thrombosis and glomerulonephritis. All of these diseases are associated with increased IL-8 production which is responsible for the chemotaxis of neutrophils into the inflammatory site. In contrast to other inflammatory cytokines (IL-1, TNF, and IL-6), IL-8 has the unique property of promoting neutrophil chemotaxis and activation. Therefore, the inhibition of IL-8 production would lead to a direct reduction in the neutrophil infiltration.

The compounds of Formula (I) are administered in an amount sufficient to inhibit a cytokine, in particular IL-1, IL-6, IL-8 or TNF, production such that it is regulated down to normal levels, or in some case to subnormal levels, so as to ameliorate or prevent the disease state. Abnormal levels of IL-1, IL-6, IL-8 or TNF, for instance in the context of the present invention, constitute: (i) levels of free (not cell bound) IL-1, IL-6, IL-8 or TNF greater than or equal to 1 picogram per ml; (ii) any cell associated IL-1, IL-6, IL-8 or TNF; or (iii) the presence of IL-1, IL-6, IL-8 or TNF mRNA above basal levels in cells or tissues in which IL-1, IL-6, IL-8 or TNF, respectively, is produced.

The discovery that the compounds of Formula (I) are inhibitors of cytokines, specifically IL-1. IL-6, IL-8 and TNF is based upon the effects of the compounds of Formula (I) on the production of the IL-1, IL-8 and TNF in in vitro assays which are described herein or are well known to those skilled in the art.

As used herein, the term "inhibiting the production of IL-1 (IL-6, IL-8 or TNF)" refers to:

a) a decrease of excessive in vivo levels of the cytokine (IL-1, IL-6, IL-8 or TNF) in a human to normal or sub-normal levels by inhibition of the in vivo release of the cytokine by all cells, including but not limited to monocytes or macrophages;

b) a down regulation, at the genomic level, of excessive in vivo levels of the cytokine (IL-1, IL-6, IL-8 or TNF) in a human to normal or sub-normal levels;

c) a down regulation, by inhibition of the direct synthesis of the cytokine (IL-1, IL-6, IL-8 or TNF) as a postranslational event to normal or sub-normal levels; or d) a down regulation, at the translational level, of excessive in vivo levels of the cytokine (IL-1, IL-6, IL-8 or TNF) in a human to normal or sub-normal levels.

As used herein, the term "TNF mediated disease or disease state" refers to any and all disease states in which TNF plays a role, either by production of TNF itself, or by TNF causing another monokine to be released, such as but not limited to IL-1, IL-6 or IL-8. A disease state in which, for instance, IL-1 is a major component, and whose production or action, is exacerbated or secreted in response to TNF, would therefore be considered a disease state mediated by TNF.

As used herein, the term "cytokine" refers to any secreted polypeptide that affects the functions of cells and is a molecule which modulates interactions between cells in the immune, inflammatory or hematopoietic response. A cytokine includes, but is not limited to, monokines and lymphokines, regardless of which cells produce them. For instance, a monokine is referred to as being produced and secreted by a mononuclear cell, such as a macrophage and/or monocyte. Many other cells however also produce monokines, such as natural killer cells, fibroblasts, basophils, neutrophils, endothelial cells, brain astrocytes, bone marrow stromal cells, epideral keratinocytes and B-lymphocytes. Lymphokines are generally referred to as being produced by lymphocyte cells. Examples of cytokines include, but are not limited to Interleukin-1 (IL-1), Interleukin-6 (IL-6), Interleukin-8 (IL-8), Tumor Necrosis Factor-alpha (TNF-α) and Tumor Necrosis Factor beta (TNF-β).

As used herein, the term "cytokine interfering" or "cytokine suppressive amount" refers to an effective amount of a compound of Formula (I) which will cause a decrease in the in vivo levels of the cytokine to normal or sub-normal levels, when given to a patient for the treatment of a disease state which is exacerbated by, or caused by, excessive or unregulated cytokine production.

As used herein, the cytokine referred to in the phrase "inhibition of a cytokine for use in the treatment of a HIV-infected human" is a cytokine which is implicated in (a) the initiation and/or maintenance of T cell activation and/or activated T cell-mediated HIV gene expression and/or replication and/or (b) any cytokine-mediated disease associated problem such as cachexia or muscle degeneration.

As TNF-β (also known as lymphotoxin) has close structural homology with TNF-α (also known as cachectin) and since each induces similar biologic responses and binds to the same cellular receptor, both TNF-α and TNF-β are inhibited by the compounds of the present invention and thus are herein referred to collectively as "TNF" unless specifically delineated otherwise.

A relatively new member of the MAP kinase family, alternatively termed CSBP, p38 or RK, has been identified by several laboratories [See Lee et al., Nature, Vol. 300, n(72), 739–746 (1994)]. Activation of this protein kinase via dual phosphorylation has been observed in different cell systems upon stimulation by a wide spectrum of stimuli, such as physicochemical stress and treatment with lipopolysaccharide or proinflammatory cytokines such as interleukin-1 and tumor necrosis factor. The cytokine biosynthesis inhibitors, of the, present invention, compounds of Formula (I) have been determined to be potent and selective inhibitors of CSBP/p38/RK kinase activity, These inhibitors are of aid in determining the signaling pathways involvement in inflammatory responses. In particular, a definitive signal transduction pathway can be prescribed to the action of lipopolysaccharide in cytokine production in macrophages. In addition to those diseases already noted herein, treatment of stroke, neurotrauma/CNS head injury, cardiac, brain and renal reperfusion injury, thrombosis, glomerulonephritis, diabetes and pancreatic β cells, multiple sclerosis, muscle degeneration, eczema, psoriasis, sunburn, and conjunctivitis are also included.

The cytokine inhibitors were subsequently tested in a number of animal models for anti-inflammatory activity. Model systems were chosen that were relatively insensitive to cyclooxygenase inhibitors in order to reveal the unique activities of cytokine suppressive agents. The inhibitors exhibited significant activity in many such in vivo studies. Most notable are its effectiveness in the collagen-induced arthritis model and inhibition of TNF production in the endotoxic shock model. In the latter study, the reduction in plasma level of TNF correlated with survival and protection from endotoxic shock related mortality. Also of great importance is the compound's effectiveness in inhibiting bone resorption in a rat fetal long bone organ culture system. Griswold et al., (1988) Arthritis Rheum. 31:1406–1412; Badger, et al., (1989) Circ. Shock 27, 51–61, Votta et al., (1994) in vitro. Bone 15, 533–538; Lee et al., (1993.). B Ann. N. Y. Acad. Sci. 696, 149–170.

It is also recognized that both IL-6 and IL-8 are produced during rhinovirus (HRV) infections and contribute to the pathogenesis of common cold and exacerbation of asthma associated with HRV infection (Turner et al., (1998), Clin. Infec. Dis., Vol. 26, p. 840; Teren et al. (1997), Am. J. Respir. Crit. Care Med., Vol. 155, p. 1362; Grunberg et al. (1997), Am. J. Respir. Crit. Care Med., Vol. 156, p. 609 and Zhu et al., J. Clin. Invest. (1996), Vol. 97, p 421). It has also been demonstrated in vitro that infection of pulmonary epithelial cells with HRV results in production of IL-6 and IL-8 (Subauste et al., J. Clin. Invest. (1995), Vol. 96, p. 549). Epithelial cells represent the primary site of infection of HRV. Therefore, another aspect of the present invention is a method of treatment to reduce inflammation associated with a rhinovirus infection, not necessarily a direct effect of the virus itself.

Another aspect of the present invention involves the novel use of these p38/cytokine inhibitors for the treatment of chronic inflammatory or proliferative or angiogenic diseases, which are caused by excessive, or inappropriate angiogenesis.

Chronic diseases which have an inappropriate angiogenic component are various ocular neovascularizations, such as diabetic retinopathy and macular degeneration. Other chronic diseases which have an excessive or increased proliferation of vasculature are tumor growth and metastasis, atherosclerosis and certain arthritic conditions. Therefore, cytokine inhibitors will be of utility in the blocking of the angiogenic component of these disease states.

The term "excessive or increased proliferation of vasculature inappropriate angiogenesis" as used herein includes, but is not limited to, diseases which are characterized by hemangiomas and ocular diseases.

The term "inappropriate angiogenesis" as used herein includes, but is not limited to, diseases which are characterized by vesicle proliferation with accompanying tissue proliferation, such as occurs in cancer, metastasis, arthritis and atherosclerosis.

This invention also encompasses methods of treating or preventing disorders that can be treated or prevented by the inhibition of ERK/MAP in a mammal, preferably a human, comprising administering to said mammal an effective amount of a compound of the formula I.

Accordingly, the present invention provides a method of treating a p38 kinase mediated disease in a mammal in need thereof, preferably a human, which comprises administering to said mammal, an effective amount of a compound of Formula (I) or a pharmaceutically acceptable salt thereof.

Preferred p38 mediated diseases for treatment include, but are not limited to psoriatic arthritis, Reiter's syndrome, rheumatoid arthritis, gout, traumatic arthritis, rubella arthritis and acute synovitis, rheumatoid spondylitis, osteoarthritis, gouty arthritis and other arthritic conditions, sepsis, septic shock, endotoxic shock, gram negative sepsis, toxic shock syndrome, Alzheimer's disease, stroke, ischemic and hemorrhagic stroke, neurotrauma/closed head injury, asthma, adult respiratory distress syndrome, chronic obstructive pulmonary disease, cerebral malaria, meningitis, chronic pulmonary inflammatory disease, silicosis, pulmonary sarcostosis, bone resorption disease, osteoporosis, restenosis, cardiac reperfusion injury, brain and renal reperfusion injury, chronic renal failure, thrombosis, glomerularonephritis, diabetes, diabetic retinopathy, macular degeneration, graft vs. host reaction, allograft rejection, inflammatory bowel disease, Crohn's disease, ulcerative colitis, neurodegenerative disease, multiple sclerosis, muscle degeneration, diabetic retinopathy, macular degeneration, tumor growth and metastasis, angiogenic disease, rhinovirus infection, peroral disease, such as gingivitis and periodontitis, eczema, contact dermatitis, psoriasis, sunburn, and conjunctivitis.

The term "treating", as used herein, refers to reversing, alleviating, inhibiting the progress of, or preventing the disorder or condition to which such term applies, or one or more symptoms of such disorder or condition. The term "treatment", as used herein, refers to the act of treating, as "treating" is defined immediately above.

This invention also encompasses pharmaceutical compositions for the treatment of a condition selected from the group consisting of arthritis, psoriatic arthritis, Reiter's syndrome, gout, traumatic arthritis, rubella arthritis and acute synovitis, rheumatoid arthritis, rheumatoid spondylitis, osteoarthritis, gouty arthritis and other arthritic conditions, sepsis, septic shock, endotoxic shock, gram negative sepsis, toxic shock syndrome, Alzheimer's disease, stroke, neurotrauma, asthma, adult respiratory distress syndrome, cerebral malaria, chronic pulmonary inflammatory disease, silicosis, pulmonary sarcoidosis, bone resorption disease, osteoporosis, restenosis, cardiac and renal reperfusion injury, thrombosis, glomerularonephritis, diabetes, graft vs. host reaction, allograft rejection, inflammatory bowel disease, Crohn's disease, ulcerative colitis, multiple sclerosis, muscle degeneration, eczema, contact dermatitis, psoriasis, sunburn, or conjunctivitis shock in a mammal, including a human, comprising an amount of a compound of formula I effective in such treatment and a pharmaceutically acceptable carrier.

This invention also encompasses pharmaceutical compositions for the treatment of a condition which can be treated by the inhibition of ERK/MAP kinase in a mammal, including a human, comprising an amount of a compound of claim 1 effective in such treatment and a pharmaceutically acceptable carrier.

This invention also encompasses pharmaceutical compositions for the treatment of a condition which can be treated by the inhibition of p38 kinase in a mammal, including a human, comprising an amount of a compound of claim 1 effective in such treatment and a pharmaceutically acceptable carrier.

This invention also encompasses pharmaceutical compositions containing prodrugs of compounds of the formula I. Compounds of formula I having free amino, amido, hydroxy or carboxylic groups can be converted into prodrugs. Prodrugs include compounds wherein an amino acid residue, or a polypeptide chain of two or more (e.g., two, three or four) amino acid residues which are covalently joined through peptide bonds to free amino, hydroxy or carboxylic acid groups of compounds of formula I. The amino acid residues include the 20 naturally occurring amino acids commonly designated by three letter symbols and also include, 4-hydroxyproline, hydroxylysine, demosine, isodemosine, 3-methylhistidine, norvalin, beta-alanine, gamma-aminobutyric acid, citrulline, homocysteine, homoserine, ornithine and methionine sulfone. Prodrugs also include compounds wherein carbonates, carbamates, amides and alkyl esters which are covalently bonded to the above substituents of formula I through the carbonyl carbon prodrug sidechain.

The invention also encompasses sustained release compositions.

One of ordinary skill in the art will appreciate that the compounds of the invention are useful in treating a diverse array of diseases. One of ordinary skill in the art will also appreciate that when using the compounds of the invention in the treatment of a specific disease that the compounds of the invention may be combined with various existing therapeutic agents used for that disease.

For the treatment of rheumatoid arthritis, the compounds of the invention may be combined with agents such as TNF-α inhibitors such as anti-TNF monoclonal antibodies (such as Remicade, CDP-870 and $D_2E_7$) and TNF receptor immunoglobulin molecules (such as Enbrel®), COX-2 inhibitors (such as celecoxib, rofecoxib, valdecoxib and etoricoxib) low dose methotrexate, lefunomide, hydroxychloroquine, d-penicillamine, auranofin or parenteral or oral gold.

The compounds of the invention can also be used in combination with existing therapeutic agents for the treatment of osteoarthritis. Suitable agents to be used in combination include standard non-steroidal anti-inflammatory agents (hereinafter NSAID's) such as piroxicam, diclofenac, propionic acids such as naproxen, flubiprofen, fenoprofen, ketoprofen and ibuprofen, fenamates such as mefenamic acid, indomethacin, sulindac, apazone, pyrazolones such as phenylbutazone, salicylates such as aspirin, COX-2 inhibitors such as celecoxib, valdecoxib, rofecoxib and etoricoxib, analgesics and intraarticular therapies such as corticosteroids and hyaluronic acids such as hyalgan and synvisc.

The compounds of the present invention may also be used in combination with anticancer agents such as endostatin and angiostatin or cytotoxic drugs such as adriamycin, daunomycin, cis-platinum, etoposide, taxol, taxotere and alkaloids, such as vincristine, farnesyl transferase inhibitors, VegF inhibitors, and antimetabolites such as methotrexate.

The compounds of the invention may also be used in combination with antiviral agents such as Viracept, AZT, aciclovir and famciclovir, and antisepsis compounds such as Valant.

The compounds of the present invention may also be used in combination with cardiovascular agents such as calcium channel blockers, lipid lowering agents such as statins, fibrates, beta-blockers, Ace inhibitors, Angiotensin-2 receptor antagonists and platelet aggregation inhibitors.

The compounds of the present invention may also be used in combination with CNS agents such as antidepressants (such as sertraline), anti-Parkinsonian drugs (such as deprenyl, L-dopa, Requip, Mirapex, MAOB inhibitors such as selegine and rasagiline, comP inhibitors such as Tasmar, A-2 inhibitors, dopamine reuptake inhibitors, NMDA antagonists, Nicotine agonists, Dopamine agonists and inhibitors of neuronal nitric oxide synthase), and anti-Alzheimer's drugs such as donepezil, tacrine, COX-2 inhibitors, propentofylline or metryfonate.

The compounds of the present invention may also be used in combination with osteoporosis agents such as roloxifene, droloxifene, lasofoxifene or fosomax and immunosuppressant agents such as FK-506 and rapamycin.

DETAILED DESCRIPTION OF THE INVENTION

Compounds of the formula I may be prepared according to the following reaction schemes and discussion. Unless otherwise indicated, m, n, p, s, B, $R^1$ through $R^{16}$ and Het and structural formula I in the reaction schemes and discussion that follow are as defined above.

Scheme 1

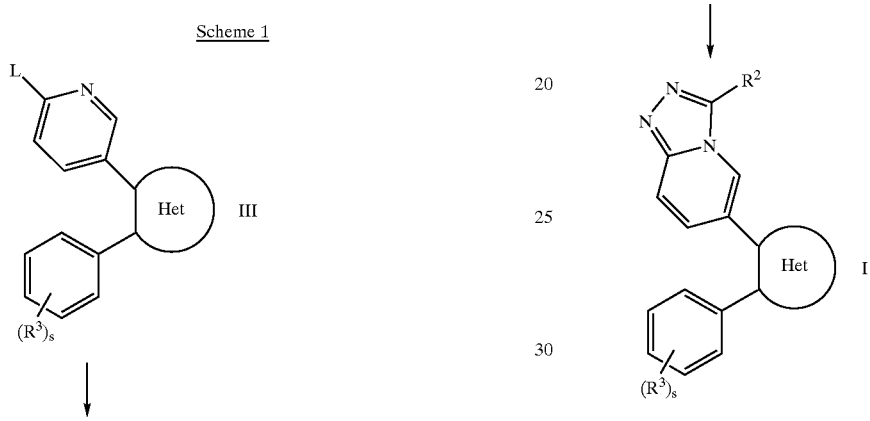

Scheme 2

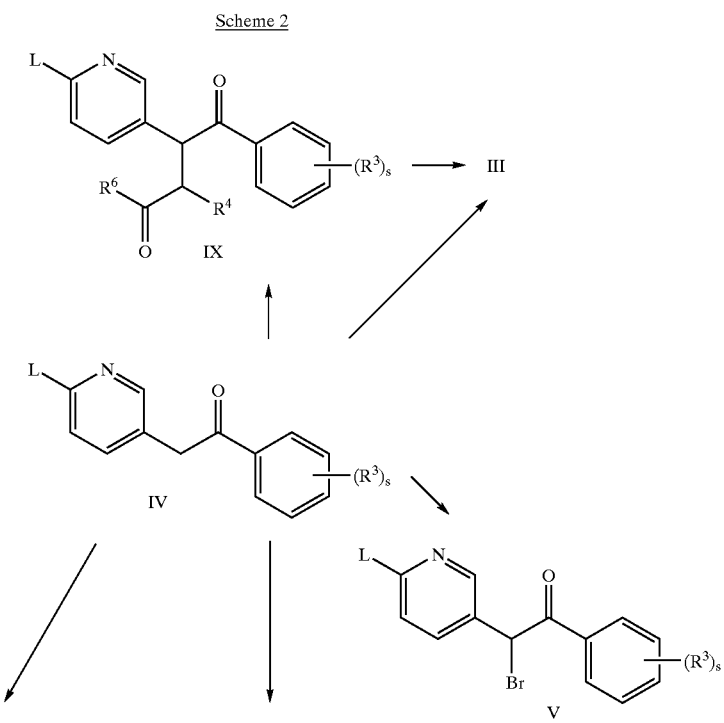

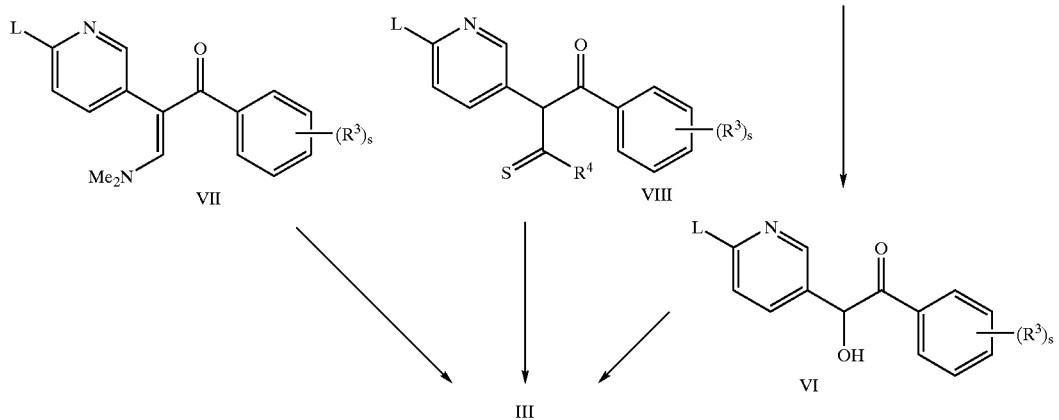
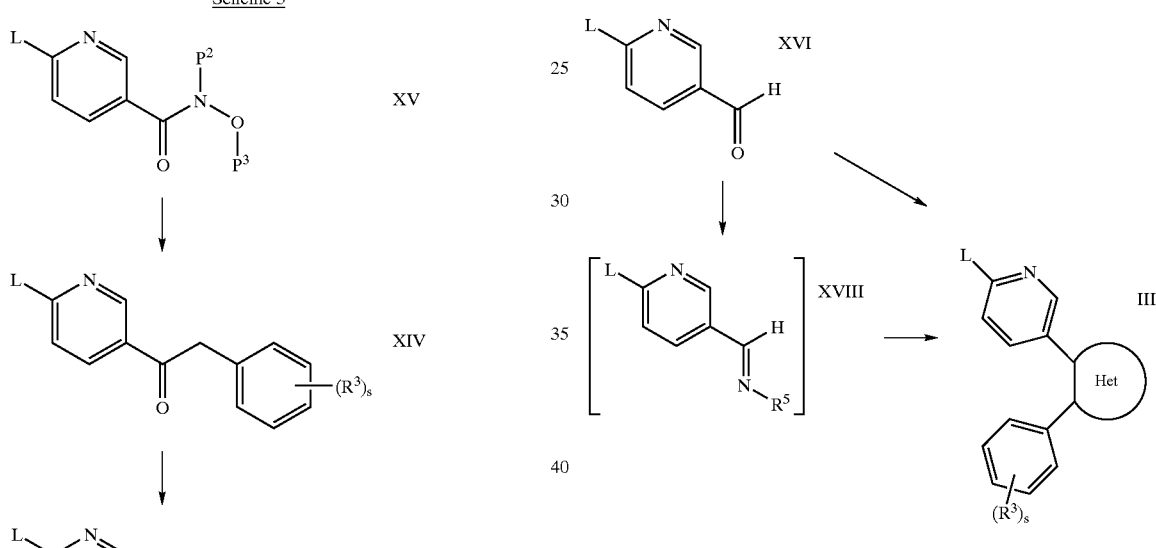
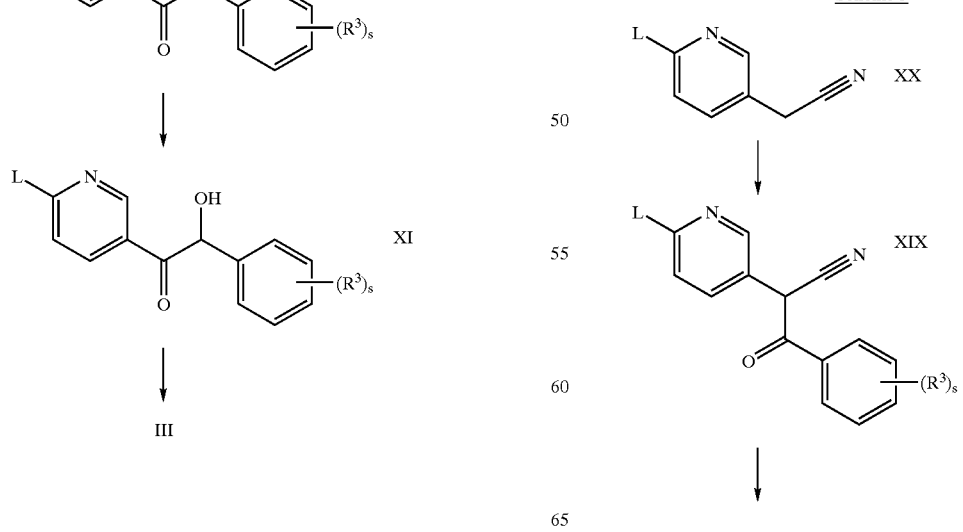

-continued
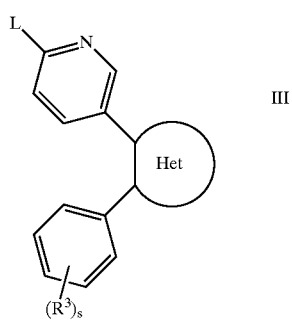
III
Scheme 6
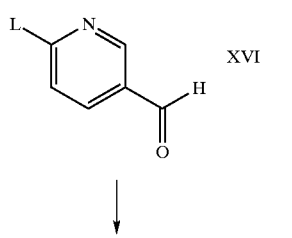
XVI
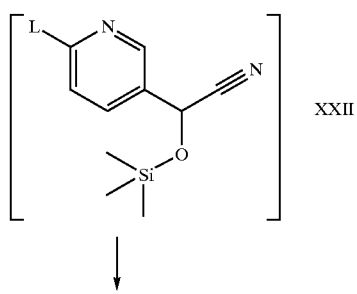
XXII
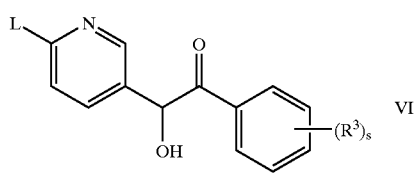
VI
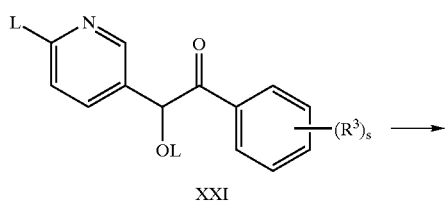
XXI
-continued
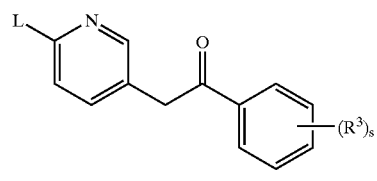
IV
Scheme 7
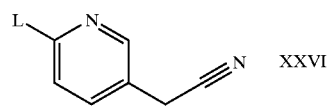
XXVI
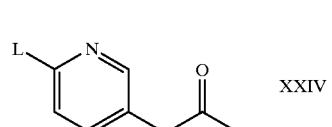
XXIV
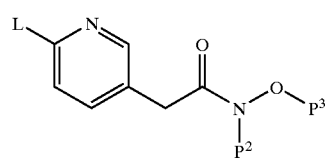
XXIII
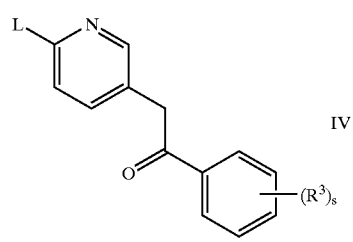
IV
Scheme 8
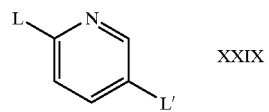
XXIX

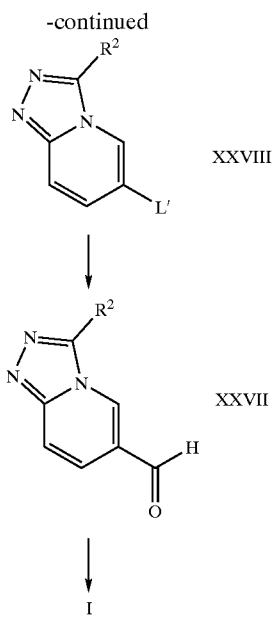

Scheme 1 refers to the preparation of compounds of the formula I in two steps from compounds of formula III. Referring to Scheme 1 compounds of the formula III, wherein L is a suitable leaving group such as fluoro, bromo, chloro or mesyl (MeSO$_2$), preferably bromo or chloro, are converted to the corresponding compound of formula II by reaction with hydrazine to form a hydrazino-pyridine, followed by reaction with an acylating reagent. The reaction of a compound of formula III with hydrazine is conducted in a polar solvent such as pyridine, ethanol or tert-butanol, or in neat hydrazine, preferably in neat hydrazine. The hydrazine reaction is conducted at a temperature between about 40° C. to about 80° C., preferably about 70° C. for about 10 minutes to about 60 minutes, preferably about 15 minutes. Acylation of the resulting hydrazino-pyridine to give compounds of the formula II is conducted with an acid chloride in the presence of a base such as triethylamine in a solvent such as dichloromethane, tetrahydrofuran, N,N-dimethylformamide, preferably dichloromethane, for a time period between about 10 minutes to about 120 minutes, preferably about 30 minutes, at a temperature of about 0° C. to about 22° C., preferably at about 0° C. Alternatively, the hydrazino-pyridine can be acylated with a carboxylic acid to give compounds of the formula II using amide coupling agents in a manner well known to one skilled in the art.

The compound of formula II can be converted to a compound of formula I using a suitable dehydrating agent or under conditions that promote cyclo-dehydration. Suitable dehydrating agents for the conversion of compounds of formula II to compounds of formula I include phosphorous oxychloride and dichlorotriphenylphosphorane, preferably phosphorous oxychloride. Reactions using phosphorous oxychloride are conducted in neat phosphorous oxychloride at a temperature between about 60° C. to about 110° C., for a time period between about 2 hours to about 16 hours. Reactions using dichlorotriphenylphosphorane are conducted in the presence of a base, such as triethylamine, in a polar solvent such as acetonitrile, at temperatures of about 60° C. and reflux for a time period from about 1 hour and about 8 hours.

Compounds of the formula III can be made according to the methods of Scheme 2.

Scheme 2 refers to the preparation of compounds of the formula II, which are intermediates useful in the preparation of compounds of the formula I, in Scheme 1. Referring to Scheme 2, a compound of the formula II, wherein (R$^3$)$_s$-phenyl-Het is of the formula (c) or (f), can be prepared from compounds of the formula VII by reaction with an aminating reagent. Suitable aminating reagents include hydrazines of the formula H$_2$N—NH—R$^7$, in a polar solvent. Suitable solvents include alcohols such as ethanol, propanol, butanol or mixtures of alcohols and acetic acid, preferably ethanol or ethanol/acetic acid. The aforesaid reaction is conducted at a temperature of about 10° C. to about 100° C., preferably at about 22° C. to 65° C., for a period from about 1 hour to about 24 hours, preferably about 3 hours.

Alternatively compounds of the formula III, wherein (R$^3$)$_s$-phenyl-Het is of the formula (e), can be prepared from compounds of the formula VII by reaction with hydroxylamine hydrochloride, and a base. Suitable bases include pyridine or a trialkylamine, preferably pyridine. Suitable solvents include N,N-dimethylformamide, tetrahydrofuran or pyridine, preferably pyridine. The aforesaid reaction is conducted at a temperature from about 0° C. to about 100° C., preferably at about 60° C., for a period from about 1 hour to about 48 hours, preferably about 20 hours.

The compound of formula VII is prepared from a compound of formula IV by reaction with an acetal, such as dimethylformamide-dimethylacetal, at a temperature of about 60° C. to about 90° C., preferably about 80° C. for a period from about 1 hour to about 6 hours, preferably about 3 hours.

Alternatively, compounds of the formula III, wherein (R$^3$)$_s$-phenyl-Het is of the formula (c) or (f), can be prepared from compounds of the formula VIII by reaction with an aminating reagent such as H$_2$N—NH—R$^7$ according to methods analogous to the conversion of compounds of formula VII to formula III.

Alternatively, compounds of the formula III, wherein (R$^3$)$_s$-phenyl-Het is of the formula (e), can be prepared from compounds of the formula VIII by reaction with hydroxylaminehydrochloride according to methods analogous to the conversion of compounds of formula VII to formula III.

The compound of formula VIII is prepared from a compound of formula IV by reaction with an isothiocyanate. Suitable isothiocyanates include compounds of the formula R$^4$—N═C═S. Reactions with isothiocyanates are facilitated by the addition of a base, such as sodium hydride, lithium diisopropylamide or other suitable strong bases. Suitable solvents for the aforesaid reaction include pyridine, N,N-dimethylformamide or tetrahydrofuran, preferably pyridine. The aforesaid reaction is performed from a period of about 0.5 hour to about 4 hours at a temperature of about 0° C. to about 30° C. The deprotonation reaction with above said bases is followed by the addition of a suitable isothiocyanate and is performed for a period from about 10 minutes to about 20 hours, at a temperature of about 0° C. to about 30° C., preferably about 22° C. for a period from about 0.5 hour to about 24 hours.

Alternatively, a compound of the formula III, wherein (R$^3$)$_s$-phenyl-Het is of the formula (d), can be prepared from a compound of formula VI, by reaction with an aldehyde of the formula R$^3$—(C═O)—H in the presence of cuprous acetate and an ammonia source in a polar solvent. Suitable ammonia sources include ammonium trifluoroacetate, ammonia, and ammonium acetate, preferably ammonium acetate. The aforesaid reaction can be run neat or in the presence of a solvent such as alcohols (methanol, ethanol or butanol) and acetic acid. The aforesaid reaction can be run at a temperature from about 20° C. to about 80° C. for a period from about 15 minutes to about 4 hours, preferably neat conditions at about 60° C. for about 2 hours.

The compound of formula VI is prepared from a compound of formula V by reaction with sodium methoxide, or sodium ethoxide, or sodium tert-butoxide, preferably sodium methoxide, in an alcohol solvent, such as methanol, ethanol, isopropanol, preferably methanol, at a temperature of 0° C. to 30° C., preferably at 22° C., for a period of time from 15 minutes to about 3 hours, preferably 30 minutes. The aforesaid reaction is followed by an aqueous acidic work-up.

The compound of formula V is prepared from a compound of formula IV by reaction with $Br_2$ in a polar solvent. Suitable solvents include acetic acid, chloroform or methylene chloride, preferably acetic acid. The aforesaid reaction is conducted at a temperature of about 0° C. to about 30° C. preferably at about 22° C. (room temperature) for a period from about 10 minutes to about 4 hours, preferably about 30 minutes.

Alternatively, a compound of the formula III, wherein $(R^3)_s$-phenyl-Het is of the formula (a), can be prepared from compounds of the formula IX, by reaction with an ammonia source and cuprous acetate and a polar solvent. Suitable ammonia sources include ammonium trifluoroacetate, ammonia, and ammonium acetate, preferably ammonium acetate. The aforesaid reaction can be run neat or in the presence of a solvent such as alcohols (methanol, ethanol or butanol) and acetic acid. The aforesaid reaction can be run at a temperature from about 20° C. to about 80° C. for a period from about 15 minutes to about 4 hours, preferably neat conditions at about 60° C. for about 2 hours.

The compound of formula IX is prepared from a compound of formula IV by reaction with a reagent of the formula

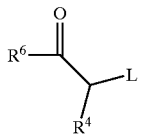

X wherein L is a leaving group such as chloro, bromo, iodo or mesylate, in the presence of a base and a solvent. Suitable bases include NaH and n-butyllithium. Suitable solvents include THF and DMF. The aforesaid reaction can be conducted at a temperature from about −30° C. to about the reflux temperature of the solvent, for a period of about 5 minutes to about 24 hours.

Alternatively, compounds of the formula III(e), can be made from formula IV according to methods described in U.S. Pat. Nos. 5,859,257 or 5,633,272.

The compounds of formulae IV and VI are prepared according to the methods of Scheme 6. Additional routes for the synthesis of compounds related to formula IV are described in the literature: Davies, I. W.; Marcoux, J. F.; Corley, E. G.; Journet, M.; Cai, D. W.; Palucki, M.; Wu, J.; Larsen, R. D.; Rossen, K.; Pye, P. J.; DiMichele, L.; Dormer, P.; Reider, P. J.; *J. Org. Chem.*, Vol. 65, pp. 8415–8420 (2000). The compound of formula X is prepared by methods well known to those skilled in the art.

Alternatively, compounds of formula III(g) and (h) can be prepared from compounds of formula IV according to methods described in the literature (Gauthier, J. Y.; Leblanc, Y.; Black, C.; Chan, C. -C.; Cromlish, W. A.; Gordon, R.; Kennedey, B. P.; Lau, C. K.; Léger, S.; Wang, Z.; Ethier, D.; Guay, J.; Mancini, J.; Riendeau, D.; Tagari, P.; Vickers, P.; Wong, E.; Xu, L.; Prasit, P. Bioorg. Med. Chem. Lett. 1996, 6, 87–92).

Scheme 3 refers to the preparation of compounds of the formula III, wherein $(R^3)_s$-phenyl-Het is of the formula (b) or (d), which are intermediates in Scheme 1, useful in the preparation of compounds of formula I. Referring to Scheme 3, a compound of the formula III, wherein $(R^3)_s$-phenyl-Het is of the formula (b), can be prepared from a compound of the formula XI by reaction with a compound of the formula

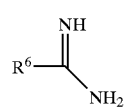

XIII in the presence of a polar solvent. Suitable solvents include N,N-dimethylformamide chloroform, dimethylsulfoxide, tetrahydrofuran, and ethanol, preferably N,N-dimethylformamide. The aforesaid reaction is conducted at a temperature of about 15° C. to about 80° C., preferably 60° C., for a period from about 4 hours to about 4 days, preferably 4 hours.

Alternatively, a compound of the formula III, wherein $(R^3)_s$-phenyl-Het is of the formula (d), can be prepared from a compound of formula XI, by reaction with an aldehyde of the formula $R^6$—(C=O)—H in the presence of a catalyst and a source of ammonia according to methods analogous to those for the conversion of compounds of formula VI to formula III in Scheme 2.

The compound of formula XI, wherein $(R^3)_s$-phenyl-Het is of formula (d), is prepared from a compound of formula XII by reaction with sodium methoxide, or sodium ethoxide, or sodium tert-butoxide, preferably sodium methoxide, in an alcohol solvent, such as methanol, ethanol, isopropanol, preferably methanol, at a temperature of 0° C. to 30° C., preferably at 22° C., for a period of time from 15 minutes to about 3 hours, preferably 30 minutes. The aforesaid reaction is followed by an aqueous acidic work-up.

The compound of formula XII is prepared from a compound of the formula XIV by reaction with $Br_2$ in a polar or nonpolar solvent. Suitable solvents include acetic acid, dichloromethane, chloroform, preferably acetic acid. The aforesaid reaction is conducted at a temperature of about 0° C. to about 30° C. preferably at about 22° C. (room temperature) for a period from about 10 minutes to four hours, preferably 30 minutes.

The compound of formula XIV is prepared from a compound of the formula XV, wherein $p^2$ and $p^3$ are independently $(C_1-C_6)$alkyl, by reaction with a Grignard reagent of the formula $(R^3)_s$-phenyl-$(CH_2)$-M, wherein M is an activating group such as magnesium bromide or chloride in a solvent. Suitable solvents include tetrahydrofuran, diethyl ether, dioxane, dimethylethyl ether, preferably tetrahydrofuran. The aforesaid reaction is run at a temperature of about 0° C. to about 30° C., preferably about 22° C., for a period of about 6 hours to about 48 hours, preferably about 6 hours.

The compound of formula XV can be made by methods well known to those of ordinary skill in the art, see Gomtsyan, A., *Org. Lett.*, 2, 11–13 (2000). Reagents of the formula $(R^3)_s$-phenyl-$(CH_2)$-M are commercially available or may be prepared by one skilled in the art.

Scheme 4 refers to the preparation of compounds of formula III, wherein $(R^3)_s$-phenyl-Het is of the formula (b)

or (d), $R^6$ is hydrogen and L is a suitable leaving group as described in Scheme 1. Referring to Scheme 4, compounds of the formula II, wherein $(R^3)_s$-phenyl-Het is of the formula (d), can be prepared from compounds of formula XVI by reaction with an isocyanide of formula

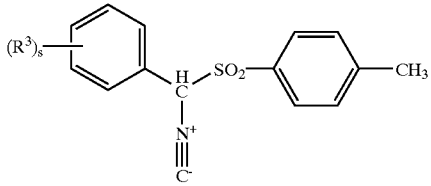

XVII in the presence of a base. Suitable bases include potassium carbonate, triethylamine, and piperazine, preferably potassium carbonate. Suitable solvents include polar solvents such as tetrahydrofuran, or N,N-dimethylformamide, preferably in N,N-dimethylformamide. The aforesaid reaction may be run at a temperature between about 22° C. and about 70° C., preferably at about 22° C. for a period from about 2 hours to about 4 hours, followed by about 6 hours to about 10 hours at a temperature of about 70° C.

Compounds of formula III, wherein $(R^3)_s$-phenyl-Het is of the formula (b), can be prepared in an analogous way by first preparation of the intermediate imine of formula XVIII by reaction of compounds of formula XVI with a suitable amine of the formula $NH_2R^5$ under dehydrating conditions. Such conditions include the treatment of compounds of formula XVI and an amine $NH_2R^5$ in a solvent such as tetrahydrofuran or dichloromethane with a dehydrating agent such as anhydrous magnesium sulfate or molecular sieves. Alternatively, the imine of formula XVIII can be prepared and subsequently reacted in an aqueous media as described in the literature: (Sisko, J.; Kassik, A. J.; Mellinger, M.; Filan, J. J.; Allen, A; Olsen, M. A.; J. Org. Chem. 2000, 65, 1516–1524). Reactions of imines of formula XVI with suitable isocyanides of formula XVII are conducted at about 22° C. for a time period from about 1 day to about 21 days, preferably about 1 day.

Compounds of formula XVI are known in the literature (when L is chloro see: Corey, E. J.; Loh, T P.; Achyutha Rao, S.; Daley, D. C.; Sarshar, S. J. Org. Chem., 1993, 58, 5600–5602) or can be prepared in a manner well known to one skilled in the art.

Scheme 5 refers alternative preparations of compounds of the formula III, which are intermediates in Scheme 1, useful in the preparation of compounds of formula I. Referring to Scheme 5, a compound of the formula III can be prepared from a compound of the formula XIX by methods described previously in Scheme 2.

A compound of formula XIX can be prepared from a compound of the formula XX by reaction with an ester of the formula $(R^3)_s$-phenyl-$CO_2P^1$, wherein $P^1$ is methyl or ethyl, in the presence of a base and a solvent. Suitable bases include sodium hydride, lithium diisopropylamide, or sodium alkoxides, preferably sodium ethoxide. Suitable solvents include alcohols such as methanol, ethanol, propanol, butanol, or tetrahydrofuran, preferably ethanol. The aforesaid reaction is conducted at a temperature from about 23° C. to about 65° C., preferably at about 50° C., for a period from about 2 hours to about 24 hours, preferably about 20 hours.

The compound of the formula XX can be prepared by methods well known to those skilled in the art.

Scheme 6 refers to the preparation of compounds of formulas IV and VI, which are intermediates in Scheme 2, useful in the preparation of compounds of formula I.

Compounds of formula IV can be prepared from compounds of formula XXI, wherein OL is acetoxy, bromo or chloro, by reaction with a reducing agent. Suitable reducing agents for the reduction of compounds of the formula XXI, when OL is acetoxy, include titanium on graphite, nickel chloride and sodium borohydride. Suitable reducing agents for the reduction of compounds of the formula XXI, when OL is bromo or chloro, include zinc dust, sodium naphthalide, and samarium iodide.

Compounds of formula XXI, wherein OL is a leaving group such as acetoxy, can be prepared from compounds of formula VI by reaction with an acylating reagent such as acetyl chloride or acetic anhydride in the presence of a base such as pyridine at a temperature from about 10° C. to about 65° C., preferably at about 50° C., for a period from about 1 hour to about 4 hours, preferably about 2 hours. Compounds of formula XXI, wherein OL is a leaving group such as chloro or bromo, can be prepared from compounds of formula VI by reaction with halogenating reagent such as oxalyl chloride, thionyl chloride, phosphorous pentachloride and phosphorous oxychloride, bromine in acetic acid, at a temperature from about 10° C. to about 65° C., preferably at about 50° C., for a period from about 1 hour to about 4 hours, preferably about 2 hours.

Compounds of formula VI can be prepared from compounds of formula XXII by reaction with a suitably substituted Grignard reagent of the formula $(R^3)_s$-phenyl-M, wherein M is an activation group such as magnesium bromide or chloride (see for example: Jackson, W. R.; Jacobs, H. A.; Jayatilake, G. S.; Matthews, B. R.; Watson, K. G. Aust. J. Chem. 1990, 43, 2045–2062). Reagents of the formula $(R^3)_s$-phenyl-M are commercially available or may be prepared by one skilled in the art.

The preparation and conversion of compounds of formula XVI into trimethylsilyl cyanohydrins of formula XXII can be performed by methods known to those skilled in the art such as for example Pirrung, M.; Shuey, S. W.; J. Org. Chem. 1994, 59, 3890–3897.

Scheme 7 refers to the preparation of compounds of the formula IV, which are intermediates for the preparation of compounds of formula III in Scheme 2. Referring to Scheme 7, a compound of the formula IV is prepared from a compound of formula XXIII by reaction with a Grignard reagent of the formula $(R^3)_s$-phenyl-M, wherein M is an activating group such as magnesium bromide or magnesium chloride in a solvent. Suitable solvents include tetrahydrofuran, dioxane, dimethylethyl ether or diethyl ether, preferably tetrahydrofuran. The aforesaid reaction is conducted at a temperature of about −78° C. to 0° C. for a period from about 10 minutes to about 24 hours preferably about 2 hours. Reagents of the formula $(R^3)_s$-phenyl-M are commercially available or may be prepared by one skilled in the art.

A compound of formula XXIII is prepared from a compound of formula XXIV by reaction with a hydroxylamine of the formula

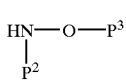

XXV wherein $P^2$ and $P^3$ are independently $(C_1-C_6)$alkyl, preferably methyl, and an activating agent. Suitable activating agents include carbonyldiimidazole or oxalyl chloride, preferably carbonyldiimidazole. Suitable solvents include methylene chloride or dichloroethane.

Compounds of the formula XXIV are prepared from compounds of formula XXVI by acid hydrolysis, such as by reaction with sulfuric acid/water (preferably 1:1) at a temperature of about 100° C. to about 120° C., preferably about 110° C. for a period from about 1 hour to about 6 hours, preferably about 4 hours. Alternatively, a compound of the formula XXII is prepared by base hydrolysis, such as by reaction with lithium hydroxide in water at a temperature of about 23° C. to about 100° C., preferably at a temperature of about 80° C. for a period of about 4 to 10 hours.

Scheme 8 refers to the preparation of compounds of formula I, wherein $(R^3)_s$-phenyl-Het is (b) or (d), and $R^6$ is hydrogen, which are intermediates in Scheme 1, useful in the preparation of compounds of formula I. Referring to Scheme 8, a compound of the formula I. wherein $(R^3)_s$-phenyl-Het is of the formula (b) or (d), and $R^6$ is hydrogen, can be prepared from aldehydes of formula XXVII as described previously in Scheme 4 for the conversion of compounds of formula XVI to compounds of formula III. Compounds of formula XXVII are prepared from compounds of formula XXVIII by a formylation reaction. Suitable conditions for formylation include metal halogen exchange with isopropylmagnesium chloride in a solvent such as tetrahydrofuran at a temperature of about 0° C., for a period of time of about 30 minutes, followed by the addition of N,N-dimethylformamide at a temperature of about 0° C., followed by a period of time of about 2.5 hours at a temperature of about 50° C.

Compounds of formula XXVIII are prepared as described in the literature (Moran, D. B.; Morton, G. O.; Albright, J. D., *J. Heterocycl. Chem.*, Vol. 23, pp. 1071–1077 (1986)) or from compounds of formula XXIX wherein L' is bromo or fluoro as described in Scheme 1 for the conversion of compounds of formula III to compounds of formula I. Compounds of formula XXIX are commercially available.

The compounds of the formula I which are basic in nature are capable of forming a wide variety of different salts with various inorganic and organic acids. Although such salts must be pharmaceutically acceptable for administration to animals, it is often desirable in practice to initially isolate a compound of the formula I from the reaction mixture as a pharmaceutically unacceptable salt and then simply convert the latter back to the free base compound by treatment with an alkaline reagent, and subsequently convert the free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent such as methanol or ethanol. Upon careful evaporation of the solvent, the desired solid salt is obtained.

The acids which are used to prepare the pharmaceutically acceptable acid addition salts of the base compounds of this invention are those which form non-toxic acid addition salts, i.e., salts containing pharmacologically acceptable anions, such as hydrochloride, hydrobromide, hydroiodide, nitrate, sulfate or bisulfate, phosphate or acid phosphate, acetate, lactate, citrate or acid citrate, tartrate or bitartrate, succinate, maleate, fumarate, gluconate, saccharate, benzoate, methanesulfonate and pamoate [i.e., 1,1'-methylene-bis-(2-hydroxy-3-naphthoate)] salts.

Those compounds of the formula I which are also acidic in nature, e.g., where $R^1$–$R^{16}$ includes a COOH or tetrazole moiety, are capable of forming base salts with various pharmacologically acceptable cations. Examples of such salts include the alkali metal or alkaline-earth metal salts and particularly, the sodium and potassium salts. These salts are all prepared by conventional techniques. The chemical bases which are used as reagents to prepare the pharmaceutically acceptable base salts of this invention are those which form non-toxic base salts with the herein described acidic compounds of formula I. These non-toxic base salts include those derived from such pharmacologically acceptable cations as sodium, potassium, calcium and magnesium, etc. These salts can easily be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum product yields.

The activity of the compounds of the invention for the various disorders described above can be determined according to one or more of the following assays. All of the compounds of the invention, that were tested, had an $IC_{50}$ of less than 10 μM in the TNFα and MAPKAP in vitro assays and an $ED_{50}$ of less than 50 mg/kg in the in vivo TNFα assay.

The compounds of the present invention also possess differential activity (i.e. are selective for) for one or more p38 kinases (i.e. α, β, γ, and δ). Certain compounds are selective for p38α over p38β, γ, and δ, other compounds are selective for p38β over p38α, γ, and δ, other compounds are selective for p38 α and β over p38 γ and δ. Selectivity is measured in standard assays as a $IC_{50}$ ratio of inhibition in each assay.

Inhibition of TNF-Alpha Production by Human LPS-Treaded Monocytes

Mononuclear cells are isolated from heparinized blood (1.5 ml of 1000 units/ml heparin for injection, Elkins-Sinn, Inc. added to each 50 ml sample) using Accuspin System-Histopaque-1077 tubes (Sigma A-7054). Thirty-five milliliters of whole blood are added to each tube and the tubes are centrifuged at 2100 rpm for 20 minutes in a Beckman GS-6KR centrifuge with the brake off at room temperature. The mononuclear cells which collect at the interface are removed, diluted with Macrophage serum free medium (Gibco-BRL) (Medium) to achieve a final volume of 50 ml, and collected by centrifugation for 10 minutes. The supernatant is discarded and the cell pellet is washed 2 times with 50 ml of Medium. A sample of the suspended cells is taken before the second wash for counting. Based on this count, the washed cells are diluted with Medium containing 1% FBS to a final concentration of $2.7 \times 10^6$ cells/ml and 75 μl of the cell suspension is added to each well of a 96 well plate.

Compound Preparation

Compounds are routinely tested at final concentrations from 2 μM to 0.016 μM, but may be tested at other concentrations, depending on activity. Test agents are diluted with DMSO to a final concentration of 2 mM. From this stock solution, compounds are first diluted 1:25 (5 μl of 2 mM stock+120 μl Medium containing 400 ng/ml LPS and 1% FBS then 40 μl of this dilution is diluted with 360 μl of Medium with LPS. Serial dilutions (1/5) are performed by transferring 20 μl of this dilution to 80 μl of Medium containing both LPS and 0.4% DMSO, resulting in solutions containing 8 μM, 1.6 μM, 0.32 μM and 0.064 μM of test agent.

Assay

The assay is initiated by adding 25 µl of the diluted compounds to the mononuclear cell suspension and incubating the cells at 37 C. and 5% $CO_2$ for 4 hours.

The 96-well plates are then centrifuged for 10 minutes at 2000 rpm at 4° C. in a Beckman GS-6KR centrifuge to remove cells and cell debris. A 90 µl aliquot of each supernatant is removed and transferred to a 96 well round bottom plate, and this plate is centrifuged a second time to insure that all cell debris is removed. 80 µl of the supernatant is removed and transferred to a new round bottom plate.

Supernatants are analyzed for TNF-α content using R&D ELISA. 25 µl of each sample is added to an ELISA well containing 25 µl of assay diluent RD1F and 75 µl of assay diluent RD5. The assay is run following kit directions except 100 µl of conjugate and substrate solutions are used.

Interpretation

The amount of TNF-α immunoreactivity in the samples is calculated as follows:

% Control=(X-B)/(TOT-B)×100 where X=$OD_{450}$ nm of the test compound well

B=$OD_{450}$ of Reagent Blank wells on the ELISA

Total=$OD_{450}$ of cells that were treated with 0.1% DMSO only.

MAPKAP Kinase-2 Assay

Monocyte Preparation

Mononuclear cells are collected from heparinized human blood as detailed above. The washed cells are seeded into 6-well cluster plates at a density of 1×10$^7$ cells/well (in 2 ml of Medium). The plates are incubated at 37° C. in a 5% $CO_2$ environment for 2 hours to allow adherence of the monocytes, after which time media supernatants containing non-adherent cells are removed by aspiration and 2 ml of fresh medium are added to each well. Plates are incubated overnight at 37° C. in a 5% $CO_2$ environment.

Cell Activation

Media are removed by aspiration. The attached cells are rinsed twice with fresh Medium, then 2 ml of D-MEM medium containing 10% heat inactivated FBS are added to each well. Test compounds are prepared as 30 mM stock solutions in DMSO and diluted to 1250, 250, 50, 10, 2, and 0.4 µM in D-MEM containing 1% DMSO and 10% FBS. To individual wells of the monocyte cultures, 20 µl of these test agent dilutions are added resulting in final test agent concentrations of 12.5, 2.5, 0.5, 0.1, 0.02 and 0.004 µM. After a 10 minute preincubation period, 20 µl of a 10 µg/ml LPS solution are added to each well and the plates are incubated at 37° C. for 30 min. Media subsequently are removed by aspiration, the attached monocytes are rinsed twice with phosphate buffered saline, then 1 ml of phosphate buffered saline containing 1% Triton X-100 (Lysis Buffer; also containing 1 Complete™ tablet [Boehringer #1697498] per 10 ml of buffer) is added to each well. The plates are incubated on ice for 10 minutes, after which the lysates are harvested and transferred to centrifugation tubes. After all samples are harvested, they are clarified by centrifugation (45,000 rpm for 20 min) and the supernatants recovered.

MAPKAP Kinase-2 Immunoprecipitation

5 µl of anti-MAPKAP kinase-2 antiserum (Upstate Biotechnology #06-534) is added to a microcentrifuge tube (1 tube for each of the above cell lysates) containing 1 ml of a 5% suspension of Protein G-Sepharose (Sigma #P3296) in PBS. These mixtures are incubated for 1 hour at 4° C. (with rocking) after which the beads, containing bound IgG, are recovered by centrifugation and washed twice with 1 ml of 50 mM Tris, pH 7.5, 1 mM EDTA, 1 mM EGTA, 0.5 mM orthovanadate, 0.1% 2-mercaptoethanol, 1% Triton X-100, 5 mM sodium pyrophosphate, 10 mM sodium β-glycerophosphate, 0.1 mM phenylmethylsulfonyl fluoride, 1 µg/ml leupeptin, 1 µg/ml pepstatin, and 50 mM sodium fluoride (Buffer A) by repeated centrifugation. An individual monocyte cell extract (prepared above) is then transferred to each tube containing a pellet of IgG-coated Protein G-Sepharose, and these mixtures are incubated for 2 hours at 4° C. (with rocking). The beads subsequently are harvested by centrifugation, and the resulting bead pellets are washed once with 0.5 ml of Buffer A containing 0.5 M NaCl, once with 0.5 ml of Buffer A, and once with 0.1 ml of a buffer composed of 20 mM MOPS, pH 7.2, 25 mM sodium β-glycerophosphate 5 mM EGTA, 1 mM orthovanadate, and 1 mM dithiothreitol (Buffer B).

MAPKAP Kinase-2 Activity Assessment

A kinase reaction mixture stock is prepared as follows: 2.2 µl of 10 mCi/ml γ[$^{32}$P]ATP, 88 µl of 1.3 µg/ml solution of MAPKAP Kinase-2 substrate peptide (Upstate Biotechnology #12-240), 11 µl of 10 mM ATP, 8.8 µl of 1 M $MgCl_2$, and 770 µl of Buffer B. To each of the immune complex-Protein G-pellets, 40 µl of the kinase reaction mixture are added and the tubes are incubated for 30 minutes at 30° C. The tubes then are clarified by centrifugation and 25 µl of each supernatant is spotted onto a P81 filter paper disk (Whatman #3698-023). After allowing all fluid to soak into the filter, each disk is placed into an individual well of 6-well cluster plates and the filters are washed sequentially with 2 ml of 0.75% phosphoric acid (3 washes/15 min each) and once with acetone (10 min). The filters then are air dried and transferred to liquid scintillation vials containing 5 ml of scintillation fluid. Radioactivity is determined in a liquid scintillation counter. The amount of radioactivity bound to the filter at each test agent concentration is expressed as a percentage of that observed from cells stimulated with LPS in the absence of a test agent.

In Vivo Inhibition of TNFα

Rats were weighed and dosed with vehicle (0.5% methyl cellulose, Sigma) or drug. One hour later, animals were injected i.p. with LPS (50 ug/rat, Sigma L-4130). Ninety minutes later, animals were sacrificed by asphyxiation with $CO_2$ and bled by cardiac puncture. Blood was collected in Vaccutainer tubes and spun for 20 minutes at 3000 rpm. Serum was assayed for TNFα levels using an ELISA (R&D Systems).

This invention also encompasses pharmaceutical compositions containing and methods of treating or preventing comprising administering prodrugs of compounds of the formula I. Compounds of formula I having free amino, amido, hydroxy or carboxylic groups can be converted into prodrugs. Prodrugs include compounds wherein an amino acid residue, or a polypeptide chain of two or more (e.g., two, three or four) amino acid residues which are covalently joined through peptide bonds to free amino, hydroxy or carboxylic acid groups of compounds of formula I. The amino acid residues include the 20 naturally occurring amino acids commonly designated by three letter symbols and also include, 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone. Prodrugs also include compounds wherein carbonates, carbamates, amides and alkyl esters which are covalently bonded to the above substituents of formula I through the carbonyl carbon prodrug sidechain.

The compositions of the present invention may be formulated in a conventional manner using one or more pharmaceutically acceptable carriers. Thus, the active compounds of the invention may be formulated for oral, buccal, intranasal, parenteral (e.g., intravenous, intramuscular or subcutaneous) or rectal administration or in a form suitable for administration by inhalation or insufflation.

For oral administration, the pharmaceutical compositions may take the form of, for example, tablets or capsules prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, methyl cellulose or hydrogenated edible fats); emulsifying agents (e.g., lecithin or acacia); non-aqueous vehicles (e.g., almond oil, oily esters or ethyl alcohol); and preservatives (e.g., methyl or propyl p-hydroxybenzoates or sorbic acid).

For buccal administration, the composition may take the form of tablets or lozenges formulated in conventional manner.

The compounds of formula I can also be formulated for sustained delivery according to methods well known to those of ordinary skill in the art. Examples of such formulations can be found in U.S. Pat. Nos. 3,538,214, 4,060,598, 4,173,626, 3,119,742, and 3,492,397, which are herein incorporated by reference in their entirety.

The active compounds of the invention may be formulated for parenteral administration by injection, including using conventional catheterization techniques or infusion. Formulations for injection may be presented in unit dosage form, e.g., in ampules or in multi-dose containers, with an added preservative. The compositions may take such forms as suspensions, solutions or emulsions in oily or aqueous vehicles, and may contain formulating agents such as suspending, stabilizing and/or dispersing agents. Alternatively, the active ingredient may be in powder form for reconstitution with a suitable vehicle, e.g., sterile pyrogen-free water, before use.

The active compounds of the invention may also be formulated in rectal compositions such as suppositories or retention enemas, e.g., containing conventional suppository bases such as cocoa butter or other glycerides.

For intranasal administration or administration by inhalation, the active compounds of the invention are conveniently delivered in the form of a solution or suspension from a pump spray container that is squeezed or pumped by the patient or as an aerosol spray presentation from a pressurized container or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. The pressurized container or nebulizer may contain a solution or suspension of the active compound. Capsules and cartridges (made, for example, from gelatin) for use in an inhaler or insufflator may be formulated containing a powder mix of a compound of the invention and a suitable powder base such as lactose or starch.

A proposed dose of the active compounds of the invention for oral, parenteral or buccal administration to the average adult human for the treatment of the conditions referred to above (e.g., inflammation) is 0.1 to 200 mg of the active ingredient per unit dose which could be administered, for example, 1 to 4 times per day.

Aerosol formulations for treatment of the conditions referred to above (e.g., adult respiratory distress syndrome) in the average adult human are preferably arranged so that each metered dose or "puff" of aerosol contains 20 $\mu$g to 1000 $\mu$g of the compound of the invention. The overall daily dose with an aerosol will be within the range 100 $\mu$g to 10 mg. Administration may be several times daily, for example 2, 3, 4 or 8 times, giving for example, 1, 2 or 3 doses each time.

Aerosol combination formulations for treatment of the conditions referred to above in the average adult human are preferably arranged so that each metered dose or "puff" of aerosol contains from about 0.01 mg to about 100 mg of the active compound of this invention, preferably from about 1 mg to about 10 mg of such compound. Administration may be several times daily, for example 2, 3, 4 or 8 times, giving for example, 1, 2 or 3 doses each time.

Aerosol formulations for treatment of the conditions referred to above in the average adult human are preferably arranged so that each metered dose or "puff" of aerosol contains from about 0.01 mg to about 2000 mg of an ERK kinase inhibitor, preferably from about 1 mg to about 200 mg of p38 kinase inhibitor. Administration may be several times daily, for example 2, 3, 4 or 8 times, giving for example, 1, 2 or 3 doses each time.

The following Examples illustrate the preparation of the compounds of the present invention. Melting points are uncorrected. NMR data are reported in parts per million (d) and are referenced to the deuterium lock signal from the sample solvent (deuteriochloroform unless otherwise specified). Mass Spectral data were obtained using a Micromass ZMD APCI Mass Spectrometer equipped with a Gilson gradient high performance liquid chromatograph. The following solvents and gradients were used for the analysis. Solvent A; 98% water/2% acetonirile/0.01% formic acid and solvent B; acetonitrile containing 0.005% formic acid. Typically, a gradient was run over a period of about 4 minutes starting at 95% solvent A and ending with 100% solvent B. The mass spectrum of the major eluting component was then obtained in positive or negative ion mode scanning a molecular weight range from 165 amu to 1100 amu. Specific rotations were measured at room temperature using the sodium D line (589 nm). Commercial reagents were utilized without further purification. THF refers to tetrahydrofuran. DMF refers to N,N-dimethylformamide. Chromatography refers to column chromatography performed using 32–63 mm silica gel and executed under nitrogen pressure (flash chromatography) conditions. Room or ambient temperature refers to 20–25° C. All non-aqueous

EXAMPLE 1

3-Isopropyl-6-(4-phenyl-oxazol-5-yl)-[1,2,4]triazolo[4,3-a]pyridine

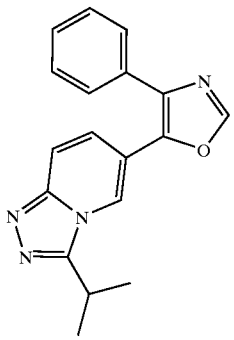

A) 6-Chloro-N-methoxy-N-methyl-nicotinamide

To a solution of 6-chloronicotine carboxylic acid (40 g, 284 mmol) in dichloromethane (500 mL) was added 5 mL of N,N-dimethylformamide (DMF). At ambient temperature, a 2 M solution of oxalyl chloride in dichloromethane (167 mL, 330 mmol) was added dropwise. The reaction mixture was heated to 40° C. for two hours and then stirred at room temperature for 18 hours. The acid chloride solution was concentrated in vacuo, and placed under vacuum for one hour. To a solution of N,O-dimethylhydroxylamine hydrochloride (32 g, 330 mmol) in dichloromethane (400 mL) was added triethylamine (70 mL); the mixture was then cooled to 0° C. A solution of the previously formed acid chloride in dichloromethane (100 mL) was added dropwise at a rate keeping the temperature at 0° C. After the addition, the ice bath was removed and the reaction mixture was allowed to warm to room temperature and stirred for 20 hours. The reaction mixture was then layered with saturated sodium hydrogenphosphate and the organic layer was extracted, washed with water, brine, dried with sodium sulfate and filtered. The solution was concentrated in vacuo yielding the title compound (48.9 g, 96%).

B) 6-Chloro-pyridine-3-carbaldehyde

Corey, E. J.; Loh, T-P.; Achyutha Rao, S.; Daley, D. C.; Sarshar, S. J. Org. Chem. 1993, 58, 5600–5602. In a flame-dried flask under nitrogen a solution of 6-Chloro-N-methoxy-N-methyl-nicotinamide (5 g, 25 mmol) in tetrahydrofuran (50 mL) was cooled in an ice bath. A 1.5 M solution of diisobutylaluminum hydride in toluene (24.9 mL, 37 mmol) was added at a rate keeping the internal temperature of the reaction below 20° C. The reaction then stirred for 3 hours at room temperature. The completed reaction was cooled in an ice bath and carefully quenched with 1N hydrochloric acid. Stirring continued for 15 minutes more without the ice bath. The reaction mixture was extracted with ethyl acetate; the extracts were washed with brine, dried over magnesium sulfate, filtered and the filtrate was concentrated in vacuo to yield a yellow solid (3.3 g). The solids were dissolved in ether and filtered through diatomaceous earth to remove some insoluble material. The filtrate was diluted with hexanes and petroleum ether and the named compound was allowed to crystallize out over night. The precipitate was collected and dried (850 mg, 24%). Melting point 77–78° C. Second crop was collected and dried (375 mg, 11%).

C) 2-Chloro-5-(4-phenyl-oxazol-5-yl)-pyridine

A solution of 6-Chloro-pyridine-3-carbaldehyde (1.98 g, 14.0 mmol), phenyl-toylsulfonomethylisocyanide (Joseph Sisko, Mark Mellinger, Peter W. Sheldrake, and Neil H. Baine, Organic Synthesis, Vol. 77, 198–205 (1999)) (3.8 g, 14.0 mmol), and potassium carbonate (2.13 g, 15.4 mmol) dissolved in DMF (20 mL) stirred at ambient temperature for 4 hours, then it was heated at 70° C. for 18 hours. The reaction was cooled to room temperature, quenched with water, and the mixture was extracted with ethyl acetate (3×). The combined organic layers were washed with water, brine, dried over sodium sulfate, filtered and the filtrate was concentrated in vacuo to a dark oil. The residue was purified by flash chromatography (eluting with hexanes/ethyl acetate 4:1) to afford the title compound as a yellow solid 2.55 g (71%).

D) 5-(4-Phenyl-oxazol-5-yl)-pyridin-2-yl-hydrazine

A suspension of 2-Chloro-5-(4-phenyl-oxazol-5-yl)-pyridine (2.55 g, 9.9 mmol) in hydrazine (8 mL) was heated at 70° C. until a solution formed (approximately 20 minutes). The hydrazine product was removed from the heat and concentrated in vacuo affording the above named compound as a dark solid (2.5 g, 100%).

E) Isobutyric Acid N'-[5-(4-Phenyl-oxazol-5-yl)-pyridin-2-yl]-hydrazide

To a solution of 5-(4-Phenyl-oxazol-5-yl)-pyridin-2-yl-hydrazine (2.5 g, 9.9 mmol), and N,N-diisopropylethylamine (8.6 mL, 50 mmol) in dichloromethane (8 mL) at 0° C. was added dropwise isobutyryl chloride (1.04 mL, 9.9 mmol); the mixture was stirred at 0° C. for 2 hours. The reaction was quenched with water and extracted with dichloromethane (3×). The combined organic layers were washed with water, brine, dried over sodium sulfate, filtered, and the filtrate was concentrated in vacuo to a dark sticky solid. The residue was purified by flash chromatography (eluting with ethyl acetate/hexanes 3:1) to give the title compound as a yellow solid.

F) 3-Isopropyl-6-(4-phenyl-oxazol-5-yl)-[1,2,4]triazolo[4,3-a]pyridine

Isobutyric acid N'-[5-(4-phenyl-oxazol-5-yl)-pyridin-2-yl]-hydrazide (730 mg, 2.26 mmol) was taken up in phosphorous oxychloride (10 mL) and heated at 75° C. for 18 hours. The reaction was cooled with an ice bath, added to a beaker of water (50 mL), and the mixture was made basic by dropwise addition with 3 N sodium hydroxide. The basic mixture was extracted with ethyl acetate (3×); the combined organic layers were washed with brine, dried over sodium sulfate, filtered and the filtrate was concentrated in vacuo to a yellow oil. The residue was recrystallized from ethyl acetate/methanol (95/5) affording the title compound as yellow crystals (294 mg, 43%). The filtrate was purified by flash chromatography (eluting with ethyl acetate/methanol 97:3) to give more of the title compound (220 mg, 32%). LCMS (m/z) 305 M+1. $^1$H NMR (400 MHz, CDCl$_3$) δ 8.22 (s 1 H), 8.05 (s, 1 H), 7.84 (d, 1 H, J=9.8 Hz), 7.64–7.66 (m, 2 H), 7.44 7.49 (m, 4 H), 3.29–3.34 (m, 1 H), 1.51 (d, 6 H, J=7.2 Hz).

EXAMPLE 2

3-Ethyl-6-(4-m-tolyl-oxazol-5-yl)-[1,2,4]triazolo[4,3-a]pyridine

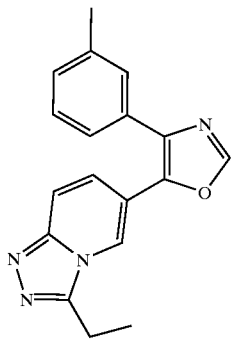

This compound was prepared in an analogous manner to Example 1, starting with 3-methylphenyl-toylsulfonomethylisocyanide (Joseph Sisko, Mark Mellinger, Peter W. Sheldrake, and Neil H. Baine, *Organic Synthesis*, Vol. 77, 198–205 (1999); Joseph Sisko, Mark Mellinger, Peter W. Sheldrake, and Neil H. Baine, *Tetrahedron Letters*, Vol. 37, No. 45, 8113–8116, (1996); U.S. Pat. No. 5,756,499; prepared in an analogous manner starting with 3-methylbenzylaldehyde) in step C and propionyl chloride in step E. LCMS (m/z) 305 M+1.

EXAMPLE 3

3-Cyclopropyl-6-[4-(4-fluoro-phenyl)-oxazol-5-yl]-[1,2,4]triazolo[4,3-a]pyridine

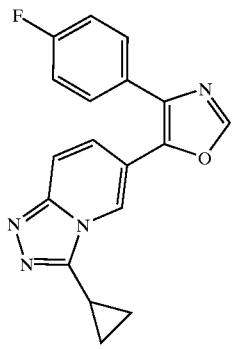

This compound was prepared in an analogous manner to Example 1, starting with 4-fluorophenyl-toylsulfonomethylisocyanide (Joseph Sisko, Mark Mellinger, Peter W. Sheldrake, and Neil H. Baine, *Tetrahedron Letters*, Vol. 37, No. 45, 8113–8116, (1996); U.S. Pat. No. 5,756,499) in step C and cyclopropanecarbonyl chloride in step E. LCMS (m/z) 321 M+1.

EXAMPLE 4

3-Cyclobutyl-6-[4-(4-fluoro-phenyl)-oxazol-5-yl-)-[1,2,4]triazolo[4,3-a]pyridine

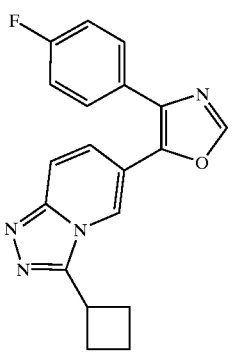

This compound was prepared in an analogous manner to Example 1, starting with 4-fluorophenyl-toylsulfonomethylisocyanide in step C and cyclobutanecarbonyl chloride in step E. LCMS (m/z) 335 M+1.

EXAMPLE 5

3-Difluoromethyl-6-(4-phenyl-oxazol-5-yl)-[1,2,4]triazolo[4,3-a]pyridine

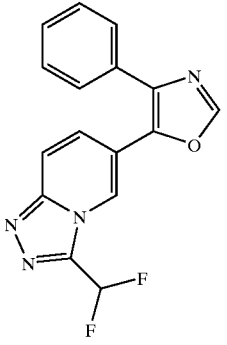

This compound was prepared in an analogous manner to Example 1, starting with the acid chloride of difluoroacetic acid (made using oxalyl chloride in dichloromethane with 1 drop of DMF) in step E and using dichlorotriphenyl phosphorane in acetonitrile with triethylamine in step F. LCMS (m/z) 313 M+1.

EXAMPLE 6

3-Isoxazol-5-yl-6-(4-phenyl-oxazol-5-yl)-[1,2,4]triazolo[4,3-a]pyridine

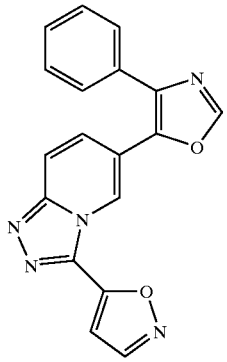

This compound was prepared in an analogous manner to Example 1, starting with the acid chloride of isoxazol-5-carboxylic acid (made using oxalyl chloride in dichloromethane with 1 drop of DMF) in step E. LCMS (m/z) 330 M+1.

EXAMPLE 7

6-(4-Phenyl-oxazol-5-yl)-3-(2,2,2-trifluoro-ethyl)-[1,2,4]triazolo[4,3-a]pyridine

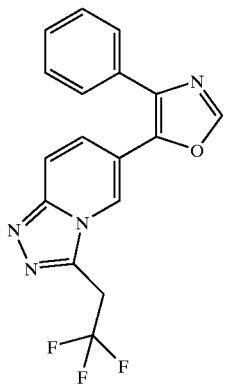

This compound was prepared in an analogous manner to Example 1, starting with the acid chloride of 3,3,3-trifluoropropionic acid (made using oxalyl chloride in dichloromethane with 1 drop of DMF) in step E and using dichlorotriphenyl phosphorane in acetonitrile with triethylamine in step E. LCMS (m/z) 345 M+1.

EXAMPLE 8

3-Cyclobutyl-6-(4-phenyl-oxazol-5-yl)-[1,2,4]triazolo[4,3-a]pyridine

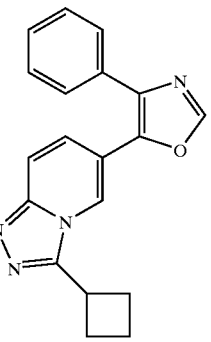

This compound was prepared in an analogous manner to Example 1, starting with cyclobutanecarbonyl chloride in step E. LCMS (m/z) 317 M+1.

EXAMPLE 9

3-Cyclopropyl-6-(4-phenyl-oxazol-5-yl)-[1,2,4]triazolo[4,3-a]pyridine

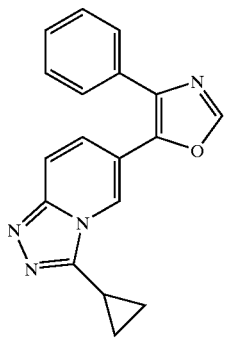

This compound was prepared in an analogous manner to Example 1, starting with cyclopropanecarbonyl chloride in step E. LCMS (m/z) 303 M+1.

EXAMPLE 10

3-Ethyl-6-(4-phenyl-oxazol-5-yl)-[1,2,4]triazolo[4,3-a]pyridine

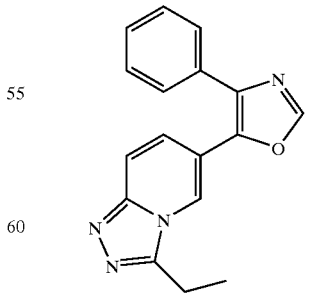

This compound was prepared in an analogous manner to Example 1, starting with propionyl chloride in step E. LCMS (m/z) 291 M+1.

EXAMPLE 11

3-Ethyl-6-[4-(4-fluoro-phenyl)-oxazol-5-yl]-[1,2,4]triazolo[4,3-a]pyridine

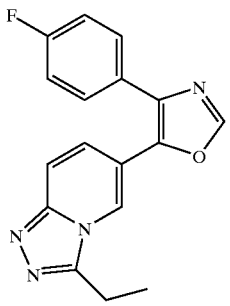

This compound was prepared in an analogous manner to Example 1, starting with 4-fluorophenyl-toylsulfonomethylisocyanide in step C and propionyl chloride in step E. LCMS (m/z) 309 M+1.

EXAMPLE 12

6-[4-(4-Fluoro-phenyl)-oxazol-5-yl]-3-isopropyl-[1,2,4]triazolo[4,3-a]pyridine

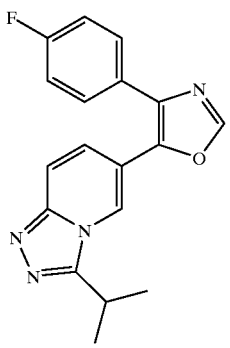

This compound was prepared in an analogous manner to Example 1, starting with 4-fluorophenyl-toylsulfonomethylisocyanide in step C. LCMS (m/z) 323 M+1.

EXAMPLE 13

3-Cyclobutyl-6-(4-m-tolyl-oxazol-5-yl)-[1,2,4]triazolo[4,3-a]pyridine

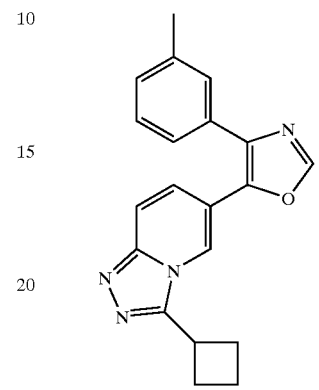

This compound was prepared in an analogous manner to Example 1, starting with 3-methylphenyl-toylsulfonomethylisocyanide in step C and cyclobutanecarbonyl chloride in step E. LCMS (m,z) 331 M+1.

EXAMPLE 14

3-Isopropyl-6-(4-m-tolyl-oxazol-5-yl)-[1,2,4]triazolo[4,3-a]pyridine

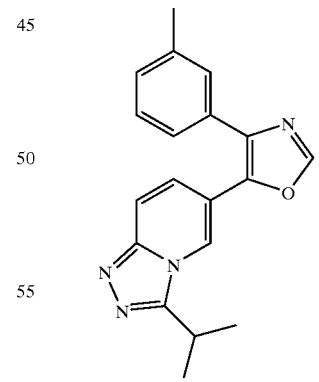

This compound was prepared in an analogous manner to Example 1, starting with 3-methylphenyl-toylsulfonomethylisocyanide in step C. LCMS (m/z) 319 M+1.

EXAMPLE 15

6-[4-(4-Fluoro-3-methyl-phenyl)-oxazol-5-yl]-3-isopropyl-[1,2,4]triazolo[4,3-a]pyridine

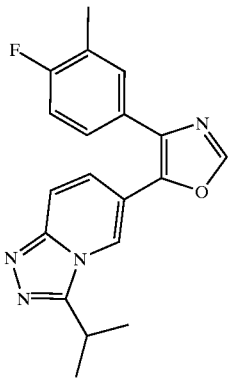

This compound was prepared in an analogous manner to Example 1, starting with 4-fluoro-3-methylphenyl-toylsulfonomethylisocyanide (made from 4-fluoro-3-methylbenzaldehyde, prepared from 4-fluoro-3-methylphenylmagnesium bromide and DMF) in step C. LCMS (m/z) 337 M+1.

EXAMPLE 16

3-Cyclopropyl-6-[4-(4-fluoro-3-methyl-phenyl)-oxazol-5-yl]-[1,2,4]triazolo[4,3-a]pyridine

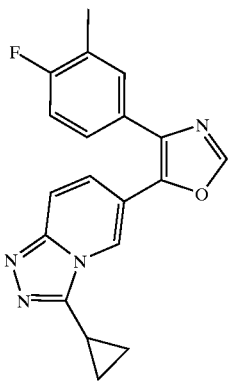

This compound was prepared in an analogous manner to Example 1, starting with 4-fluoro-3-methylphenyl-toylsulfonomethylisocyanide in step C and cyclopropanecarbonyl chloride in step E. LCMS (m/z) 335 M+1.

EXAMPLE 17

6-[4-(4-Fluoro-phenyl)-oxazol-5-yl]-3-phenyl-[1,2,4]triazolo[4,3-a]pyridine

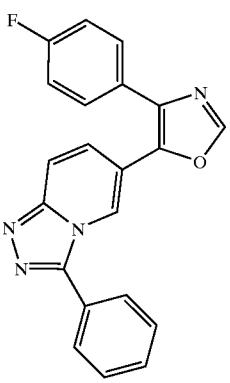

This compound was prepared in an analogous manner to Example 1, starting with 4-fluorophenyl-toylsulfonomethylisocyanide in step C and benzoyl chloride in Step E. LCMS (m/z) 357 M+1.

EXAMPLE 18

3-Isopropyl-6-(2-methyl-4-phenyl-oxazol-5-yl)-[1,2,4]triazolo[4,3-a]pyridine

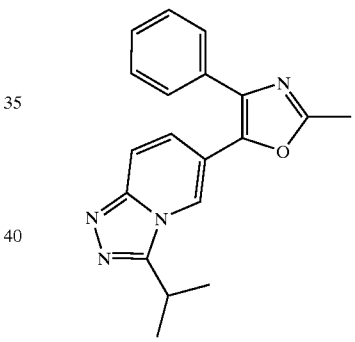

A) 2-Chloro-5-(2-methyl-4-phenyl-oxazol-5-yl)-pyridine

To a stirred, cold (0° C.) solution of 6-chloro-pyridine-3-carbaldehyde and 5 mg of zinc iodide in 3 mL of dichloromethane was added 0.40 mL trimethylsilyl cyanide under a nitrogen atmosphere via syringe. The ice bath was removed and the yellow solution/suspension was stirred at 22° C. for 1.5 hours. The mixture was diluted with dilute aqueous sodium bicarbonate and extracted with dichloromethane (2×). The extracts were washed with water, dried (magnesium sulfate), filtered, and the filtrate was concentrated to a yellow oil. This oil was diluted with 1 mL of dry diethyl ether (Et$_2$O) and added slowly via syringe to a stirred mixture of 1.1 mL of phenylmagnesium bromide (3 M in Et$_2$O) and 1 mL of Et$_2$O at 0° C. The resulting paste was heated at reflux after the addition of 2 mL more of Et$_2$O. After 1.75 hours the mixture was cooled to 22° C. and diluted with 6 mL of 2 N hydrochloric acid, 2 mL of Et$_2$O, and 2 mL of ethyl acetate. The mixture was stirred for 1 hour then extracted with ethyl acetate (3×). The ethyl acetate extracts were washed with water, brine, dried (magnesium sulfate), filtered, and the filtrate was concentrated to a yellow oil. This material was purified by flash chromatography (eluting with 35:65 ethyl acetate/hexanes) to give the benzoin 2-(6-chloro-pyridin-3-yl)-2-hydroxy-1-phenyl-ethanone. This material was then concentrated twice from 1 mL of pyridine and 0.75 mL of acetic anhydride. The resulting acetate was heated at reflux in 15 mL of acetic acid and 1.6 g of ammonium acetate. The mixture was cooled to 22° C. and concentrated to a yellow oil, which was diluted with aqueous sodium bicarbonate, and extracted with ethyl acetate (2×). The combined extracts were washed with brine, dried (magnesium sulfate), filtered, and the filtrate was concentrated to an orange oil which was purified by flash chromatography (eluting with 1:3 ethyl acetate/hexanes) to give 273 mg of 2-chloro-5-(2-methyl-4-phenyl-oxazol-5-yl)-pyridine as a light yellow solid.

B) 5-(2-Methyl-4-phenyl-oxazol-5-yl)-pyridin-2-yl-hydrazine

A mixture of 120 mg of 2-chloro-5-(2-methyl-4-phenyl-oxazol-5-yl)-pyridine in 1 mL of hydrazine (98%) was heated at 70° C. for 45 min before adding 0.5 mL of dichloromethane to get better mixing of the hydrazine and the chloro-pyridine. When the dichloromethane had evaporated 0.5 mL of ethanol was added and the mixture was heated for 11 hours. The layers were separated. The ethanol layer was diluted with ethyl acetate and washed with aqueous sodium carbonate (2×), dried (magnesium sulfate), filtered, and the filtrate was evaporated to give 110 mg of crude 5-(2-Methyl-4-phenyl-oxazol-5-yl)-pyridin-2-yl-hydrazine as an orange solid. This material was used without purification in the next step.

C) Isobutyric Acid N'-[5-(2-Methyl-4-phenyl-oxazol-5-yl)-pyridin-2-yl]-hydrazide To a stirred, cold (0° C.) solution of 5-(2-Methyl-4-phenyl-oxazol-5-yl)-pyridin-2-yl-hydrazine in 0.5 mL of dichloromethane and 0.3 mL of DMF and 0.325 mL of N,N-diisopropylethylamine was added 0.02 mL of isobutyryl chloride. After 5 minutes an additional 0.005 mL of isobutyryl chloride was added and the reaction was quenched a minute later with water. The mixture was extracted with dichloromethane (3×), washed with water (2×), brine (1×), dried (sodium sulfate), filtered, and the filtrate was concentrated to a dark orange oil. This oil was purified by flash chromatography (eluting with 5:1 ethyl acetate/hexanes) to give 23 mg of isobutyric acid N'-[5-(2-methyl-4-phenyl-oxazol-5-yl)-pyridin-2-yl]-hydrazide as an orange solid.

D) 3-Isopropyl-6-(2-methyl-4-phenyl-oxazol-5-yl)-[1,2,4]triazolo[4,3-a]pyridine

A mixture of 23 mg of isobutyric acid N'-[5-(2-methyl-4-phenyl-oxazol-5-yl)-pyridin-2-yl]-hydrazide in 0.68 mL of phosphorous oxychloride was heated at 60° C. for 16 hours. The mixture was cooled to 22° C. and carefully added to 25 mL of water. The aqueous mixture was made basic with 3 N sodium hydroxide and extracted with ethyl acetate (3×). The combined extracts were washed with brine, dried (sodium sulfate), filtered, and the filtrate was concentrated to a dark yellow oil. This oil was purified by flash chromatography (eluting with 97:3 ethyl acetate/methanol) to give 14 mg of 3-isopropyl-6-(2-methyl-4-phenyl-oxazol-5-yl)-[1,2,4]triazolo[4,3-a]pyridine as a light yellow solid. LCMS (m/z) 319 M+1. $^1$H NMR (400 MHz, CDCl$_3$ δ8.18 (s, 1 H), 7.85 (d, 1 H, J=9.8 Hz), 7.60–7.62 (m, 2 H), 7.42–7.49 (m, 4 H), 3.32–3.34 (m, 1 H), 2.63 (s, 3 H), 1.51 (d, 6 H, J=6.7 Hz).

EXAMPLE 19

6-[4-(4-Fluoro-phenyl)-2-methyl-oxazol-5-yl]-3-isopropyl-[1,2,4]triazolo[4,3a]-pyridine

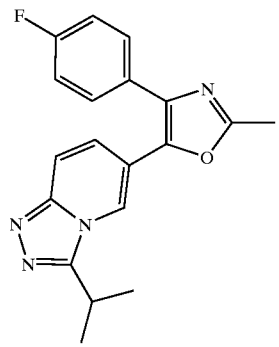

This compound was prepared in an analogous manner to Example 18, starting with 4-fluorophenylmagnesium bromide in step A. LCMS (m/z) 337 M+1.

The compounds of Examples 20–33 can be prepared according to the method of Examples 1–19.

TABLE 1

| EXAMPLE # | MOLSTRUCTURE | IUPAC NAME | DATA LCMS M/Z |
|---|---|---|---|
| 20 |  | {6-[4-(4-Fluoro-phenyl)-oxazol-5-yl]-[1,2,4]triazolo[4,3-a]pyridin-3-yl}-acetic acid ethyl ester | 367 |

TABLE 1-continued

| EXAMPLE # | MOLSTRUCTURE | IUPAC NAME | DATA LCMS M/Z |
|---|---|---|---|
| 21 | | 3-(2-Chloro-phenyl)-6-(4-m-tolyl-oxazol-5-yl)-[1,2,4]triazolo[4,3-a]pyridine | 387 |
| 22 | | 6-[4-(2-Fluoro-5-methyl-phenyl)-oxazol-5-yl]-3-isopropyl-[1,2,4]triazolo[4,3-a]pyridine | 337 |
| 23 | | 6-[4-(4-Fluoro-phenyl)-oxazol-5-yl]-3-o-tolyl-[1,2,4]triazolo[4,3-a]pyridine | 371 |
| 24 | | 3-(2-Fluoro-phenyl)-6-(4-m-tolyl-oxazol-5-yl)-[1,2,4]triazolo[4,3-a]pyridine | 371 |

TABLE 1-continued
| EXAMPLE # | MOLSTRUCTURE | IUPAC NAME | DATA LCMS M/Z |
|---|---|---|---|
| 25 | 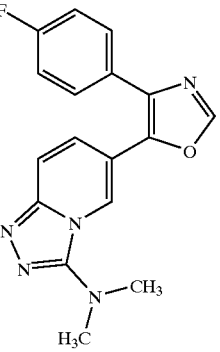 | {6-[4-(4-Fluoro-phenyl)-oxazol-5-yl]-[1,2,4]triazolo[4,3-a]pyridin-3-yl}-dimethyl-amine | 324 |
| 26 | 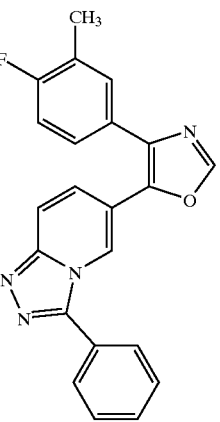 | 6-[4-(4-Fluoro-3-methyl-phenyl)-oxazol-5-yl]-3-phenyl-[1,2,4]triazolo[4,3-a]pyridine | 371 |
| 27 | 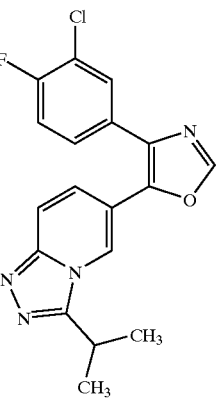 | 6-[4-(3-Chloro-4-fluoro-phenyl)-oxazol-5-yl]-3-isopropyl-[1,2,4]triazolo[4,3-a]pyridine | 357 |
| 28 | 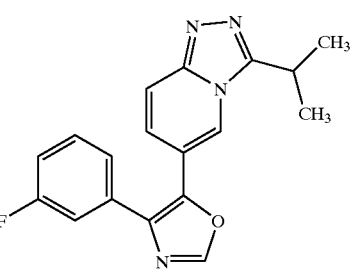 | 6-[4-(3-Fluoro-phenyl)-oxazol-5-yl]-3-isopropyl-[1,2,4]triazolo[4,3-a]pyridine | 323 |

TABLE 1-continued
| EXAMPLE # | MOLSTRUCTURE | IUPAC NAME | DATA LCMS M/Z |
|---|---|---|---|
| 29 | 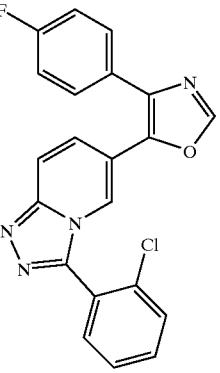 | 3-(2-Chloro-phenyl)-6-[4-(4-fluoro-phenyl)-oxazol-5-yl]-[1,2,4]triazolo[4,3-a]pyridine | 391 |
| 30 | 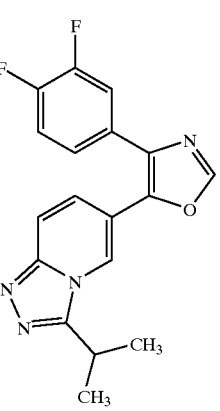 | 6-[4-(3,4-Difluoro-phenyl)-oxazol-5-yl]-3-isopropyl-[1,2,4]triazolo[4,3-a]pyridine | 341 |
| 31 | 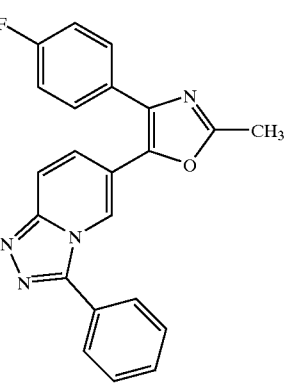 | 6-[4-(4-Fluoro-phenyl)-2-methyl-oxazol-5-yl]-3-phenyl-[1,2,4]triazolo[4,3-a]pyridine | 371 |

TABLE 1-continued

| EXAMPLE # | MOLSTRUCTURE | IUPAC NAME | DATA LCMS M/Z |
|---|---|---|---|
| 32 | | 6-[4-(3-Fluoro-phenyl)-oxazol-5-yl]-3-phenyl-[1,2,4]triazolo[4,3-a]pyridine | 357 |

EXAMPLE 33

6-[5-(4-Fluoro-phenyl)-3H-imidazol-4-yl]-3-isopropyl-1,2,4]triazolo[4,3-a]pyridine

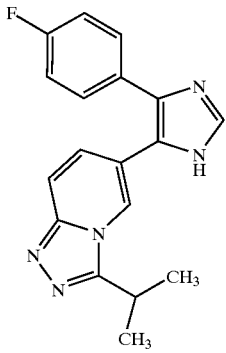

A) 3-Isopropyl-[1,2,4]triazolo[4,3-a]pyridine-6-carbaldehyde

A mixture of 22.1 g 5-bromo-2-fluoropyridine and 10 mL of 55% aqueous hydrazine in 165 mL of pyridine was heated at reflux for 7 hours. The mixture was cooled to 22° C. concentrated to near dryness. The resulting light yellow solids were suspended in aqueous sodium hydroxide and toluene, stirred, and the solids were collected by vacuum filtration to give 22 g of 5-bromo-pyridin-2-yl-hydrazine as a faint yellow solid.

To a stirred cold (0° C.) solution of 5.5 g of 5-bromo-pyridin-2-yl-hydrazine in 40 mL of dichloromethane, 30 mL of N,N-dimethylformamide, and 26 mL of N,N-diisopropylethylamine was added 3.1 ml of isobutyryl chloride dropwise. The mixture was stirred at 0° C. for 1 hour and a precipitate formed. The mixture was diluted with water and the solids were collected by filtration to give 5.9 g of isobutyric acid N'-(5-bromo-pyridin-2-yl)-hydrazide as a light yellow solid.

A mixture of 3 g of isobutyric acid N'-(5-bromo-pyridin-2-yl)-hydrazide in 25 mL of phosphorous oxychloride was heated at 80° C. for 18 hours. The mixture was cooled with an ice bath and added slowly to a beaker of dilute sodium hydroxide. The mixture was extracted with ethyl acetate (3×); the extracts were washed with brine, dried (sodium sulfate), filtered, and the filtrate was concentrated to give 3.4 g of a dark oil. This oil was purified by flash chromatography (eluting with 6:1 ethyl acetate hexanes) to give 2.0 g of 6-bromo-3-isopropyl-[1,2,4]triazolo[4,3-a]pyridine as a dark oil.

To a stirred, cold (0° C.), dark brown solution of 0.48 g of 6-bromo-3-isopropyl-[1,2,4]triazolo[4,3-a]pyridine in 5 mL of tetrahydrofuran was added slowly 1.3 mL of 2 M isopropylmagnesium chloride in tetrahydrofuran. After 30 minutes N,N-dimethylformamide was added; the ice bath was removed, and the mixture was heated to 50° C. for 150 minutes. The mixture was cooled to 22° C., diluted with 1 M hydrochloric acid, and stirred for 10 minutes. The mixture was made basic with saturated aqueous sodium carbonate, and extracted with ethyl acetate (3×). The combined extracts were washed with brine (2×), dried (sodium sulfate), filtered, and the filtrate was concentrated to give a light yellow solid which was crystallized (ethyl acetate, hexanes, and methanol) to give 0.19 g of 3-isopropyl-[1,2,4]triazolo[4,3-a]pyridine-6-carbaldehyde as a faint yellow solid.

B) 6-[5-(4-Fluoro-phenyl)-3H-imidazol-4-yl]-3-isopropyl-[1,2,4]triazolo[4,3-a]pyridine A solution of 0.2 g of 3-isopropyl-[1,2,4]triazolo[4,3-a]pyridine-6-carbaldehyde in 50 mL of tetrahydrofuran and 0.1 g of concentrated ammonium hydroxide was stirred at 22° C. for 18 hours. To the intermediate imine thus formed was added 0.09 g of piperazine and 0.3 g of 4-fluorophenyl-toylsulfonomethylisocyanide. The resulting mixture was stirred at 22° C. for 24 hours before the mixture was diluted with water and extracted with dichloromethane. The extracts were washed with water, brine, dried (sodium sulfate), filtered, and the filtrate was concentrated. The residue was purified by flash chromatography (eluting with 85:15 ethyl acetate/methanol) to give 6-[5-(4-Fluoro-phenyl)-3H-imidazol-4-yl]-3-isopropyl-[1,2,4]triazolo[4,3-a]pyridine which crystallized on standing to a white solid. LCMS m/z 322 (M+1). For related work see Sisko, J.; Kassick, A. J.; Mellinger, M.; Filan, J. J.; Allen, A.; Olsen, M. A. J. Org. Chem. 2000, 65, 1516–1524.

What is claimed is:

1. A compound of the formula

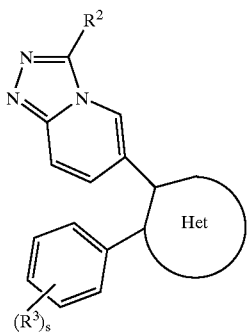

wherein Het is an optionally substituted 5-membered heteroaryl which taken together with $(R^3)_s$-phenyl is selected from the group consisting of (a)
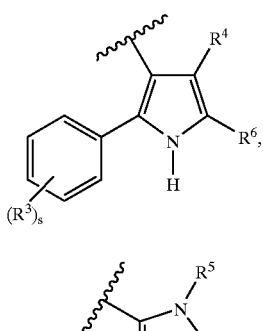

(b)
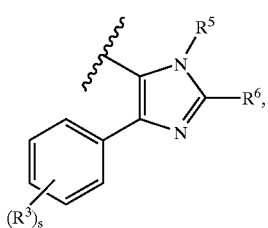

(c)
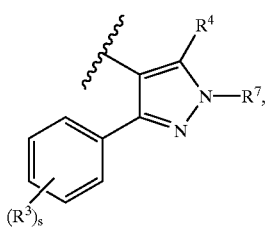

(d)
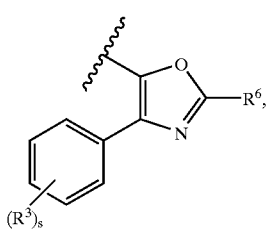

(e)
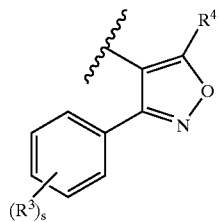

(f)
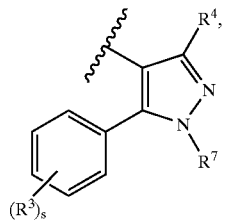

(g)
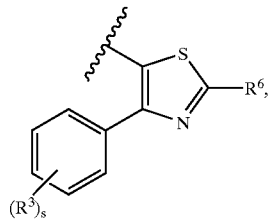

(h)
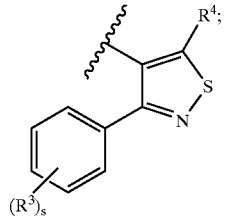

each $R^1$ is independently selected from hydrogen, $(C_1-C_6)$alkyl, phenyl, $(C_1-C_{10})$heteroaryl, $(C_1-C_{10})$ heterocyclic and $(C_3-C_{10})$cycloalkyl; wherein each of the aforesaid $R^1$ $(C_1-C_6)$alkyl, phenyl, $(C_1-C_{10})$ heteroaryl, $(C_1-C_{10})$heterocyclic and $(C_3-C_{10})$ cycloalkyl substituents may optionally be substituted by one to four moieties independently selected from the group consisting of halo, $(C_1-C_6)$alkyl, $(C_2-C_6)$ alkenyl, $(C_2-C_6)$alkynyl, perhalo$(C_1-C_6)$alkyl, phenyl, $(C_1-C_{10})$heteroaryl, $(C_1-C_{10})$heterocyclic, $(C_3-C_{10})$ cycloalkyl, hydroxy, $(C_1-C_6)$alkoxy, perhalo$(C_1-C_6)$ alkoxy, phenoxy, $(C_1-C_{10})$heteroaryl-O—, $(C_1-C_{10})$ heterocyclic-O—, $(C_3-C_{10})$cycloalkyl-O—, $(C_1-C_6)$ alkyl-S—, $(C_1-C_6)$alkyl-SO$_2$—, $(C_1-C_6)$alkyl-NH— SO$_2$—, —NO$_2$, amino, $(C_1-C_6)$alkylamino, [$(C_1-C_6$, alkyl]$_2$-amino, $(C_1-C_6)$alkyl-SO$_2$—N H—, $(C_1-C_6)$ alkyl-(C=O)—NH—, $(C_1-C_6)$alkyl-(C=O)— [$((C_1-C_6)$alkyl)-N)]—, phenyl-(C=O)—NH—, phenyl-(C=O)—[$((C_1-C_6)$alkyl)-N]—, —CN, $(C_1-C_6)$alkyl-(C=O)—, phenyl-(C=O)—, $(C_1-C_{10})$ heteroaryl-(C=O)—, $(C_1-C_{10})$heterocyclic- (C=O)—, $(C_3-C_{10})$cycloalkyl-(C=O)—, HO— (C=O)—, $(C_1-C_6)$alkyl-O—(C=O)—, H$_2$N (C=O)— $(C_1-C_6)$alkyl-NH—(C=O)—, [$(C_1-C_6)$ alkyl]$_2$-N—(C=O)—, phenyl-NH—(C=O)—, phenyl-[$((C_1-C_6)$alkyl)-N]—(C=O)—, $(C_1-C_{10})$ heteroaryl-NH—(C=O)—, $(C_1-C_{10})$heterocyclic-NH—(C=O)—, $(C_3-C_{10})$cycloalkyl-NH—(C=O)—, $(C_1-C_6)$alkyl-(C=O)—O— and phenyl-(C=O)—O—; wherein two $R^1$ $(C_1-C_6)$alkyl groups may be taken together with the nitrogen atom to which they are attached to form a five to six membered heterocyclic or heteroaryl ring;

$R^2$ is selected from the group consisting of hydrogen, —C≡N, $(C_1-C_6)$alkyl, $(C_2-C_6)$alkenyl, $(C_2-C_6)$alkynyl, $(C_3-C_{10})$cycloalkyl, phenyl, $(C_1-C_{10})$heteroaryl, $(C_1-C_{10})$heterocyclic and $(R^1)_2$—N—; wherein each of the aforesaid $(C_1-C_6)$alkyl, $(C_3-C_{10})$cycloalkyl, phenyl, $(C_1-C_{10})$heteroaryl and $(C_1-C_{10})$heterocyclic substituents may optionally be independently substituted by one to four moieties independently selected from the group consisting of halo, $(C_1-C_6)$alkyl, $(C_2-C_6)$alkenyl, $(C_2-C_6)$alkynyl, perhalo$(C_1-C_6)$alkyl, phenyl, $(C_3-C_{10})$cycloalkyl, $(C_1-C_{10})$heteroaryl, $(C_1-C_{10})$heterocyclic, formyl, —CN, $(C_1-C_6)$alkyl-(C=O)—, phenyl-(C=O)—, HO—(C=O)—, $(C_1-C_6)$alkyl-O—(C=O)—, $(C_1-C_6)$alkyl-NH—(C=O)—, $[(C_1-C_6)alkyl]_2$-N—(C=O)—, phenyl-NH—(C=O)—, phenyl-$[((C_1-C_6)alkyl)$-N]—(C=O)—, —NO$_2$, amino, $(C_1-C_6)$alkylamino, $[(C_1-C_6)alkyl]_2$-amino, $(C_1-C_6)$alkyl-(C=O)—NH—, $(C_1-C_6)$alkyl-(C=O)—$[((C_1-C_6)$alkyl)-N]—, phenyl-(C=O)—NH—, phenyl-(C=O)—$[((C_1-C_6)$alkyl)-N]—, H$_2$N—(C=O)—NH—, $(C_1-C_6)$alkyl-HN—(C=O)—NH—, $[(C_1-C_6)alkyl)]_2$—N—(C=O)—NH—, $(C_1-C_6)$alkyl-HN—(C=O)—$[((C_1-C_6)$alkyl)-N]—, $[(C_1-C_6)alkyl)]_2$N—(C=O)-$[((C_1-C_6)$alkyl)-N]—, phenyl-HN—(C=O)—NH—, (phenyl-)$_2$N—(C=O)—NH—, phenyl-HN—(C=O)—$[((C_1-C_6)$alkyl)-N]—, (phenyl-)$_2$N—(C=O)—$[((C_1-C_6)$alkyl)-N]—, $(C_1-C_6)$alkyl-O—(C=O)—NH—, $(C_1-C_6)$alkyl-O—(C=O)—$[((C_1-C_6)$alkyl)-N]—, phenyl-O—(C=O)—NH—, phenyl-O—(C=O)—$[((C_1-C_6)$alkyl)-N]—, $(C_1-C_6)$alkyl-SO$_2$NH—, phenyl-SO$_2$NH—, $(C_1-C_6)$alkyl-SO$_2$—, phenyl-SO$_2$—, hydroxy, $(C_1-C_6)$alkoxy, perhalo$(C_1-C_6)$alkoxy, phenoxy, $(C_1-C_6)$alkyl-(C=O)—O—, phenyl-(C=O)—O—, H$_2$N—(C=O)—O—, $(C_1-C_6)$alkyl-HN—(C=O)—O—, $[(C_1-C_6)alkyl-]_2$N—(C=O)—O—, phenyl-HN—(C=O)—O—, (phenyl-)$_2$N—(C=O)—O—; wherein when said $R^2$ phenyl contains two adjacent substituents, such substituents may optionally be taken together with the carbon atoms to which they are attached to form a five to six membered carbocyclic or heterocyclic ring; wherein each of said moieties containing a phenyl alternative may optionally be substituted by one or two radicals independently selected from the group consisting of $(C_1-C_6)$alkyl, halo, $(C_1-C_6)$alkoxy, perhalo$(C_1-C_6)$alkyl and perhalo$(C_1-C_6)$alkoxy;

each $R^3$ is independently selected from the group consisting of halo, $(C_1-C_6)$alkyl, $(C_2-C_6)$alkenyl, $(C_2-C_6)$alkynyl, perhalo$(C_1-C_6)$alkyl, phenyl, $(C_1-C_{10})$heteroaryl, $(C_1-C_{10})$heterocyclic, $(C_3-C_{10})$cycloalkyl, hydroxy, $(C_1-C_6)$alkoxy, perhalo$(C_1-C_6)$alkoxy, phenoxy, $(C_1-C_{10})$heteroaryl-O—, $(C_1-C_{10})$heterocyclic-O—, $(C_3-C_{10})$cycloalkyl-O—, $(C_1-C_6)$alkyl-S—, $(C_1-C_6)$alkyl-SO$_2$—, $(C_1-C_6)$alkyl-NH—SO$_2$—, —NO$_2$, amino, $(C_1-C_6)$alkylamino, $[(C_1-C_6)alkyl]_2$-amino, $(C_1-C_6)$alkyl-SO$_2$—NH—, $(C_1-C_6)$alkyl-(C=O)—NH—, $(C_1-C_6)$alkyl-(C=O)—$[((C_1-C_6)$alkyl)-N]—, phenyl-(C=O)—NH—, phenyl-(C=O)—$[((C_1-C_6)$alkyl)-N]—, —CN, $(C_1-C_6)$alkyl-(C=O)—, phenyl-(C=O)—, $(C_1-C_{10})$heteroaryl-(C=O)—, $(C_1-C_{10})$heterocyclic-(C=O)—, $(C_3-C_{10})$cycloalkyl-(C=O)—, HO—(C=O)—, $(C_1-C_6)$alkyl-O—(C=O)—, H$_2$N—(C=O)—, $(C_1-C_6)$alkyl-NH—(C=O)—, $[(C_1-C_6)alkyl]_2$-N—(C=O)—, phenyl-NH—(C=O)—, phenyl-$[((C_1-C_6)alkyl)$-N]—(C=O)—, $(C_1-C_{10})$heteroaryl-NH—(C=O)—, $(C_1-C_{10})$heterocyclic-NH—(C=O)—, $(C_3-C_{10})$cycloalkyl-NH—(C=O)— and $(C_1-C_6)$alkyl-(C=O)—O—; wherein two adjacent $R^3$ substituents may be optionally taken together with the carbon atoms to which they are attached to form a five to six membered carbocyclic or heterocyclic ring;

s is an integer from zero to five;

$R^4$ and $R^6$ are each independently selected from the group consisting of hydrogen, halo or $R^9$-B-$(CH_2)_n$—;

n is an integer from zero to six;

each B is independently a bond, —(CHR$^{10}$)—, —O—, —S—, —(SO$_2$)—, —(C=O)—, —O—(C=O)—, —(C=O)—O—, —(C=O)—NR$^{10}$—, —(R$^{10}$—N)—, —(R$^{10}$—N)—SO$_2$—, —(R$^{10}$—N)—(C=O)—, —SO$_2$—(NR$^{10}$)—, —(R$^{10}$—N)—(C=O)—(NR$^{11}$)—, —(O)—(C=O)—(NR$^{10}$)— or —(R$^{10}$—N)—(C=O)—O—;

$R^5$ and $R^7$ are each independently selected from the group consisting of hydrogen, $R^{14}$—(CR$^{15}$H)$_p$—, phenyl, $(C_1-C_{10})$heteroaryl, $(C_1-C_{10})$heterocyclic, $(C_3-C_{10})$cycloalkyl, $(C_1-C_6)$alkyl-(SO$_2$)—, phenyl-(SO$_2$)—, H$_2$N—(SO$_2$)—, $(C_1-C_6)$alkyl-NH—(SO$_2$)—, $[(C_1-C_6)alkyl-]_2$N—(SO$_2$)—, phenyl-NH—(SO$_2$)—, (phenyl-)$_2$N—(SO$_2$)—, $R^{16}$—$(C_1-C_6)$alkyl-(C=O)—, phenyl-(C=O)—, $(C_1-C_{10})$heteroaryl-(C=O)—, $(C_1-C_{10})$heterocyclic-(C=O)—, $(C_3-C_{10})$cycloalkyl-(C=O)—, $(C_1-C_6)$alkyl-O—(C=O)—, $(C_1-C_{10})$heterocyclic-O—(C=O)—, $(C_3-C_{10})$cycloalkyl-O—(C=O)—, H$_2$N—(C=O)—, $(C_1-C_6)$alkyl-NH—(C=O)—, phenyl-NH—(C=O)—, $(C_1-C_{10})$heteroaryl-NH—(C=O)—, $(C_1-C_{10})$heterocyclic-NH—(C=O)—, $(C_3-C_{10})$cycloalkyl-NH—(C=O)—, $[(C_1-C_6)alkyl-]_2$N—(C=O)—, (phenyl-)$_2$N—(C=O)—, phenyl-$[((C_1-C_6)alkyl)$-N]—(C=O)—, $(C_1-C_{10})$heteroaryl-$[((C_1-C_6)alkyl)$-N]—(C=O)—, $(C_1-C_{10})$heterocyclic-$[((C_1-C_6)alkyl)$-N]—(C=O)—, and $(C_3-C_{10})$cycloalkyl-$[((C_1-C_6)alkyl)$-N]—(C=O)—; wherein each of the aforesaid phenyl, heterocyclic, heteroaryl or cycloalkyl $R^5$ and $R^7$ substituents may optionally be independently substituted by one to four moieties independently selected from the group consisting of halo, $R^{16}$—$(C_1-C_6)$alkyl, $(C_2-C_6)$alkenyl, $(C_2-C_6)$alkynyl, perhalo$(C_1-C_6)$alkyl, $(C_3-C_{10})$cycloalkyl phenyl, benzyl, $(C_1-C_{10})$heterocyclic, $(C_1-C_{10})$heteroaryl, $(C_1-C_6)$alkyl-SO$_2$—, formyl, —CN, $(C_1-C_6)$alkyl-(C=O)—, $(C_3-C_{10})$cycloalkyl-(C=O)—, phenyl-(C=O)—, $(C_1-C_{10})$heterocyclic-(C=O)—, $(C_1-C_{10})$heteroaryl-(C=O)—, HO—(C=O)—, $(C_1-C_6)$alkyl-O—(C=O)—, $(C_3-C_{10})$cycloalkyl-O—(C=O)—, $(C_1-C_{10})$heterocyclic-O—(C=O)—, $(C_1-C_5)$alkyl-NH—(C=O)—, $(C_3-C_{10})$cycloalkyl-NH—(C=O)—, phenyl-NH—(C=O)—, $(C_1-C_{10})$heterocyclic-NH—(C=O)—, $(C_1-C_{10})$heteroaryl-NH—(C=O)—, $[(C_1-C_6)alkyl]_2$-N—(C=O)—, phenyl-$[((C_1-C_6)alkyl)$-N]—(C=O)—, hydroxy, $(C_1-C_6)$alkoxy, perhalo$(C_1-C_6)$alkoxy, $(C_3-C_{10})$cycloalkyl-O—, phenoxy, $(C_1-C_{10})$heterocyclic-O—, $(C_1-C_{10})$ heteroaryl-O—, $(C_1$–$C_6)$alkyl-(C=O)—, —$(C_3$–$C_{10})$ cycloalkyl-(C=O)—O—, phenyl-(C=O)—O—, $(C_1$–$C_{10})$heterocyclic-(C=O)—O—, $(C_1$–$C_{10})$ heteroaryl-(C=O)—O—, —$NO_2$, amino, $(C_1$–$C_6)$ alkylamino, [$(C_1$–$C_6)$alkyl]$_2$-amino, formamidyl, $(C_1$–$C_6)$alkyl-(C=O)—NH—, $(C_3$–$C_{10})$cycloalkyl-(C=)—NH—, phenyl-(C=O)—NH—, $(C_1$–$C_{10})$ heterocyclic-(C=O)—NH—, $(C_1$–$C_{10})$)heteroaryl-(C=O)—NH—, $(C_1$–$C_6)$alkyl-(C=O)—[(($C_1$–$C_6)$ alkyl)-N]—, phenyl-(C=O)—[$(C_1$–$C_6)$alkyl-N]—, $(C_1$–$C_6)$alkyl-$SO_2$NH—, $(C_3$–$C_{10})$cycloalkyl-$SO_2$NH—, phenyl-$SO_2$NH—, $(C_1$–$C_{10})$heterocyclic-$SO_2$NH— and $(C_1$–$C_{10})$heteroaryl-$SO_2$NH—; wherein each of said phenyl and heteroaryl moieties may optionally be substituted by one or two radicals independently selected from halo, $(C_1$–$C_6)$alkyl, $(C_1$–$C_6)$ alkoxy, perfluoro$(C_1$–$C_6)$alkyl and perfluoro$(C_1$–$C_6)$ alkoxy;

p is an integer from one to six;

$R^9$ is selected from the group consisting of hydrogen, —$CF_3$, —C≡N, $R^{13}$—$(R^{12}CH)_m$—, phenyl, $(C_1$–$C_{10})$ heterocyclic, $(C_1$–$C_{10})$heteroaryl, and $(C_3$–$C_{10})$ cycloalkyl; wherein each of the aforesaid $R^9$ phenyl, $(C_1$–$C_{10})$heteroaryl, $(C_1$–$C_{10})$heterocyclic and $(C_3$–$C_{10})$cycloalkyl substituents may optionally be substituted by one to four moieties independently selected from the group consisting of halo, $(C_1$–$C_6)$alkyl, $(C_2$–$C_6)$alkenyl, $(C_2$–$C_6)$alkynyl, perhalo$(C_1$–$C_6)$alkyl, phenyl, $(C_1$–$C_{10})$heteroaryl, $(C_1$–$C_{10})$heterocyclic, $(C_3$–$C_{10})$cycloalkyl, hydroxy, $(C_1$–$C_6)$alkoxy, perhalo $(C_1$–$C_6)$alkoxy, phenoxy, $(C_1$–$C_{10})$heteroaryl-O—, $(C_1$–$C_{10})$heterocyclic-O—, $(C_3$–$C_{10})$cycloalkyl-O—, $(C_1$–$C_6)$alkyl-S—, $(C_1$–$C_6)$alkyl-$SO_2$—, $(C_1$–$C_6)$alkyl-NH—$SO_2$—, —$NO_2$, amino, $(C_1$–$C_6)$alkylamino, [$(C_1$–$C_6)$alkyl]$_2$-amino, $(C_1$–$C_6)$alkyl-$SO_2$—NH—, $(C_1$–$C_6)$alkyl-(C=O)—NH—, $(C_1$–$C_6)$alkyl-(C=O)—[(($C_1$–$C_6)$alkyl)-N]—, phenyl-(C=O)—NH—, phenyl-(C=O)—[(($C_1$–$C_6)$alkyl)-N]—, —CN, $(C_1$–$C_6)$alkyl-(C=O)—, phenyl-(C=O)—, $(C_1$–$C_{10})$ heteroaryl-(C=O)—, $(C_1$–$C_{10})$heterocyclic-(C=O)—, $(C_3$–$C_{10})$cycloalkyl-(C=O)—, HO—(C=O)—, $(C_1$–$C_6)$alkyl-O—(C=O)—, $H_2$N (C=O)— $(C_1$–$C_6)$alkyl-NH—(C=O)—, [$(C_1$–$C_6)$ alkyl]$_2$—N—(C=O)—, phenyl-NH—(C=O)—, phenyl-[(($C_1$–$C_6)$alkyl)-N]—(C=O)—, $(C_1$–$C_{10})$ heteroaryl-NH—(C=O)—, $(C_1$–$C_{10})$heterocyclic-NH—(C=O)—, $(C_3$–$C_{10})$cycloalkyl-NH—(C=O)—, $(C_1$–$C_6)$alkyl-(C=O)—O— and phenyl-(C=O)—O—; wherein two adjacent $R^9$ substituents of said phenyl, $(C_1$–$C_{10})$heteroaryl, $(C_1$–$C_{10})$heterocyclic and $(C_3$–$C_{10})$cycloalkyl may optionally be taken together with the carbon or heteroatom to which they are attached to form a five or six membered carbocyclic or heterocyclic ring;

m is an integer from one to six;

$R^{10}$ is hydrogen, $(C_1$–$C_6)$alkyl-$SO_2$— or $(C_1$–$C_6)$alkyl;

$R^{11}$ is hydrogen or $(C_1$–$C_6)$alkyl;

each $R^{12}$ is independently selected from the group consisting of hydrogen, amino, $(C_1$–$C_6)$alkoxy and $(C_1$–$C_6)$alkyl;

$R^{13}$ is selected from the group consisting of hydrogen, $(C_1$–$C_6)$alkyl, $(C_2$–$C_6)$alkenyl, $(C_2$–$C_6)$alkynyl, phenyl, $(C_1$–$C_{10})$heteroaryl, $(C_1$–$C_{10})$heterocyclic, $(C_3$–$C_{10})$cycloalkyl, hydroxy $(C_1$–$C_6)$alkoxy, perhalo $(C_1$–$C_6)$alkoxy, phenoxy, $(C_1$–$C_{10})$heteroaryl-O—, $(C_1$–$C_{10})$heterocyclic-O—, $(C_3$–$C_{10})$cycloalkyl-O—, $(C_1$–$C_6)$alkyl-S—, $(C_1$–$C_6)$alkyl-$SO_2$—, $(C_1$–$C_6)$alkyl-NH—$SO_2$—, —$NO_2$, amino $(C_1$–$C_6)$alkylamino, [$(C_1$–$C_6)$alkyl]$_2$-amino, $(C_1$–$C_6)$alkyl-$SO_2$—NH—, phenyl-$SO_2$—NH—, $(C_1$–$C_6)$alkyl-$SO_2$—[(($C_1$–$C_6)$ alkyl)-N]—, phenyl-$SO_2$—[(($C_1$–$C_6)$alkyl)-N]—, $(C_1$–$C_6)$alkyl-(C=O)—NH—, $(C_1$–$C_6)$alkyl-(C=O)—[(($C_1$–$C_6)$alkyl)-N]—, phenyl-(C=O)—NH—, phenyl-(C=O)—[(($C_1$–$C_6)$alkyl)-N]—, —CN, $(C_1$–$C_6)$alkyl-(C=O)—, phenyl-(C=O)—, $(C_1$–$C_{10})$ heteroaryl-(C=O)—, $C_1$–$C_{10}$heterocyclic-(C=O)—, $(C_3$–$C_{10})$cycloalkyl-(C=O)—, HO—(C=O)—, $(C_1$–$C_6)$alkyl-O—(C=O)—, $H_2$N(C=O)—, $(C_1$–$C_6)$ alkyl-NH—(C=O)—, [$(C_1$–$C_6)$alkyl]$_2$-N—(C=O)—, phenyl-NH—(C=O)—, phenyl-[(($C_1$–$C_6)$alkyl)-N]—(C=O)—, $(C_1$–$C_{10})$heteroaryl-NH—(C=O)—, $(C_1$–$C_{10})$heterocyclic-NH—(C=O)—, $(C_3$–$C_{10})$ cycloalkyl-NH—(C=O)—, $(C_1$–$C_6)$alkyl-(C=O)—O— and phenyl-(C=O)—O—;

$R^{14}$ is selected from the group consisting of hydrogen, halo, $(C_1$–$C_6)$alkyl, $(C_2$–$C_6)$alkenyl, $(C_2$–$C_6)$alkynyl, perhalo$(C_1$–$C_6)$alkyl, $(C_3$–$C_{10})$cycloalkyl, phenyl, $(C_1$–$C_{10})$heterocyclic, $(C_1$–$C_{10})$heteroaryl, phenyl-(S=O)—, $(C_1$–$C_6)$alkyl-$SO_2$—, phenyl-$SO_2$—, $H_2$N—$SO_2$—, $(C_1$–$C_6)$alkyl-NH—$SO_2$—, phenyl-NH—$SO_2$—, [$(C_1$–$C_6)$alkyl-]$_2$N—$SO_2$—, (phenyl-)$_2$N—$SO_2$—, formyl, —CN, $(C_1$–$C_6)$alkyl-(C=O)—, phenyl-(C=O)—, $(C_1$–$C_{10})$heteroaryl-(C=O)—, $(C_1$–$C_{10})$heterocyclic-(C=O)—, $(C_3$–$C_{10})$cycloalkyl-(C=O)—, HO—(C=O)—, $R^{16}$—$(C_1$–$C_6)$alkyl-O—(C=O)—, $(C_3$–$C_{10})$cycloalkyl-O—(C=O)—, $(C_1$–$C_{10})$heterocyclic-O—(C=O)—, $H_2$N—(C=O)—, $R^{16}$—$(C_1$–$C_6)$alkyl-NH—(C=O)—, $(C_3$–$C_{10})$cycloalkyl-NH—(C=O)—, phenyl-NH—(C=O)—, $(C_1$–$C_{10})$heterocyclic-NH—(C=O)—, $(C_1$–$C_{10})$heteroaryl-NH—(C=O)—, [$(C_1$–$C_6)$alkyl]$_2$-N—(C=O)—, phenyl-[(($C_1$–$C_6)$alkyl)-N]—(C=O)—, $(C_1$–$C_{10})$heterocyclic-[(($C_1$–$C_6)$alkyl)-N]—(C=O)—, $(C_1$–$C_{10})$heterocyclic-[(($C_1$–$C_6)$alkyl)-N]—(C=O)—, $(C_3$–$C_{10})$cycloalkyl[(($C_1$–$C_6)$alkyl)-N]—(C=O)—, hydroxy, $R^{16}$—$(C_1$–$C_6)$alkoxy, perhalo$(C_1$–$C_6)$alkoxy, $(C_3$–$C_{10})$cycloalkyl-O—, phenoxy, $(C_1$–$C_{10})$heterocyclic-O—, $(C_1$–$C_{10})$ heteroaryl-O—, $R^{16}$—$(C_1$–$C_6)$alkyl-(C=O)—O—, $(C_3$–$C_{10})$cycloalkyl-(C=O)—O—, phenyl-(C=O)—O—, $(C_1$–$C_{10})$heterocyclic-(C=O)—O—, $(C_1$–$C_{10})$ heteroaryl-(C=O)—O—, —$NO_2$, amino, $R^{16}$—$(C_1$–$C_6)$alkylamino, [$(C_1$–$C_6)$alkyl]$_2$-amino, formamidyl, $R^{16}$—$(C_1$–$C_6)$alkyl-(C=O)—NH—, $(C_3$–$C_{10})$cycloalkyl-(C=C)—NH—, phenyl-(C=O)—NH—, $(C_1$–$C_{10})$heterocyclic-(C=O)—NH—, $(C_1$–$C_{10})$heteroaryl-(C=O)—NH—, $R^{16}$—$(C_1$–$C_6)$alkyl-(C=O)—[(($C_1$–$C_6)$alkyl)-N]—, phenyl-(C=O)—[(($C_1$–$C_6)$alkyl)-N]—, $R^{16}$—$(C_1$–$C_6)$alkyl-$SO_2$NH—, $(C_3$–$C_{10})$cycloalkyl-$SO_2$NH—, phenyl-$SO_2$NH—, $(C_1$–$C_{10})$heterocyclic-$SO_2$NH— and $(C_1$–$C_{10})$heteroaryl-$SO_2$NH—; wherein each of the aforesaid phenyl, heterocyclic, heteroaryl or cycloalkyl $R^{14}$ substituents may optionally be independently substituted by one to four moieties independently selected from the group consisting of halo, $R^{16}$—$(C_1$–$C_6)$alkyl, $(C_2$–$C_6)$alkenyl, $(C_2$–$C_6)$alkynyl, perhalo$(C_1$–$C_6)$alkyl, $(C_3$–$C_{10})$cycloalkyl, phenyl, benzyl, $(C_1$–$C_{10})$ heterocyclic, $(C_1$–$C_{10})$heteroaryl, $(C_1$–$C_6)$alkyl-$SO_2$—, formyl, —CN, $R^{16}$—$(C_1$–$C_6)$alkyl-(C=O)—, $(C_3$–$C_{10})$cycloalkyl-(C=O)—, phenyl-(C=O)—, $(C_1$–$C_{10})$heterocyclic-(C=O)—, $(C_1$–$C_{10})$heteroaryl-(C=O)—, HO—(C=O)—, $(C_1$–$C_6)$alkyl-O—

(C=O)—, $(C_3-C_{10})$cycloalkyl-O—(C=O)—, $(C_1-C_{10})$heterocyclic-O—(C=O)—, $(C_1-C_{10})$heteroaryl-O—(C=O)—, $H_2N$—(C=O)—, $R^{16}$—$(C_1-C_6)$alkyl-NH—(C=O)—, $(C_3-C_{10})$cycloalkyl-NH—(C=O)—, phenyl-NH—(C=O)—, $(C_1-C_{10})$heterocyclic-NH—(C=O)—, $(C_1-C_{10})$heteroaryl-NH—(C=O)—, $[(C_1-C_6)$alkyl$]_2$-N—(C=O)—, phenyl-$[((C_1-C_6)$alkyl)-N]$—(C=O)—, hydroxy, $R^{16}$—$(C_1-C_6)$alkoxy, perhalo$(C_1-C_6)$alkoxy, $(C_3-C_{10})$cycloalkyl-O—, phenoxy, $(C_1-C_{10})$heterocyclic-O—, $(C_1-C_{10})$heteroaryl-O—, $R^{16}$—$(C_1-C_6)$alkyl-(C=O)—O—, $(C_3-C_{10})$cycloalkyl-(C=O)—O—, phenyl-(C=O)—O—, $(C_1-C_{10})$heterocyclic-(C=O)—O—, $(C_1-C_{10})$heteroaryl-(C=O)—O—, —$NO_2$, amino, $R^{16}$—$(C_1-C_6)$alkylamino, $[(C_1-C_6)$alkyl$]_2$-amino, formamidyl, $R^{16}$—$(C_1-C_6)$alkyl-(C=O)—NH—, $(C_3-C_{10})$cycloalkyl-(C=O)—NH—, phenyl-(C=O)—NH—, $(C_1-C_{10})$heterocyclic-(C=O)—NH—, $(C_1-C_{10})$heteroaryl-(C=O)—NH—, $R^{16}$—$(C_1-C_6)$alkyl-(C=O)—$[((C_1-C_6)$alkyl)-N]$—, phenyl-(C=O—$[((C_1-C_{10})$alkyl)-N]$—, $R^{16}$—$(C_1-C_6)$alkyl-$SO_2NH$—, $(C_3-C_{10})$cycloalkyl-$SO_2NH$—, phenyl-$SO_2NH$—, $(C_1-C_{10})$heterocyclic-$SO_2NH$— and $(C_1-C_{10})$heteroaryl-$SO_2NH$—; wherein each of said phenyl and heteroaryl moieties may optionally be substituted by one or two radicals independently selected from the group consisting of halo, $(C_1-C_6)$alkyl, $(C_1-C_6)$alkoxy, perfluoro$(C_1-C_6)$alkyl and perfluoro$(C_1-C_6)$alkoxy;

each $R^{15}$ is independently selected from the group consisting of hydrogen, halo, $(C_1-C_6)$alkyl, $(C_2-C_6)$alkenyl, perhalo$(C_1-C_6)$alkyl, HO—(C=O)—, $(C_1-C_6)$alkyl-O—(C=O)—, $H_2N$—(C=O)—, $(C_1-C_6)$alkyl-NH—(C=O)—, $[(C_1-C_6)$alkyl$]_2$-N—(C=O)—, hydroxy, $(C_1-C_6)$alkoxy, $(C_1-C_6)$alkyl-(C=O)—O—, amino, $(C_1-C_6)$alkylamino, $[(C_1-C_6)$alkyl$]_2$-amino, formamidyl and $(C_1-C_6)$alkyl-(C=O)—NH—;

each $R^{16}$ is independently selected from the group consisting of hydrogen, halo, $(C_1-C_6)$alkyl, $(C_2-C_6)$alkenyl, $(C_2-C_6)$alkynyl, perhalo$(C_1-C_6)$alkyl, $(C_2-C_{10})$heterocyclic, HO—(C=O)—, $(C_1-C_6)$alkyl-O—(C=O)—, $H_2N$—(C=O)—, $(C_1-C_6)$alkyl-NH—(C=O)—, $[(C_1-C_6)$alkyl$]_2$-N—(C=O)—, hydroxy, $(C_1-C_6)$alkoxy, perhalo$(C_1-C_6)$alkoxy, $(C_1-C_6)$alkyl-(C=O)—O—, —$NO_2$, amino, $(C_1-C_6)$alkylamino, $[(C_1-C_6)$alkyl$]_2$-amino, formamidyl and $(C_1-C_6)$alkyl-(C=O)—NH—; wherein said $(C_1-C_{10})$heterocyclic may optionally be substituted by one to three substituents independently selected from the group consisting of halo, $(C_1-C_6)$alkyl, $(C_1-C_6)$alkoxy, benzyl, amino, $(C_1-C_6)$alkylamino and $[(C_1-C_6)$alkyl$]_2$-amino;

or $R^4$ and $R^6$ or $R^4$ and $R^7$ or $R^5$ and $R^5$ may be taken together with the atoms to which they are attached to form an optionally substituted five to ten membered saturated, unsaturated or aromatic ring optionally containing two to three heteroatoms independently selected from NH, N, O, S, SO or $SO_2$; wherein said ring may be optionally substituted by one to three substituents independently selected from the group consisting of oxo, halo, $(C_1-C_6)$alkyl, phenyl, $(C_1-C_{10})$heteroaryl, $(C_1-C_{10})$heterocyclic, $(C_3-C_{10})$cycloalkyl, hydroxy, $(C_1-C_6)$alkoxy, phenoxy, $(C_1-C_{10})$heteroaryl-O—, $(C_1-C_{10})$heterocyclic-O—, $(C_3-C_{10})$cycloalkyl-O—, $(C_1-C_6)$alkyl-S—, $(C_1-C_6)$alkyl-$SO_2$—, phenyl-S—, phenyl-(S=O)—, phenyl-$SO_2$—, $(C_1-C_6)$alkyl-NH—$SO_2$—, $[(C_1-C_6)$alkyl$]_2$-N—$SO_2$—, phenyl-NH—$SO_2$—, (phenyl)$_2$-N—$SO_2$—, phenyl-[N$(C_1-C_6)$alkyl]-$SO_2$—, formyl, $(C_1-C_6)$alkyl-(C=O)—, phenyl-(C=O)—, $(C_1-C_{10})$heteroaryl-(C=O)—, $(C_1-C_{10})$heterocyclic-(C=O)—, $(C_3-C_{10})$cycloalkyl-(C=O)—, HO—(C=O)—, $(C_1-C_6)$alkyl-O—(C=O)—, $(C_1-C_{10})$heterocyclic-O—(C=O)—, $(C_3-C_{10})$cycloalkyl-O—(C=O)—, $H_2N$—(C=O)—, $(C_1-C_6)$alkyl-NH—(C=O)—, $[(C_1-C_6)$alkyl$]_2$-N—(C=O)—, phenyl-NH—(C=O)—, phenyl-$[((C_1-C_6)$alkyl)-N]$—(C=O)—, $(C_1-C_{10})$heteroaryl-NH—(C=O)—, $(C_1-C_{10})$heteroaryl-$[((C_1-C_6)$alkyl)-N]$—(C=O)—, $(C_1-C_{10})$heterocyclic-NH—(C=O)—, $(C_1-C_{10})$heterocyclic-$[((C_1-C_6)$alkyl)-N]$—(C=O)—, $(C_3-C_{10})$cycloalkyl-NH—(C=O)—, $(C_3-C_{10})$cycloalkyl-$[((C_1-C_6)$alkyl)-N]$—(C=O)—, amino, $(C_1-C_6)$alkylamino, $[(C_1-C_6)$alkyl$]_2$amino, $(C_1-C_6)$alkyl-$SO_2$—NH—, phenyl-$SO_2$—NH—, $(C_1-C_6)$alkyl-$SO_2$—$[((C_1-C_6)$alkyl)-N]$—, phenyl-$SO_2$—$[((C_1-C_6)$alkyl)-N]$—, formamidyl, $(C_1-C_6)$alkyl-(C=O)—NH—, $(C_1-C_6)$alkyl-(C=O)—$[((C_1-C_6)$alkyl)-N]$—, phenyl-(C=O)—NH—, phenyl-(C=O)—$[((C_1-C_6)$alkyl)-N]$—, $(C_1-C_{10})$heteroaryl-(C=O)—NH—, $(C_1-C_{10})$heteroaryl-(C=O)—$[((C_1-C_6)$alkyl)-N]$—, $(C_1-C_{10})$heterocyclic-(C=O)—NH—, $(C_1-C_{10})$heterocyclic-(C=O)—$[((C_1-C_6)$alkyl)-N]$—, $(C_3-C_{10})$cycloalkyl-(C=O)—NH—, $(C_3-C_{10})$cycloalkyl-(C=O)—$[((C_1-C_6)$alkyl)-N]$—, $H_2N$(C=O)—NH—, $(C_1-C_6)$alkyl-HN—(C=O)—NH—, $(C_1-C_6)$alkyl-HN—(C=O)—$[((C_1-C_6)$alkyl)-N]$—, $[(C_1-C_6)$alkyl$]_2$-N—(C=O)—NH—, $[(C_1-C_6)$alkyl$]_2$-N—(C=O)—$[((C_1-C_6)$alkyl)-N]$—, phenyl-HN—(C=O)—NH—, phenyl-HN—(C=O)—$[((C_1-C_6)$alkyl)-N]$—, (phenyl)$_2$-N—(C=O)—NH—, (phenyl)$_2$-N—(C=O)-$[((C_1-C_6)$alkyl)-N]$—, $(C_1-C_{10})$heteroaryl-HN—(C=O)—NH—, $(C_1-C_{10})$heteroaryl-HN—(C=O)-$[((C_1-C_6)$alkyl)-N]$—, $[(C_1-C_{10})$heteroaryl$]_2$-N—(C=O)—$[((C_1-C_6)$alkyl)-N]$—, $[(C_1-C_{10})$heteroaryl$]_2$-N—(C=O)—NH—, $(C_1-C_{10})$heterocyclic-HN—(C=O)—NH—, $(C_1-C_{10})$heterocyclic-HN—(C=O)—$[((C_1-C_6)$alkyl)-N]$—, $[(C_1-C_{10})$heterocyclic$]_2$-N—(C=O)—$[((C_1-C_6)$alkyl)-N]$—, $[(C_1-C_{10})$heterocyclic$]_2$-N—(C=O)—NH—, $(C_3-C_{10})$cycloalkyl-HN—(C=O)—NH—, $(C_3-C_{10})$cycloalkyl-HN—(C=O)-$[((C_1-C_6)$alkyl)-N]$—, $[(C_3-C_{10})$cycloalkyl$]_2$-N—(C=O)—$[((C_1-C_6)$alkyl)-N]$—, $[(C_3-C_{10})$cycloalkyl$]_2$-N—(C=O)—NH—, $(C_1-C_6)$alkyl-(C=O)—O—, phenyl-(C=O)—O—, $(C_1-C_{10}))$heteroaryl-(C=O)—O—, $(C_1-C_{10})$heterocyclic-(C=O)—O—, $(C_3-C_{10})$cycloalkyl-(C=O)—O—, $(C_1-C_6)$alkyl-NH—(C=O)—O—, $[(C_1-C_6)$alkyl$]_2$-N—(C=O)—O—, phenyl-NH—(C=O)—O—, $(C_1-C_{10})$heteroaryl-NH—(C=O)—O—, $(C_1-C_{10}))$heterocyclic-NH—(C=O)—O— and $(C_3-C_{10})$cycloalkyl-NH—(C=O)—O—;

or a pharmaceutically acceptable salt thereof.

2. A compound according to claim 1 wherein $R^2$ is optionally substituted $(C_1-C_6)$alkyl, phenyl, $(C_3-C_{10})$cycloalkyl, $(C_1-C_{10})$heteroaryl or $(C_1-C_{10})$heterocyclic.

3. A compound according to claim 1 wherein $R^2$ is $(C_1-C_6)$alkyl, optionally substituted with one to four groups independently selected from halo, hydroxy, $(C_1-C_6)$alkyl, $(C_2-C_6)$alkenyl, $(C_2-C_6)$alkynyl, $(C_1-C_6)$alkoxy, perhalo ($C_1$-$C_6$)alkyl, perhalo($C_1$-$C_6$)alkoxy, —CN, —$NO_2$, amino, ($C_1$-$C_6$)alkylamino, [($C_1$-$C_6$)alkyl]$_2$-amino, HO—(C═O)—, ($C_1$-$C_6$)alkyl-(C═O)—, ($C_1$-$C_6$)alkyl-O—(C═O)—, ($C_1$-$C_6$)alkyl-$CO_2$—, ($C_1$-$C_6$)alkyl-(C═O)—NH—, ($C_1$-$C_6$)alkyl-NH—(C═O)—, ($C_1$-$C_6$)alkyl-(C═O)—[(($C_1$-$C_6$)alkyl)-N]—, ($C_1$-$C_6$)alkyl-[(($C_1$-$C_6$)alkyl)-N]—(C═O)—, ($C_1$-$C_6$)alkyl-$SO_2$NH—, ($C_1$-$C_6$)alkyl-$SO_2$—, optionally substituted phenyl-(C═O)—, optionally substituted phenyl-(C═O)—O—, optionally substituted phenoxy, optionally substituted phenyl-NH—(C═O)—, optionally substituted phenyl-[(($C_1$-$C_6$)alkyl)-N]—(C═O)—, optionally substituted phenyl-(C═O)—NH— and optionally substituted phenyl-(C═O)—[(($C_1$-$C_6$)alkyl)-N]—.

4. A compound according to claim 1 wherein $R^2$ is ($C_1$-$C_4$)alkyl.

5. A compound according to claim 1 wherein $R^2$ is optionally substituted ($C_3$-$C_6$)cycloalkyl.

6. A compound according to claim 1 wherein $R^2$ is optionally substituted phenyl.

7. A compound according to claim 1 wherein $R^2$ is optionally substituted phenyl, wherein said substituents are independently selected from the group consisting of halo, ($C_1$-$C_6$)alkyl, ($C_2$-$C_6$)alkenyl, ($C_2$-$C_6$)alkynyl, perhalo($C_1$-$C_6$)alkyl, phenyl, ($C_3$-$C_{10}$)cycloalkyl, ($C_1$-$C_{10}$)heteroaryl, ($C_1$-$C_{10}$)heterocyclic, formyl, —CN, ($C_1$-$C_6$)alkyl-(C═O)—, phenyl-(C═O)—, HO—(C═O)—, ($C_1$-$C_6$)alkyl-O—(C═O)—, ($C_1$-$C_6$)alkyl-NH—(C═O)—, [($C_1$-$C_6$)alkyl]$_2$-N—(C═O)—, phenyl-NH—(C═O)—, phenyl-[(($C_1$-$C_6$)alkyl)-N]—(C═O)—, —$NO_2$, amino, ($C_1$-$C_6$)alkylamino, [($C_1$-$C_6$)alkyl]$_2$-amino, ($C_1$-$C_6$)alkyl-(C═O)—NH—, ($C_1$-$C_6$)alkyl-(C═O)—[(($C_1$-$C_6$)alkyl)-N]—, phenyl-(C═O)—NH—, phenyl-(C═O)—[(($C_1$-$C_6$)alkyl)-N]—, $H_2$N—(C═O)—NH—, ($C_1$-$C_6$)alkyl-HN—(C═O)—NH—, [($C_1$-$C_6$)alkyl-]$_2$N—(C═O)—NH—, ($C_1$-$C_6$)alkyl-HN—(C═O)—[(($C_1$-$C_6$)alkyl)-N]—, [($C_1$-$C_6$)alkyl-]$_2$N—(C═O)—[(($C_1$-$C_6$)alkyl)-N]—, phenyl-HN—(C═O)—NH—, (phenyl-)$_2$N—(C═O)—NH—, phenyl-HN—(C═O)-[(($C_1$-$C_6$)alkyl)-N]—, (phenyl-)$_2$N—(C═O)—[(($C_1$-$C_6$)alkyl)-N]—, ($C_1$-$C_6$)alkyl-O—(C═O)—NH—, ($C_1$-$C_6$)alkyl-O—(C═O)—[(($C_1$-$C_6$)alkyl)-N]—, phenyl-O—(C═O)—NH—, phenyl-O—(C═O)—[(($C_1$-$C_6$)alkyl)-N]—, ($C_1$-$C_6$)alkyl-$SO_2$NH—, phenyl-$SO_2$NH—, ($C_1$-$C_6$)alkyl-$SO_2$—, phenyl-$SO_2$—, hydroxy, ($C_1$-$C_6$)alkoxy, perhalo($C_1$-$C_6$)alkoxy, phenoxy, ($C_1$-$C_6$)alkyl-(C═O)—O—, phenyl-(C═O)—O—, $H_2$N—(C═O)—O—, ($C_1$-$C_6$)alkyl-HN—(C═O)—O—, [($C_1$-$C_6$)alkyl-]$_2$N—(C═O)—O—, phenyl-HN—(C═O)—O—, (phenyl-)$_2$N—(C═O)—O—; wherein each of said moieties containing a phenyl alternative may optionally be substituted by one or two radicals independently selected from the group consisting of ($C_1$-$C_6$) alkyl, halo, ($C_1$-$C_6$)alkoxy, perhalo($C_1$-$C_6$)alkyl and perhalo($C_1$-$C_6$)alkoxy.

8. A compound according to claim 1 wherein $R^2$ is optionally substituted phenyl wherein said substituents are independently selected from the group consisting of halo, ($C_1$-$C_6$)alkyl, ($C_2$-$C_6$)alkenyl, perhalo($C_1$-$C_6$)alkyl, —CN, ($C_1$-$C_6$)alkyl-(C═O)—, HO—(C═O)—, ($C_1$-$C_6$)alkyl-O—(C═O)—, ($C_1$-$C_6$)alkyl-NH—(C═O)—, [($C_1$-$C_6$)alkyl]$_2$-N—(C═O)—, amino, ($C_1$-$C_6$)alkylamino, [($C_1$-$C_6$)alkyl]$_2$-amino, ($C_1$-$C_6$)alkyl-(C═O)—NH—, ($C_1$-$C_6$)alkyl-(C═O)—[(($C_1$-$C_6$)alkyl)-N]—, $H_2$N—(C═O)—NH—, ($C_1$-$C_6$)alkyl-HN—(C═O)—NH—, [($C_1$-$C_6$)alkyl-]$_2$N—(C═O)—NH—, ($C_1$-$C_6$)alkyl-HN—(C═O)—[(($C_1$-$C_6$)alkyl)-N]—, [($C_1$-$C_6$)alkyl-]$_2$N—(C═O)-[(($C_1$-$C_6$)alkyl)-N]—, hydroxy, ($C_1$-$C_6$)alkoxy, perhalo($C_1$-$C_6$)alkoxy, ($C_1$-$C_6$)alkyl-(C═O)—O—, $H_2$N—(C═O)—O—, ($C_1$-$C_6$)alkyl-HN—(C═O)—O— and [($C_1$-$C_6$)alkyl-]$_2$N—(C═O)—O—.

9. A compound according to claim 1 wherein $R^2$ is optionally substituted phenyl containing two adjacent substituents which taken together with the carbon atoms to which they are attached form a five to six membered carbocyclic or heterocyclic ring.

10. A compound according to claim 1 wherein $R^2$ is ($R^1$)$_2$—N—, wherein each $R^1$ is independently selected from hydrogen, ($C_1$-$C_6$)alkyl, phenyl, ($C_1$-$C_{10}$)heterocyclic and ($C_3$-$C_{10}$)cycloalkyl; wherein each of the aforesaid $R^1$, ($C_1$-$C_6$)alkyl, phenyl, ($C_1$-$C_{10}$)heteroaryl, ($C_1$-$C_{10}$)heterocyclic and ($C_3$-$C_{10}$)cycloalkyl substituents may optionally be substituted by one to four moieties independently selected from the group consisting of halo, ($C_1$-$C_6$)alkyl, ($C_2$-$C_6$)alkenyl, ($C_2$-$C_6$)alkynyl, perhalo($C_1$-$C_6$)alkyl, phenyl, ($C_1$-$C_{10}$)heteroaryl, ($C_1$-$C_{10}$)heterocyclic, ($C_3$-$C_{10}$)cycloalkyl, hydroxy, ($C_1$-$C_6$)alkoxy, perhalo($C_1$-$C_6$)alkoxy, phenoxy, ($C_1$-$C_{10}$)heteroaryl-O—, ($C_1$-$C_{10}$)heterocyclic-O—, ($C_3$-$C_{10}$)cycloalkyl-O—, ($C_1$-$C_6$)alkyl-S—, ($C_1$-$C_6$)alkyl-$SO_2$—, ($C_1$-$C_6$)alkyl-NH—$SO_2$—, —$NO_2$, amino, ($C_1$-$C_6$)alkylamino, [($C_1$-$C_6$)alkyl]$_2$-amino, ($C_1$-$C_6$)alkyl-$SO_2$—NH—, ($C_1$-$C_6$)alkyl-(C═O)—NH—, ($C_1$-$C_6$)alkyl-(C═O)—[(($C_1$-$C_6$)alkyl)-N]—, phenyl-(C═O)—NH—, phenyl-(C═O)—[(($C_1$-$C_6$)alkyl)-N]—, —CN, ($C_1$-$C_6$)alkyl-(C═O)—, phenyl-(C═O)—, ($C_1$-$C_{10}$)heteroaryl-(C═O)—, ($C_1$-$C_{10}$)heterocyclic-(C═O)—, ($C_3$-$C_{10}$)cycloalkyl-(C═O)—, HO—(C═O)—, ($C_1$-$C_6$)alkyl-O—(C═O)—, $H_2$N(C═O)— ($C_1$-$C_6$)alkyl-NH—(C═O)—, [($C_1$-$C_6$)alkyl]$_2$-N—(C═O)—, phenyl-NH—(C═O)—, phenyl-[(($C_1$-$C_6$)alkyl)-N]—(C═O)—, ($C_1$-$C_{10}$)heteroaryl-NH—(C═O)—, ($C_1$-$C_{10}$)heterocyclic-NH—(C═O)—, ($C_3$-$C_{10}$)cycloalkyl-NH—(C═O)—, ($C_1$-$C_6$)alkyl-(C═O)—O— and phenyl-(C═O)—O—; wherein two $R^1$ ($C_1$-$C_6$)alkyl groups may be taken together with the nitrogen atom to form a five to six membered heterocyclic or heteroaryl ring.

11. A compound according to claim 1 wherein $R^2$ is ($R^1$)$_2$—N— and wherein each $R^1$ is independently selected from hydrogen, ($C_1$-$C_4$)alkyl, phenyl and ($C_1$-$C_{10}$)heterocyclic.

12. A compound according to claim 1, wherein the compound has the formula

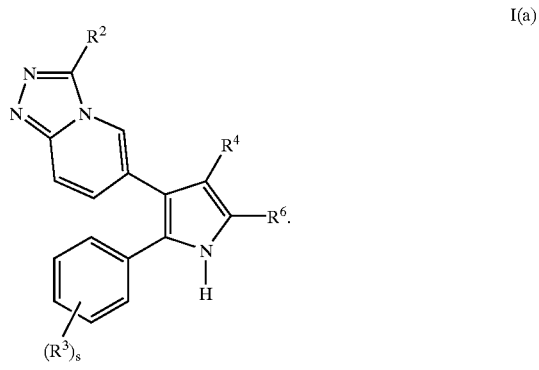

I(a)

13. A compound according to claim 1, wherein the compound has the formula

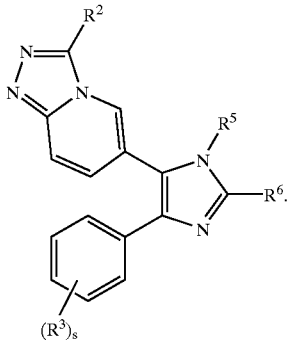

14. A compound according to claim 1, wherein the compound has the formula

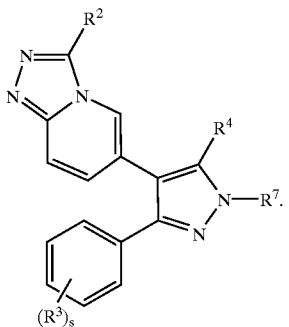

15. A compound according to claim 1, wherein the compound has the formula

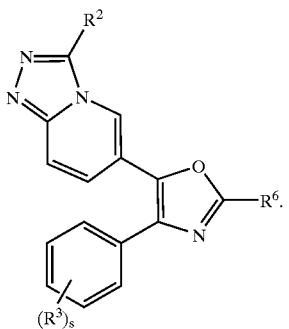

16. A compound according to claim 1, wherein the compound has the formula

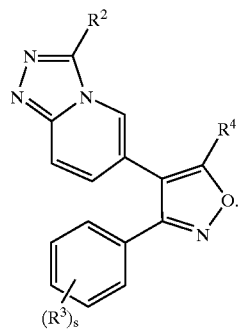

17. A compound according to claim 1, wherein the compound has the formula

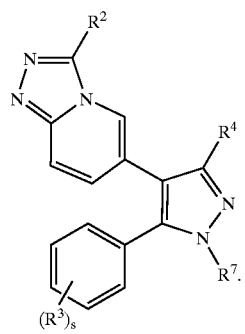

18. A compound according to claim 1, wherein the compound has the formula

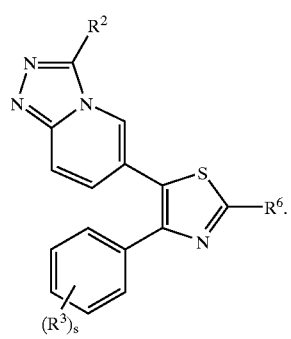

19. A compound according to claim 1, wherein the compound has the formula

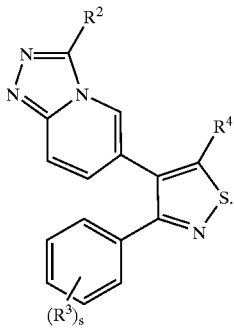

I(h)

20. A compound according to claim 1, wherein $R^4$ is hydrogen.

21. A compound according to claim 1, wherein $R^4$ is $R^9$—B—$(CH_2)_n$— and n is zero.

22. A compound according to claim 1, wherein $R^4$ is $R^9$—B—$(CH_2)_n$— and n is an integer from one to five.

23. A compound according to claim 1, wherein $R^4$ is $R^9$—B—$(CH_2)_n$—; n is zero; B is a bond and $R^9$ is $R^{13}$—$(R^{12}CH)_m$—.

24. A compound according to claim 1, wherein $R^4$ is $R^9$—B—$(CH_2)_n$—; n is zero; B is —(C=O)—$(R^{10}$—N)—, —$(R^{10}$—N)—, —$SO_2$—$(R^{10}$—N)—, —$(R^{10}$—N)—(C=O)—$(NR^{11})$— or —$(R^{10}$—N)—(C=O)—O—; and $R^9$ is selected from the group consisting of hydrogen and $R^{13}$—$(R^{12}CH)_m$—.

25. A compound according to claim 1, wherein $R^4$ is $R^9$—B—$(CH_2)_y$—; n is zero; B is —(C=O)—$(R^{10}$—N)—, —$(R^{10}$—N)—, —$SO_2$—$(R^{10}$—N)—, —$(R^{10}$—N)—(C=O)—$(NR^{11})$— or —$(R^{10}$—N)—(C=O)—O—, $R^9$ is $R^{13}$—$(R^{12}CH)_m$—; m is 1-6; $R^{10}$ is hydrogen or methyl; each $R^{12}$ is independently selected from the groups consisting of hydrogen or methyl; and $R^{13}$ is selected from the group consisting of hydrogen, $(C_1-C_6)$alkyl, $(C_2-C_6)$alkenyl, phenyl, $(C_1-C_{10})$heteroaryl, $(C_1-C_{10})$heterocyclic, $(C_3-C_{10})$cycloalkyl, hydroxy, $(C_1-C_6)$alkoxy, perhalo $(C_1-C_6)$alkoxy, phenoxy; $(C_1-C_{10})$heteroaryl-, $(C_1-C_{10})$heterocyclic-O—, $(C_3-C_{10})$cycloalkyl-O—, $(C_1-C_6)$alkyl-S—, $(C_1-C_6)$alkyl-$SO_2$—, $(C_1-C_6)$alkyl-NH—$SO_2$—, —$NO_2$, amino, $(C_1-C_6)$alkylamino, $[(C_1-C_6)$alkyl$]_2$-amino, $(C_1-C_6)$alkyl-$SO_2$—NH—, $(C_1-C_6)$alkyl-(C=O)—NH—, $(C_1-C_6)$alkyl-(C=O)—$[((C_1-C_6)$alkyl)-N]$—, phenyl-(C=O)—NH—, phenyl-(C=O)—$[((C_1-C_6)$alkyl)-N]$—, $(C_1-C_6)$alkyl-$SO_2$—NH—, phenyl-$SO_2$—NH—, $(C_1-C_6)$alkyl-$SO_2$—$[((C_1-C_6)$alkyl)-N]$—, phenyl-$SO_2$—$[((C_1-C_6)$alkyl)-N]$—, —CN, $(C_1-C_6)$alkyl-(C=O)—, phenyl-(C=O)—, $(C_1-C_{10})$heteroaryl-(C=O)—, $(C_1-C_{10})$heterocyclic-(C=O)—, $(C_3-C_{10})$cycloalkyl-(C=O)—, $(C_1-C_{10})$heteroaryl-NH—(C=O)—, $(C_1-C_{10})$heterocyclic-NH—(C=O)—, $(C_3-C_{10})$cycloalkyl-NH—(C=O)—, HO—(C=O)—, $(C_1-C_6)$alkyl-O—(C=O)—, $H_2N$(C=O)—, $(C_1-C_6)$alkyl-NH—(C=O)—, $[(C_1-C_6)$alkyl$]_2$-N—(C=O)—, phenyl-NH—(C=O)—, phenyl-$[((C_1-C_6)$alkyl)-N]$—(C=O)—, $(C_1-C_6)$alkyl-(C=O)—O— and phenyl-(C=O)—O—.

26. A compound according to claim 1, wherein $R^4$ is $R^9$—B—$(CH_2)_n$—; n is zero; B is —$(R^{10}$—N)—; $R^9$ is hydrogen or $R^{13}$—$(R^{12}CH)_m$—; m is 1-6; $R^{10}$ is hydrogen or methyl; $R^{12}$ is hydrogen or methyl; and $R^{13}$ is selected from the group consisting of hydrogen, $(C_1-C_6)$alkyl, hydroxy, $(C_1-C_6)$alkoxy, amino, $(C_1-C_6)$alkylamino, $[(C_1-C_6)$alkyl$]_2$amino, $(C_2-C_6)$alkenyl, $(C_2-C_6)$alkynyl, phenyl, $(C_1-C_{10})$heteroaryl, $(C_1-C_{10})$heterocyclic and $(C_3-C_{10})$cycloalkyl.

27. A compound according to claim 1, wherein $R^7$ is selected from the group consisting of $R^{16}$—$(C_1-C_6)$alkyl-(C=O)—, phenyl-(C=O)—, $(C_1-C_{10})$heteroaryl-(C=O)—, $(C_1-C_{10})$heterocyclic-(C=O)—, $(C_3-C_{10})$cycloalkyl-(C=O)—, $(C_1-C_6)$alkyl-O—(C=O)—, $H_2N$—(C=O)—, $(C_1-C_6)$alkyl-NH—(C=O)—, phenyl-NH—(C=O)—, $(C_1-C_{10})$heteroaryl-NH—(C=O)—, $(C_1-C_{10})$heterocyclic-NH—(C=O)— and $(C_3-C_{10})$cycloalkyl-NH—(C=O)—; wherein each of the aforesaid phenyl, heterocyclic, heteroaryl or cycloalkyl $R^7$ substituents may optionally be independently substituted by one to four moieties independently selected from the group consisting of halo, $R^{16}(C_1-C_6)$alkyl, $(C_2-C_6)$alkenyl, $(C_2-C_6)$alkynyl, perhalo$(C_1-C_6)$alkyl, $(C_3-C_{10})$cycloalkyl, phenyl, benzyl, $(C_1-C_{10})$heterocyclic, $(C_1-C_{10})$heteroaryl, $(C_1-C_6)$alkyl-$SO_2$—, formyl, —CN, $(C_1-C_6)$alkyl-(C=O)—, $(C_3-C_{10})$cycloalkyl-(C=O)—, phenyl-(C=O)—, $(C_1-C_{10})$heterocyclic-(C=O)—, $(C_1-C_{10})$heteroaryl-(C=O)—, HO—(C=O)—, $(C_1-C_6)$alkyl-O—(C=O)—, $(C_3-C_{10})$cycloalkyl-O—(C=O)—, $(C_1-C_{10})$heterocyclic-O—(C=O)—, $(C_1-C_{10})$heteroaryl-O—(C=O)—, $(C_1-C_6)$alkyl-NH—(C=O)—, $(C_3-C_{10})$cycloalkyl-NH—(C=O)—, phenyl-NH—(C=O)—, $(C_1-C_{10})$heterocyclic-NH—(C=O)—, $(C_1-C_{10})$heteroaryl-NH—(C=O)—, $[(C_1-C_6)$alkyl$]_2$-N—(C=O)—, phenyl-$[((C_1-C_6)$alkyl)-N]$—(C=O)—, hydroxy, $(C_1-C_6)$alkoxy, perhalo$(C_1-C_6)$alkoxy, $(C_3-C_{10})$cycloalkyl-O—, phenoxy, $(C_1-C_{10})$heterocyclic-O—, $(C_1-C_{10})$heteroaryl-O—, $(C_1-C_6)$alkyl-(C=O)—O—, $(C_3-C_{10})$cycloalkyl-(C=O)—O—, phenyl-(C=O)—O—, $(C_1-C_{10})$heterocyclic-(C=O)—O—, $(C_1-C_{10})$heteroaryl-(C=O)—O—, —$NO_2$, amino, $(C_1-C_6)$alkylamino, $[(C_1-C_6)$alkyl$]_2$-amino, formamidyl, $(C_1-C_6)$alkyl-(C=O)—NH—, $(C_3-C_{10})$cycloalkyl-(C=O)—, phenyl-(C=O)—NH—, $(C_1-C_{10})$heterocyclic-(C=O)—NH—, $(C_1-C_{10})$heteroaryl-(C=O)—NH—, $(C_1-C_6)$alkyl-(C=O)—$[((C_1-C_6)$alkyl)-N]$—, phenyl-(C=O)—$[((C_1-C_6)$alkyl)-N]$—, $(C_1-C_6)$alkyl-$SO_2NH$—, $(C_3-C_{10})$cycloalkyl-$SO_2NH$—, phenyl-$SO_2NH$—, $(C_1-C_{10})$heterocyclic-$SO_2NH$— and $(C_1-C_{10})$heteroaryl-$SO_2NH$—; wherein each of said phenyl and heteroaryl moieties may optionally be substituted by one or two radicals independently selected from the group consisting of halo, $(C_1-C_6)$alkyl, $(C_1-C_6)$alkoxy, amino, $(C_1-C_6)$alkylamino and $[(C_1-C_6)$alkyl$]_2$-amino.

28. A compound according to claim 1, wherein $R^7$ is selected from the group consisting of hydrogen and optionally substituted phenyl, $(C_1-C_{10})$heteroaryl, $(C_1-C_{10})$heterocyclic and $(C_3-C_{10})$cycloalkyl.

29. A compound according to claim 1, wherein $R^7$ is selected from the group consisting of $R^{16}$—$(C_1-C_6)$alkyl-(C=O)—, phenyl-(C=O)—, $(C_1-C_{10})$heteroaryl-(C=O)—, $(C_1-C_{10})$heterocyclic-(C=O)—, $(C_3-C_{10})$cycloalkyl-(C=O)—, $(C_1-C_6)$alkyl-O—(C=O)—, $H_2N$—(C=O)—, $(C_1-C_6)$alkyl-NH—(C=O)—, phenyl-NH—(C=O)—, $(C_1-C_{10})$heteroaryl-NH—(C=O)—, $(C_1-C_{10})$heterocyclic-NH—(C=O)— and $(C_3-C_{10})$cycloalkyl-NH—(C=O)—.

30. A compound according to claim 1, wherein $R^7$ is $R^{14}$—$(CR^{15}H)_p$—; p is one to four; $R^{14}$ is selected from the group consisting of hydrogen, halo, $(C_1-C_6)$alkyl, $(C_2-C_6)$alkenyl, $(C_2-C_6)$alkynyl, perhalo$(C_1-C_6)$alkyl, $(C_3-C_{10})$cycloalkyl, phenyl, $(C_1-C_{10})$heterocyclic, $(C_1-C_{10})$heteroaryl, formyl, —CN, $(C_1-C_6)$alkyl-(C=O)—, phenyl-(C=O)—, $(C_1-C_{10})$heteroaryl-(C=O)—, $(C_1-C_{10})$ heterocyclic-(C=O)—, $(C_3-C_{10})$cycloalkyl-(C=O)—, HO—(C=O)—, $R^{16}$—$(C_1-C_6)$alkyl-O—(C=O)—, $(C_3-C_{10})$cycloalkyl-O—(C=O)—, $(C_1-C_{10})$heterocyclic-O—(C=O)—, $(C_1-C_{10})$heteroaryl-O—(C=O)—, $H_2N$—(C=O)—, $R^{16}$—$(C_1-C_6)$alkyl-NH—(C=O)—, $(C_3-C_{10})$cycloalkyl-NH—(C=O)—, phenyl-NH—(C=O)—, $(C_1-C_{10})$heterocyclic-NH—(C=O)—, $(C_1-C_{10})$heteroaryl-NH—(C=O)—, $[(C_1-C_6)$alkyl$]_2$-N—(C=O)—, phenyl-$[((C_1-C_6)$alkyl)-N]$—(C=O)—, $(C_1-C_{10})$heteroaryl-$[((C_1-C_6)$alkyl)-N]$—(C=O)—, $(C_1-C_{10})$heterocyclic-$[((C_1-C_6)$alkyl)-N]$—(C=O)—, $(C_3-C_{10})$cycloalkyl-$[((C_1-C_6)$alkyl-N]$—(C=O)—, hydroxy, $R^{16}$—$(C_1-C_6)$alkoxy, perhalo$(C_1-C_6)$alkoxy, $(C_3-C_{10})$cycloalkyl-O—, phenoxy, $(C_1-C_{10})$heterocyclic-O—, $(C_1-C_{10})$heteroaryl-O—, $R^{16}$—$(C_1-C_6)$alkyl-(C=O)—O—, $(C_3-C_{10})$cycloalkyl-(C=O)—O—, phenyl-(C=O)—O—, $(C_1-C_{10})$heterocyclic-(C=O)—O—, $(C_1-C_{10})$heteroaryl-(C=O)—O—, amino, $R^{16}$—$(C_1-C_6)$alkylamino, $[(C_1-C_6)$alkyl$]_2$-amino, formamidyl, $R^{16}$—$(C_1-C_6)$alkyl-(C=O)—NH—, $(C_3-C_{10})$cycloalkyl-(C=O)—NH—, phenyl-(C=O)—NH—, $(C_1-C_{10})$heterocyclic-(C=O)—NH—, $(C_1-C_{10})$heteroaryl-(C=O)—NH—, $R^{16}$—$(C_1-C_6)$alkyl-(C=O)-$[((C_1-C_6)$alkyl)-N]$-, phenyl-(C=O)-$[(C_1-C_6)$alkyl-N]$—, $R^{16}$—$(C_1-C_6)$alkyl-$SO_2NH$—, $(C_3-C_{10})$cycloalkyl-$SO_2NH$—, phenyl-$SO_2NH$—, $(C_1-C_{10})$heterocyclic-$SO_2NH$— and $(C_1-C_{10})$heteroaryl-$SO_2NH$—; wherein each of the aforesaid phenyl, heterocyclic, heteroaryl or cycloalkyl $R^{14}$ substituents may optionally be independently substituted by one to four moieties independently selected from the group consisting of halo, $R^{16}$—$(C_1-C_6)$alkyl, $(C_2-C_6)$alkenyl, $(C_2-C_6)$alkynyl, perhalo$(C_1-C_6)$alkyl, $(C_3-C_{10})$cycloalkyl, phenyl, benzyl, $(C_1-C_{10})$heterocyclic, $(C_1-C_{10})$heteroaryl, $(C_1-C_6)$alkyl-$SO_2$—, formyl, —CN, $R^{16}$—$(C_1-C_6)$alkyl-(C=O)—, $(C_3-C_{10})$cycloalkyl-(C=O)—, phenyl-(C=O)—, $(C_1-C_{10})$heterocyclic-(C=O)—, $(C_1-C_{10})$heteroaryl-(C=O)—, HO—(C=O)—, $(C_1-C_6)$alkyl-O—(C=O)—, $(C_3-C_{10})$cycloalkyl-O—(C=O)—, $(C_1-C_{10})$heterocyclic-O—(C=O)—, $(C_1-C_{10})$heteroaryl-O—(C=O)—, $H_2N$—(C=O)—, $R^{16}$—$(C_1-C_6)$alkyl-NH—(C=O)—, $(C_3-C_{10})$cycloalkyl-NH—(C=O)—, phenyl-NH—(C=O)—, $(C_1-C_{10})$heterocyclic-NH—(C=O)—, $(C_1-C_{10})$heteroaryl-NH—(C=O)—, $[(C_1-C_6)$alkyl$]_2$-N—(C=O)—, phenyl-$[((C_1-C_6)$alkyl)-N]$—(C=O)—, hydroxy, $R^{16}$—$(C_1-C_6)$alkoxy, perhalo$(C_1-C_6)$alkoxy, $(C_3-C_{10})$cycloalkyl-O—, phenoxy, $(C_1-C_{10})$heterocyclic-O—, $(C_1-C_{10})$heteroaryl-O—, $R^{16}$—$(C_1-C_6)$alkyl-(C=O)—O—, $(C_3-C_{10})$cycloalkyl-(C=O)—O—, phenyl-(C=O)—O—, $(C_1-C_{10})$heterocyclic-(C=O)—O—, $(C_1-C_{10})$heteroaryl-(C=O)—O—, —$NO_2$, amino, $R^{16}$—$(C_1-C_6)$alkylamino, $[(C_1-C_6)$alkyl$]_2$-amino, formamidyl, $R^{16}$—$(C_1-C_6)$alkyl-(C=O)—NH—, $(C_3-C_{10})$cycloalkyl-(C=O)—NH—, phenyl-(C=O)—NH—, $(C_1-C_{10})$heterocyclic-(C=O)—NH—, $(C_1-C_{10})$heteroaryl-(C=O)—NH—, $R^{16}$—$(C_1-C_6)$alkyl-(C=O)-$[((C_1-C_6)$alkyl)-N]$—, phenyl-(C=O)-$[((C_1-C_6)$alkyl)-N]$—, $R^{16}$—$(C_1-C_6)$alkyl-$SO_2NH$—, $(C_3-C_{10})$cycloalkyl-$SO_2NH$—, phenyl-$SO_2NH$—, $(C_1-C_{10})$heterocyclic-$SO_2NH$— and $(C_1-C_{10})$heteroaryl-$SO_2NH$—; wherein each of said phenyl and heteroaryl moieties may optionally be substituted by one or two radicals independently selected from the group consisting of halo, $(C_1-C_6)$alkyl, $(C_1-C_6)$alkoxy, amino, $(C_1-C_6)$alkylamino or $[(C_1-C_6)$alkyl$]_2$-amino;

each $R^{15}$ is independently selected from the group consisting of hydrogen, halo, $(C_1-C_6)$alkyl, $(C_2-C_6)$alkenyl, perhalo$(C_1-C_6)$alkyl, HO—(C=O)—, $(C_1-C_6)$alkyl-O—(C=O)—, $H_2N$—(C=O)—, $(C_1-C_6)$alkyl-NH—(C=O)—, $[(C_1-C_6)$alkyl$]_2$-N—(C=O)—, hydroxy, $(C_1-C_6)$alkoxy, perhalo$(C_1-C_6)$alkoxy, amino, $(C_1-C_6)$alkylamino, $[(C_1-C_6)$alkyl$]_2$-amino, formamidyl and $(C_1-C_6)$alkyl-(C=O)—NH—; and each $R^{16}$ is independently selected from the group consisting of hydrogen, halo, $(C_1-C_6)$alkyl, $(C_2-C_6)$alkenyl, $(C_2-C_6)$alkynyl, perhalo$(C_1-C_6)$alkyl, HO—(C=O)—, $C_1-C_6)$alkyl-O—(C=O)—, $H_2N$—(C=O)—, $(C_1-C_6)$alkyl-NH—(C=O)—, $[(C_1-C_6)$alkyl$]_2$-N—(C=O)—, hydroxy, $(C_1-C_6)$alkoxy, perhalo$(C_1-C_6)$alkoxy, $(C_1-C_6)$alkyl-(C=O)—, —$NO_2$, amino, $(C_1-C_6)$alkylamino, $[(C_1-C_6)$alkyl$]_2$-amino, formamidyl and $(C_1-C_6)$alkyl-(C=O)—NH—.

31. A compound according to claim 1, wherein $R^7$ is $R^{14}$—$(CR^{15}H)_p$—; p is one to four; $R^{14}$ is selected from the group consisting of hydrogen, halo, $(C_1-C_6)$alkyl, $(C_2-C_6)$alkenyl, $(C_3-C_{10})$cycloalkyl, phenyl, $(C_1-C_{10})$heterocyclic, $(C_1-C_{10})$heteroaryl, HO—(C=O)—, $R^{16}$—$(C_1-C_6)$alkyl-O—(C=O)—, $H_2N$—(C=O)—, $R^{16}$—$(C_1-C_6)$alkyl-NH—(C=O)—, phenyl-NH—(C=O)—, $(C_1-C_{10})$heterocyclic-NH—(C=O)—, $[(C_1-C_6)$alkyl$]_2$-N—(C=O)—, phenyl-$[N$—$((C_1-C_6)$alkyl$)]$—(C=O)—, hydroxy, $R^{16}$—$(C_1-C_6)$alkoxy, phenoxy, amino, $R^{16}$—$(C_1-C_6)$alkylamino, $[(C_1-C_6)$alkyl$]_2$-amino and $R^{16}$—$(C_1-C_6)$alkyl-(C=O)—NH—; wherein each of the aforesaid phenyl, heterocyclic, heteroaryl or cycloalkyl $R^{14}$ substituents may optionally be independently substituted by one to four moieties independently selected from the group consisting of halo, $R^{16}$—$(C_1-C_6)$alkyl, $(C_2-C_6)$alkenyl, $(C_2-C_6)$alkynyl, perhalo$(C_1-C_6)$alkyl, $(C_1-C_6)$alkyl-$SO_2$—, formyl, —CN, $R^{16}$—$(C_1-C_6)$alkyl-(C=O)—, HO—(C=O)—, $(C_1-C_6)$alkyl-O—(C=O)—, $H_2N$—(C=O)—, $R^{16}$—$(C_1-C_6)$alkyl-NH—(C=O)—, $[(C_1-C_6)$alkyl$]_2$-N—(C=O)—, hydroxy, $R^{16}$—$(C_1-C_6)$alkoxy, perhalo$(C_1-C_6)$alkoxy, $R^{16}$—$(C_1-C_6)$alkyl-(C=O)—O—, amino, $R^{16}$—$(C_1-C_6)$alkylamino, $[(C_1-C_6)$alkyl$]_2$-amino, formamidyl, $R^{16}$—$(C_1-C_6)$alkyl-(C=O)—NH—, $R^{16}$—$(C_1-C_6)$alkyl-(C=O)-$[((C_1-C_6)$alkyl)-N]$— and $R^{16}$—$(C_1-C_6)$alkyl-$SO_2NH$—;

each $R^{15}$ is independently selected from the group consisting of hydrogen, halo, $(C_1-C_6)$alkyl, $(C_2-C_6)$alkenyl, perhalo$(C_1-C_6)$alkyl, HO—(C=O)—, $(C_1-C_6)$alkyl-O—(C=O)—, $H_2N$—(C=O)—, $(C_1-C_6)$alkyl-NH—(C=O)—, $[(C_1-C_6)$alkyl$]_2$-N—(C=O)—, hydroxy, $(C_1-C_6)$alkoxy, perhalo$(C_1-C_6)$alkoxy, amino, $(C_1-C_6)$alkylamino, $[(C_1-C_6)$alkyl$]_2$-amino, formamidyl and $(C_1-C_6)$alkyl-(C=O)—NH—; wherein no more than two of said $R^{15}$ groups may be other than hydrogen; and each $R^{16}$ is independently selected from the group consisting of hydrogen, halo, $(C_1-C_6)$alkyl, $(C_2-C_6)$alkenyl, $(C_2-C_6)$alkynyl, perhalo$(C_1-C_6)$alkyl, HO—(C=O)—, $(C_1-C_6)$alkyl-O—(C=O)—, $H_2N$—(C=O)—, $(C_1-C_6)$alkyl-NH—(C=O)—, $[(C_1-C_6)$alkyl$]_2$-N—(C=O)—, hydroxy, $(C_1-C_6)$alkoxy, perhalo$(C_1-C_6)$alkoxy, $(C_1-C_6)$alkyl-(C=O)—O—, —$NO_2$, amino, $(C_1-C_6)$alkylamino, $[(C_1-C_6)$alkyl$]_2$-amino, formamidyl and $(C_1-C_6)$alkyl-(C=O)—NH—.

32. A compound according to claim 1, wherein $R^5$ is hydrogen.

33. A compound according to claim 1, wherein $R^5$ is $(C_1-C_{10})$heterocyclic or $(C_1-C_{10})$heteroaryl; wherein each of the aforesaid heterocyclic and heteroaryl substituents may optionally be independently substituted by one to four moieties independently selected from the group consisting of halo, $(C_1-C_6)$alkyl, $(C_1-C_6)$alkoxy, HO—(C=O)—, ($C_1$–$C_6$)alkyl-O—(C=O)—, $H_2N$—(C=O)—, ($C_1$–$C_6$)alkyl-NH—(C=O)— and [($C_1$–$C_6$)alkyl]$_2$-N—(C=O)—.

34. A compound according to claim 1, wherein $R^5$ is $R^{14}$—(CHR$^{15}$)$_p$—, p is 1–6; and $R^{14}$ is selected from the group consisting of hydrogen, ($C_1$–$C_6$)alkyl, ($C_2$–$C_6$)alkenyl, perhalo($C_1$–$C_6$)alkyl, ($C_3$–$C_{10}$)cycloalkyl, phenyl, ($C_1$–$C_{10}$)heterocyclic, ($C_1$–$C_{10}$)heteroaryl, phenyl-(S=O)—, ($C_1$–$C_6$)alkyl-SO$_2$—, phenyl-SO$_2$—, $H_2N$—SO$_2$—, ($C_1$–$C_6$)alkyl-NH—SO$_2$—, phenyl-NH—SO$_2$—, [($C_1$–$C_6$)alkyl-]$_2$N—SO$_2$—, ($C_1$–$C_6$)alkyl-(C=O)—, phenyl-(C=O)—, ($C_1$–$C_{10}$)heteroaryl-(C=O)—, ($C_1$–$C_{10}$)heterocyclic-(C=O)—, ($C_3$–$C_{10}$)cycloalkyl-(C=O)—, HO—(C=O)—, $R^{16}$—($C_1$–$C_6$)alkyl-O—(C=O)—, ($C_3$–$C_{10}$)cycloalkyl-O—(C=O)—, ($C_1$–$C_{10}$)heterocyclic-O—(C=O)—, ($C_1$–$C_{10}$)heteroaryl-O—(C=O)—, $H_2N$—(C=O)—, ($C_1$–$C_6$)alkyl-NH—(C=O)—, ($C_3$–$C_{10}$)cycloalkyl-NH—(C=O)—, phenyl-NH—(C=O)—, ($C_1$–$C_{10}$))heterocyclic-NH—(C=O)—, ($C_1$–$C_{10}$)heteroaryl-NH—(C=O)—, [($C_1$–$C_6$)alkyl]$_2$-N—(C=O)—, phenyl-[(($C_1$–$C_6$)alkyl)-N]—(C=O)—, ($C_1$–$C_{10}$)heteroaryl-[N-($C_1$–$C_6$)alkyl]-(C=O)—, ($C_1$–$C_{10}$))heterocyclic-[(($C_1$–$C_6$)alkyl)-N]—(C=O)—, ($C_3$–$C_{10}$)cycloalkyl[(($C_1$–$C_6$)alkyl)-N]—(C=O)—, hydroxy, $R^{16}$—($C_1$–$C_6$)alkoxy, perhalo($C_1$–$C_6$)alkoxy, ($C_3$–$C_{10}$)cycloalkyl-O—, phenoxy, ($C_1$–$C_{10}$)heterocyclic-O—, ($C_1$–$C_{10}$)heteroaryl-O—, $R^{16}$—($C_1$–$C_6$)alkyl-(C=O)—O—, ($C_3$–$C_{10}$)cycloalkyl-(C=O)—O—, phenyl-(C=O)—O—, ($C_1$–$C_{10}$)heterocyclic-(C=O)—O—, ($C_1$–$C_{10}$)heteroaryl-(C=O)—O—, —NO$_2$, amino, $R^{16}$—($C_1$–$C_6$)alkylamino, [($C_1$–$C_6$)alkyl]$_2$-amino, formamidyl, $R^{16}$—($C_1$–$C_6$)alkyl-(C=O)—NH—, ($C_3$–$C_{10}$)cycloalkyl-(C=O)—NH—, phenyl-(C=O)—NH—, $R^{16}$—($C_1$–$C_6$)alkyl-SO$_2$NH—, ($C_3$–$C_{10}$)cycloalkyl-SO$_2$NH—, phenyl-SO$_2$NH—, ($C_1$–$C_{10}$)heterocyclic-SO$_2$NH— and ($C_1$–$C_{10}$)heteroaryl-SO$_2$NH—; wherein each of the aforesaid phenyl, heterocyclic, heteroaryl or cycloalkyl $R^{14}$ substituents may optionally be independently substituted by one to four moieties independently selected from the group consisting of halo, $R^{16}$—($C_1$–$C_6$)alkyl, ($C_2$–$C_6$)alkenyl, ($C_2$–$C_6$)alkynyl, perhalo($C_1$–$C_6$)alkyl, ($C_3$–$C_{10}$)cycloalkyl, phenyl, benzyl, ($C_1$–$C_{10}$)heterocyclic, ($C_1$–$C_{10}$)heteroaryl, ($C_1$–$C_6$)alkyl-SO$_2$—, formyl, —CN, $R^{16}$—($C_1$–$C_6$)alkyl-(C=O)—, ($C_3$–$C_{10}$)cycloalkyl-(C=O)—, phenyl-(C=O)—, ($C_1$–$C_{10}$)heterocyclic-(C=O)—, ($C_1$–$C_{10}$)heteroaryl-(C=O)—, HO—(C=O)—, ($C_1$–$C_6$)alkyl-O—(C=O)—, ($C_3$–$C_{10}$)cycloalkyl-O—(C=O)—, ($C_1$–$C_{10}$)heterocyclic-O—(C=O)—, ($C_1$–$C_{10}$)heteroaryl-O—(C=O)—, $H_2N$—(C=O)—, $R^{16}$—($C_1$–$C_6$)alkyl-NH—(C=O)—, ($C_3$–$C_{10}$)cycloalkyl-NH—(C=O)—, phenyl-NH—(C=O)—, ($C_1$–$C_{10}$)heterocyclic-NH—(C=O)—, ($C_1$–$C_{10}$)heteroaryl-NH—(C=O)—, [($C_1$–$C_6$)alkyl]$_2$-N—(C=O)—, phenyl-[(($C_1$–$C_6$)alkyl)-N]—(C=O)—, hydroxy, $R^{16}$—($C_1$–$C_6$)alkoxy, perhalo($C_1$–$C_6$)alkoxy, ($C_3$–$C_{10}$)cycloalkyl-O—, phenoxy, ($C_1$–$C_{10}$)heterocyclic-O—, ($C_1$–$C_{10}$)heteroaryl-O—, $R^{16}$—($C_1$–$C_6$)alkyl-(C=O)—O—, ($C_3$–$C_{10}$)cycloalkyl-(C=O)—O—, phenyl-(C=O)—O—, ($C_1$–$C_{10}$)heterocyclic-(C=O)—O—, ($C_1$–$C_{10}$)heteroaryl-(C=O)—O—, —NO$_2$, amino, $R^{16}$—($C_1$–$C_6$)alkylamino, [($C_1$–$C_6$)alkyl]$_2$-amino, formamidyl, $R^{16}$—($C_1$–$C_6$)alkyl-(C=O)—NH—, ($C_3$–$C_{10}$)cycloalkyl-(C=O)—NH—, phenyl-(C=O)—NH—, ($C_1$–$C_{10}$)heterocyclic-(C=O)—NH—, ($C_1$–$C_{10}$)heteroaryl-(C=O)—NH—, $R^{16}$—($C_1$–$C_6$)alkyl-(C=O)—[(($C_1$–$C_6$)alkyl)-N]—, phenyl-(C=O)—[($C_1$–$C_6$)alkyl-N]—, $R^{16}$—($C_1$–$C_6$)alkyl-SO$_2$NH—, ($C_3$–$C_{10}$)cycloalkyl-SO$_2$NH—, phenyl-SO$_2$NH—, ($C_1$–$C_{10}$)heterocyclic-SO$_2$NH— and ($C_1$–$C_{10}$)heteroaryl-SO$_2$NH—; and wherein each of said phenyl and heteroaryl moieties may optionally be substituted by one or two radicals independently selected from halo, ($C_1$–$C_6$)alkyl, ($C_1$–$C_6$)alkoxy, amino, ($C_1$–$C_6$)alkylamino and [($C_1$–$C_6$)alkyl]$_2$-amino.

35. A compound according to claim 1, wherein $R^5$ is $R^{14}$—(CHR$^{15}$)$_p$—, p is 1–6; and $R^{14}$ is selected from the group consisting of hydrogen, ($C_1$–$C_6$)alkyl, ($C_2$–$C_6$)alkenyl, ($C_3$–$C_{10}$)cycloalkyl, phenyl, ($C_1$–$C_{10}$)heterocyclic, ($C_1$–$C_{10}$)heteroaryl, HO—(C=O)—, $R^{16}$—($C_1$–$C_6$)alkyl-O—(C=O)—, $H_2N$—(C=O)—, $R^{16}$—($C_1$–$C_6$)alkyl-NH—(C=O)—, phenyl-NH—(C=O)—, ($C_1$–$C_{10}$)heterocyclic-NH—(C=O)—, [($C_1$–$C_6$)alkyl]$_2$-N—(C=O)—, phenyl-[(($C_1$–$C_6$)alkyl)-N]—(C=O)—, hydroxy, $R^{16}$—($C_1$–$C_6$)alkoxy, phenoxy, amino, $R^{16}$—($C_1$–$C_6$)alkylamino, [($C_1$–$C_6$)alkyl]$_2$-amino, $R^{16}$—($C_1$–$C_6$)alkyl-(C=O)—NH—; wherein each of the aforesaid phenyl, heterocyclic, heteroaryl or cycloalkyl $R^{14}$ substituents may optionally be independently substituted by one to four moieties independently selected from the group consisting of halo, $R^{16}$—($C_1$–$C_6$)alkyl, ($C_2$–$C_6$)alkenyl, ($C_2$–$C_6$)alkynyl, perhalo($C_1$–$C_6$)alkyl, ($C_1$–$C_6$)alkyl-SO$_2$—, formyl, —CN, $R^{16}$—($C_1$–$C_6$)alkyl-(C=O)—, HO—(C=O)—, ($C_1$–$C_6$)alkyl-O—(C=O)—, $H_2N$—(C=O)—, $R^{16}$—($C_1$–$C_6$)alkyl-NH—(C=O)—, [($C_1$–$C_6$)alkyl]$_2$-N—(C=O)—, hydroxy, $R^{16}$—($C_1$–$C_6$)alkoxy, perhalo($C_1$–$C_6$)alkoxy, $R^{16}$—($C_1$–$C_6$)alkyl-(C=O)—O—, amino, $R^{16}$—($C_1$–$C_6$)alkylamino, [($C_1$–$C_6$)alkyl]$_2$-amino, formamidyl, $R^{16}$—($C_1$–$C_6$)alkyl-(C=O)—NH—, $R^{16}$—($C_1$–$C_6$)alkyl-(C=O)—[(($C_1$–$C_6$)alkyl)-N]— and $R^{16}$—($C_1$–$C_6$)alkyl-SO$_2$NH—;

each $R^{15}$ is independently selected from the group consisting of hydrogen, halo, ($C_1$–$C_6$)alkyl, ($C_2$–$C_6$)alkenyl, perhalo($C_1$–$C_6$)alkyl, HO—(C=O)—, ($C_1$–$C_6$)alkyl-O—(C=O)—, $H_2N$—(C=O)—, ($C_1$–$C_6$)alkyl-NH—(C=O)—, [($C_1$–$C_6$)alkyl]$_2$-N—(C=O)—, hydroxy, ($C_1$–$C_6$)alkoxy, perhalo($C_1$–$C_6$)alkoxy, amino, ($C_1$–$C_6$)alkylamino, [($C_1$–$C_6$)alkyl]$_2$-amino, formamidyl and ($C_1$–$C_6$)alkyl-(C=O)—NH—; wherein no more than two of said $R^{15}$ groups may be other than hydrogen; and each $R^{16}$ is independently selected from the group consisting of hydrogen, halo, ($C_1$–$C_6$)alkyl, ($C_2$–$C_6$)alkenyl, ($C_2$–$C_6$)alkynyl, perhalo($C_1$–$C_6$)alkyl, HO—(C=O)—, ($C_1$–$C_6$)alkyl-O—(C=O)—, $H_2N$—(C=O)—, ($C_1$–$C_6$)alkyl-NH—(C=O)—, [($C_1$–$C_6$)alkyl]$_2$-N—(C=O)—, hydroxy, ($C_1$–$C_6$)alkoxy, perhalo($C_1$–$C_6$)alkoxy, ($C_1$–$C_6$)alkyl-(C=O)—O—, —NO$_2$, amino, ($C_1$–$C_6$)alkylamino, [($C_1$–$C_6$)alkyl]$_2$-amino, formamidyl and ($C_1$–$C_6$)alkyl-(C=O)—NH—.

36. A compound according to claim 1, wherein $R^6$ is hydrogen.

37. A compound according to claim 1, wherein $R^6$ is $R^9$—B—(CH$_2$)$_n$— and n is zero.

38. A compound according to claim 1, wherein $R^6$ is $R^9$—B—(CH$_2$)$_n$— and n is an integer from one to five.

39. A compound according to claim 1, wherein $R^6$ is $R^9$—B—(CH$_2$)$_n$—; n is zero; B is a bond and $R^9$ is selected from the group consisting of hydrogen, —CF$_3$, —C≡N, ($C_1$–$C_{10}$)heteroaryl, ($C_1$–$C_{10}$)heterocyclic or ($C_3$–$C_{10}$)cycloalkyl; wherein each of the aforesaid ($C_1$–$C_{10}$)heteroaryl, ($C_1$–$C_{10}$)heterocyclic and ($C_3$–$C_{10}$)cycloalkyl may optionally be substituted by one to three moieties independently selected from the group consisting of halo, ($C_1$–$C_6$)alkyl, ($C_2$–$C_6$)alkenyl, ($C_1$–$C_6$)alkynyl, perhalo ($C_1$–$C_6$)alkyl, hydroxy, ($C_1$–$C_6$)alkoxy, perhalo($C_1$–$C_6$)alkoxy, ($C_1$–$C_6$)alkyl-S—, ($C_1$–$C_6$)alkyl-SO$_2$—, ($C_1$–$C_6$)alkyl-NH—SO$_2$—, —NO$_2$, amino, ($C_1$–$C_6$)alkylamino, [($C_1$–$C_6$)alkyl]$_2$-amino, ($C_1$–$C_6$)alkyl-SO$_2$—NH—, (C₁-C₆)alkyl-(C=O)—NH—, (C₁-C₆)alkyl-(C=O)—[((C₁-C₆)alkyl)-N]—, —CN, (C₁-C₆)alkyl-(C=O)—, HO—(C=O)—, (C₁-C₆)alkyl-O—(C=O)—, H₂N(C=O)—, (C₁-C₆)alkyl-NH—(C=O)—, [(C₁-C₆)alkyl]₂-N—(C=O)— and (C₁-C₆)alkyl-(C=O)—O—.

40. A compound according to claim 1, wherein R⁶ is R⁹—B—(CH₂)ₙ—; n is zero; B is —(C=O)—NR¹⁰—, —(R¹⁰—N)—, —(R¹⁰—N)—SO₂—, —(R¹⁰—N)—(C=O)—, >C=O, —O—(C=O)—, —SO₂—(NR¹⁰)—, —(R¹⁰—N)—(C=O)—(NR¹¹)—; and R⁹ is selected from the group consisting of hydrogen, (C₃-C₁₀)cycloalkyl or phenyl; wherein the aforesaid phenyl and (C₃-C₁₀)cycloalkyl may optionally be substituted by one to three moieties independently selected from the group consisting of halo, (C₁-C₆)alkyl, (C₂-C₆)alkenyl, (C₂-C₆)alkynyl, perhalo(C₁-C₆)alkyl, hydroxy, (C₁-C₆)alkoxy, perhalo(C₁-C₆)alkoxy, (C₁-C₆)alkyl-S—, (C₁-C₆)alkyl-SO₂—, (C₁-C₆)alkyl-NH—SO₂—, —NO₂, amino (C₁-C₆)alkylamino, [(C₁-C₆)alkyl]₂-amino, (C₁-C₆)alkyl-SO₂—NH—, (C₁-C₆)alkyl-(C=O)—NH—, (C₁-C₆)alkyl-(C=O)—[N(C₁-C₆)alkyl]-, —CN, (C₁-C₆)alkyl-(C=O)—, HO—(C=O)—, (C₁-C₆)alkyl-O—(C=O)—, H₂N(C=O)— (C₁-C₆)alkyl-NH—(C=O)—, [(C₁-C₆)alkyl]₂-N—(C=O)— and (C₁-C₆)alkyl-(C=O)—O—.

41. A compound according to claim 1, wherein R⁶ is R⁹—B—(CH₂)ₙ—; n is zero; B is —(C=O)—NR¹⁰—, —(R¹⁰—N)—, >C=O, —O—(C=O)—, —(R¹⁰—N)—(C=O)— or —(R¹⁰—N)—(C=O)—(NR¹¹)—; R⁹ is R¹³—(R¹²CH)ₘ—; m is 1–6; R¹⁰ is hydrogen or methyl; R¹² is hydrogen or methyl; and R¹³ is selected from the group consisting of hydrogen, (C₁-C₆)alkyl, (C₁-C₆)alkoxy, phenyl, (C₁-C₁₀)heteroaryl, (C₁-C₁₀)heterocyclic, (C₃-C₁₀)cycloalkyl, amino, (C₁-C₆)alkylamino, [(C₁-C₆)alkyl]₂amino, (C₁-C₆)alkyl-SO₂—NH—phenyl-SO₂—NH—, (C₁-C₆)alkyl-SO₂—[N—(C₁-C₆)alkyl]-, phenyl-SO₂—[N—(C₁-C₆)alkyl]-, hydroxy, (C₁-C₆)alkoxy, perhalo(C₁-C₆)alkoxy, phenoxy, (C₁-C₁₀)heteroaryl-O—, (C₁-C₁₀)heterocyclic-O—, (C₃-C₁₀)cycloalkyl-O—, (C₁-C₆)alkyl-S—, (C₁-C₆)alkyl-SO₂—, (C₁-C₆)alkyl-NH—SO₂—, —NO₂, amino, (C₁-C₆)alkylamino, [(C₁-C₆)alkyl]₂-amino, (C₁-C₆)alkyl-SO₂—NH—, (C₁-C₆)alkyl-(C=O)—NH—, (C₁-C₆)alkyl-(C=O)—[N (C₁-C₆)alkyl]-, phenyl-(C=O)—NH—, phenyl-(C=O)—[N—(C₁-C₆)alkyl]-, —CN, (C₁-C₆)alkyl-(C=O)—, phenyl-(C=O)—, (C₁-C₁₀)heteroaryl-(C=O)—, (C₁-C₁₀)heterocyclic-(C=O)—, (C₃-C₁₀)cycloalkyl-(C=O)—, (C₁-C₁₀)heteroaryl-NH—(C=O)—, (C₁-C₁₀)heterocyclic-NH—(C=O)—, (C₃-C₁₀)cycloalkyl-NH—(C=O)—, HO—(C=O)—, (C₁-C₆)alkyl-O—(C=O)—, H₂N(C=O)—, (C₁-C₆)alkyl-NH—(C=O)—, [(C₁-C₆)alkyl]₂-N—(C=O)—, phenyl-NH—(C=O)—, phenyl-[N—((C₁-C₆)alkyl)]-(C=O)—, (C₁-C₆)alkyl-(C=O)—O— and phenyl-(C=O)—O—.

42. A compound according to claim 1, wherein R⁶ is R⁹—B—(CH₂)ₙ—; n is zero; B is —(R¹⁰—N)—; R⁹ is hydrogen or R¹³—(R¹²CH)ₘ—; m is 1–6; R¹⁰ is hydrogen or methyl; R¹² is hydrogen or methyl; and R¹³ is selected from the group consisting of hydrogen, (C₁-C₆)alkyl, hydroxy, (C₁-C₆)alkoxy, amino, (C₁-C₆)alkylamino, [(C₁-C₆)alkyl]₂amino, (C₂-C₆)alkenyl, (C₂-C₆)alkynyl, phenyl, (C₁-C₁₀)heteroaryl, (C₁-C₁₀)heterocyclic and (C₃-C₁₀)cycloalkyl.

43. A compound according to claim 1, wherein R⁶ is R⁹—B—(CH₂)ₙ—; n is one to four; B is —(C=O)—NR¹⁰—, (R¹⁰—N)—, —(R¹⁰—N)—(C=O)— or —(R¹⁰—N)—(C=O)—(NR¹¹)—; R⁹ is R¹³—(R¹²CH)ₘ—; m is 1–6; R¹⁰ is hydrogen or methyl; R¹² is hydrogen or methyl; and R¹³ is selected from the group consisting of hydrogen, (C₁-C₆)alkyl, (C₁-C₆)alkoxy, phenyl, (C₁-C₁₀)heteroaryl, (C₁-C₁₀)heterocyclic, (C₃-C₁₀)cycloalkyl, amino, (C₁-C₆)alkylamino, [(C₁-C₆)alkyl]₂amino, (C₁-C₆)alkyl-SO₂—NH—, phenyl-SO₂—NH—, (C₁-C₆)alkyl-SO₂—[N—(C₁-C₆)alkyl]-, phenyl-SO₂—[N—(C₁-C₆)alkyl]-, hydroxy, (C₁-C₆)alkoxy, perhalo(C₁-C₆)alkoxy, phenoxy, (C₁-C₁₀)heteroaryl-O—, (C₁-C₁₀)heterocyclic-O—, (C₃-C₁₀)cycloalkyl-O—, (C₁-C₆)alkyl-S—, (C₁-C₆)alkyl-SO₂—, (C₁-C₆)alkyl-NH—SO₂—, —NO₂, amino, (C₁-C₆)alkylamino, [(C₁-C₆)alkyl]₂-amino, (C₁-C₆)alkyl-SO₂—NH—, (C₁-C₆)alkyl-(C=O)—NH—, (C₁-C₆)alkyl-(C=O)—[((C₁-C₆)alkyl)-N]—, phenyl-(C=O)—NH—, phenyl-(C=O)—[((C₁-C₆)alkyl)-N]—, —CN, (C₁-C₆)alkyl-(C=O)—, phenyl-(C=O)—, (C₁-C₁₀)heteroaryl-(C=O)—, (C₁-C₁₀)heterocyclic-(C=O)—, (C₃-C₁₀)cycloalkyl-(C=O)—, (C₁-C₁₀)heteroaryl-NH—(C=O)—, (C₁-C₁₀)heterocyclic-NH—(C=O)—, (C₃-C₁₀)cycloalkyl-NH—(C=O)—, HO—(C=O)—, H₂N(C=O)— (C₁-C₆)alkyl-NH—(C=O)—, [(C₁-C₆)alkyl]₂-N—(C=O)—, phenyl-NH—(C=O)—, phenyl-[((C₁-C₆)alkyl)-N]—(C=O)—, (C₁-C₆)alkyl-(C=O)—O— and phenyl-(C=O)—O—.

44. A compound according to claim 1, wherein s is an integer from zero to four and each R³ is independently selected from the group consisting of halo, (C₁-C₆)alkyl, (C₂-C₆)alkenyl, (C₂-C₆)alkynyl, perhalo(C₁-C₆)alkyl, phenyl, (C₁-C₁₀)heteroaryl, (C₁-C₁₀)heterocyclic, (C₃-C₁₀)cycloalkyl, hydroxy, (C₁-C₆)alkoxy, perhalo(C₁-C₆)alkoxy, phenoxy, (C₁-C₁₀)heteroaryl-O—, (C₁-C₁₀)heterocyclic-O—, (C₃-C₁₀)cycloalkyl-O—, (C₁-C₆)alkyl-S—, (C₁-C₆)alkyl-SO₂—, (C₁-C₆)alkyl-NH—SO₂—, —NO₂, amino, (C₁-C₆)alkylamino, [(C₁-C₆)alkyl]₂—, amino, (C₁-C₆)alkyl-SO₂—NH—, (C₁-C₆)alkyl-(C=O)—NH—, (C₁-C₆)alkyl-(C=O)—[((C₁-C₆)alkyl)-N]—, phenyl-(C=O)—NH—, phenyl-(C=O)—[((C₁-C₆)alkyl)-N]—, —CN, (C₁-C₆)alkyl-(C=O)—, phenyl-(C=O)—, (C₁-C₁₀)heteroaryl-(C=O)—, (C₁-C₁₀)heterocyclic-(C=O)—, (C₃-C₁₀)cycloalkyl-(C=O)—, HO—(C=O)—, (C₁-C₆)alkyl-O—(C=O)—, H₂N(C=O)— (C₁-C₆)alkyl-NH—(C=O)—, [(C₁-C₆)alkyl]₂-N—(C=O)—, phenyl-NH—(C=O)—, phenyl-[((C₁-C₆)alkyl)-N]—(C=O)—, (C₁-C₁₀)heteroaryl-NH—(C=O)—, (C₁-C₁₀)heterocyclic-NH—(C=O)—, (C₃-C₁₀)cycloalkyl-NH—(C=O)— and (C₁-C₆)alkyl-(C=O)—O—.

45. A compound according to claim 1, wherein s is an integer from zero to four and each R³ is independently selected from the group consisting of halo, —CN, (C₁-C₆)alkyl, (C₂-C₆)alkenyl, (C₂-C₆)alkynyl and perhalo(C₁-C₆)alkyl.

46. A compound according to claim 1, wherein s is an integer from zero to four and zero, one or two of R³ are independently selected from the group consisting of halo, (C₁-C₆)alkyl, perhalo(C₁-C₆)alkyl, hydroxy, (C₁-C₆)alkoxy, perhalo(C₁-C₆)alkoxy, amino, (C₁-C₆)alkylamino, [(C₁-C₆)alkyl]₂-amino, —CN, and H₂N(C=O)—.

47. A compound according to claim 1, wherein s is an integer from zero to three and each R³ is independently selected from the group consisting of halo, (C₁-C₆)alkyl, perhalo(C₁-C₆)alkyl, hydroxy, (C₁-C₆)alkoxy, perhalo(C₁-C₆)alkoxy, —NO₂, amino, (C₁-C₆)alkylamino, [(C₁-C₆)alkyl]₂-amino, —CN, and H₂N(C=O)—.

48. A compound according to claim 1, wherein s is an integer from zero to two and each R³ is independently selected from the group consisting of halo, $(C_1-C_6)$alkyl, perhalo$(C_1-C_6)$alkyl, $(C_1-C_6)$alkoxy, perhalo$(C_1-C_6)$alkoxy and —CN.

49. A compound according to claim 1, wherein s is an integer from zero to three and each $R^3$ is independently selected from the group consisting of fluoro, chloro and methyl.

50. A compound according to claim 1, wherein said compound is selected from the group consisting of:

3-Isopropyl-6-(4-phenyl-oxazol-5-yl)-[1,2,4]triazolo[4,3-a]pyridine;

3-Ethyl-6-(4-m-tolyl-oxazol-5-yl)-[1,2,4]triazolo[4,3-a]pyridine;

3-Cyclopropyl-6-[4-(4-fluoro-phenyl)-oxazol-5-yl]-[1,2,4]triazolo[4,3-a]pyridine;

3-Cyclobutyl-6-[4-(4-fluoro-phenyl)-oxazol-5-yl]-[1,2,4]triazolo[4,3-a]pyridine;

3-Cyclobutyl-6-(4-phenyl-oxazol-5-yl)-[1,2,4]triazolo[4,3-a]pyridine;

3-Cyclopropyl-6-(4-phenyl-oxazol-5-yl)-[1,2,4]triazolo[4,3-a]pyridine;

3-Ethyl-6-(4-phenyl-oxazol-5-yl)-[1,2,4]triazolo[4,3-a]pyridine;

3-Ethyl-6-[4-(4-fluoro-phenyl)-oxazol-5-yl]-[1,2,4]triazolo[4,3-a]pyridine;

6-[4-(4-Fluoro-phenyl)-oxazol-5-yl]-3-isopropyl-[1,2,4]triazolo[4,3-a]pyridine;

3-Cyclobutyl-6-(4-m-tolyl-oxazol-5-yl)-[1,2,4]triazolo[4,3-a]pyridine;

3-Isopropyl-6-(4-m-tolyl-oxazol-5-yl)-[1,2,4]triazolo[4,3-a]pyridine;

6-[4-(4-Fluoro-3-methyl-phenyl)-oxazol-5-yl]-3-isopropyl-[1,2,4]triazolo[4,3-a]pyridine;

3-Cyclopropyl-6-[4-(4-fluoro-3-methyl-phenyl)-oxazol-5-yl]-[,1,2,4]triazolo[4,3-a]pyridine;

6-[4-(4-Fluoro-phenyl)-oxazol-5-yl]-3-phenyl-[1,2,4]triazolo[4,3-a]pyridine;

3-Isopropyl-6-(2-methyl-4-phenyl-oxazol-5-yl)-[1,2,4]triazolo[4,3-a]pyridine; and 6-[4-(4-Fluoro-phenyl)-2-methyl-oxazol-5-yl]-3-isopropyl-[,2,4]triazolo[4,3-a]pyridine.

51. A method for treating a condition selected from the group consisting of arthritis, psoriatic arthritis, Reiter's syndrome, rheumatoid arthritis, gout, traumatic arthritis, rubella arthritis and acute synovitis, rheumatoid arthritis, rheumatoid spondylitis, osteoarthritis, gouty arthritis and other arthritic condition, sepsis, septic shock, endotoxic shock, gram negative sepsis, toxic shock syndrome, Alzheimer's disease, stroke, neurotrauma, asthma, adult respiratory distress syndrome, cerebral malaria, chronic pulmonary inflammatory disease, silicosis, pulmonary sarcoidosis, bone resorption disease, osteoporosis, restenosis, cardiac and renal reperfusion injury, thrombosis, glomerularonephritis, diabetes, graft vs. host reaction, allograft rejection, inflammatory bowel disease, Crohn's disease, ulcerative colitis, multiple sclerosis, muscle degeneration, eczema, contact dermatitis, psoriasis, sunburn, and conjunctivitis shock in a mammal, including a human, comprising administering to said mammal an amount of a compound according to claim 1, effective in treating such a condition.

52. A pharmaceutical composition for the treatment of a condition selected from the group consisting of arthritis, psoriatic arthritis, Reiter's syndrome, rheumatoid arthritis, gout, traumatic arthritis, rubella arthritis and acute synovitis, rheumatoid arthritis, rheumatoid spondylitis, osteoarthritis, gouty arthritis and other arthritic condition, sepsis, septic shock, endotoxic shock, gram negative sepsis, toxic shock syndrome, Alzheimer's disease, stroke, neurotrauma, asthma, adult respiratory distress syndrome, cerebral malaria, chronic pulmonary inflammatory disease, silicosis, pulmonary sarcoidosis, bone resorption disease, osteoporosis, restenosis, cardiac and renal reperfusion injury, thrombosis, glomerularonephritis, diabetes, graft vs. host reaction, allograft rejection, inflammatory bowel disease, Crohn's disease, ulcerative colitis, multiple sclerosis, muscle degeneration, eczema, contact dermatitis, psoriasis, sunburn, and conjunctivitis shock in a mammal, including a human, comprising an amount of a compound according to claim 1 effective in such treatment and a pharmaceutically acceptable carrier.

53. A pharmaceutical composition for the treatment of a condition which can be treated by the inhibition of ERK/MAP kinase in a mammal, including a human, comprising an amount of a compound according to claim 1 effective in such treatment and a pharmaceutically acceptable carrier.

* * * * *